US010561812B2

(12) United States Patent
Skipper et al.

(10) Patent No.: US 10,561,812 B2
(45) Date of Patent: Feb. 18, 2020

(54) MASK SYSTEM

(71) Applicant: ResMed Pty Ltd, Bella Vista (AU)

(72) Inventors: Christopher Scott Skipper, Sydney (AU); Alison Oldenburg, Sydney (AU); Karthikeyan Selvarajan, Sydney (AU); Steven John Lubke, Sydney (AU); Gregory Scott Smart, Sydney (AU); Rupert Christian Scheiner, Sydney (AU); James William Vandyke, Sydney (AU); Michael John Reid, Sydney (AU); Timothy Shawn Nelson, Sydney (AU); Philip Rodney Kwok, Sydney (AU)

(73) Assignee: ResMed Pty Ltd, Bella Vista, NSW (AU)

( * ) Notice: Subject to any disclaimer, the term of this patent is extended or adjusted under 35 U.S.C. 154(b) by 0 days.

(21) Appl. No.: 16/183,417

(22) Filed: Nov. 7, 2018

(65) Prior Publication Data
US 2019/0070381 A1 Mar. 7, 2019

Related U.S. Application Data

(63) Continuation of application No. 16/182,300, filed on Nov. 6, 2018, which is a continuation of application
(Continued)

(51) Int. Cl.
*A61M 16/06* (2006.01)
*A62B 18/08* (2006.01)

(52) U.S. Cl.
CPC ........ *A61M 16/06* (2013.01); *A61M 16/0605* (2014.02); *A61M 16/0683* (2013.01);
(Continued)

(58) Field of Classification Search
CPC .. A61M 16/00; A61M 16/06; A61M 16/0605; A61M 16/0611; A61M 16/0616;
(Continued)

(56) References Cited

U.S. PATENT DOCUMENTS

| 122,905 A | 1/1872 | O'Dell |
| 443,191 A | 12/1890 | Illing |

(Continued)

FOREIGN PATENT DOCUMENTS

| AU | 199651130 | 10/1996 |
| AU | 06/000031 | 1/2006 |

(Continued)

OTHER PUBLICATIONS

U.S. Appl. No. 10/584,711, filed Jun. 26, 2006, Davidson et al.
(Continued)

*Primary Examiner* — Colin W Stuart
(74) *Attorney, Agent, or Firm* — Fish & Richardson P.C.

(57) ABSTRACT

A mask system for use between a patient and device to deliver a breathable gas to the patient includes a mouth cushion, a pair of nasal prongs, an elbow, and a headgear assembly. The mouth cushion is structured to sealingly engage around an exterior of a patient's mouth in use, and the pair of nasal prongs are structured to sealingly communicate with nasal passages of a patient's nose in use. The elbow delivers breathable gas to the patient. The headgear assembly maintains the mouth cushion and the nasal prongs in a desired position on the patient's face. The headgear assembly provides a substantially round crown strap that cups the parietal bone and occipital bone of the patient's head in use.

22 Claims, 111 Drawing Sheets

Related U.S. Application Data

No. 14/663,499, filed on Mar. 20, 2015, which is a continuation of application No. 11/921,185, filed as application No. PCT/AU2006/000770 on Jun. 6, 2006, now Pat. No. 9,032,955.

(60) Provisional application No. 60/687,453, filed on Jun. 6, 2005, provisional application No. 60/702,581, filed on Jul. 27, 2005, provisional application No. 60/795,562, filed on Apr. 28, 2006.

(52) U.S. Cl.
CPC ..... *A61M 16/0616* (2014.02); *A61M 16/0622* (2014.02); *A61M 2016/0661* (2013.01); *A61M 2210/06* (2013.01); *A61M 2210/0606* (2013.01); *A61M 2210/0618* (2013.01); *A61M 2210/0625* (2013.01); *A62B 18/084* (2013.01); *Y10T 29/49826* (2015.01)

(58) Field of Classification Search
CPC .......... A61M 16/0622; A61M 16/0683; A61M 2016/0661; A61M 2210/06; A61M 2210/0606; A61M 2210/0618; A61M 2210/0625; A62B 18/00; A62B 18/006; A62B 18/02; A62B 18/025; A62B 18/04; A62B 18/045

See application file for complete search history.

(56) References Cited

U.S. PATENT DOCUMENTS

| | | | |
|---|---|---|---|
| 1,125,542 A | 1/1915 | Humphries | |
| 1,229,050 A | 6/1917 | Donald | |
| 1,282,527 A | 10/1918 | Bidonde | |
| 1,362,766 A | 12/1920 | Mcgargill | |
| 1,445,010 A | 2/1923 | Feinberg | |
| 1,710,160 A | 2/1925 | Gibbs | |
| 1,614,231 A | 1/1927 | Cosgrove | |
| 1,873,160 A | 8/1932 | Sturtevant | |
| 2,020,978 A | 11/1935 | Whiton | |
| 2,126,755 A | 8/1938 | Dreyfus | |
| 2,130,555 A | 9/1938 | Malcom | |
| 2,228,218 A | 1/1941 | Schwartz | |
| 2,578,621 A | 12/1951 | Yant | |
| 2,706,983 A | 4/1955 | Matheson et al. | |
| 2,837,090 A | 6/1958 | Bloom et al. | |
| 2,998,818 A | 9/1961 | Tabor et al. | |
| 3,013,556 A | 12/1961 | Galleher | |
| 3,330,273 A | 7/1967 | Bennett | |
| 3,424,633 A | 1/1969 | Corrigall et al. | |
| 3,457,564 A | 7/1969 | Holloway | |
| 3,739,774 A | 6/1973 | Gregory | |
| 3,754,552 A | 8/1973 | King | |
| 3,799,164 A | 3/1974 | Rollins | |
| 3,861,385 A | 1/1975 | Carden | |
| 3,902,486 A | 9/1975 | Guichard | |
| 3,905,361 A | 9/1975 | Hewson et al. | |
| 4,156,426 A | 5/1979 | Gold | |
| 4,248,218 A | 2/1981 | Fischer | |
| 4,263,908 A | 4/1981 | Mizerak | |
| 4,267,845 A | 5/1981 | Robertson, Jr. et al. | |
| 4,273,124 A | 6/1981 | Zimmerman | |
| 4,312,359 A | 1/1982 | Olson | |
| 4,367,735 A | 1/1983 | Dali | |
| 4,367,816 A | 1/1983 | Wilkes | |
| 4,406,283 A | 9/1983 | Bir | |
| 4,422,456 A | 12/1983 | Tiep | |
| 4,449,526 A | 5/1984 | Elam | |
| 4,454,880 A | 6/1984 | Muto et al. | |
| 4,493,614 A | 1/1985 | Chu et al. | |
| 4,549,542 A | 10/1985 | Chien | |
| 4,587,967 A | 5/1986 | Chu et al. | |
| 4,601,465 A | 7/1986 | Roy | |
| 4,617,637 A | 10/1986 | Chu et al. | |
| 4,660,555 A | 4/1987 | Payton | |
| 4,676,241 A | 6/1987 | Webb et al. | |
| 4,699,139 A | 10/1987 | Marshall et al. | |
| 4,706,664 A | 11/1987 | Snook et al. | |
| 4,753,233 A | 6/1988 | Grimes | |
| 4,774,946 A | 10/1988 | Ackerman et al. | |
| 4,782,832 A | 11/1988 | Trimble et al. | |
| 4,899,740 A | 2/1990 | Napolitano | |
| 4,915,105 A | 4/1990 | Lee | |
| 4,919,128 A | 4/1990 | Kopala et al. | |
| 4,944,310 A | 7/1990 | Sullivan | |
| 4,960,121 A | 10/1990 | Nelson et al. | |
| 4,996,983 A | 3/1991 | AmRhein | |
| 5,000,173 A | 3/1991 | Zalkin et al. | |
| 5,005,571 A | 4/1991 | Dietz | |
| 5,018,519 A * | 5/1991 | Brown .................. | A61M 16/06 128/203.29 |
| 5,022,900 A | 6/1991 | Bar-Yona et al. | |
| 5,025,805 A | 6/1991 | Nutter | |
| 5,038,772 A | 8/1991 | Kolbe et al. | |
| 5,042,478 A | 8/1991 | Kopala et al. | |
| 5,046,491 A | 9/1991 | Derrick | |
| 5,062,421 A | 11/1991 | Burns et al. | |
| D322,318 S | 12/1991 | Sullivan | |
| 5,074,297 A | 12/1991 | Venegas | |
| 5,109,839 A * | 5/1992 | Blasdell ................ | A61M 16/06 128/203.12 |
| 5,113,857 A | 5/1992 | Dickerman et al. | |
| 5,121,745 A | 6/1992 | Israel | |
| 5,127,397 A | 7/1992 | Kohnke | |
| 5,137,017 A | 8/1992 | Salter | |
| D333,015 S | 2/1993 | Farmer et al. | |
| 5,188,101 A | 2/1993 | Tumolo | |
| 5,205,832 A | 4/1993 | Tuman | |
| 5,233,978 A | 8/1993 | Callaway | |
| 5,243,971 A | 9/1993 | Sullivan et al. | |
| 5,265,592 A | 11/1993 | Beaussant | |
| 5,265,595 A | 11/1993 | Rudolph | |
| 5,269,296 A | 12/1993 | Landis | |
| 5,271,391 A | 12/1993 | Graves | |
| 5,299,599 A | 4/1994 | Farmer et al. | |
| 5,335,656 A | 8/1994 | Bowe et al. | |
| 5,355,893 A | 10/1994 | Mick et al. | |
| 5,372,130 A | 12/1994 | Stern et al. | |
| 5,375,593 A | 12/1994 | Press | |
| 5,385,141 A | 1/1995 | Granatiero | |
| 5,394,568 A | 3/1995 | Brostrom et al. | |
| 5,396,885 A | 3/1995 | Nelson | |
| 5,398,676 A | 3/1995 | Press et al. | |
| 5,400,776 A | 3/1995 | Bartholomew | |
| 5,425,359 A | 6/1995 | Liou | |
| 5,437,267 A | 8/1995 | Weinstein et al. | |
| 5,474,060 A | 12/1995 | Evans | |
| 5,477,852 A | 12/1995 | Landis et al. | |
| 5,509,409 A | 4/1996 | Weatherholt | |
| 5,513,634 A | 5/1996 | Jackson | |
| 5,526,806 A | 6/1996 | Sansoni | |
| 5,533,506 A | 7/1996 | Wood | |
| 5,540,223 A | 7/1996 | Starr et al. | |
| 5,560,354 A | 10/1996 | Berthon-Jones et al. | |
| 5,657,752 A | 8/1997 | Landis et al. | |
| D383,204 S | 9/1997 | Lomas | |
| 5,662,101 A | 9/1997 | Ogden et al. | |
| 5,724,965 A | 3/1998 | Handke et al. | |
| 5,740,799 A | 4/1998 | Nielsen | |
| 5,746,201 A | 5/1998 | Kidd | |
| 5,758,642 A | 6/1998 | Choi | |
| 5,794,619 A | 8/1998 | Edelman et al. | |
| 5,906,203 A | 5/1999 | Klockseth et al. | |
| 5,921,239 A | 7/1999 | McCall et al. | |
| 5,954,049 A | 9/1999 | Foley et al. | |
| 6,016,804 A | 1/2000 | Gleason et al. | |
| 6,019,101 A | 2/2000 | Cotner et al. | |
| 6,112,746 A | 9/2000 | Kwok et al. | |
| 6,119,694 A | 9/2000 | Correa et al. | |
| 6,123,071 A | 9/2000 | Berthon-Jones et al. | |
| 6,123,082 A | 9/2000 | Berthon-Jones | |
| 6,192,886 B1 | 2/2001 | Rudolph | |

(56) References Cited

U.S. PATENT DOCUMENTS

| | | |
|---|---|---|
| 6,269,814 B1 | 8/2001 | Blaszczykiewicz et al. |
| 6,338,342 B1 | 1/2002 | Fecteau et al. |
| 6,357,441 B1 | 3/2002 | Kwok et al. |
| 6,374,826 B1 | 4/2002 | Gunaratnam et al. |
| 6,412,487 B1 | 7/2002 | Gunaratnam et al. |
| 6,412,488 B1 | 7/2002 | Barnett et al. |
| 6,418,928 B1 | 7/2002 | Bordewick et al. |
| 6,422,238 B1 | 7/2002 | Lithgow |
| 6,431,172 B1 | 8/2002 | Bordewick |
| 6,435,181 B1 | 8/2002 | Jones, Jr. et al. |
| 6,439,230 B1 | 8/2002 | Gunaratnam et al. |
| 6,439,234 B1 | 8/2002 | Curti et al. |
| 6,457,473 B1 | 10/2002 | Brostrom et al. |
| 6,467,483 B1 | 10/2002 | Kopacko et al. |
| 6,470,886 B1 | 10/2002 | Jestrabek-Hart |
| 6,478,026 B1 | 11/2002 | Wood |
| 6,513,526 B2 | 2/2003 | Kwok et al. |
| 6,530,373 B1 | 3/2003 | Patron et al. |
| 6,532,961 B1 | 3/2003 | Kwok et al. |
| 6,561,188 B1 | 5/2003 | Ellis |
| 6,561,190 B1 | 5/2003 | Kwok |
| 6,561,193 B1 | 5/2003 | Noble |
| 6,571,798 B1 | 6/2003 | Thornton |
| 6,581,594 B1 | 6/2003 | Drew et al. |
| 6,581,602 B2 | 6/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,631,718 B1 | 10/2003 | Lovell |
| 6,637,434 B2 | 10/2003 | Noble |
| 6,644,315 B2 | 11/2003 | Ziaee |
| 6,644,316 B2 | 11/2003 | Bowman et al. |
| 6,655,385 B1 | 12/2003 | Curti et al. |
| 6,665,915 B1 | 12/2003 | Higuchi |
| 6,679,257 B1 | 1/2004 | Robertson et al. |
| 6,679,265 B2 | 1/2004 | Strickland et al. |
| 6,691,707 B1 | 2/2004 | Gunaratnam et al. |
| 6,701,927 B2 | 3/2004 | Kwok et al. |
| 6,732,733 B1 | 5/2004 | Brostrom et al. |
| 6,766,800 B2 | 7/2004 | Chu et al. |
| 6,776,162 B2 | 8/2004 | Wood |
| 6,796,308 B2 | 9/2004 | Gunaratnam et al. |
| 6,807,967 B2 | 10/2004 | Wood |
| 6,820,617 B2 | 11/2004 | Robertson et al. |
| 6,823,869 B2 | 11/2004 | Raje et al. |
| 6,851,425 B2 | 2/2005 | Jaffre et al. |
| 6,857,428 B2 | 2/2005 | Thornton |
| 6,860,270 B2 | 3/2005 | Sniadach |
| D505,489 S | 5/2005 | Sleeper |
| 6,886,564 B2 | 5/2005 | Sullivan et al. |
| 6,907,882 B2 | 6/2005 | Ging et al. |
| 7,007,696 B2 | 3/2006 | Palkon et al. |
| 7,011,090 B2 | 3/2006 | Drew et al. |
| 7,096,867 B2 | 8/2006 | Smith et al. |
| 7,152,602 B2 | 12/2006 | Bateman et al. |
| 7,178,525 B2 | 2/2007 | Matula, Jr. et al. |
| 7,178,528 B2 | 2/2007 | Lau et al. |
| 7,210,481 B1 | 5/2007 | Lovell et al. |
| 7,219,669 B1 | 5/2007 | Lovell et al. |
| 7,243,650 B2 | 7/2007 | Thornton |
| 7,353,827 B2 | 4/2008 | Geist |
| 7,357,136 B2 | 4/2008 | Ho et al. |
| 7,658,189 B2 | 2/2010 | Davidson et al. |
| 7,779,832 B1 | 8/2010 | Ho |
| 7,827,990 B1 | 11/2010 | Melidis et al. |
| 7,878,199 B2 | 2/2011 | Ging et al. |
| 7,909,035 B2 | 3/2011 | Thornton |
| 7,942,148 B2 * | 5/2011 | Davidson ............ A61M 16/06 128/206.11 |
| 7,967,013 B2 | 6/2011 | Ging et al. |
| 8,042,539 B2 | 10/2011 | Chandran et al. |
| 8,136,524 B2 | 3/2012 | Ging et al. |
| 8,342,181 B2 | 1/2013 | Selvarajan et al. |
| 8,443,807 B2 | 5/2013 | McAuley et al. |
| 8,479,741 B2 | 7/2013 | McAuley et al. |
| 8,517,024 B2 | 8/2013 | Selvarajan et al. |
| 8,714,157 B2 | 5/2014 | McAuley et al. |
| 8,944,061 B2 | 2/2015 | D'Souza et al. |
| 8,950,404 B2 | 2/2015 | Formica et al. |
| 8,960,196 B2 | 2/2015 | Henry |
| 9,981,105 B2 | 5/2018 | Selvarajan et al. |
| 2002/0005198 A1 | 1/2002 | Kwok et al. |
| 2002/0020416 A1 | 2/2002 | Namey |
| 2002/0029780 A1 | 3/2002 | Frater et al. |
| 2002/0046755 A1 | 4/2002 | De Voss |
| 2002/0069872 A1 | 6/2002 | Gradon et al. |
| 2002/0096178 A1 | 7/2002 | Ziaee |
| 2002/0108613 A1 * | 8/2002 | Gunaratnam ......... A61M 16/06 128/205.25 |
| 2002/0124849 A1 | 9/2002 | Billette De Villemeur et al. |
| 2002/0174868 A1 | 11/2002 | Kwok et al. |
| 2003/0005931 A1 | 1/2003 | Jaffre et al. |
| 2003/0011080 A1 | 1/2003 | Deshpande et al. |
| 2003/0029454 A1 | 2/2003 | Gelinas et al. |
| 2003/0034030 A1 | 2/2003 | Carlucci et al. |
| 2003/0051732 A1 | 3/2003 | Smith et al. |
| 2003/0079749 A1 | 5/2003 | Strickland et al. |
| 2003/0079751 A1 | 5/2003 | Kwok |
| 2003/0094178 A1 | 5/2003 | McAuley et al. |
| 2003/0131852 A1 | 7/2003 | Shafer et al. |
| 2003/0150460 A1 | 8/2003 | Campbell, Sr. et al. |
| 2003/0172936 A1 | 9/2003 | Wilkie et al. |
| 2003/0196655 A1 | 10/2003 | Ging et al. |
| 2003/0196656 A1 | 10/2003 | Moore et al. |
| 2003/0196658 A1 * | 10/2003 | Ging .................... A61M 16/06 128/201.22 |
| 2004/0025882 A1 | 2/2004 | Madaus et al. |
| 2004/0025885 A1 | 2/2004 | Payne, Jr. |
| 2004/0041342 A1 | 3/2004 | Frieman |
| 2004/0052438 A1 | 3/2004 | Sugita et al. |
| 2004/0065328 A1 | 4/2004 | Amarasinghe et al. |
| 2004/0067333 A1 | 4/2004 | Amarasinghe |
| 2004/0094157 A1 | 5/2004 | Dantanarayana et al. |
| 2004/0112384 A1 | 6/2004 | Lithgow et al. |
| 2004/0118406 A1 | 6/2004 | Lithgow et al. |
| 2004/0182398 A1 | 9/2004 | Sprinkle et al. |
| 2004/0186405 A1 | 9/2004 | Pinna et al. |
| 2004/0211428 A1 | 10/2004 | Jones, Jr. et al. |
| 2004/0226566 A1 | 11/2004 | Gunaratnam et al. |
| 2004/0255949 A1 | 12/2004 | Lang et al. |
| 2005/0001152 A1 | 1/2005 | Stewart et al. |
| 2005/0011523 A1 | 1/2005 | Aylsworth et al. |
| 2005/0011524 A1 | 1/2005 | Thomlinson et al. |
| 2005/0028822 A1 * | 2/2005 | Sleeper ................ A61M 16/06 128/207.18 |
| 2005/0033247 A1 | 2/2005 | Thompson |
| 2005/0051176 A1 | 3/2005 | Riggins |
| 2005/0061326 A1 | 3/2005 | Payne, Jr. |
| 2005/0076913 A1 | 4/2005 | Ho et al. |
| 2005/0098183 A1 | 5/2005 | Nash et al. |
| 2005/0121030 A1 * | 6/2005 | Bateman ............... A61M 16/06 128/201.23 |
| 2005/0155604 A1 | 7/2005 | Ging et al. |
| 2005/0199240 A1 | 9/2005 | Hall |
| 2005/0205096 A1 * | 9/2005 | Matula, Jr. ........ A61M 16/0666 128/207.11 |
| 2005/0268916 A1 | 12/2005 | Mumford et al. |
| 2006/0042629 A1 | 3/2006 | Geist |
| 2006/0060200 A1 | 3/2006 | Ho et al. |
| 2006/0081250 A1 | 4/2006 | Bordewick et al. |
| 2006/0112962 A1 | 6/2006 | Tebbutt et al. |
| 2006/0118117 A1 | 6/2006 | Berthon-Jones et al. |
| 2006/0124131 A1 | 6/2006 | Chandran et al. |
| 2006/0201514 A1 | 9/2006 | Jones et al. |
| 2006/0207597 A1 | 9/2006 | Wright |
| 2006/0272646 A1 | 12/2006 | Ho et al. |
| 2006/0283461 A1 | 12/2006 | Lubke et al. |
| 2007/0014525 A1 | 1/2007 | Sillard et al. |
| 2007/0044804 A1 | 3/2007 | Matula, Jr. et al. |
| 2007/0125385 A1 | 6/2007 | Ho et al. |
| 2007/0130067 A1 | 6/2007 | Keller |
| 2007/0139531 A1 | 6/2007 | Sagatelyan et al. |
| 2007/0175480 A1 | 8/2007 | Gradon et al. |
| 2007/0209663 A1 | 9/2007 | Marque et al. |

(56) References Cited

U.S. PATENT DOCUMENTS

| | | |
|---|---|---|
| 2008/0006277 A1 | 1/2008 | Worboys et al. |
| 2008/0007985 A1 | 1/2008 | Wilcox |
| 2008/0110464 A1 | 5/2008 | Davidson et al. |
| 2009/0044808 A1 | 2/2009 | Guney et al. |
| 2009/0159084 A1 | 6/2009 | Sher et al. |
| 2009/0277452 A1 | 11/2009 | Lubke et al. |
| 2010/0229866 A1 | 9/2010 | Sullivan |
| 2011/0072553 A1 | 3/2011 | Ho |
| 2011/0214674 A1 | 9/2011 | Ging et al. |
| 2014/0083430 A1 | 3/2014 | Matula, Jr. et al. |
| 2019/0070380 A1 | 3/2019 | Skipper |
| 2019/0091429 A1 | 3/2019 | Skipper |

FOREIGN PATENT DOCUMENTS

| | | | |
|---|---|---|---|
| AU | 06/000417 | 3/2006 | |
| AU | PCT/AU2008/906390 | 12/2008 | |
| AU | PCT/AU2009/900327 | 1/2009 | |
| AU | PCT/AU2009/902731 | 6/2009 | |
| AU | PCT/AU2009/904236 | 9/2009 | |
| CA | 996301 | 9/1976 | |
| CN | 2180279 | 10/1994 | |
| CN | 2721141 | 8/2005 | |
| DE | 146688 | 2/1981 | |
| DE | 3719009 | 12/1988 | |
| DE | 19944242 | 3/2001 | |
| EP | 0658356 | 6/1995 | |
| EP | 1481702 | 12/2004 | |
| EP | 1020201 | 7/2009 | |
| GB | 0532214 | 1/1941 | |
| GB | 2176404 | 12/1986 | |
| GB | 2368533 | 5/2002 | |
| GB | 2385533 | 8/2003 | |
| JP | 08-182769 | 7/1996 | |
| JP | 2000-254229 | 9/2000 | |
| JP | 2000-325481 | 11/2000 | |
| JP | 2002-537078 | 11/2002 | |
| JP | 2002-539899 | 11/2002 | |
| JP | 2003-527907 | 9/2003 | |
| JP | 2003-299744 | 10/2003 | |
| JP | 2006-505310 | 2/2006 | |
| WO | WO 87/01950 | 4/1987 | |
| WO | WO 92/20392 | 11/1992 | |
| WO | WO 2000/38772 | 7/2000 | |
| WO | WO 00/50122 | 8/2000 | |
| WO | WO 00/57942 | 10/2000 | |
| WO | WO-0074758 A1 * | 12/2000 | ............ A61M 16/06 |
| WO | WO 01/95965 | 12/2001 | |
| WO | WO 01/97892 | 12/2001 | |
| WO | WO 01/97893 | 12/2001 | |
| WO | WO 02/05883 | 1/2002 | |
| WO | WO 02/47749 | 6/2002 | |
| WO | WO 2002/047749 | 6/2002 | |
| WO | WO 02/051486 | 7/2002 | |
| WO | WO 03/090827 | 11/2003 | |
| WO | WO 2004/022147 | 3/2004 | |
| WO | WO 2004/041325 | 5/2004 | |
| WO | WO 2004/041341 | 5/2004 | |
| WO | WO 2004/041342 | 5/2004 | |
| WO | WO 2004/073778 | 9/2004 | |
| WO | WO 2004/096332 | 11/2004 | |
| WO | WO 2005/021075 | 3/2005 | |
| WO | WO 2005/032634 | 4/2005 | |
| WO | WO 2005/046776 | 5/2005 | |
| WO | WO 2005/051468 | 6/2005 | |
| WO | WO 2005/063326 | 7/2005 | |
| WO | WO 2005/063328 | 7/2005 | |
| WO | WO 2005/079726 | 9/2005 | |
| WO | WO 2005/123166 | 12/2005 | |
| WO | WO 2006/000046 | 1/2006 | |
| WO | WO 2006/000770 | 1/2006 | |
| WO | WO 2006/074515 | 7/2006 | |
| WO | WO 2006/074516 | 7/2006 | |
| WO | WO 96/28207 | 9/2006 | |
| WO | WO 2006/130903 | 12/2006 | |
| WO | WO 2007/006089 | 1/2007 | |
| WO | WO 2007/014088 | 2/2007 | |
| WO | WO 2007/041751 | 4/2007 | |
| WO | WO 2007/045008 | 4/2007 | |
| WO | WO 2007/048174 | 5/2007 | |
| WO | WO 2007/139531 | 12/2007 | |
| WO | WO 2007/147088 | 12/2007 | |
| WO | WO 2008/007985 | 1/2008 | |
| WO | WO 2008/030831 | 3/2008 | |
| WO | WO 2008/068966 | 6/2008 | |
| WO | WO 2009/026627 | 3/2009 | |
| WO | WO 2009/052560 | 4/2009 | |
| WO | WO 2009/059353 | 5/2009 | |
| WO | WO 2010/066004 | 6/2010 | |

OTHER PUBLICATIONS

U.S. Appl. No. 11/474,415, filed Jun. 26, 2006, Davidson et al.
U.S. Appl. No. 60/483,622, filed Jul. 1, 2003, Kwok et al.
U.S. Appl. No. 60/795,615, filed Apr. 1, 2006, Judson et al.
"If You Hate CPAP! You Need CPAP Pro," www.cpappro.com.
ACP Composites—Large Stock of Ready to Use Composite Plate, Tube, Sheet, Fabrics and Core Materials, https://www.acpsakes.com/Core-Materials-nd-Foam.html, dated Oct. 5, 2015, 4 pages.
Amended (Fourth) Statement of Case dated Apr. 27, 2017, with markups, filed by Fisher & Paykel Healthcare Limited in New Zealand Application No. 5999406 (39 pages).
Amended (Fourth) Statement of Case dated Apr. 27, 2017, with no markups, filed by Fisher & Paykel Healthcare Limited in New Zealand Application No. 5999406 (35 pages).
Amended (Third) Statement of Case filed by on Jul. 16, 2015 by Fisher & Paykel Healthcare Limited in corresponding New Zealand Application No. 5999406—Marked-up and clean formats.
Amended (Third) Statement of Case filed on Sep. 1, 2015 by Fisher & Paykel Healthcare Limited in New Zealand Application No. 5999406—Marked-up and clean formats.
Amended Fifth Statement of Case (Clean Copy) dated Aug. 13, 2018 filed by Fisher & Paykel Heathcare Limited in New Zealand Application No. 599406 (63 pages).
Amended Fifth Statement of Case (Marked Up Copy) dated Aug. 13, 2018 filed by Fisher & Paykel Heathcare Limited in New Zealand Application No. 599406 (66 pages).
Claim Amiguity filed on Jul. 20, 2015 by Fisher & Paykel Healthcare Limited in corresponding New Zealand Application No. 5999406.
Communication regarding Deadline for Counterstatement dated Jun. 9, 2017 issued in New Zealand Appliction No. 5999406 (1 pages).
Decision of Rejection issued in corresponding Chinese Appln. No. 201110448115.3 dated Jul. 30, 2014.
Examination Report issued in related New Zealand Appln. No. 591018 (dated Feb. 15, 2011).
Fisher and Paykel Co.—Product Family—http://fphcare.com/osa/products.asp/ viewed on Jul. 24, 2006.
Flexifit instructions, http://web.archive.org/web/1 9970126045828/http:/www.archive.org/ dated Jan. 26, 1997, Affidavit of Christopher Butler dated Sep. 6, 2016, 23 pages.
Fourth Notice of Opposition to Grant of Patent (Section 21), with markups, dated Apr. 27, 2017, filed by Fisher & Paykel Healthcare Limited in New Zealand Application No. 5999406 (2 pages).
Fourth Notice of Opposition to Grant of Patent (Section 21), with no markups, dated Apr. 27, 2017, filed by Fisher & Paykel Healthcare Limited in New Zealand Application No. 5999406 (2 pages).
Further Examination Report issued in a corresponding New Zealand Application No. 599406, dated Jul. 18, 2013.
Guidelines for Sandwich Core Materials, http://fibreglast.com/product/guidelines-for-sandwich-core-materials/Learnin_Center, dated Oct. 5, 2015, 3 pages.
Hans Rudolph, Inc.—Mask Products—http://rudolpkc.com/products.php?category=MASKS viewed on Jul. 24, 2006.
International Preliminary Report on Patentability for PCT/AU2004/001832 dated Jul. 3, 2006.
International Preliminary Report on Patentability, PCT/AU2006/000770, filed Jun. 6, 2006 (dated Dec. 6, 2007), 6 pages.

(56) References Cited

OTHER PUBLICATIONS

International Search Report for PCT/AU2004/001832, dated Mar. 24, 2005.
International Search Report for PCT/AU2006/000770 dated Aug. 3, 2006.
Japanese Decision of Rejection issued in corresponding Appln. No. 2012-023743 dated Oct. 20, 2014 2014.
Malloy, Plastic Part Design for Injection Molding, New York: Hanser Publishers, 1994, 14 pages.
Notice of Allowance dated Aug. 1, 2016 issued in Japanese Application No. 2013-157402 (3 pages).
Notice of Allowance dated Aug. 17, 2015 issued in corresponding Japanese Application No. 2012-023743 (3 pages).
Notice of Allowance dated Nov. 21, 2016 in a corresponding Japanese Application No. 2015-31990 (3 pages).
Notice of Opposition to Grant of Patent (Section 21) issued in corresponding New Zealand Application No. 599406, filed Mar. 19, 2014.
Notice of Reasons for Rejection dated Apr. 4, 2016 isued in Japanese Application No. 2013-157402 with English translation (8 pages).
Notice of Reasons for Rejection dated Mar. 7, 2016 issued in Japanese Application No. 2015-031990 with English translation (7 pages).
Office Action dated Apr. 14, 2016 issued in Europen Application No. 06741187.6 (5 pages).
Office Action dated Nov. 2, 2016 issued in Chinese Application No. 201410650331.X with English translation (6 pages).
Office Action issued in a corresponding Chinese Application No. 201110448115.3 dated Nov. 26, 2013.
Office Action issued in a corresponding JP Application No. 2012-023743 dated Jan. 21, 2014.
Office Action issued in a related U.S. Appl. No. 13/399,832, dated May 7, 2013, including PTO-892 listed US 2003/0131852, US 2003/0051732, and US 2007/0209663
Office Action issued in Chinese Appln. No. 200680029139.2 (dated Jun. 4, 2010).
Office Action issued in corresponding Japanese Appln. No. 2008-514996 (dated Sep. 4, 2012)200.
Office Action issued in corresponding Japanese Appln. No. 2012-023743 dated Apr. 23, 2013.
Office Action issued in related Japanese Appln. No. 2008-514996 (dated Aug. 9, 2011).
Office Action issued in related U.S. Appl. No. 13/399,832, dated Apr. 24, 2014.
Office Acttion issued in corresponding Japanese Application No. 2013-157402 dated Jul. 6, 2015, with Englih translation thereof.
Opponent's Bundle of Authorities filed May 28, 2018 by Fisher & Paykel Heathcare Limited in New Zealand Application Nos. 599406 and 703971 (286 pages).
Opponent's Submissions o Adequacy of Counterstatements filed May 28, 2018 by Fisher & Paykel Heathcare Limited in New Zealand Application Nos. 599406 and 703971 (18 pages).
Opus Brochure, Fisher & Paykel Healthcare, www.fphcare.com, 2 pages.
Proceeding Correspondence dated Aug. 31, 2018 issued in New Zealand Application No. 599406 (2 pages).
Proceeding Halt issued in corresponding New Zealand Application No. 599406 dated Jul. 23, 2015.
ResMed Co.—Mask Products—http://resmed/com/portal/site/ResMedUS/index.jsp? . . . viewed on Jul. 24, 2006.
ResMed Mask Frames, Nasal Cushions and Headgear, http://web.archive.org/web/19970 1 26045828 /http ://www.a rchive.org/ dated Jan. 26, 1997, Affidavit of Christopher Butler dated Jul. 6, 2017, 8 pages.
ResMed Mirage Swift Nasal Pillows System, www.resmed.com, 2004, 6 pages.
ResMed Mirage Vista Nasal Mask-Component Cards, www.resmed.com Reference No. 1010279/30502, dated 2005, 1 page.
ResMed Origins Brochure dated Apr. 17, 2016, 64 pages.
Respironics Co.—Mask Family—http://masksfamily.respironics.com/ viewed on Jul. 24, 2006.
Second Amended Notice of Opposition to Grant of Patent (Section 21) and Amended (Second) Statement of Case filed on Apr. 9, 2015 by Fisher & Paykel Healthcare Limited in New Zealand Patent Application No. 5999406.
Snapp Nasal Interface, Tiara Medical Systems, Inc.—http://www.tiaramed.com/asp_shops/shopdisplayproducts.asp?id=109&ct=SNAPP%2A+Nasal+Interface viewed on Jul. 24, 2006.
Statutory Declaration of Christopher Earl Nightingale filed on May 27, 2015 by Fisher & Paykel Healthcare Limited in New Zealand Patent Application No. 5999406.
Supplementary Search Report issued in EP Appln. No. 06741187.6 (dated Jan. 31, 2011).
Third Amended Notice of Opposition to Grant of Patent (Section 21) filed on Jul. 16, 2015 by Fisher & Paykel Healthcare Limited in corresponding New Zealand Application No. 5999406—Marked-up and clean formats.
Third Office Action issued in corresponding Japanese Patent Application No. 2012-023743 dated May 1, 2015, with English translation thereof.
U.S. Appl. No. 10/390,681, filed Mar. 19, 2003 (p. 23 of specification, published No. U.S. 2003/0196655).
U.S. Appl. No. 10/390,682, filed Mar. 19, 2003 (p. 50 of specification, published No. U.S. 2003/0196656).
U.S. Appl. No. 10/655,621, filed Sep. 5, 2003 (pp. 23, 62 of specofocation, now U.S. Pat. No. 7,011,090).
U.S. Appl. No. 10/655,622, filed Sep. 5, 2003 (p. 68 of specification, published as U.S. 2004/0118406).
U.S. Appl. No. 10/781,929, filed Feb. 20, 2004 (p. 43 of specification, published No. U.S. 2004/0226566).
U.S. Appl. No. 11/447,295, filed Jun. 6, 2006 (published as U.S. 2006/0283461).
U.S. Appl. No. 60/634,802, filed Dec. 10, 2004.
U.S. Appl. No. 60/643,114, filed Jan. 12, 2005 (p. 25 of specification).
U.S. Appl. No. 60/645,672, filed Jan. 21, 2005.
U.S. Appl. No. 60/667,052, filed Apr. 1, 2005 (pp. 25 of specification).
U.S. Appl. No. 60/795,615, filed Apr. 28, 2006 (pp. 54 of specification).
Ultra Mirage Full Face Mask brochure, http://web.archive.org/web/19970 126045828/http://www.archive.org/ dated Jan. 26, 1997, Affidavit of Christopher Butler dated Sep. 6, 2016, 9 pages.
Users Guide ResMed Mirage Swift Nasal Pillows System, www.myresmed.com dated May 6, 2004, 11 pages.
Written Opinion of the International Searching Authority for PCT/AU2006/00070, dated Aug. 3, 2006.

* cited by examiner

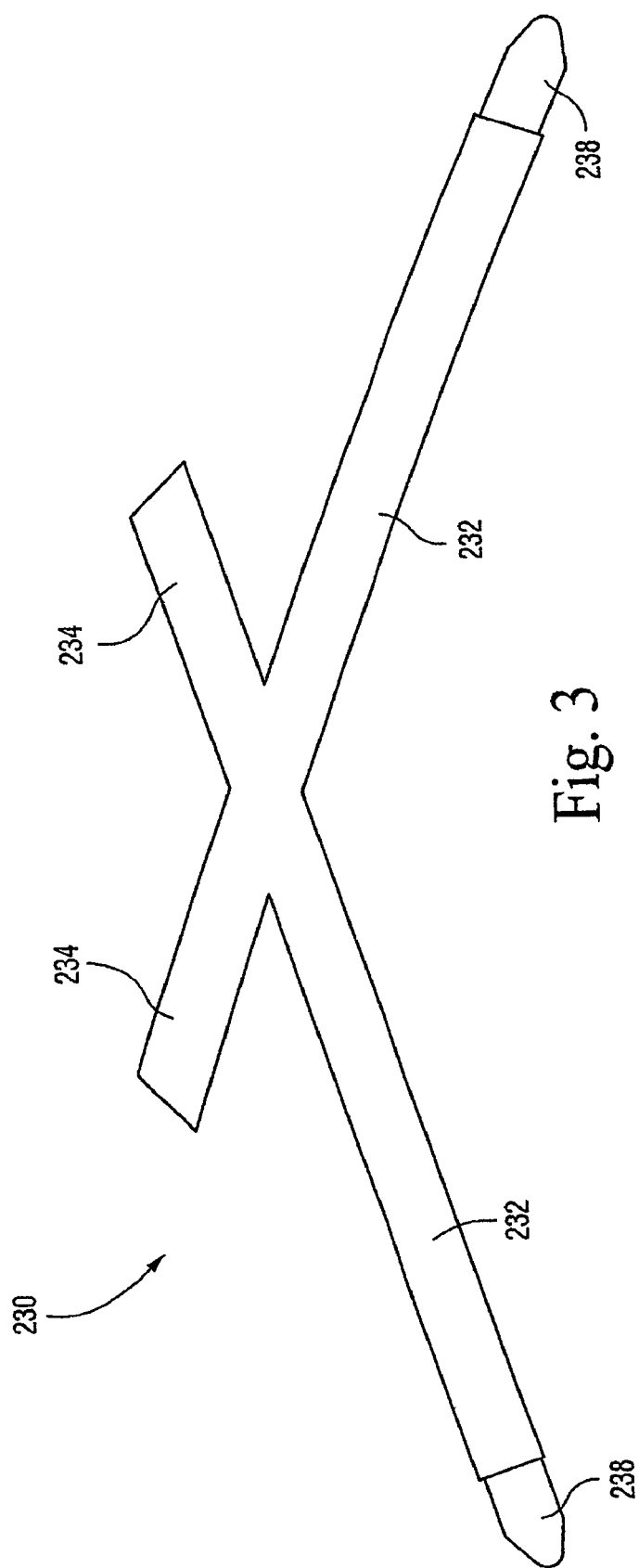

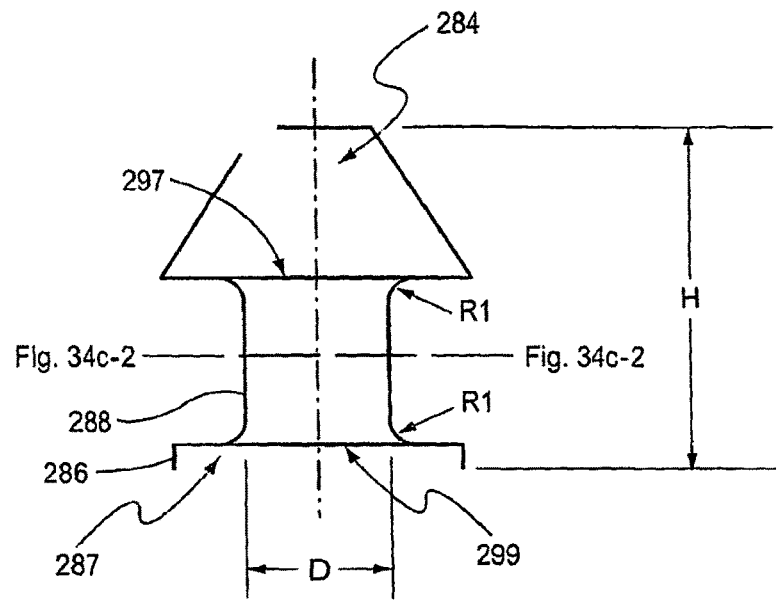
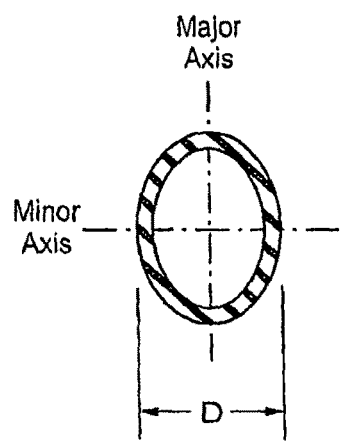
Fig. 34c-2
Fig. 34c-1
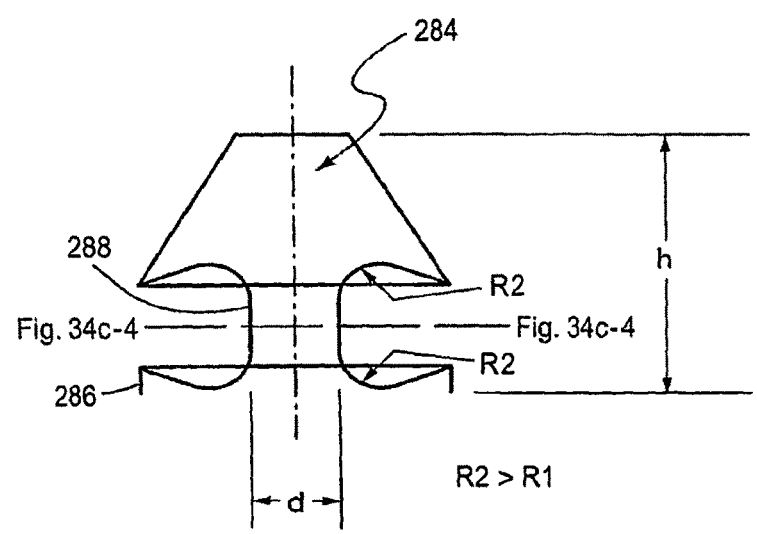
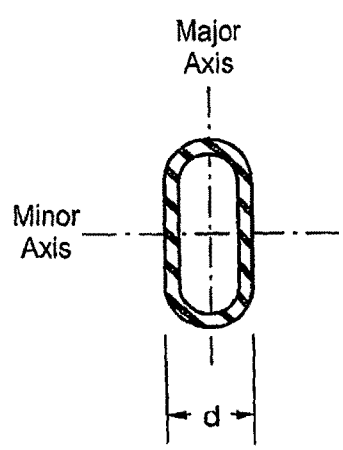
Fig. 34c-4
Fig. 34c-3

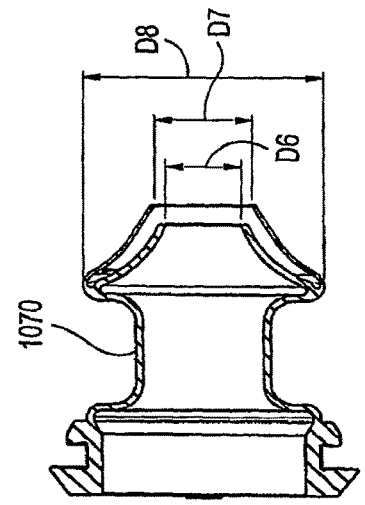
Fig. 70B-2
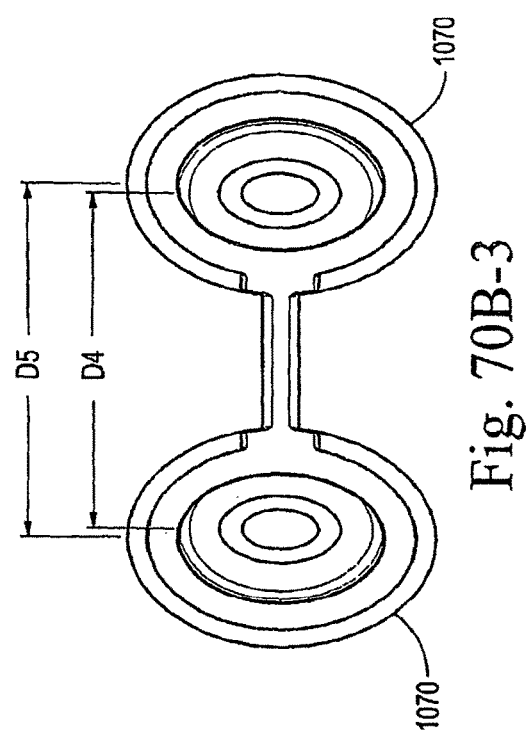
Fig. 70B-4
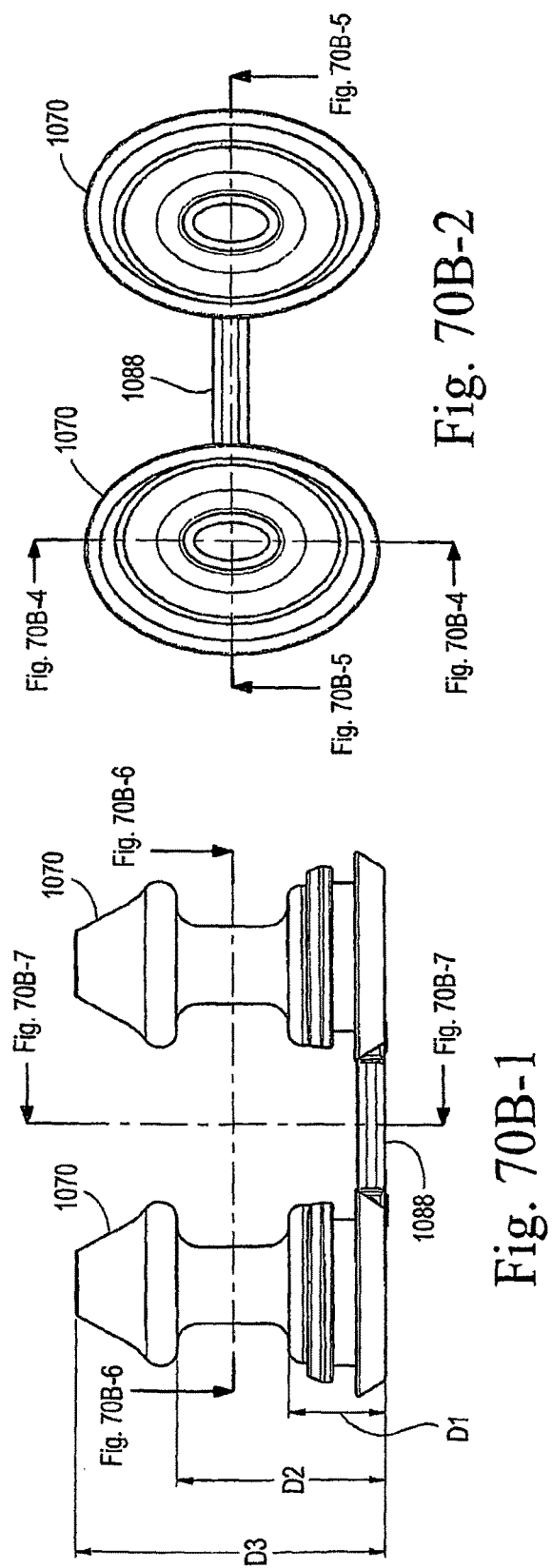
Fig. 70B-1
Fig. 70B-3

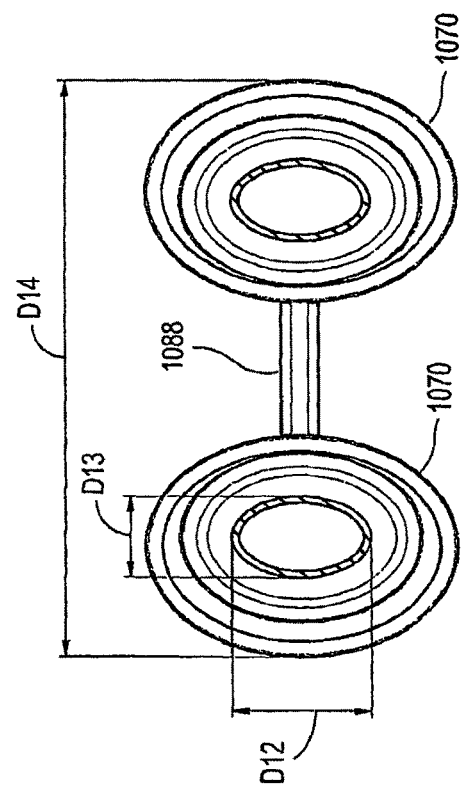
Fig. 70B-6
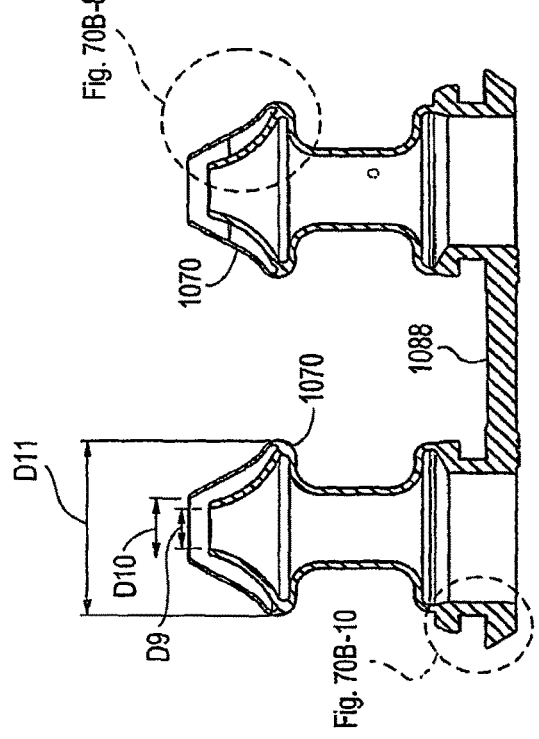
Fig. 70B-5
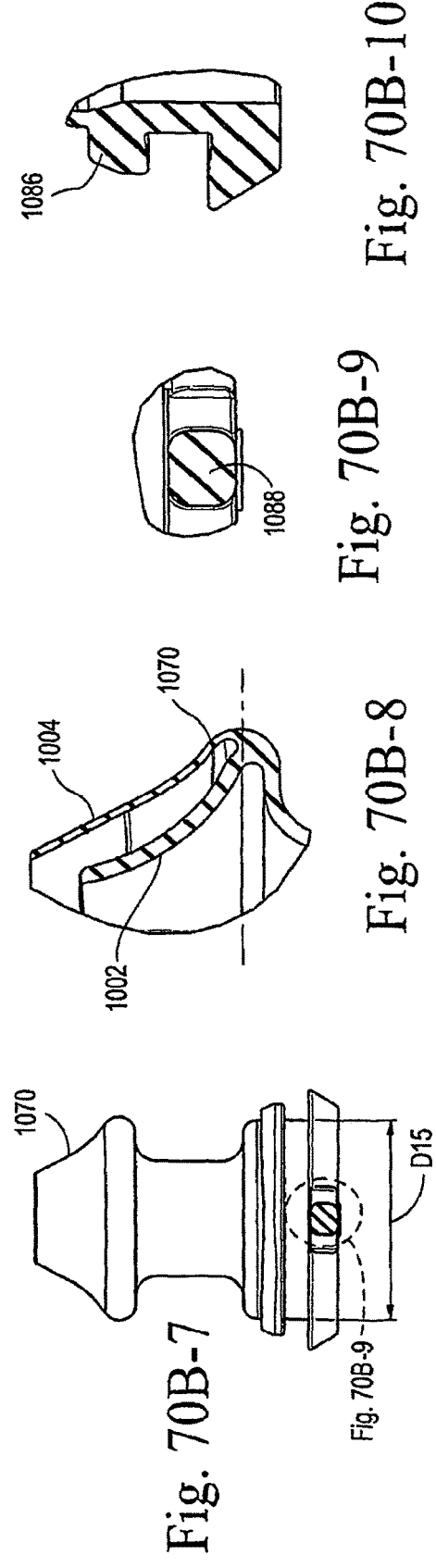
Fig. 70B-10
Fig. 70B-9
Fig. 70B-8
Fig. 70B-7

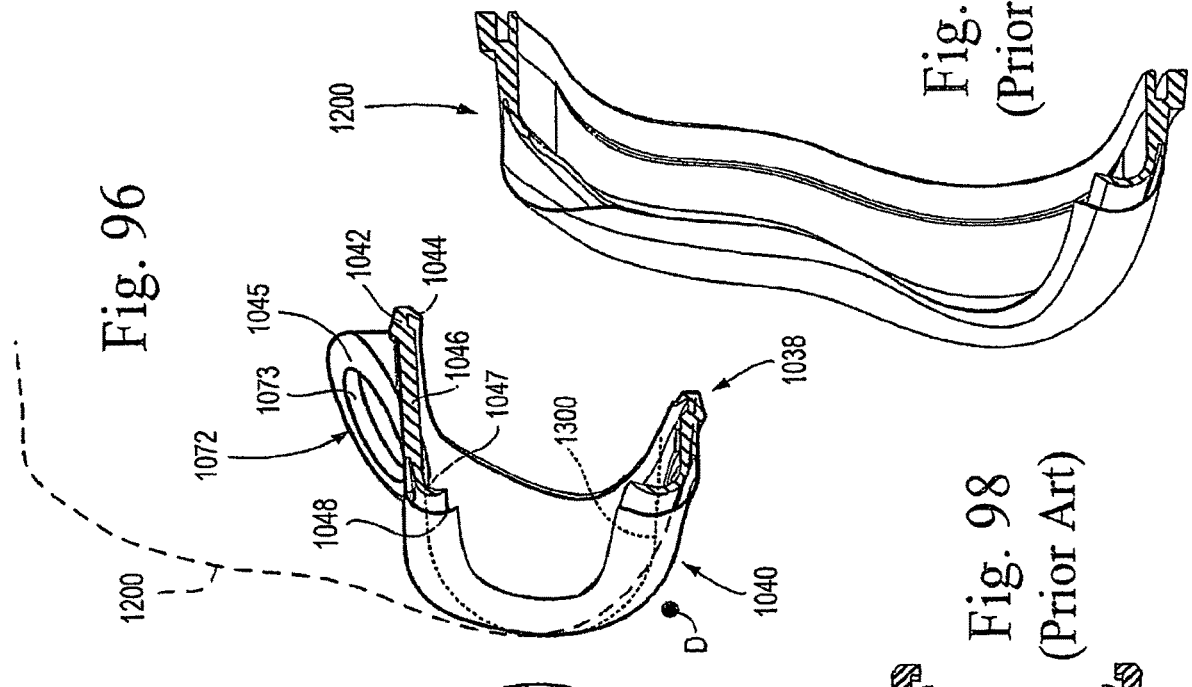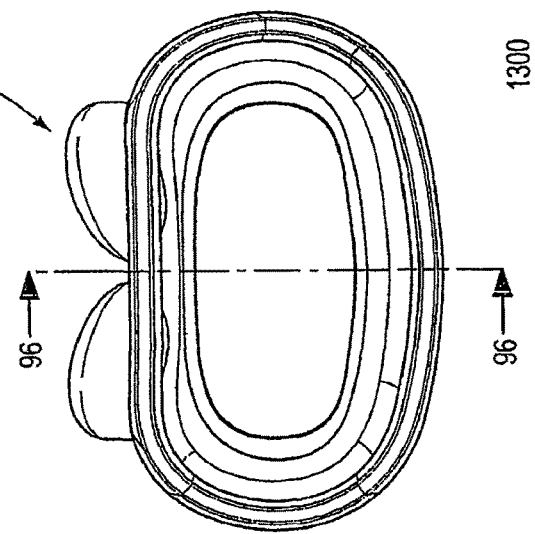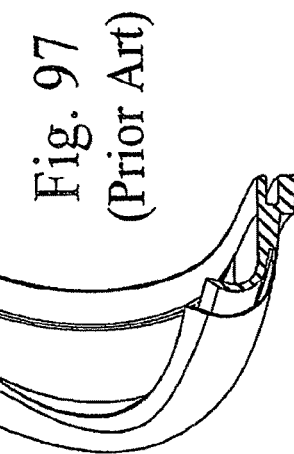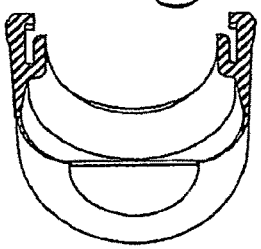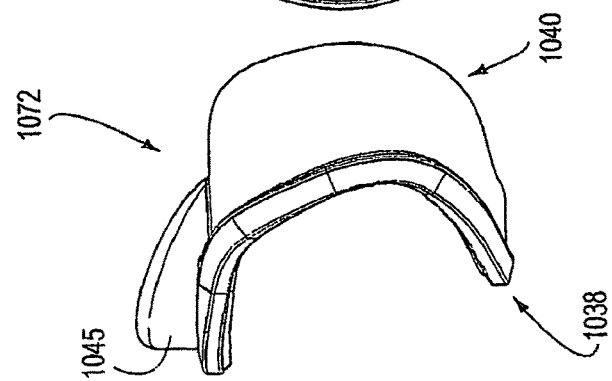

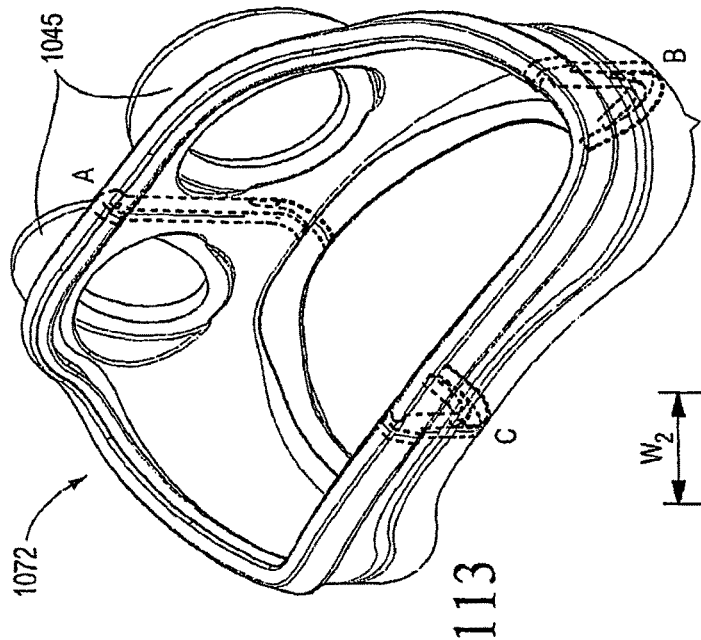
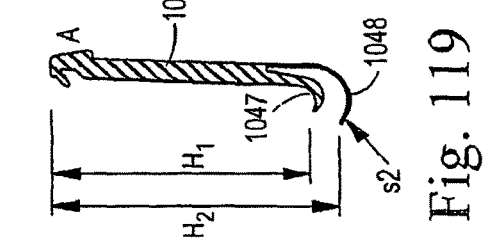
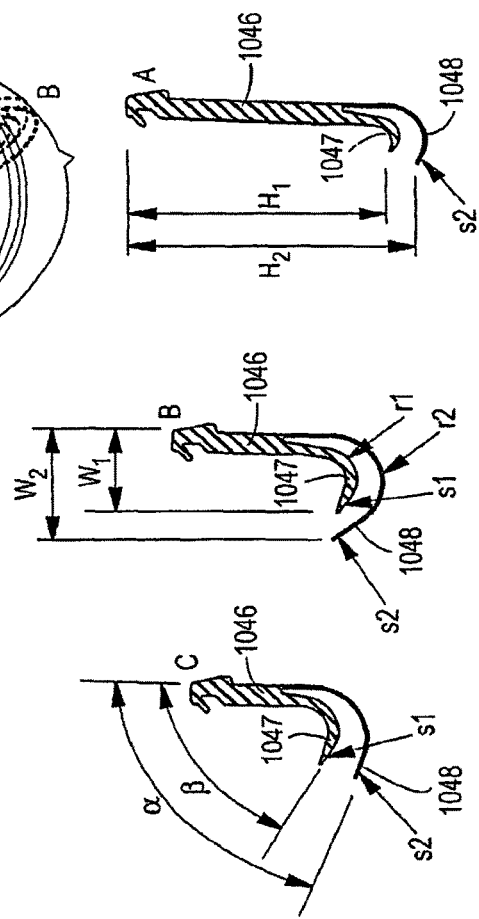
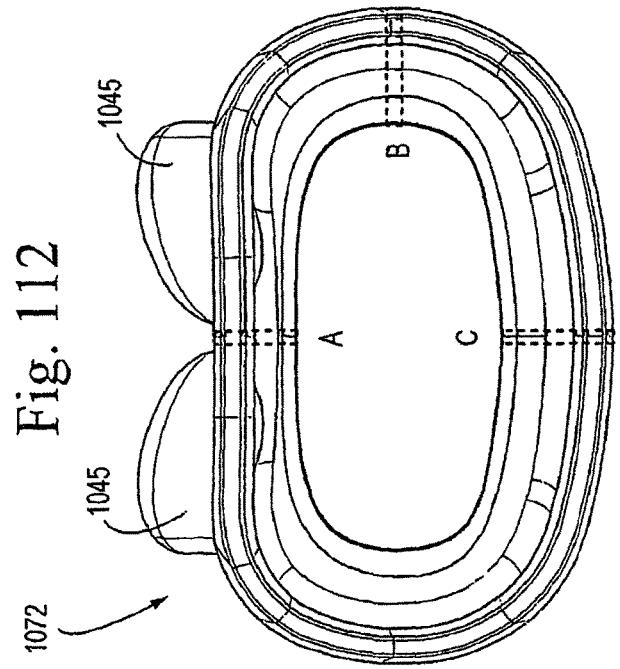
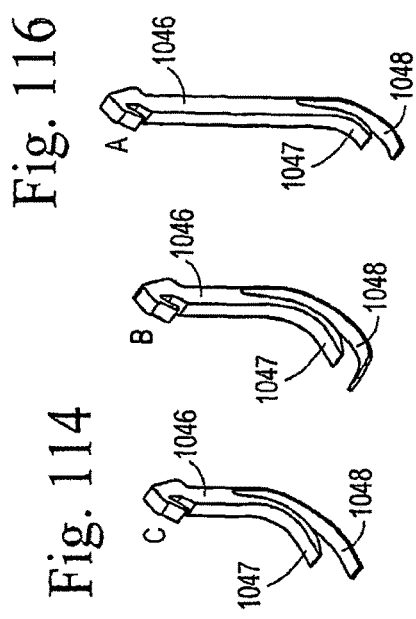

Fig. 124D
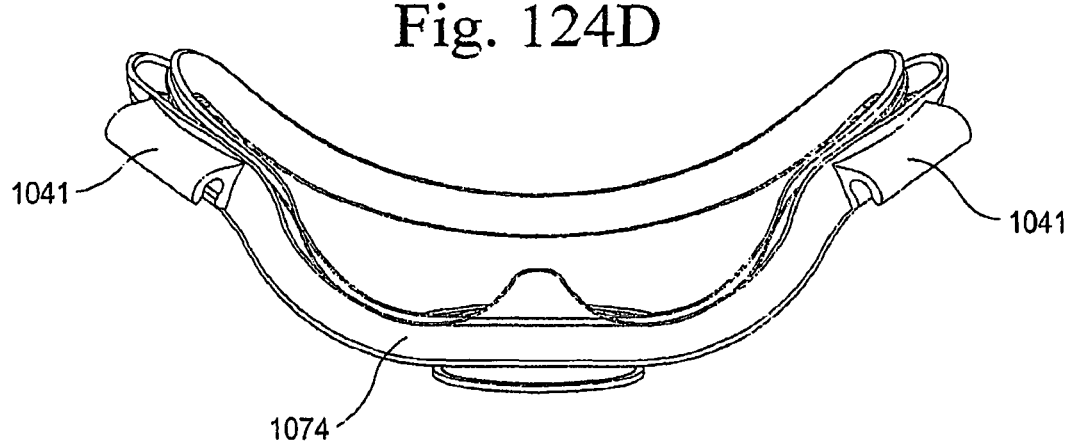
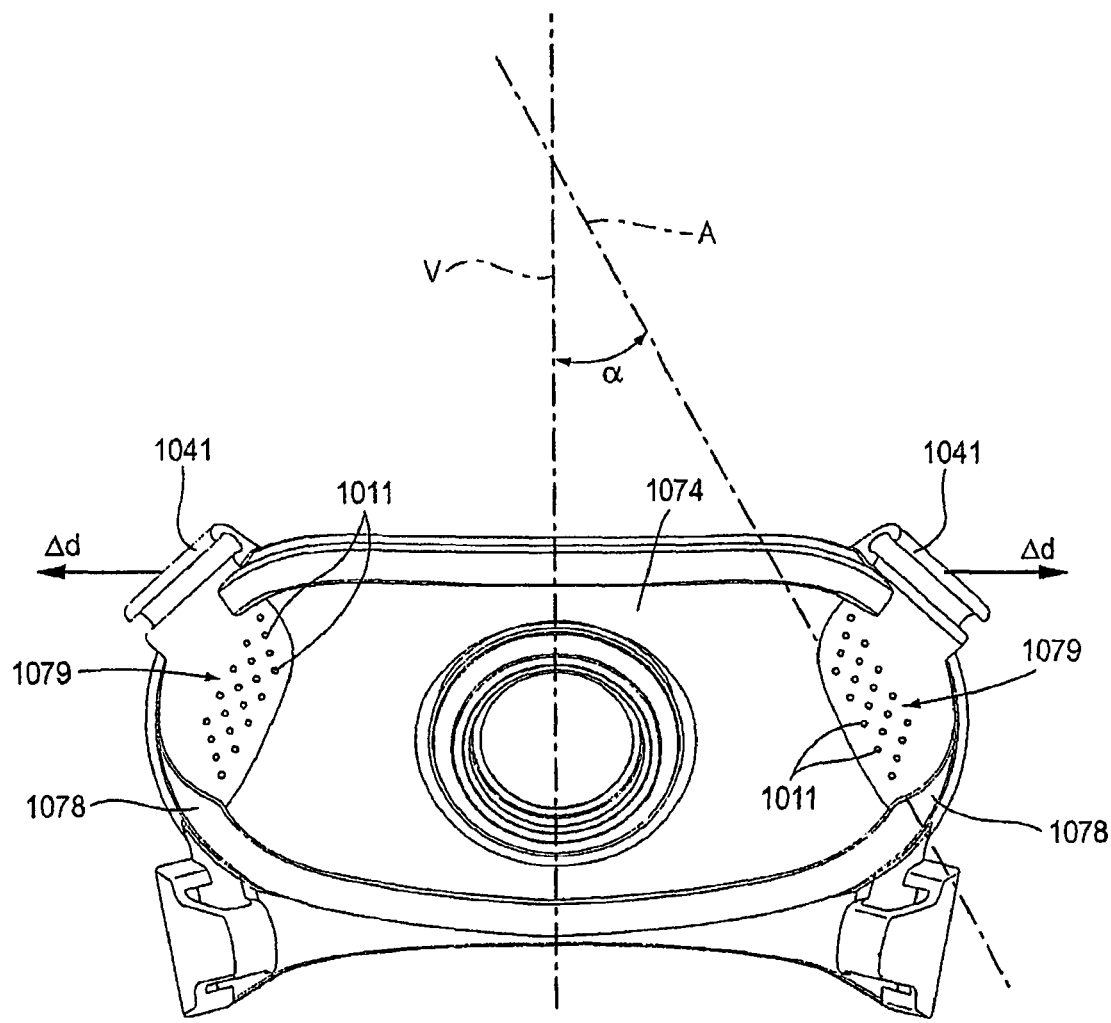
Fig. 124E

Fig. 124H
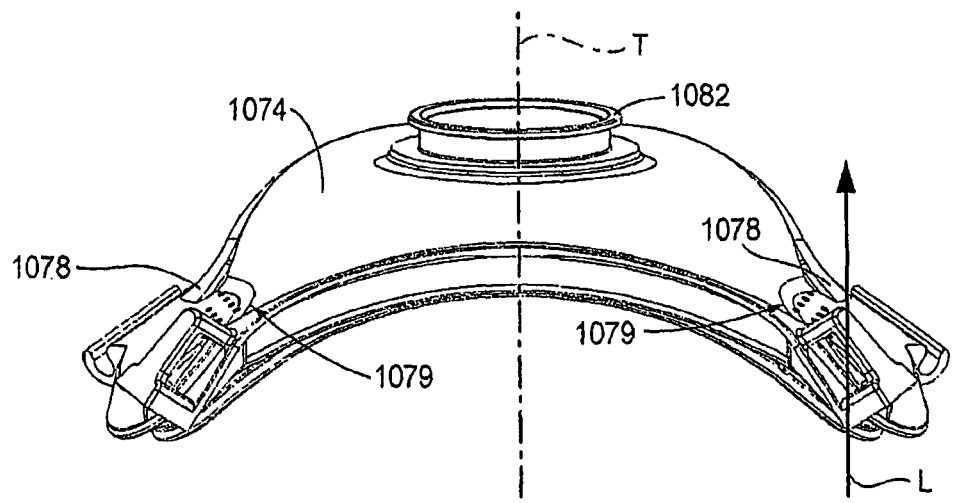
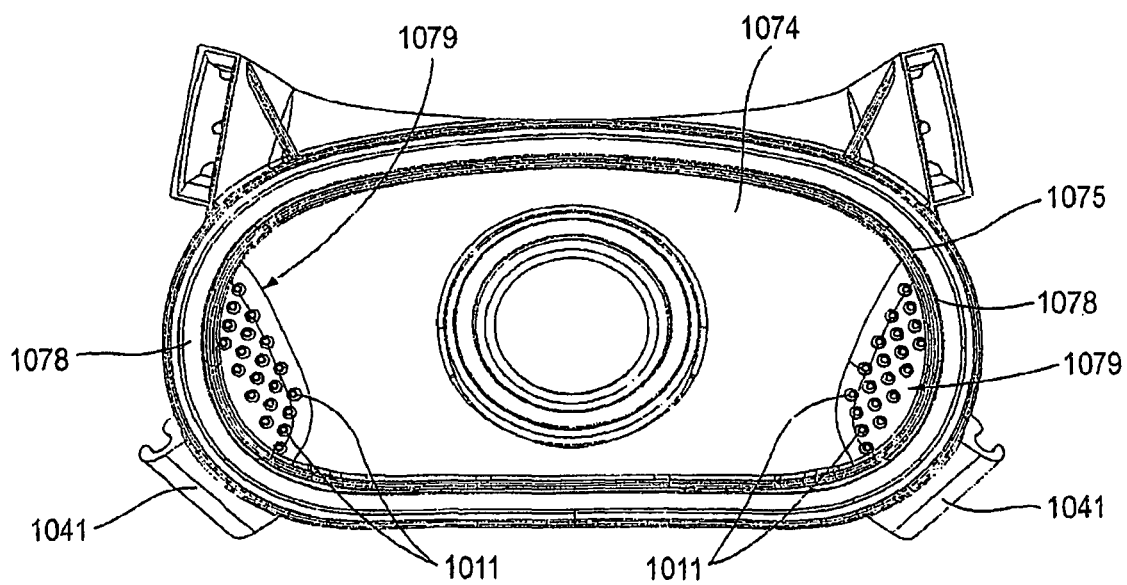
Fig. 124I

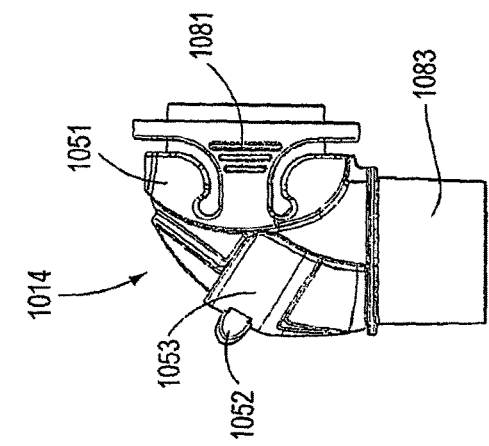
Fig. 125
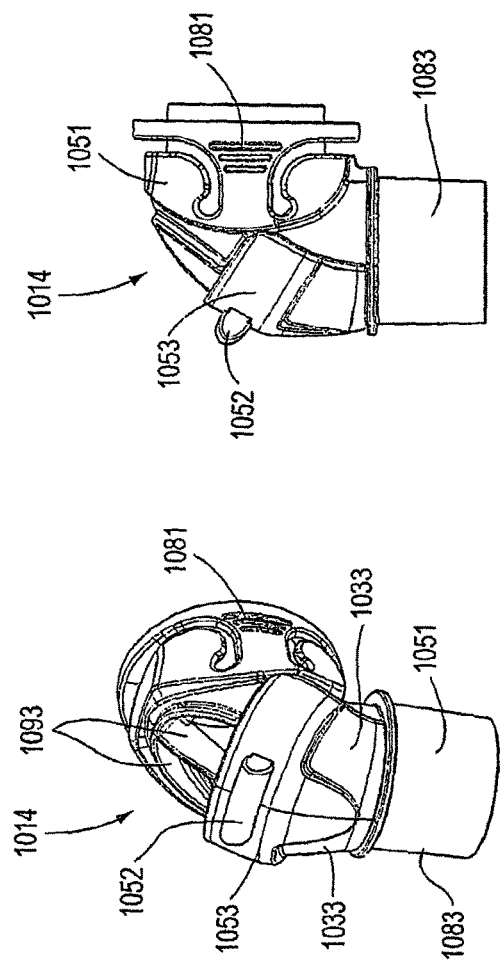
Fig. 126
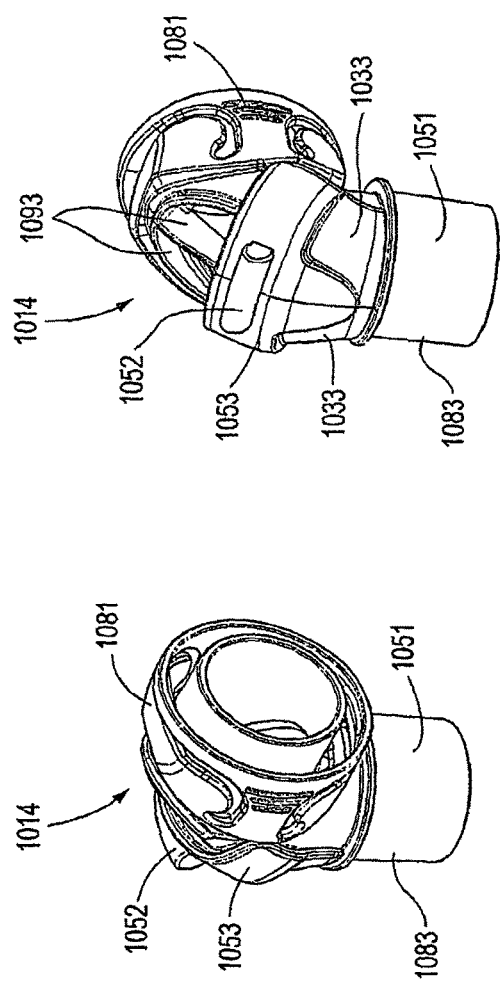
Fig. 127
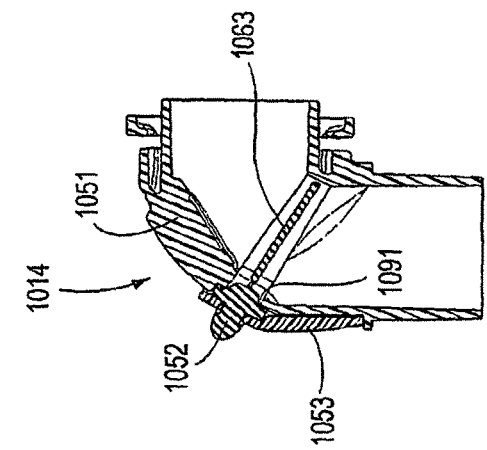
Fig. 128
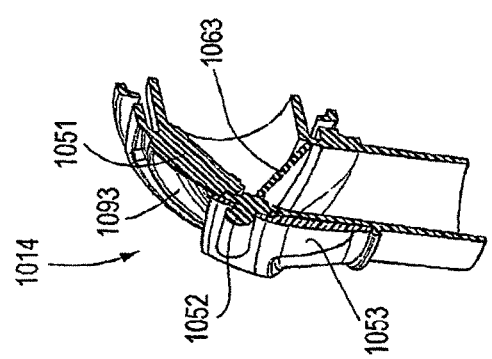
Fig. 129
Fig. 130

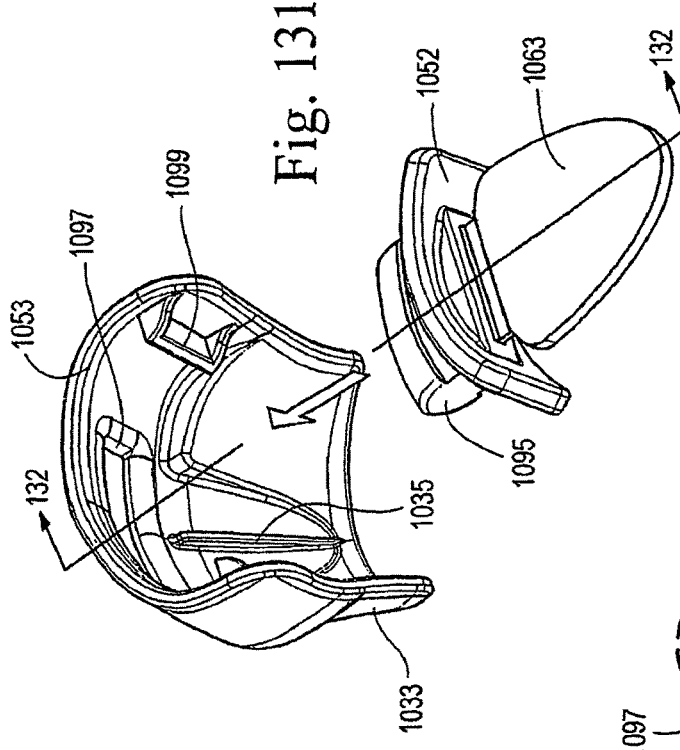
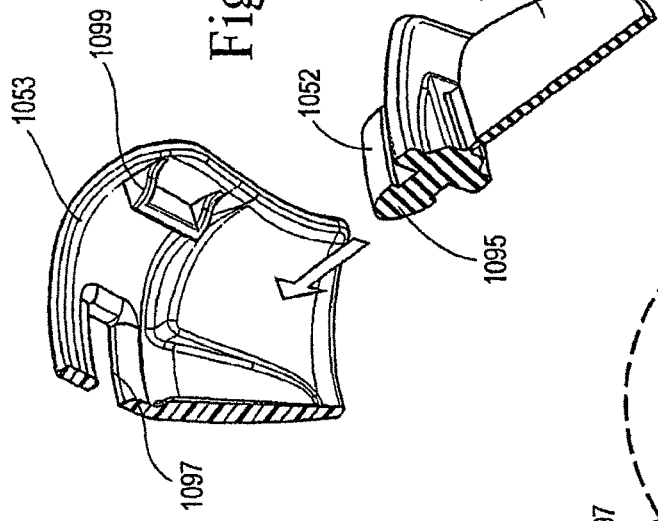
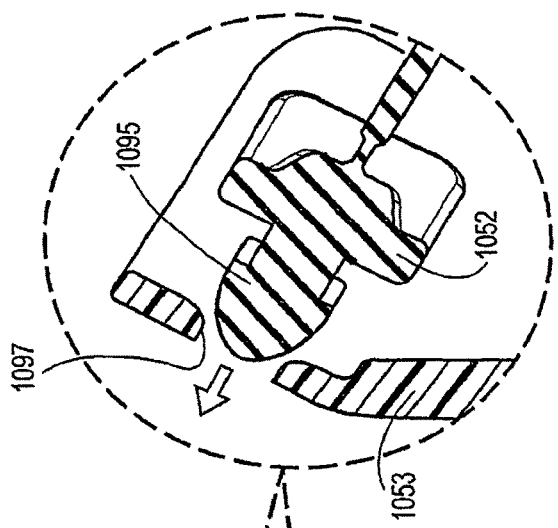
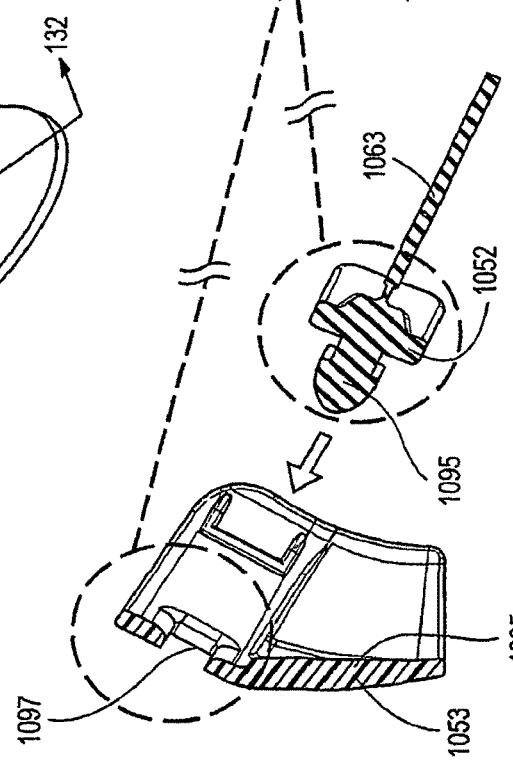

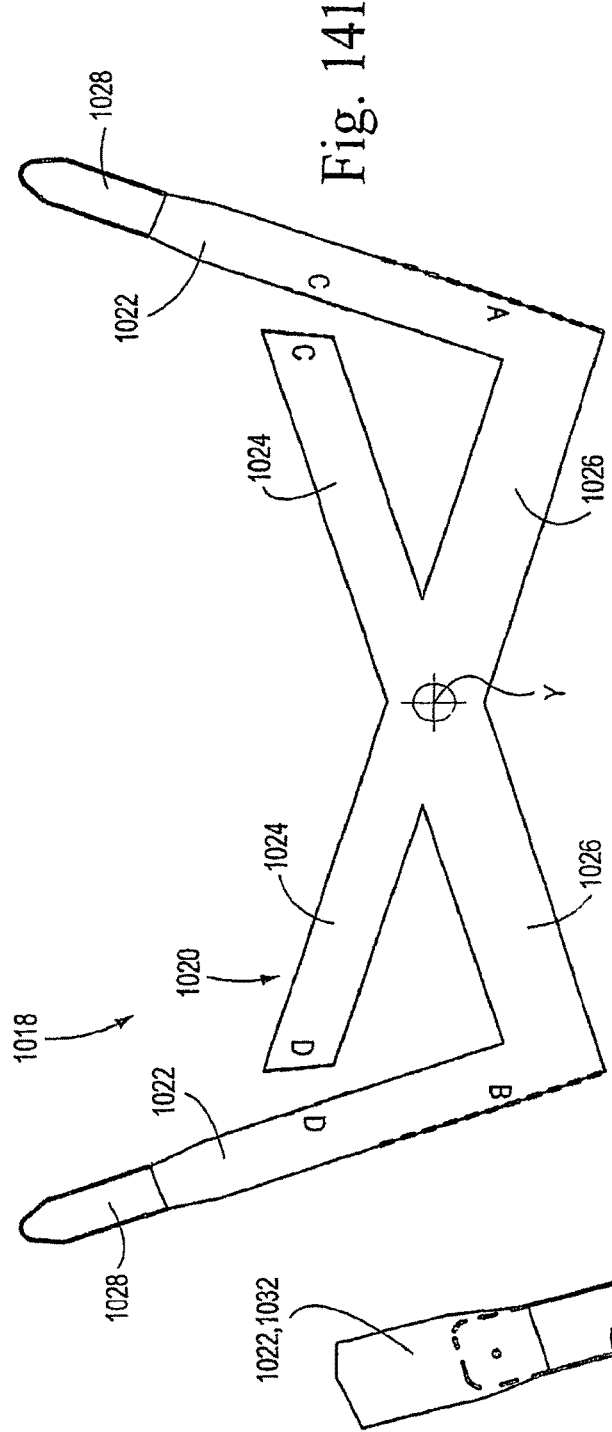
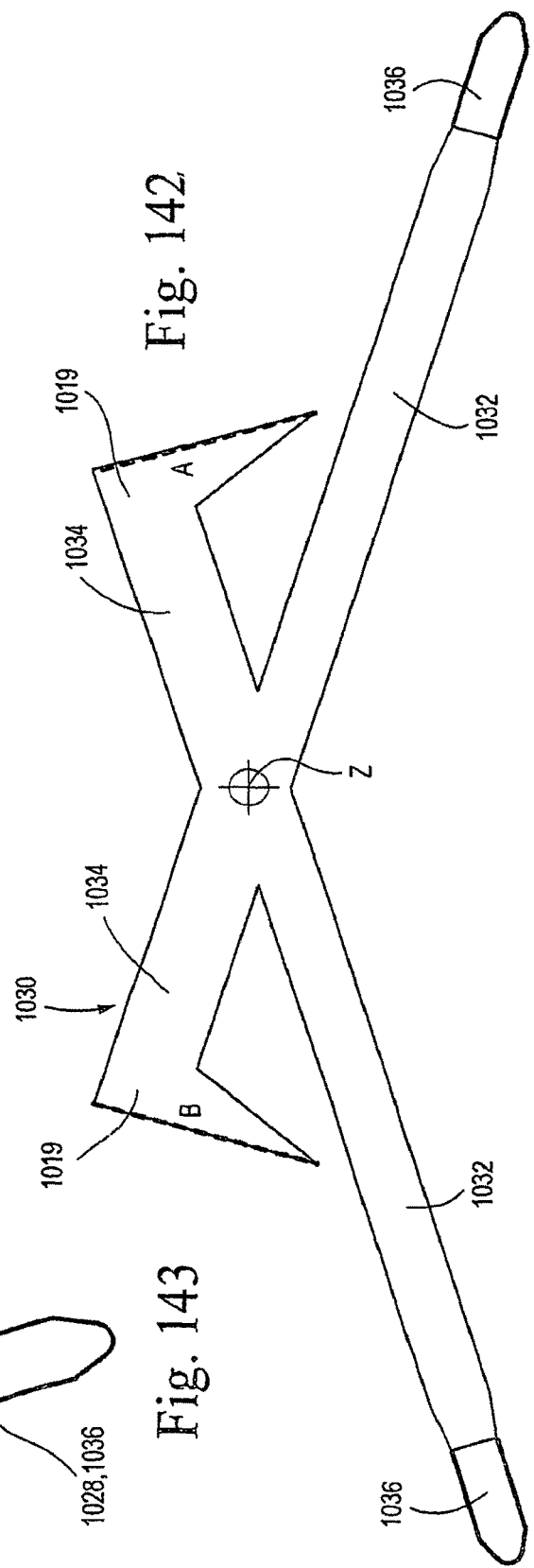

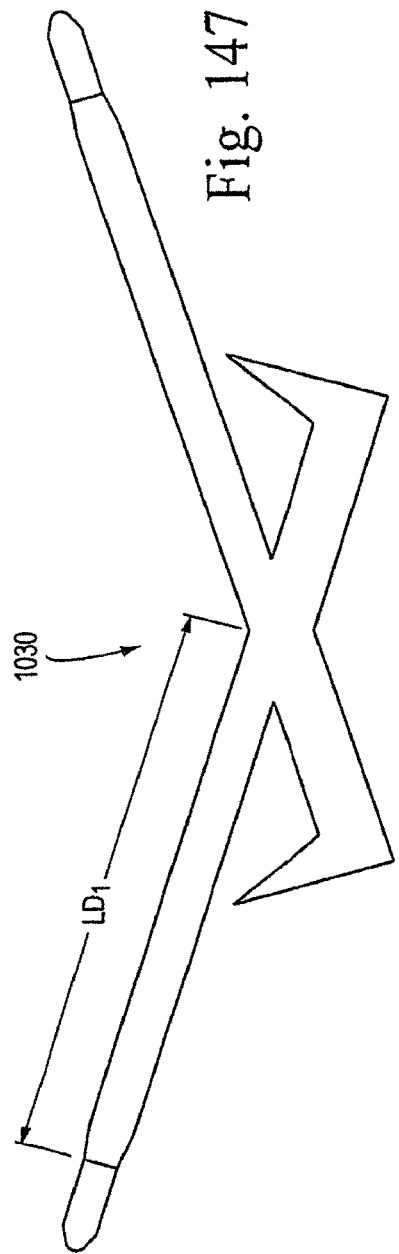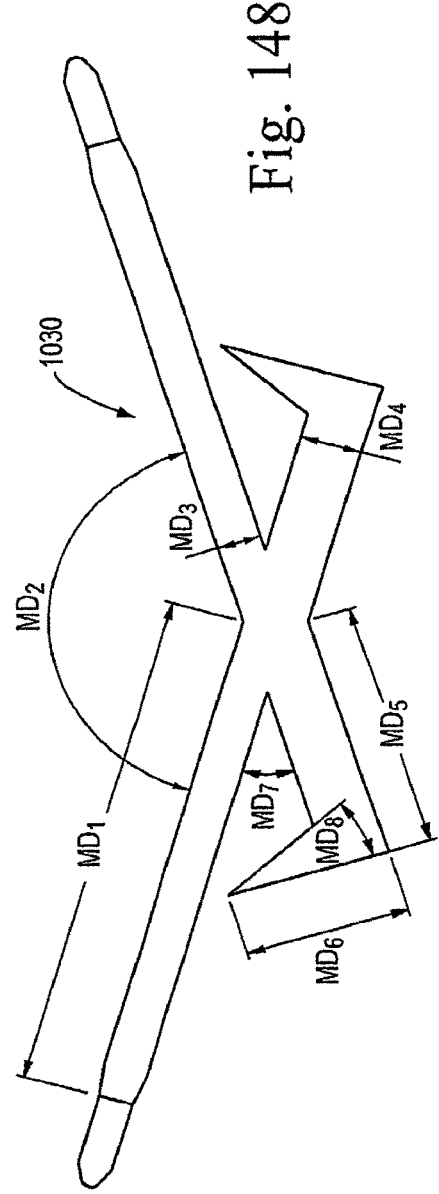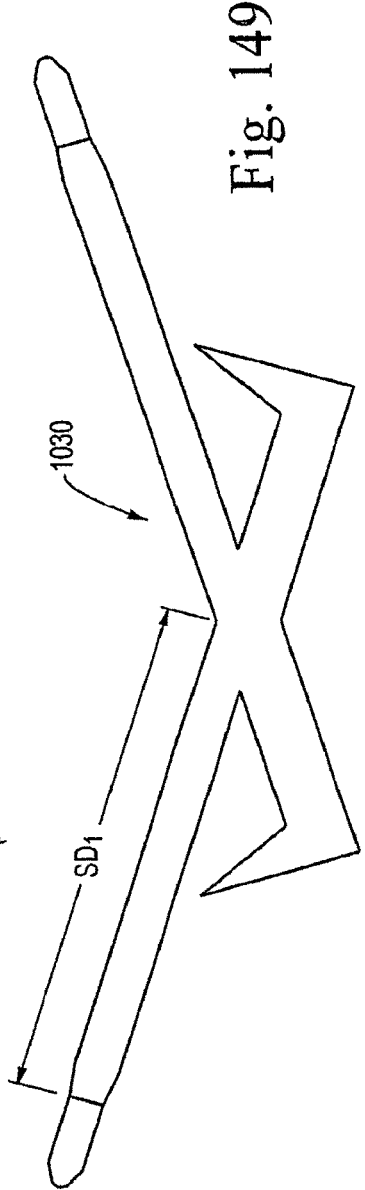

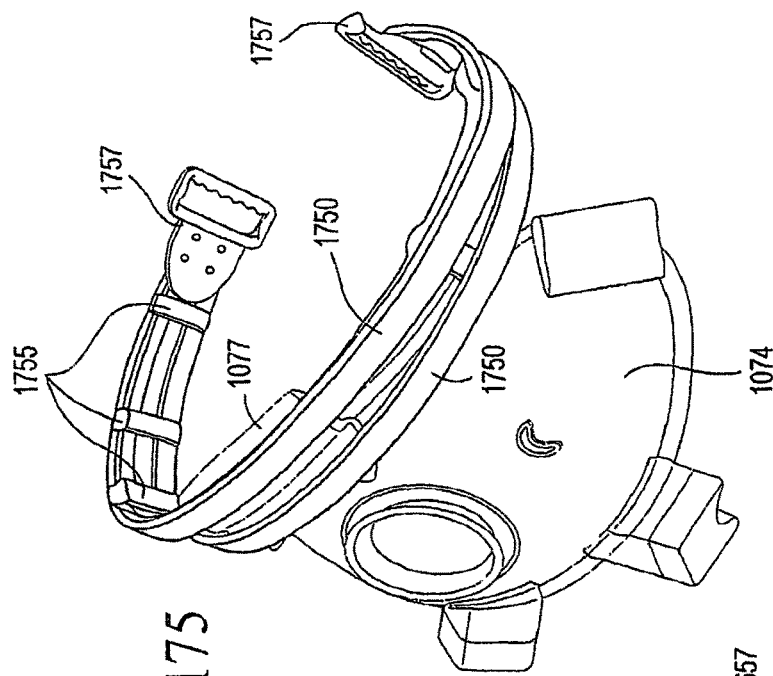
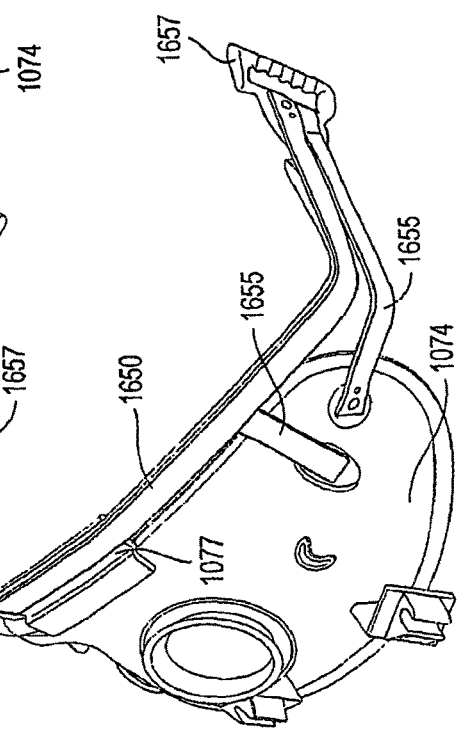
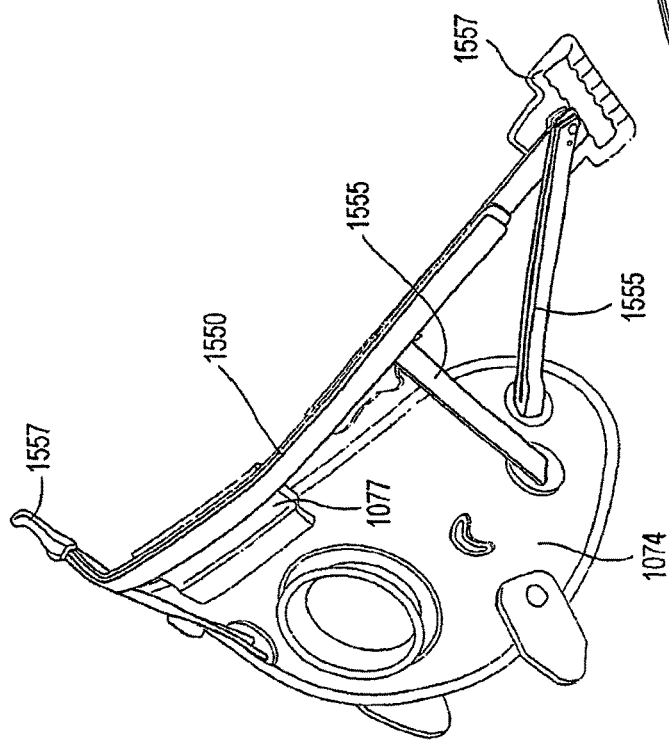
Fig. 175
Fig. 174
Fig. 173

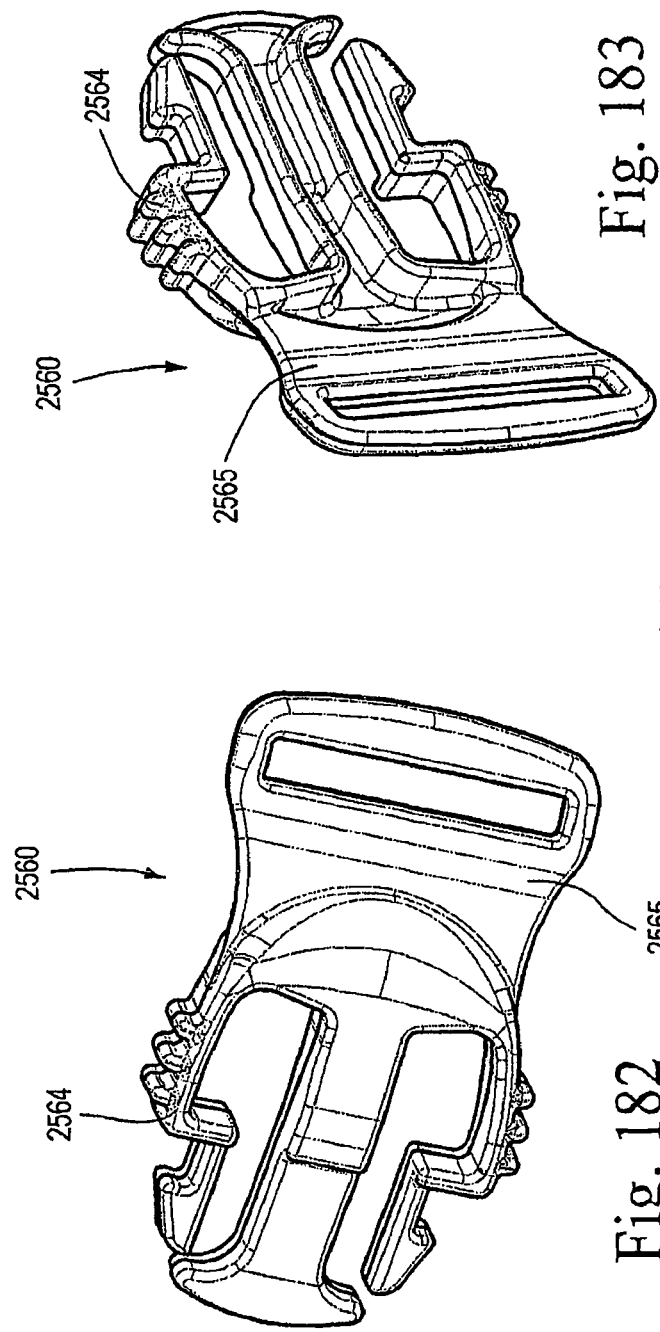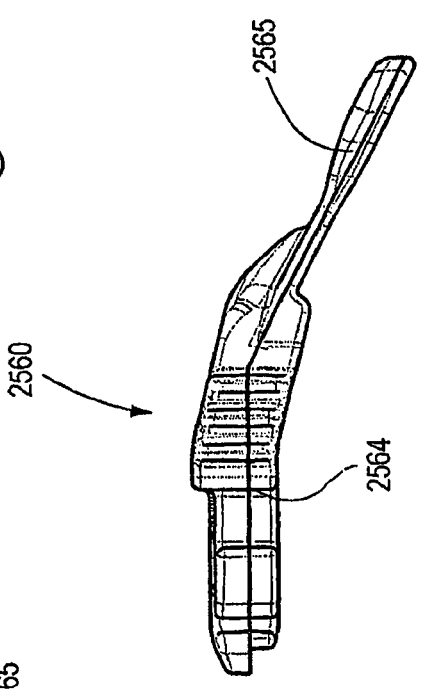
Fig. 183
Fig. 184
Fig. 182

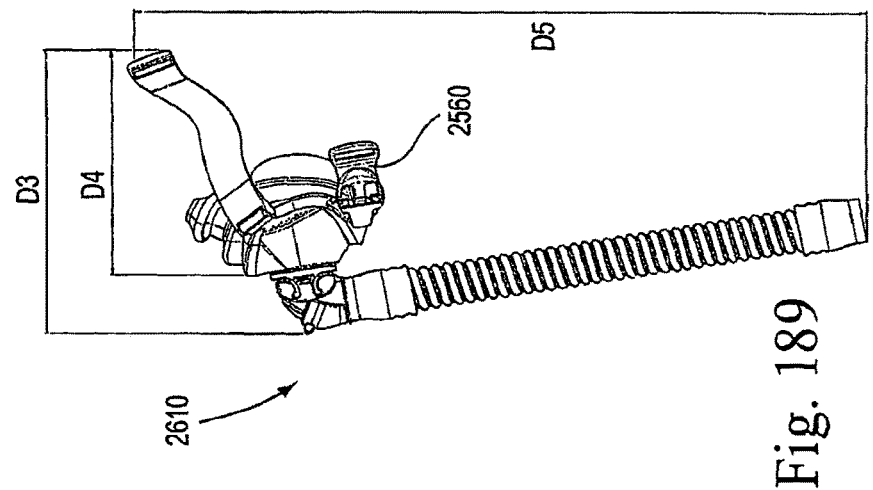
Fig. 187
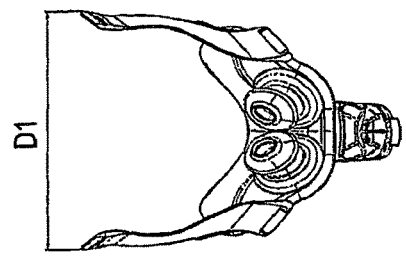
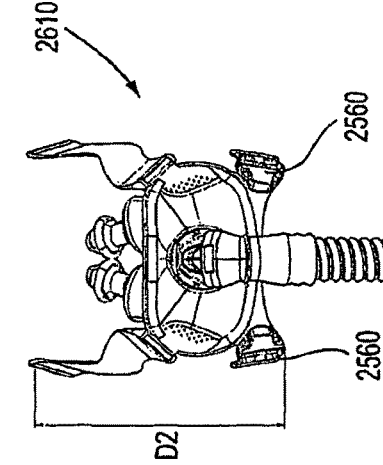
Fig. 188
Fig. 189

MASK SYSTEM

CROSS-REFERENCE TO APPLICATIONS

This application is a continuation of U.S. application Ser. No. 16/182,300 filed on Nov. 6, 2018, which is a continuation of U.S. application Ser. No. 14/663,499 filed on Mar. 20, 2015, which is continuation of U.S. application Ser. No. 11/921,185, filed Nov. 28, 2007, which is a U.S. National Phase of International Application No. PCT/AU2006/000770, which designated the U.S. and claims priority to U.S. Provisional Application Nos. 60/687,453, filed Jun. 6, 2005, 60/702,581, filed Jul. 27, 2005, and 60/795,562, filed Apr. 28, 2006, each of which is incorporated herein by reference in its entirety.

Also, PCT Application No. PCT/AU2004/001832, filed Dec. 24, 2004, is incorporated herein by reference in its entirety.

FIELD OF THE INVENTION

The present invention relates to a mask system for delivery of respiratory therapy to a patient. Examples of such therapies are Continuous Positive Airway Pressure (CPAP) treatment, Non-Invasive Positive Pressure Ventilation (NIPPV), and Variable Positive Airway Pressure (VPAP). The therapy is used for treatment of various respiratory conditions including Sleep Disordered Breathing (SDB) such as Obstructive Sleep Apnea (OSA).

BACKGROUND OF THE INVENTION

Mask systems• form an interface between a patient and apparatus providing a supply of pressurized air or breathing gas and are hence sometimes referred to as patient interfaces. In this specification, the words mask system and patient interface will be used interchangeably. Mask systems in the field of the invention differ from mask systems used in other applications such as aviation and safety in particular because of their emphasis on comfort. This high level of comfort is desired because patients must sleep wearing the masks for hours, possibly each night for the rest of their lives. Mask systems typically, although not always, comprise (i) a rigid or semi-rigid portion often referred to as a shell or frame, (ii) a soft, patient contacting portion often referred to as a cushion, and (iii) some form of headgear to hold the frame and cushion in position. Mask systems often include a mechanism for connecting an air delivery conduit. The air delivery conduit is usually connected to a blower or flow generator.

A range of patient interfaces are known including nasal masks, nose & mouth masks, full face masks and nasal prongs, pillows, nozzles & cannulae. Masks typically cover more of the face than nasal prongs, pillows, nozzles and cannulae. In this specification, all will be collectively referred to as patient interfaces or mask systems. Nasal prongs, nasal pillows, nozzles and cannulae all will be collectively referred to as nasal prongs.

An inherent characteristic of nasal masks is that they do not seal the mouth region. A number of patients thus find that during sleep when muscles relax, mouth leak may occur. Alternatively, some patients are naturally mouth breathers and thus find a nasal mask type patient interface ineffective. Mouth leak is undesirable as, among other difficulties, it may result in noise, increased treatment pressure to compensate for the leak or an increased load on the nasal passages and potentially nasal obstruction or a runny nose. Full face masks or nose & mouth masks address this issue by sealing around both the nose and the mouth.

Leak is a problem common to all designs of patient interface. Since nasal bridge anthropometry varies greatly between patients, the soft patient contacting portion or cushion must adapt to the shapes of individual patients. Typically, this is not achieved for the entire range of patients and some form of leak occurs. The problem is heightened during sleep when the jaw moves and the head position•changes. This action can often serve to dislodge the mask and cause leak. Since leak can be noisy and results in less-effective treatment, users often compensate by tightening the headgear more than is desired. This is detrimental for patient comfort and can cause skin breakdown or irritation.

A further problem encountered by patients who are using full face, nasal or nose and mouth masks is that the portion of the patient interface that seals around the nasal bridge prevents the patient from wearing spectacles. Additionally, it may give the sensation of being closed in, leading to a feeling of claustrophobia, particularly when combined with a mouth-sealing portion. A further disadvantage is that any leaks that may occur can affect the sensitive area surrounding the eyes.

Thus, there is a need for an improved mask system that does not suffer from the above-mentioned drawbacks.

SUMMARY OF THE INVENTION

A mask system in accordance with a first aspect of the invention provides unobtrusive, comfortable, quiet, effective therapy to a patient's mouth and nasal passages. In one form, this is achieved by providing a mouth cushion with nasal prongs having a mask frame held in a stable position by a headgear including stabilizing elements. The headgear according to an embodiment of the present invention uniquely provide unobtrusive sealing for both the nose and mouth. The nasal prongs and mouth cushion according to an embodiment of the present invention can accommodate and seal with a wide range of different facial shapes. A vent according to an embodiment of the present invention provides quiet washout of exhaled gases. A swiveling elbow according to an embodiment of the present invention incorporates an anti-asphyxia valve that is effective and simple to use.

A form of headgear in accordance with an embodiment of the invention provides a sealing or retaining force against the mouth and against the nares. In one form the headgear includes a stabilizing element that has a generally serpentine shape that allows a retaining force be directed against the nares and allows the headgear to circumvent the eyes.

A form of nasal prong in accordance with an embodiment of the invention has an articulated base region and an articulated head region. In one form a prong includes a base region having two joints and a head region having two joints.

A nasal prong in accordance with an embodiment of the invention includes a seal-forming portion and a structure-defining portion. In one form the prong has dual walls comprising a thin seal-forming wall and a thicker structure-defining wall.

Another aspect of the present invention relates to a mask system for use between a patient and a device to deliver a breathable gas to the patient. The mask system includes a mouth cushion, a pair of nasal prongs, an elbow, and a headgear assembly. The mouth cushion is structured to sealingly engage around an exterior of a patient's mouth in use, and the pair of nasal prongs are structured to sealingly communicate with nasal passages of a patient's nose in use. The elbow delivers breathable gas to the patient. The headgear assembly maintains the mouth cushion and the nasal prongs in a desired position on the patient's face. The headgear assembly provides a substantially round crown strap that cups the parietal bone and occipital bone of the patient's head in use. In an embodiment, the headgear assembly is constructed from two-dimensional first and second headgear sections that are attached to one another to form a three-dimensional anatomically-shaped headgear assembly.

Another aspect of the present invention relates to a mask system for use between a patient and a device to deliver a breathable gas to the patient. The mask system includes a mouth cushion, a pair of nasal prongs, an inlet conduit, and a headgear assembly. The mouth cushion is structured to sealingly engage around an exterior of a patient's mouth in use, and the pair of nasal prongs are structured to sealingly communicate with nasal passages of a patient's nose in use. The inlet conduit is structured to deliver breathable gas to the patient. The headgear assembly maintains the mouth cushion and the nasal prongs in a desired position on the patient's face. The headgear assembly includes a retainer that retains the inlet conduit so that the inlet conduit extends up and around the patient's ears in use.

Another aspect of the invention relates to a headgear assembly for a mask system including a two-dimensional first headgear section and a two-dimensional second headgear section. The two-dimensional first and second headgear sections are attached to one another to form a three-dimensional anatomically-shaped headgear assembly.

Yet another aspect of the invention relates to a method for forming a headgear assembly for a mask system. The method includes forming a two-dimensional first headgear section, forming a two-dimensional second headgear section, and attaching the two-dimensional first and second headgear sections to one another to form a three-dimensional anatomically-shaped headgear assembly.

Still another aspect of the invention relates to a nasal prong for sealing with a nasal passage of a patient. The nasal prong includes a head portion structured to seal with the patient's nasal passage and a base portion structured to mount the nasal prong to a support structure. The base portion includes a horizontal segment, a radial segment, and a vertical segment that provide the base portion with a trampoline-like structure to add flexibility at the base portion.

A further aspect of the invention relates to a mask system including a plurality of headgear straps, a sealing assembly, and a stabilizing structure extending between the sealing assembly and at least a selected one of the headgear straps. The stabilizing structure is substantially rigid and has a preformed three-dimensional shape substantially matching the shape of a portion of the patient's face.

Still another aspect of the invention relates to a sealing assembly for a mask system. The sealing assembly includes a mouth cushion adapted to sealingly engage around an exterior of a patient's mouth in use, and a nasal prong insert (e.g., nasal cushion) provided to the mouth cushion. The nasal prong insert includes a pair of nasal prongs adapted to sealingly communicate with respective nasal passages of a patient in use and a bridging strap to interconnect the pair of nasal prongs.

Still another aspect of the invention relates to a nasal prong insert including a pair of nasal prongs adapted to sealingly communicate with respective nasal passages of a patient in use and a bridging strap to interconnect the pair of nasal prongs. Still another aspect of the invention relates to a mask system for delivering breathable gas to a patient. The mask system includes a frame, a mouth cushion provided to the frame, and a pair of nasal prongs provided to the mouth cushion. The mouth cushion is adapted to sealingly engage around an exterior of a patient's mouth in use. The pair of nasal prongs is adapted to sealingly communicate with respective nasal passages of a patient in use. An elbow is provided to deliver breathable gas to the patient. A headgear assembly is removably connected to the frame so as to maintain the mouth cushion and the pair of nasal prongs in a desired position on the patient's face. The headgear assembly includes upper headgear straps, lower headgear straps, upper stabilizing elements extending between the upper headgear straps and the frame, and lower stabilizing elements extending between the lower headgear straps and the frame. The upper and lower stabilizing elements are bendable along at least one bending plane so as to conform to the shape of a portion of the patient's face.

Yet another aspect of the invention relates to a method for defining a cushion shape. The method includes selecting at least three points on the cushion, defining coordinates for each of the at least three points, and smoothly transitioning the shape of the cushion between the at least three points along the cushion perimeter.

Yet another aspect of the invention relates to a mask system including a plurality of headgear straps including at least upper straps, a sealing assembly, and an upper stabilizing element extending between the sealing assembly and the upper straps. The upper stabilizing element includes an elongated element having an intermediate portion attachable to the sealing assembly and end portions attachable to respective upper straps.

Yet another aspect of the invention relates to an integrally molded nasal prong including a first substantially frusto-conical portion, a second substantially frusto-conical portion, and a connecting portion that interconnects the first and second conical portions. The connecting portion is configured to allow the first frusto-conical portion to fold into a position adjacent the second frusto-conical portion to provide a dual wall construction.

Yet another aspect of the invention relates to an elbow assembly for a mask system. The elbow assembly includes an elbow including a slot and a port, an anti-asphyxia valve adapted to be received within the slot and including a flap portion adapted to selectively close the port depending on the presence of pressurized gas, and a clip member to secure the anti-asphyxia valve to the elbow. The clip member includes a slot that is adapted to interlock with a protrusion provided to the anti-asphyxia valve. The clip member has a vertically extending rib that is located against an outer surface of the elbow when secured to the elbow. The rib is adapted to prevent assembly of the flap portion between the rib and the outer surface.

Another aspect of the invention relates to a mask system including a sealing assembly having prongs, a trampoline base provided to the prongs, headgear, and stabilizing elements between the headgear and sealing assembly. The trampoline base allows the prongs to move axially. In an embodiment, the prongs each have dual wall construction.

Another aspect of the invention relates to an elbow assembly for a mask system. The elbow assembly includes an elbow including a slot and a port, an anti-asphyxia valve adapted to be received within the slot and including a flap portion adapted to selectively close the port depending on the presence of pressurized gas, and a clip member to secure the anti-asphyxia valve to the elbow. The clip member includes a slot that is adapted to interlock with a protrusion provided to the anti-asphyxia valve. The clip member has a vertically extending rib that is located against an outer surface of the elbow when secured to the elbow. The rib is adapted to prevent assembly of the flap portion between the rib and the outer surface.

Another aspect of the invention relates to a mask system for delivering breathable gas to a patient. The mask system includes a frame, a mouth cushion provided to the frame, a pair of nasal prongs provided to the mouth cushion, an elbow to deliver breathable gas to the patient, and a headgear assembly removably connected to the frame so as to maintain the mouth cushion and the pair of nasal prongs in a desired position on the patient's face. The mouth cushion is adapted to sealingly engage around an exterior of a patient's mouth in use. The pair of nasal prongs is adapted to sealingly communicate with respective nasal passages of a patient in use. The headgear assembly includes upper headgear straps, lower headgear straps, an upper stabilizing element extending between each upper headgear strap and the frame, and a locking clip provided to each lower headgear strap that is adapted to be interlocked with a clip receptacle provided to the frame. Each upper stabilizing element is bendable along at least one bending plane so as to conform to the shape of a portion of the patient's face.

Another aspect of the invention relates to a mask frame including a main body, a side frame portion provided on each lateral side of the main body, and a vent assembly provided to each side frame portion. Each vent assembly includes a plurality of holes arranged in a multi-column pattern and each column is vertically staggered with respect to one another.

Another aspect of the invention relates to a mask system for use between a patient and a device to deliver a breathable gas to the patient. The mask system includes a mouth cushion structured to sealingly engage around an exterior of a patient's mouth in use, a pair of nasal prongs structured to sealingly communicate with nasal passages of a patient's nose in use, an elbow to deliver breathable gas to the patient, and a headgear assembly to maintain the mouth cushion and the nasal prongs in a desired position on the patient's face. The nasal prongs each include a trampoline-like base that adds flexibility to the nasal prongs in use.

Another aspect of the invention relates to a mask system for use between a patient and a device to deliver a breathable gas to the patient. The mask system includes a mouth cushion structured to sealingly engage around an exterior of a patient's mouth in use, a pair of nasal prongs structured to sealingly communicate with nasal passages of a patient's nose in use, and a headgear assembly to maintain the mouth cushion and the nasal prongs in a desired position on the patient's face. The nasal prongs each include at least a first trampoline-like base that adds flexibility to the nasal prongs in use.

Another aspect of the invention relates to a mask system including a plurality of headgear straps, a sealing assembly, and a stabilizing element extending between the sealing assembly and at least a selected one of the headgear straps. The selected headgear strap is adjustable with respect to the stabilizing element.

Another aspect of the invention relates to a mask system for use between a patient and a device to deliver breathable gas to the patient comprising a pair of nasal prongs structured to sealingly communicate with nasal passages of the patient's nose in use, each of said prongs including an inner wall and an outer wall spaced from the inner wall prior to use, said outer wall comprising a membrane that is thinner than the inner wall and no more than 0.65 mm thick.

Another aspect of the invention relates to a mask system for use between a patient and a device to deliver breathable gas to the patient. The mask system includes a pair of nasal prongs structured to sealingly communicate with nasal passages of the patient's nose in use. Each of the prongs includes a thin membrane. The membrane has a thickness in the range of 0.1 to 0.65 mm.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 3 is a plan view of a second headgear section of a headgear assembly of the mask system shown in FIG. 1;

FIG. 28b is a perspective view of the mask system shown in FIG. 28a;

FIG. 34b is a top perspective of a mask system including a cushion having a recess adapted to receive the insertable nasal prong shown in FIG. 34a;

FIGS. 34c-1 to 34c-13 illustrate the trampoline effect of the nasal prong according to an embodiment of the present invention;

FIGS. 70B-1 to 70B-10 illustrate a paired-prong arrangement with each nasal prong including a dual-wall according to an embodiment of the present invention;

FIGS. 94-95 are side and front views of the mouth cushion shown in FIG. 90;

FIG. 96 is a cross-sectional view through line 96-96 of FIG. 95, and illustrates comparison between cushions shown in FIGS. 97-98;

FIG. 97 is a cross-sectional view of ResMed's full face mask cushion;

FIG. 98 is a cross-sectional view of ResMed's mouth mask cushion;

FIGS. 112-119 illustrate wall cross sections along the perimeter of the mouth cushion shown in FIG. 90;

FIGS. 124B-124I illustrate various views of the frame including a vent assembly according to an embodiment of the present invention;

FIGS. 125-140 illustrate an elbow assembly according to an embodiment of the present invention;

FIGS. 141-143 illustrate upper and lower headgear sections of the headgear assembly for the mask system shown in FIG. 48;

FIGS. 147-149 illustrate exemplary dimensions for large, medium, and small lower headgear sections;

FIGS. 158b-1 to 158b-6 illustrate an upper stabilizing element according to another embodiment of the present invention;

FIGS. 158c-1 to 158c-4 illustrate an upper stabilizing element and frame according to another embodiment of the present invention;

FIGS. 173-175 illustrate upper stabilizing elements according to alternative embodiments of the present invention;

FIGS. 182-184 illustrate a lower stabilizing element according to another embodiment of the present invention;

FIGS. 185-189 illustrate a mask system according to another embodiment of the present invention;

DETAILED DESCRIPTION OF ILLUSTRATED EMBODIMENTS

§ 1. First Illustrated Embodiment of Mask System

Figure 1:
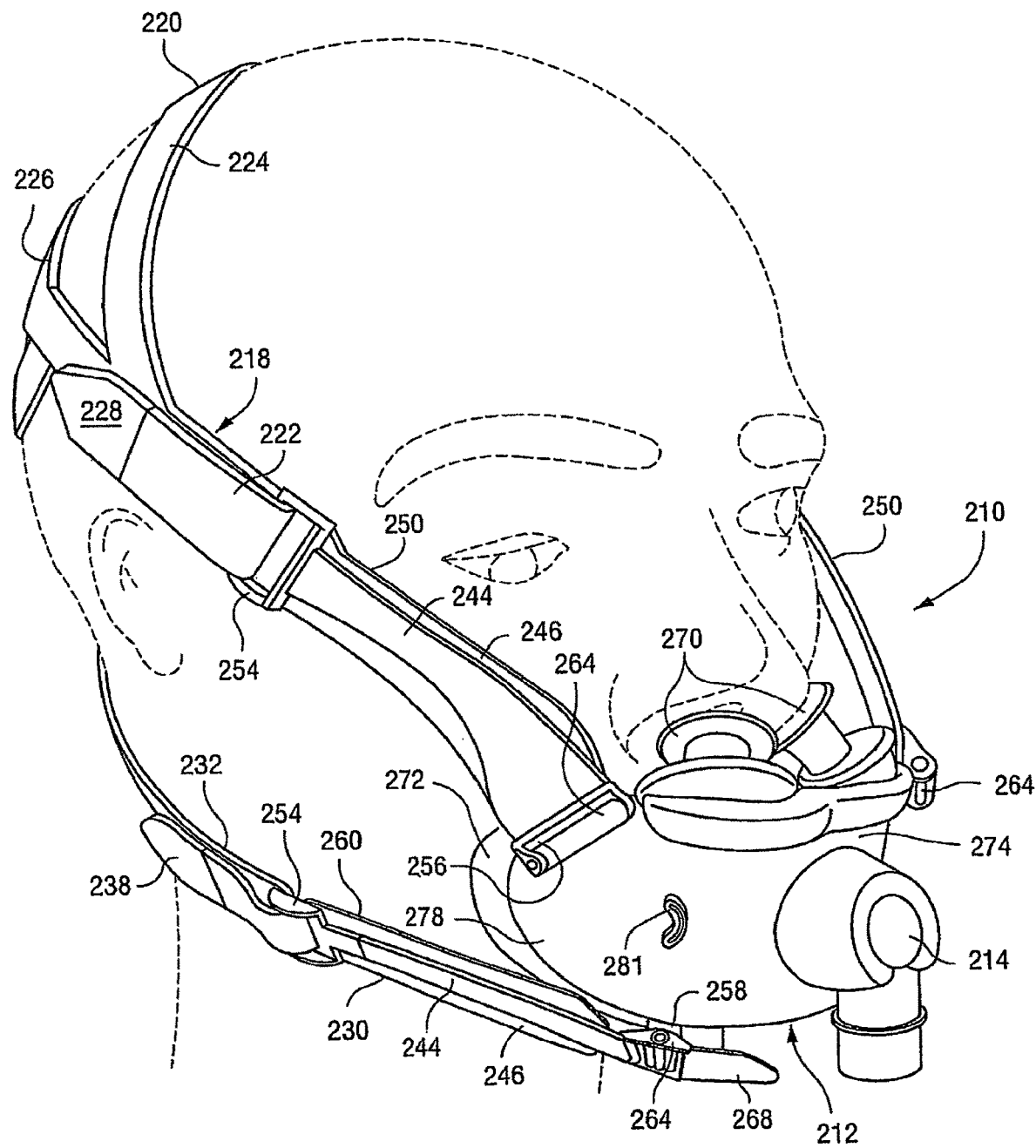
FIG. 1 is a perspective view of a mask system constructed according to an embodiment of the present invention.

FIG. 1 illustrates a mask system 210 constructed according to an embodiment of the present invention. As illustrated, the mask system 210 includes a sealing assembly 212 that provides an effective seal with both the patient's mouth and the patient's nasal passages, a swivel elbow 214 to deliver breathable gas to the patient, and a headgear assembly 218 to maintain the sealing assembly 212 in a desired position on the patient's face. In an embodiment, the swivel elbow 214 may be replaced with an elbow that is provided to a side of the mask system, e.g., see FIG. 11.

§ 1.1 Headgear

§ 1.1.1 Anatomically Shaped Headgear Assembly

Figure 2:
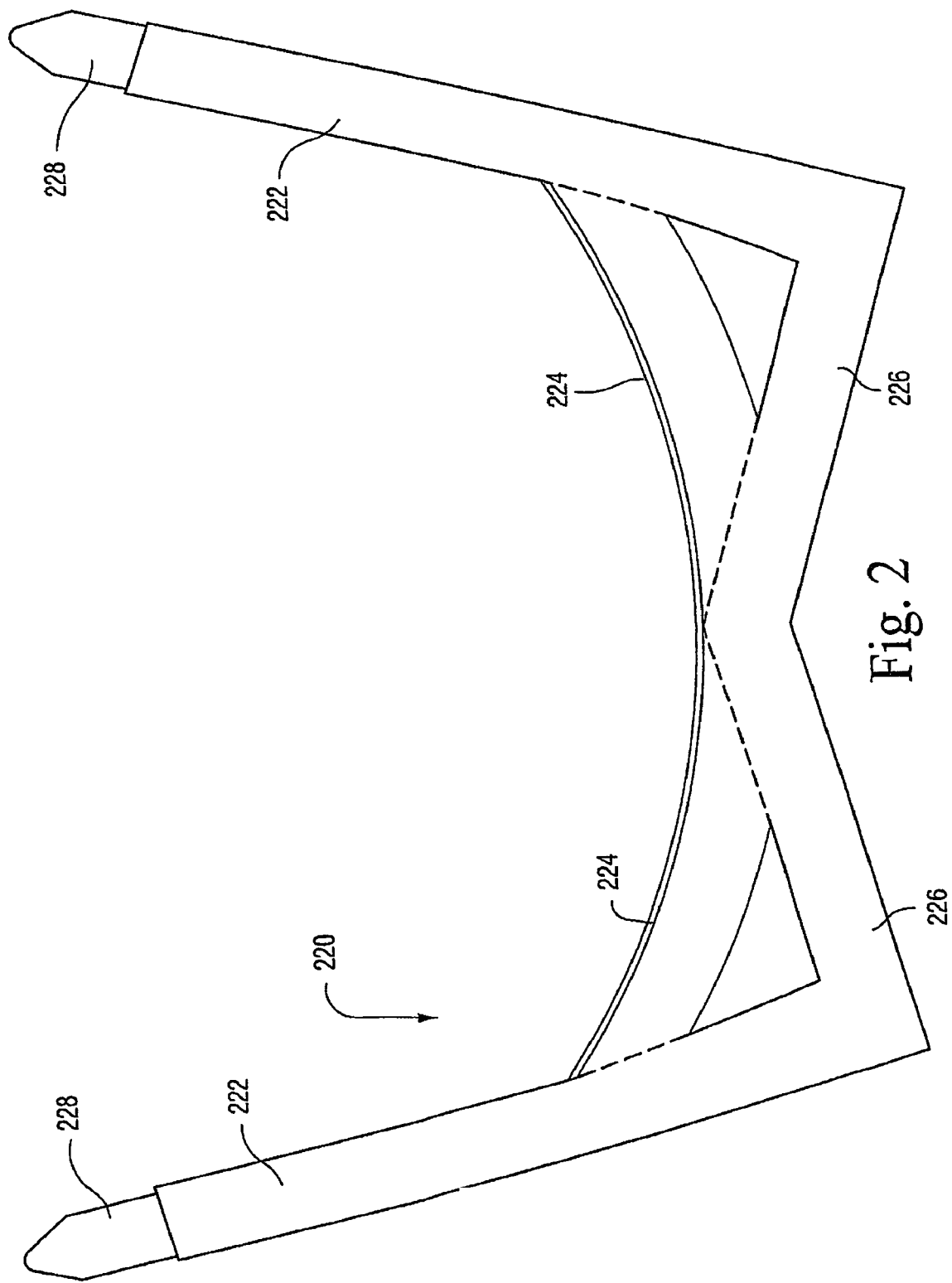
FIG. 2 is a plan view of a first headgear section of a headgear assembly of the mask system shown in FIG. 1.
Figure 4A:
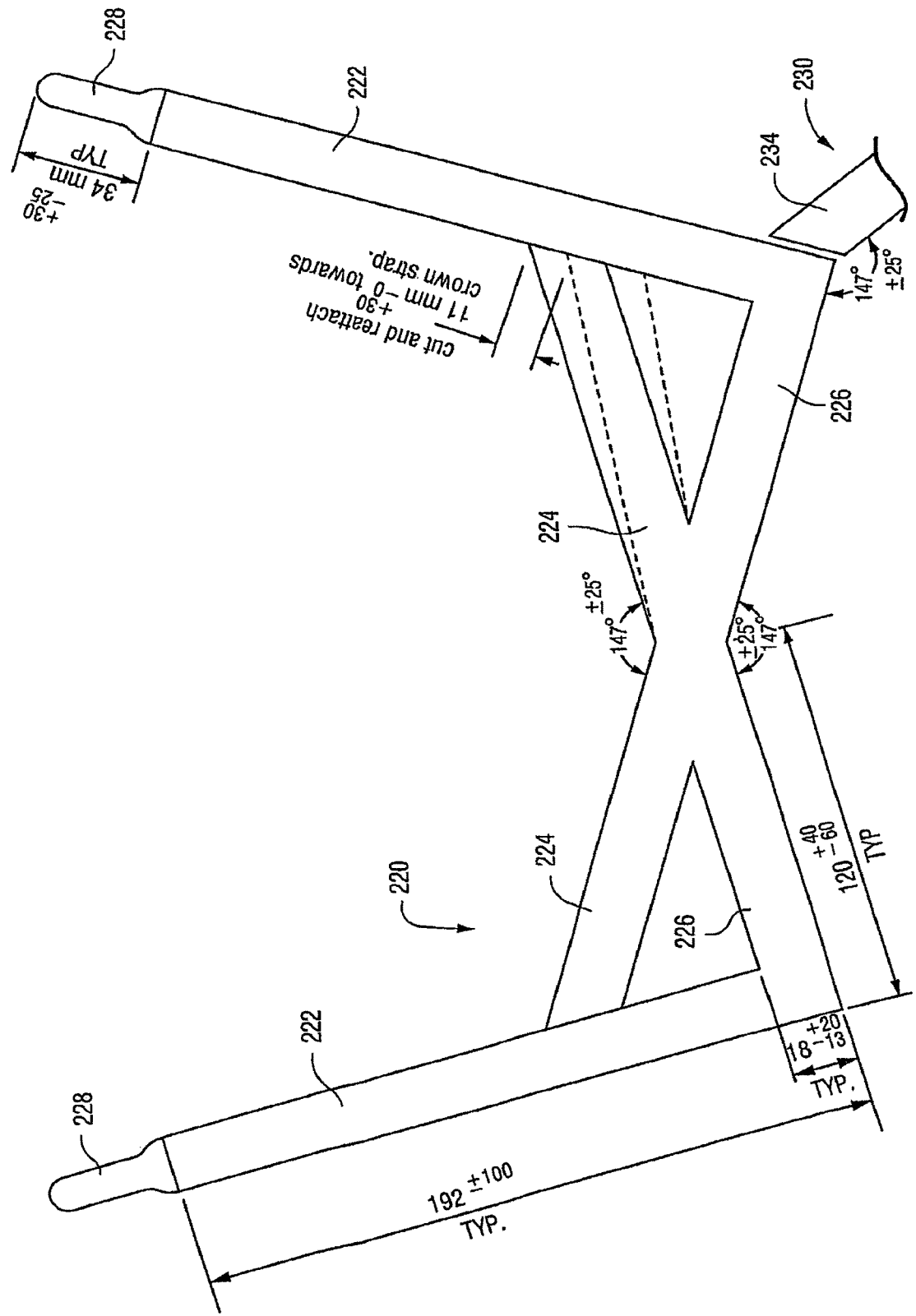
FIG. 4a is a plan view of the first headgear section shown in FIG. 2 and showing dimensions of an embodiment and an embodiment of instruction to form the three-dimensional first headgear section and instruction where second headgear section is attached.
Figure 5:
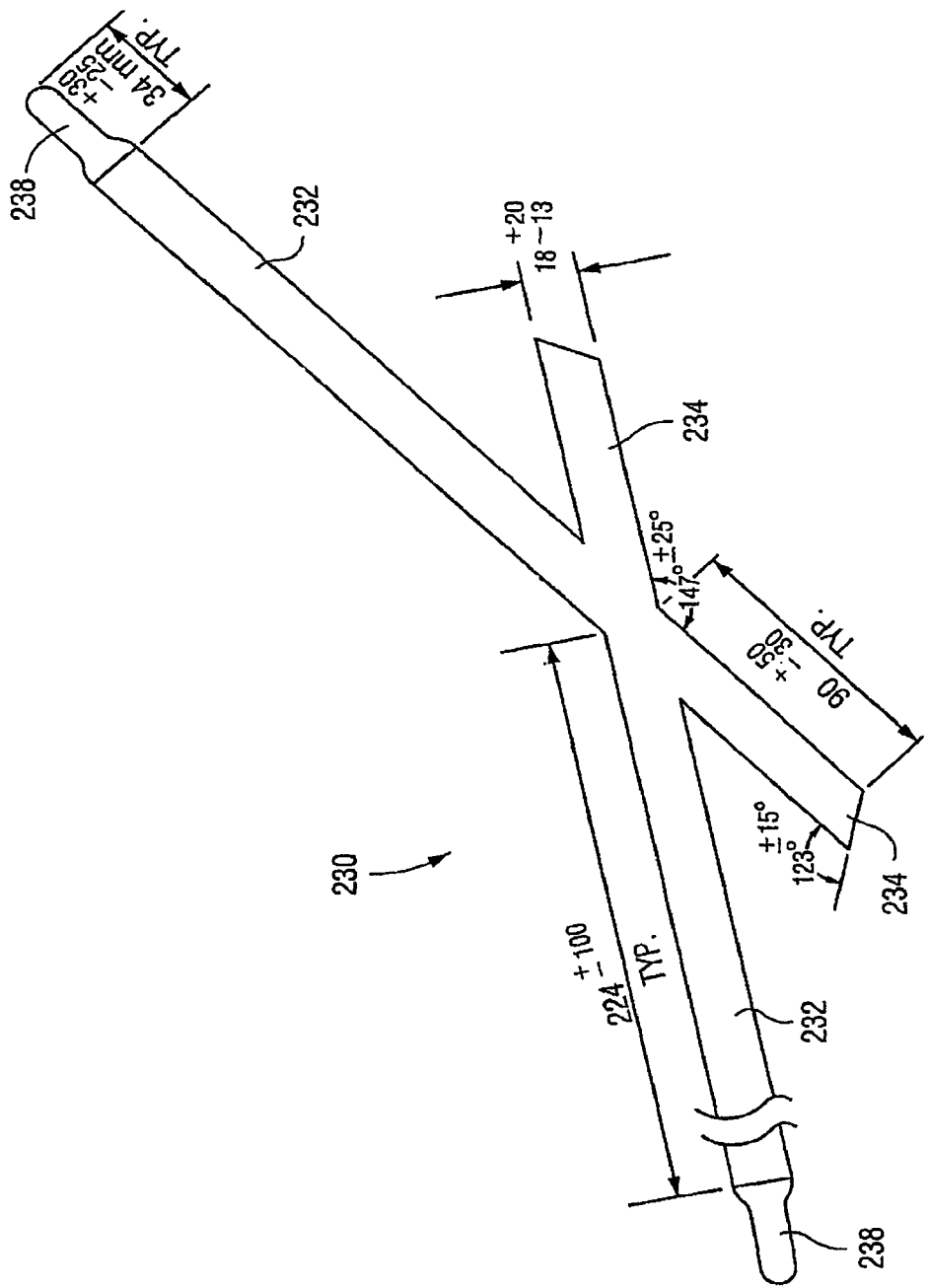
FIG. 5 is a plan view of the second headgear section shown in FIG. 3 and showing dimensions of an embodiment.
Figure 158:
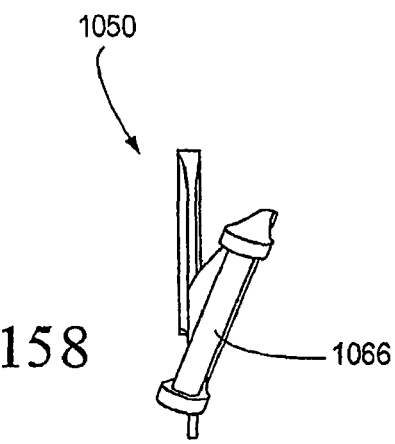
Figures 1, 158B:
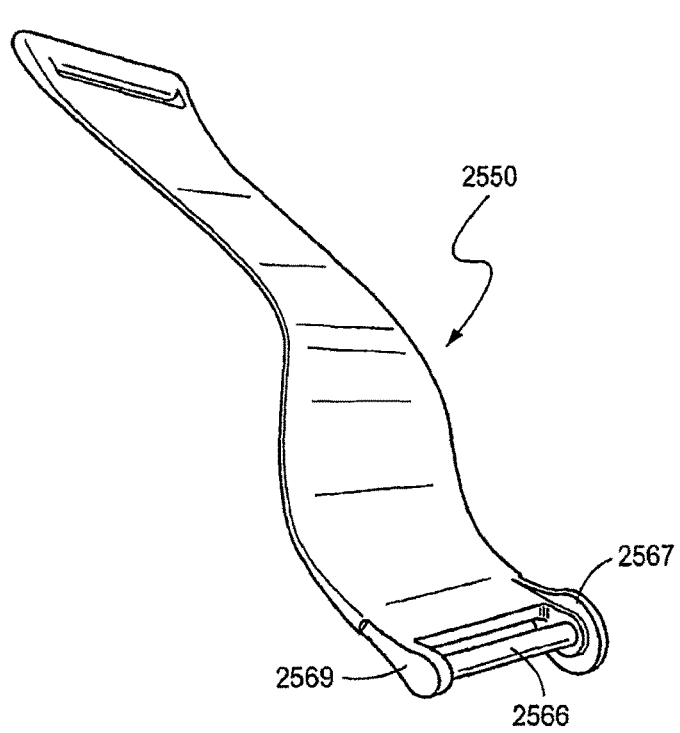
Figures 2, 158B:
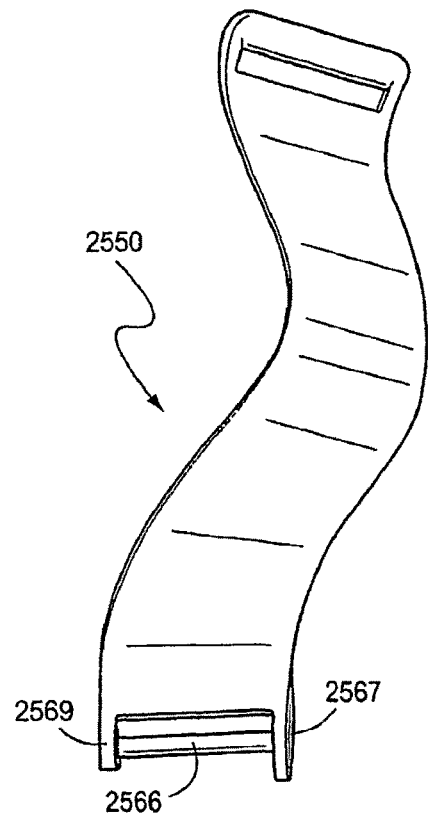
Figures 3, 158B:
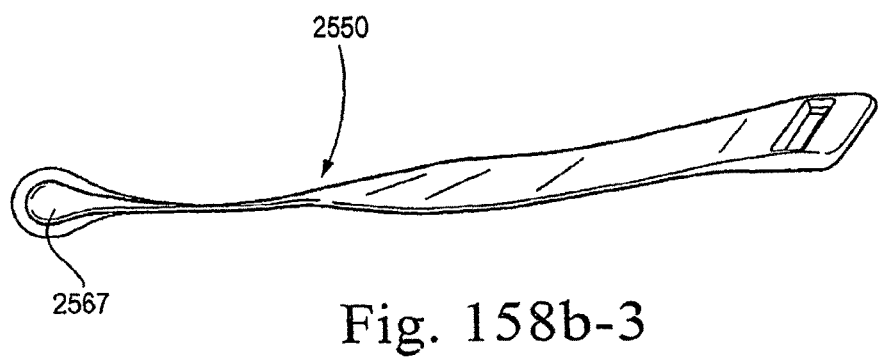

As best shown in FIGS. 2, 3, 7a, and 7b, the headgear assembly 218 includes a first headgear section 220 and a second headgear section 230 that is attached to the first headgear section 220. Specifically, the first and second headgear sections 220, 230 are constructed from two-dimensional flat headgear material, e.g., soft, flexible composite material such as Breathe-O-Prene™ manufactured by Accumed Technologies Inc. The two-dimensional flat headgear material is stamped, cut, or otherwise manufactured from a sheet, e.g., flexible material with thickness of 0.1-3 mm, to form the desired shapes of the first and second headgear sections 220, 230. As shown in FIG. 2 (which illustrates the first headgear section's bowed final form before it is attached to the second headgear section 230), the first headgear section 220 includes top strap portions 222, bridge strap portions 224, and crown strap portions 226. The free end of each top strap portion 222 includes a strip of Velcro® material 228 for use in securing the upper stabilizing straps 250 to the headgear assembly 218, and thereby securing the sealing assembly 212 to the headgear assembly 218. The dashed lines in FIG. 2 represent possible joint locations of the first headgear section 220 to achieve its bowed three-dimension final form. As shown in FIG. 3 (which illustrates the second headgear section's final form before it is attached to the first headgear section 220), the second headgear section 230 includes bottom strap portions 232 and crown strap portions 234. The free end of each bottom strap portion 232 includes a strip of Velcro® material 238 for use in securing the lower stabilizing straps 260 to the headgear assembly 218, and thereby securing the sealing assembly 212 to the headgear assembly 218. FIGS. 2 and 3 illustrate the two-dimensional first and second headgear sections 220, 230, and FIGS. 4a and 5 illustrate dimensions of embodiments of the first and second headgear sections 220, 230. Although specific dimensions and ranges of the first and second headgear sections 220, 230 are shown in FIGS. 4a and 5, it is to be understood that these dimensions and ranges are merely exemplary and other dimensions and ranges are possible depending on application. For example, ranges that vary from those provided +/−10% may be suitable for particular applications.

Figure 6:
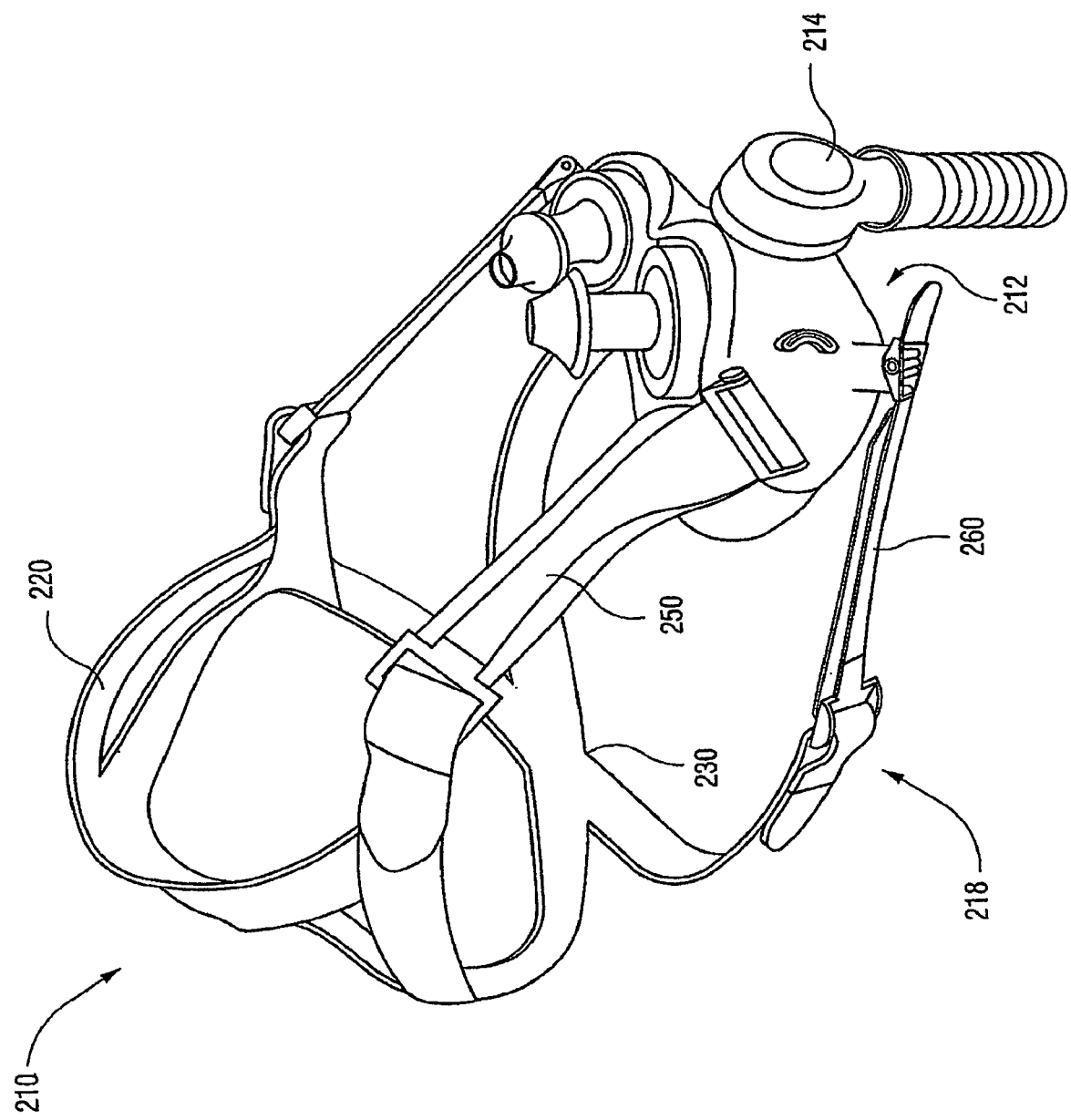
FIG. 6 is a perspective view of the mask system shown in FIG. 1 removed from the patient's head.
Figure 7A:
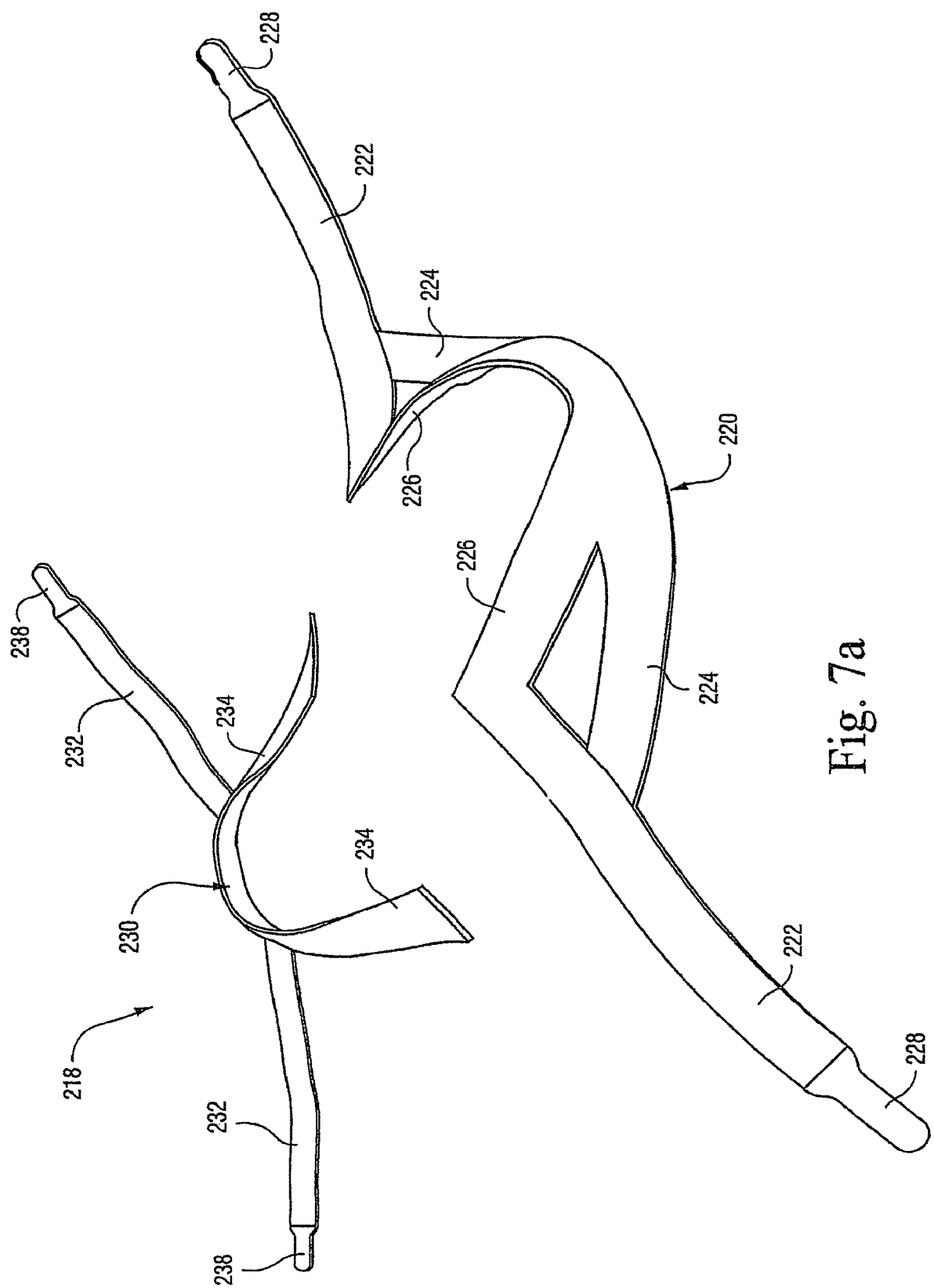
FIG. 7a is a perspective view of the headgear assembly of the mask system shown in FIG. 1 with the first and second headgear sections detached.
Figure 7B:
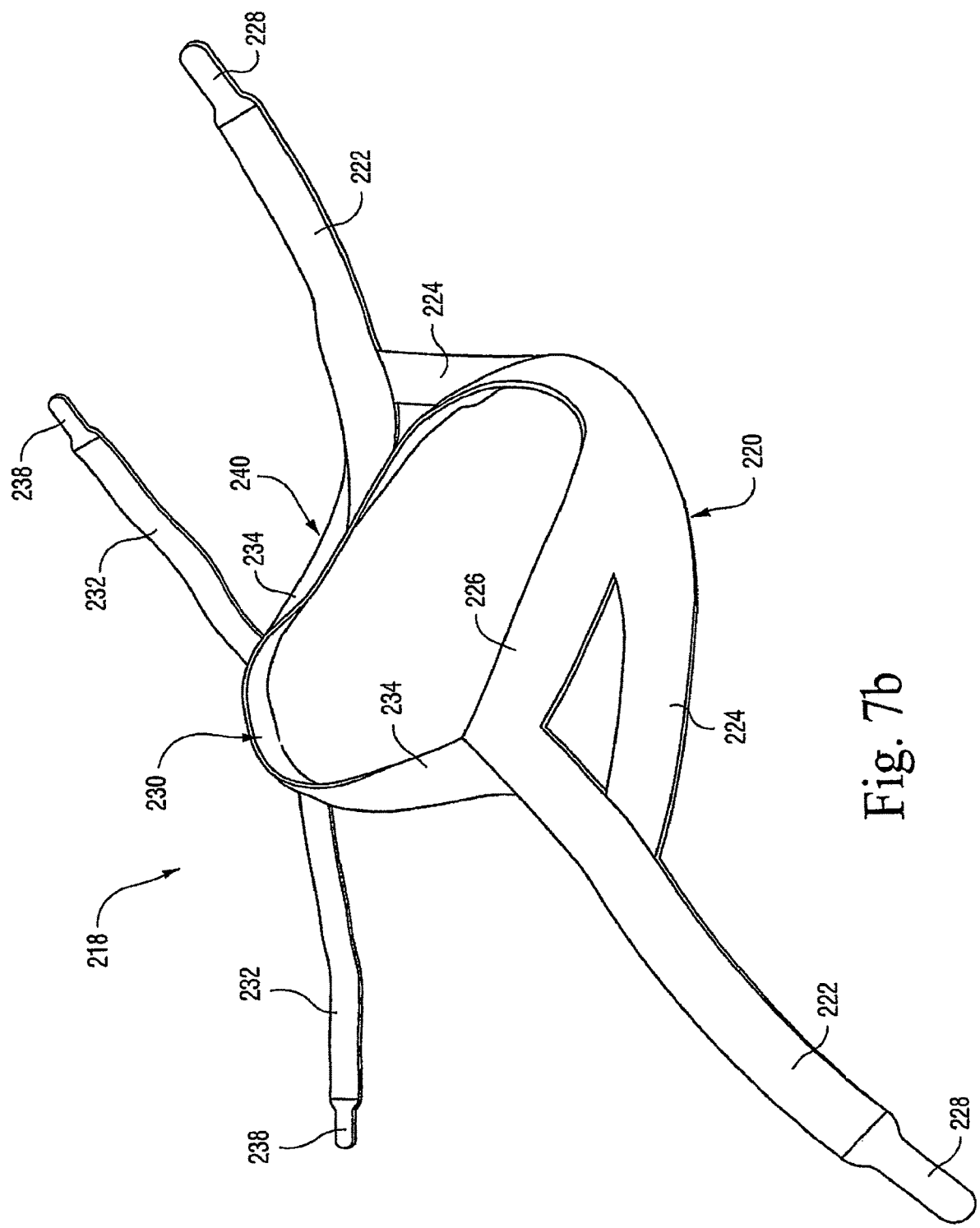
FIG. 7b is a perspective view of the headgear assembly of the mask system shown in FIG. 1 with the first and second headgear sections attached.

The two-dimensional first and second headgear sections 220, 230 are attached to one another, e.g., stitched, welded, glued or otherwise formed, to form a three-dimensional anatomically shaped headgear assembly 218. As shown in FIGS. 4a, 7a, and 7b, the first and second headgear sections 220, 230 are attached by attaching ends of respective crown strap portions 226, 234. FIG. 6 illustrates the three-dimensional headgear assembly 218 attached to the sealing assembly 212, and FIG. 7b illustrate the three-dimensional headgear assembly 218 removed from the patient's head.

Figure 8:
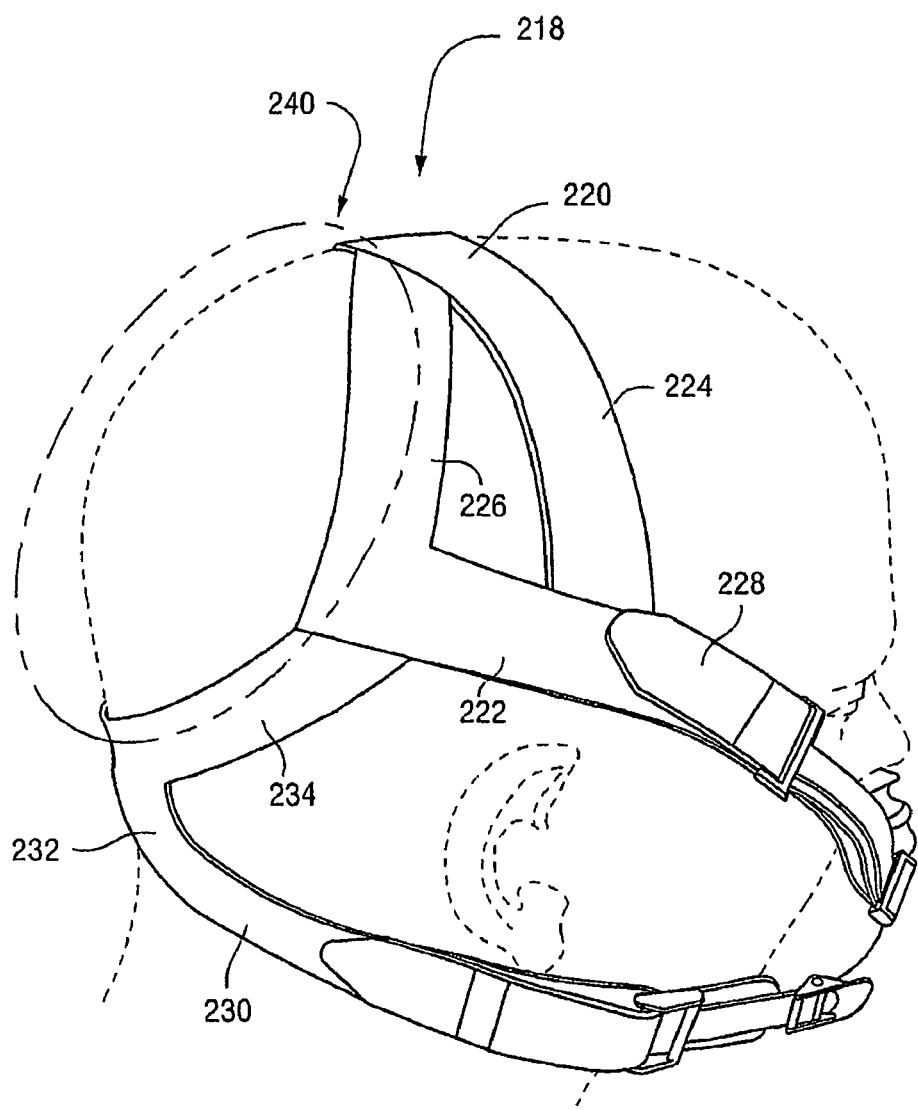
FIG. 8 is a rear perspective view of the mask system shown in FIG. 1 on the patient's head.
Figure 9:
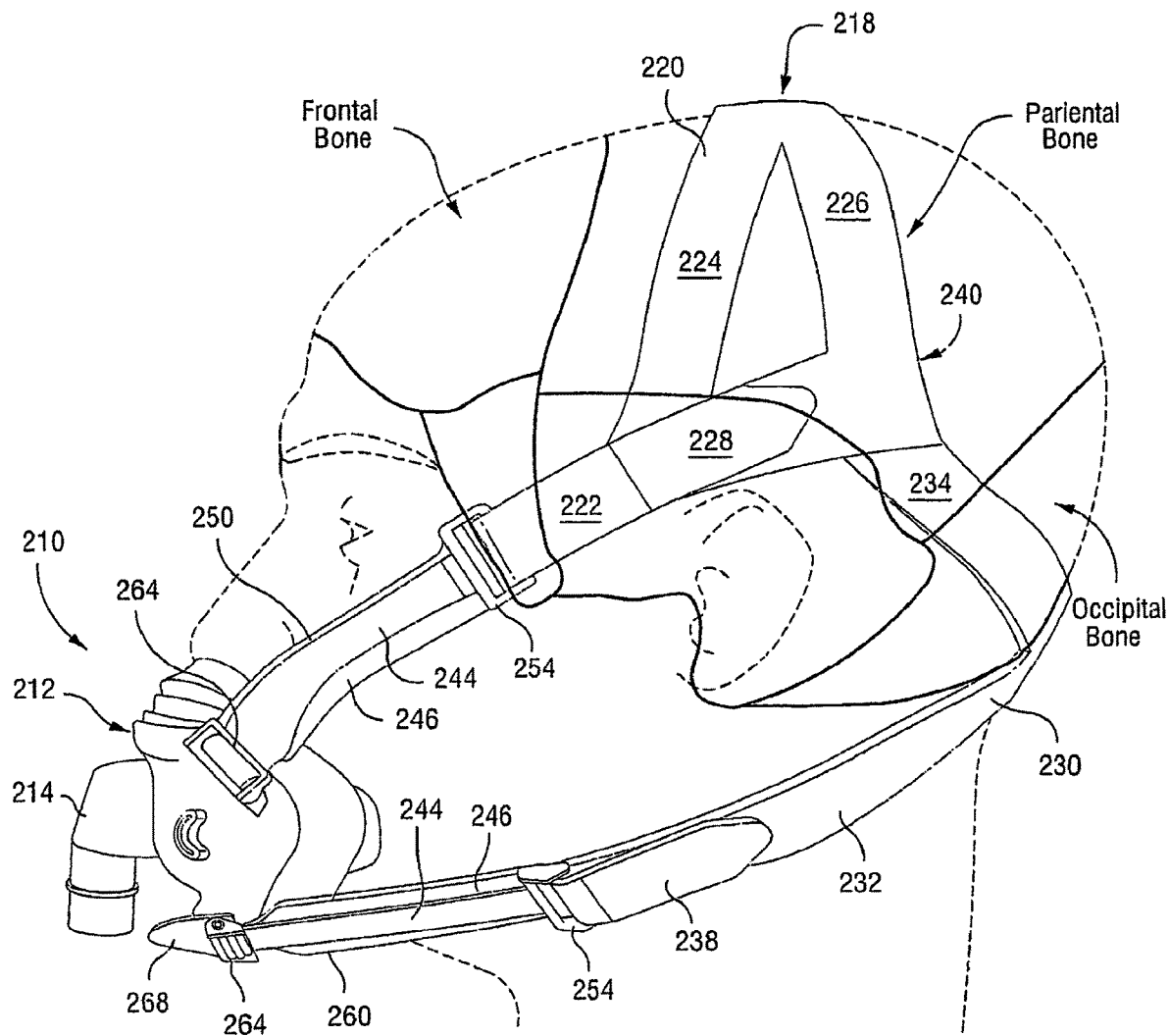
FIG. 9 is a side view of the mask system shown in FIG. 1 on the patient's head.
Figure 10:
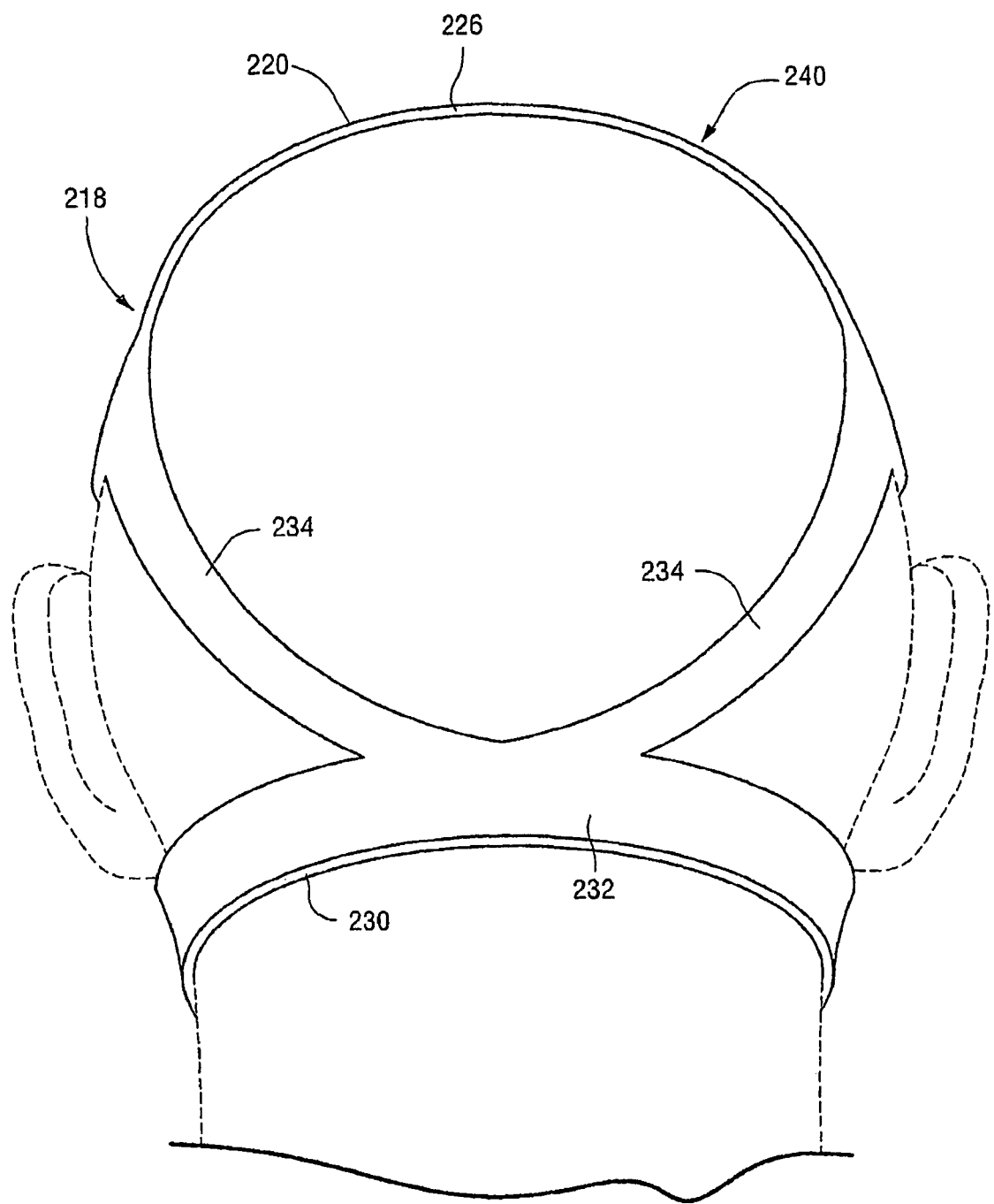
FIG. 10 is a rear view of the mask system shown in FIG. 1 on the patient's head.

As shown in FIGS. 8-10, the crown strap portions 226, 234 of the headgear assembly 218 cooperate to form a round-shaped crown strap 240 that cups the parietal bone and occipital bone of the patient's head. The crown strap 240 is preferably constructed from at least two segments of soft, flexible material that allows the crown strap 240 to conform to the shape of the patient's head. While the material may be non-elastic, in a preferred embodiment the material is elastic in order to further allow the headgear assembly 218 to conform to the patient's head shape and maybe a composite material such as Breathe-O-Prene™ manufactured by Accumed Technologies Inc.

The bridge strap portions 224 of the first headgear section 220 provides additional stability to the crown strap structure and prevent buckling. The bridge strap portions 224 may be provided to the first headgear section 220 in multiple arrangements. For example, as shown in FIG. 4a, the bridge strap portions 224 may be formed, e.g., punched, from the same piece of material where it remains attached between the top strap portion 222 and the crown strap portion 226. Then, the bridge strap portions 224 may be cut away from respective top strap portions 222 and moved slightly towards respective crown strap portions 226 where it is reattached, e.g., see dashed lines in FIG. 4a. This arrangement assists in forming the first headgear section 220 into the three-dimensional shape.

Figure 4B:
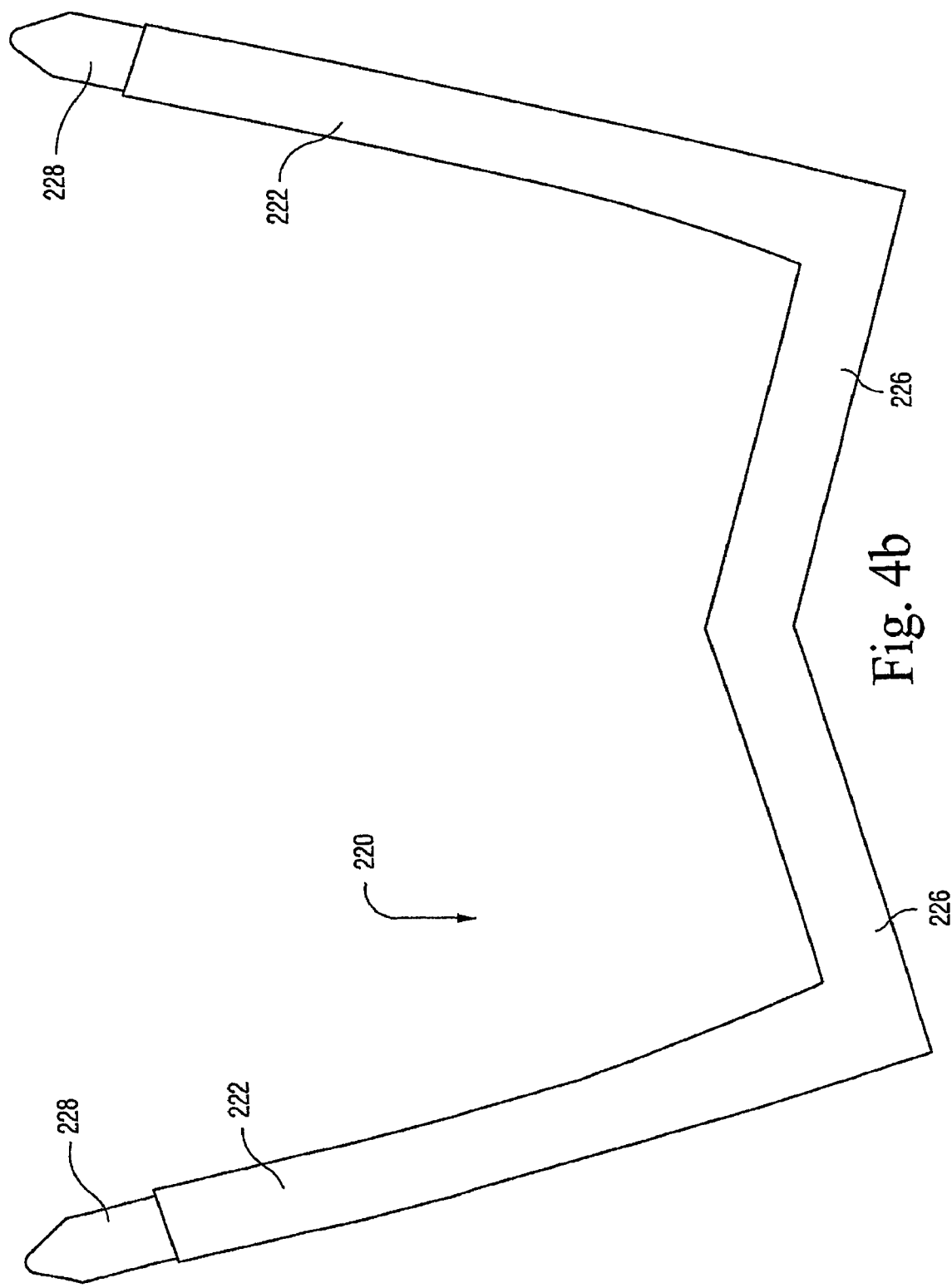
FIG. 4b is a plan view of another embodiment of the first headgear section.

In another embodiment, bridge strap portions 224 may not be provided on the first headgear section 220, as shown in FIG. 4b.

Figure 4C:
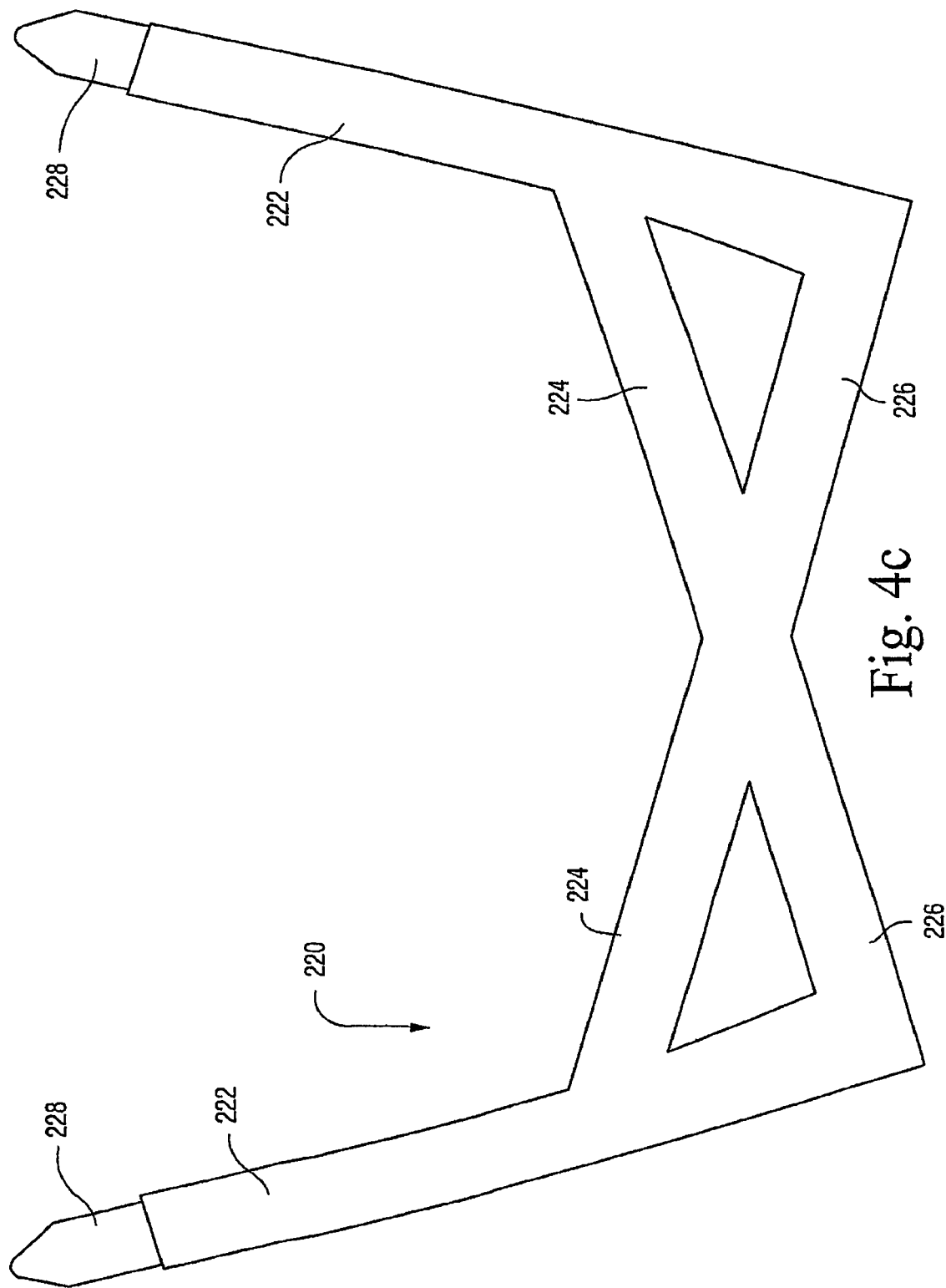
FIG. 4c is a plan view of another embodiment of the first headgear section.

In another embodiment, the bridge strap portions 224 may be formed, e.g., punched, from the same piece of material and attached between the top strap portions 222 and the crown strap portions 226, and then left in its flat configuration as shown in FIG. 4c.

Figure 4D:
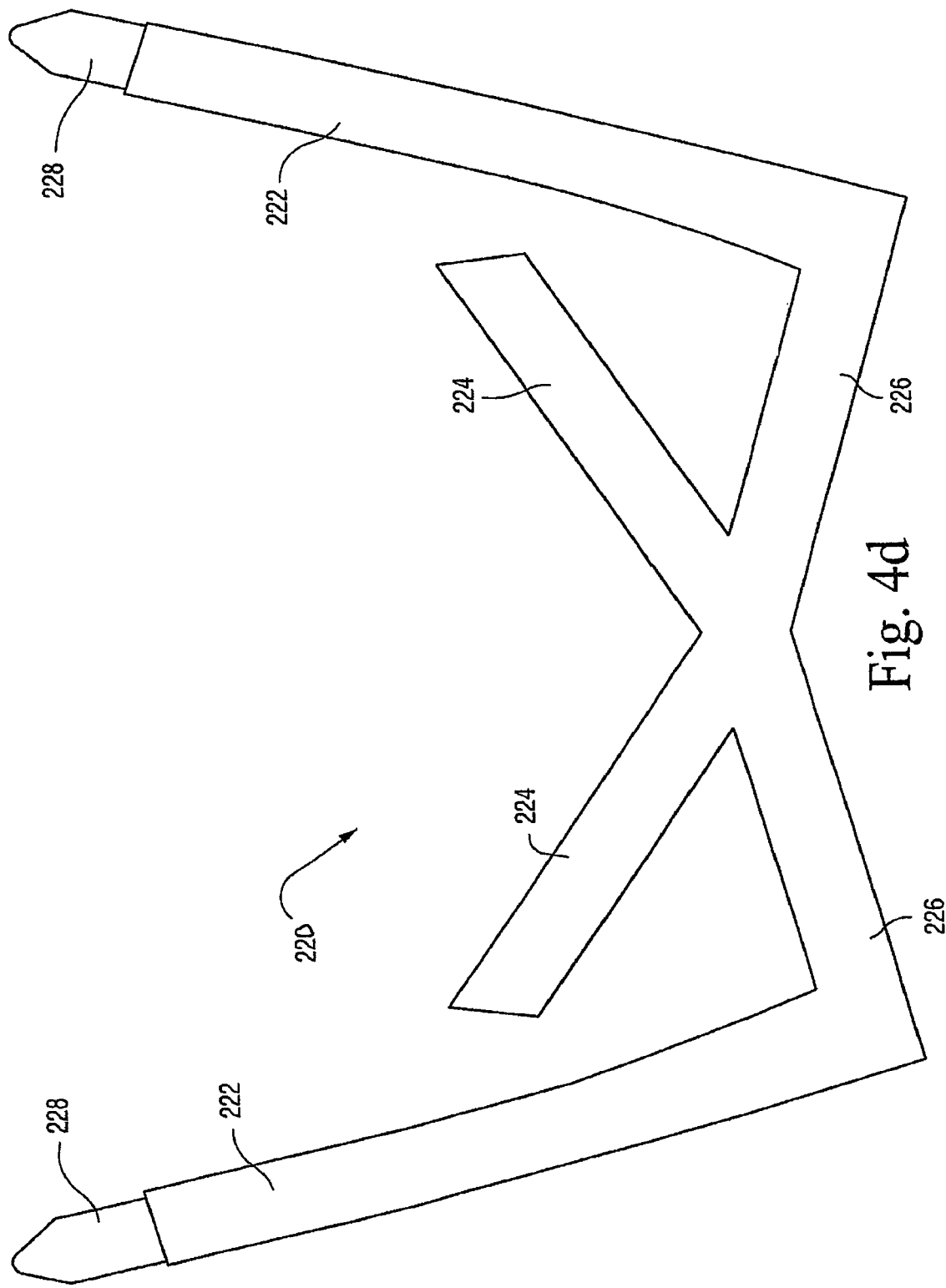
FIG. 4d is a plan view of another embodiment of the first headgear section.

In another embodiment, the bridge strap portions 224 may be formed, e.g., punched, from the same piece of material as the top strap portions 222 and the crown strap portions 226 such that the bridge strap portions 224 are separated from respective top strap portions 222 as shown in FIG. 4d. Then, the bridge strap portions 224 are reattached to respective top strap portions 222 to form a three-dimensional shape.

Figure 4E:
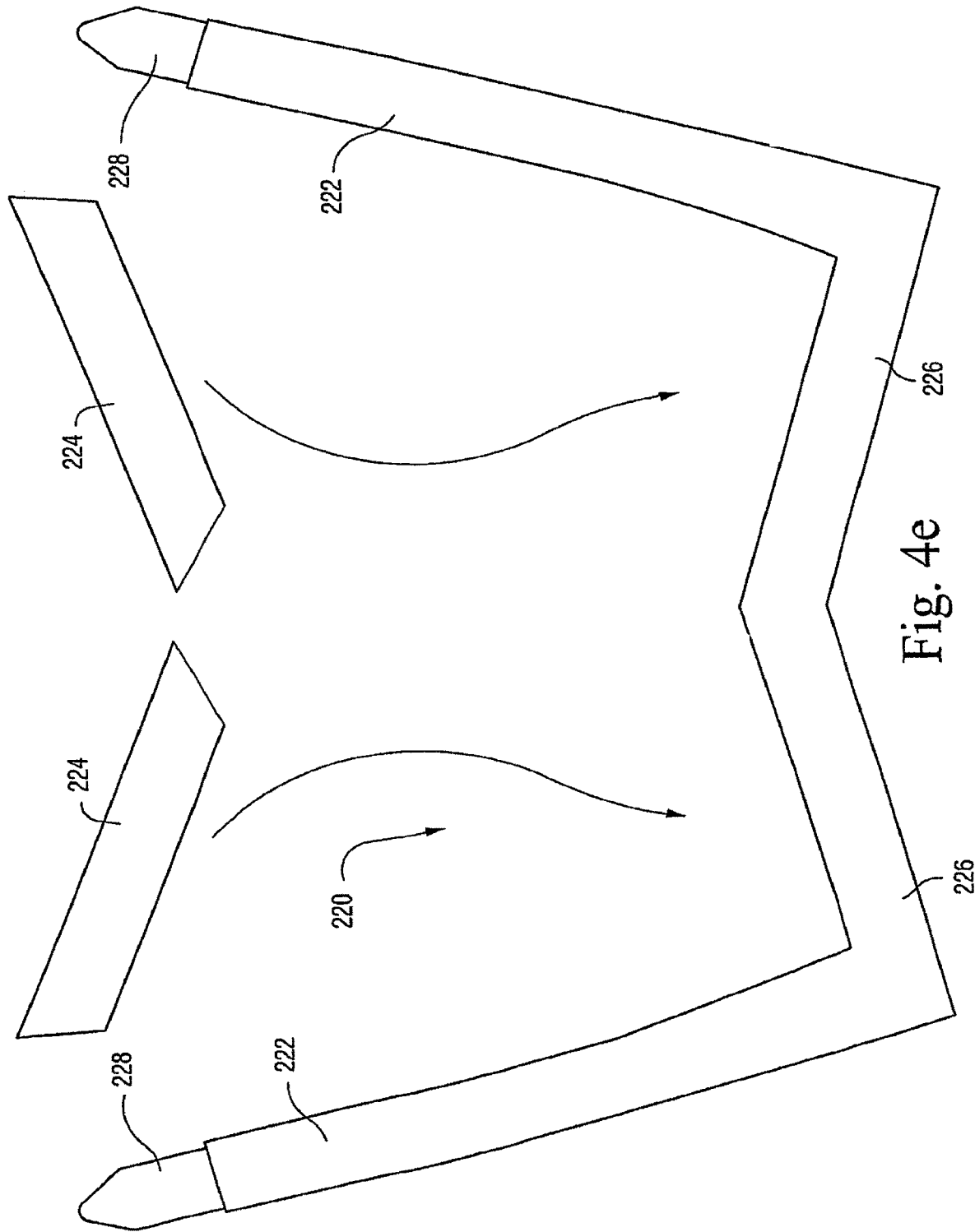
FIG. 4e is a plan view of yet another embodiment of the first headgear section.

In yet another embodiment, the bridge strap portions 224 may be formed, e.g., punched, separately from the top strap portions 222 and the crown strap portions 226 as shown in FIG. 4e. Then, the bridge strap portions 224 are attached between respective top strap portions 222 and crown strap portions 226 to form a three-dimensional shape.

Figure 4F:
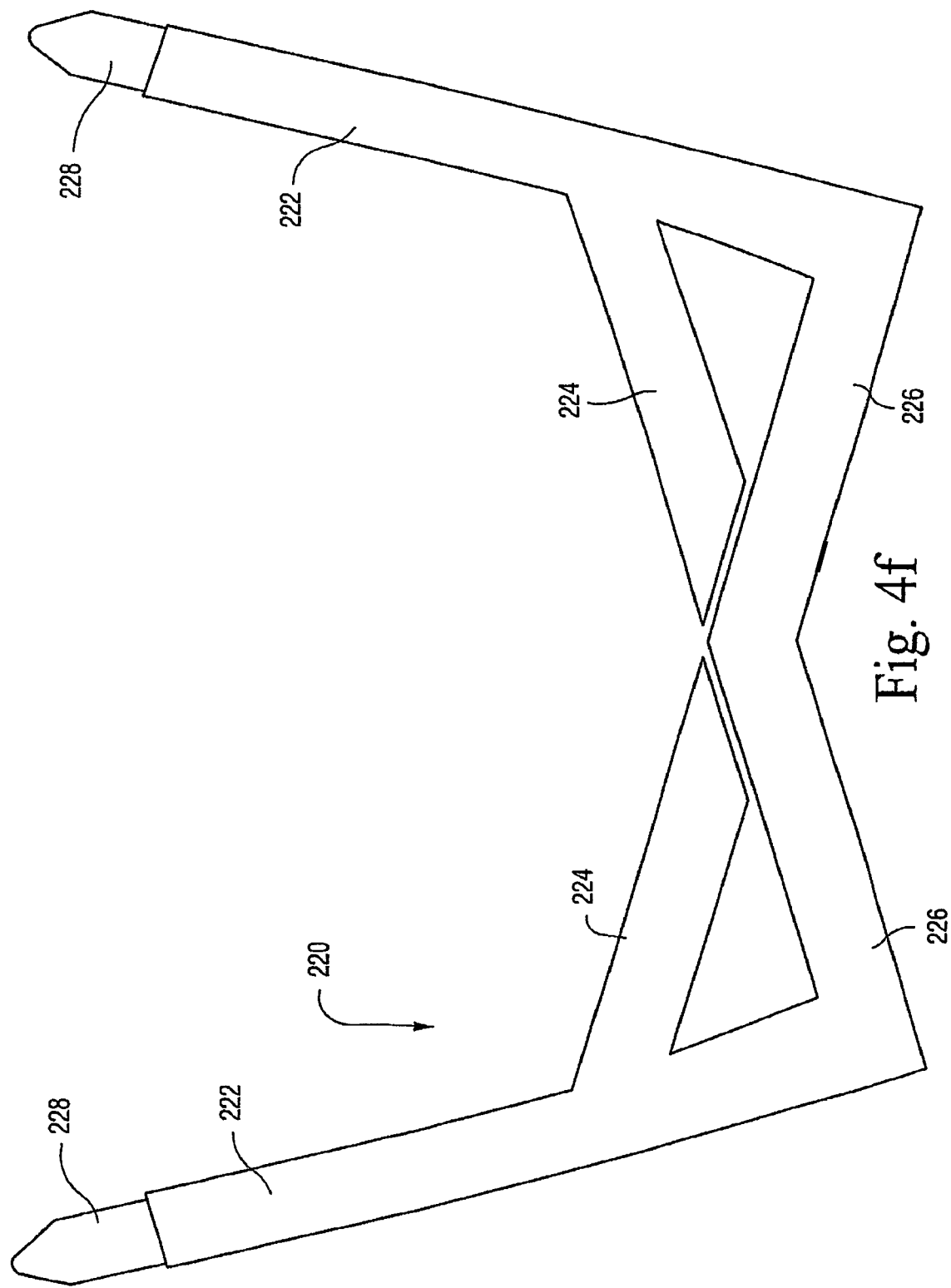
FIG. 4f is a plan view of still another embodiment of the first headgear section.

In still another embodiment, the bridge strap portions 224 may formed, e.g., punched, from the same piece of material as the top strap portions 222 and the crown strap portions 226 such that the bridge strap portions 224 are separated from respective crown strap portions 226 as shown in FIG. 4f. Then, the bridge strap portions 224 are reattached to respective crown strap portions 226 to form a three-dimensional shape. The bridge strap portions 224 may also be shortened (e.g., by cutting) if desired before reattaching depending on the particular application.

In still another embodiment, the strap portions of the headgear assembly may have different elasticity from one another depending on application.

However, the headgear assembly may have other suitable arrangements and forming methods. For example, the straps of the headgear assembly may be attached to one another in other locations to achieve a three-dimensional effect.

The headgear assembly 218 provides several advantages to both the manufacturer and the patient. For example, the formation of a three-dimensional crown strap 240 that fits snugly to the patient's head prevents the buckling of straps that is a recognized problem with some existing headgear. This increases the patient's comfort and provides stability to the mask system. In addition, the stability provided by the snug fit of the crown strap 240 allows the headgear assembly 218 to have a relatively small footprint. This in turn provides a relatively small surface area in contact with the patient's head, which increases comfort of the patient, e.g., prevents heat formation, areas that press against the head when being worn, sweating, etc., and reduces the visual bulk of the headgear assembly 218. Also, the formation of the crown strap 240 as described above removes the need to provide adjustment on the headgear assembly 218 that is known with existing headgear, and thus no relatively hard adjustment components that can lead to patient discomfort are found. Further, the use of two-dimensional components to construct the crown strap 240 provides a relatively low-cost method of manufacturing a three-dimensional shape. However, alternative methods of manufacture such as molding from heat-setting materials or foam molded headgears are possible.

Also, although the headgear assembly 218 has been described in connection with the mask system 210, it is to be understood that the headgear assembly 218 may be used in all types of mask systems, e.g., nasal mask, mouth mask, oro-nasal mask, etc.

§ 1.1.2 Substantially Rigid Stabilizing Straps

Figure 11:
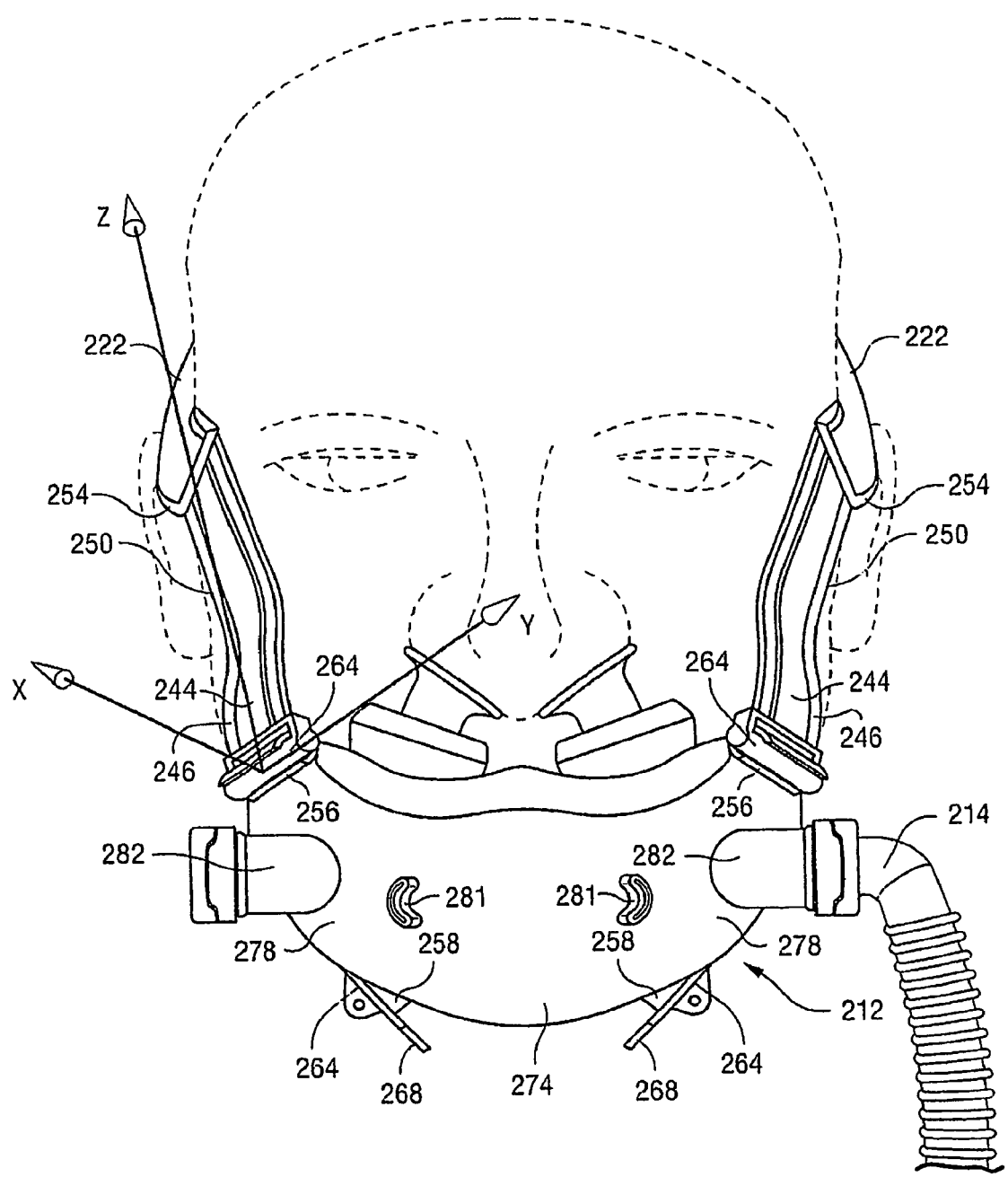
FIG. 11 is a front view of another embodiment of a mask system on the patient's head with X, Y, and Z axes.
Figure 12:
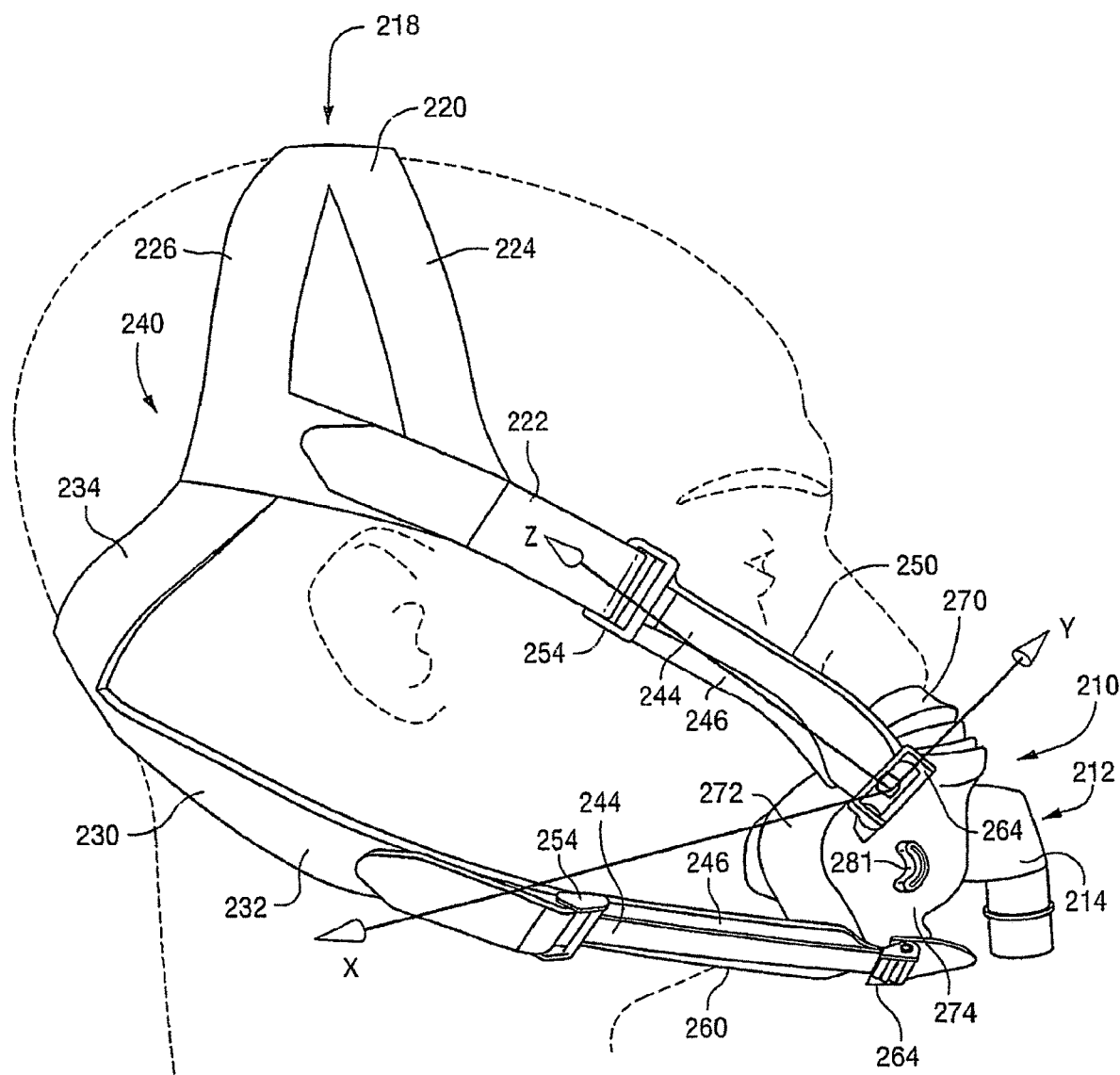
FIG. 12 is a side view of the mask system shown in FIG. 1 on the patient's head with X, Y, and Z axes.
Figure 171:
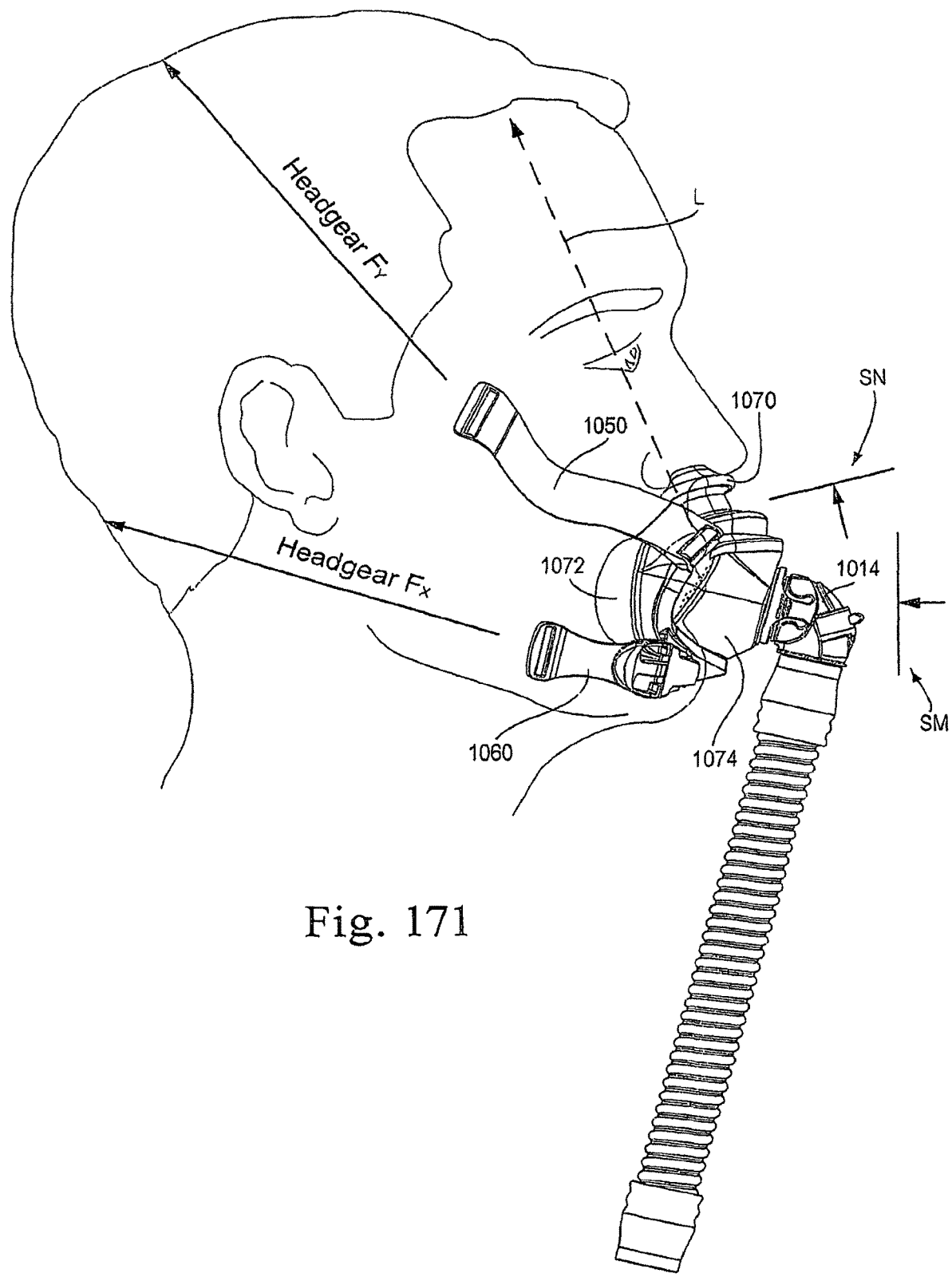
FIG. 171 illustrates forces provided by the headgear assembly according to an embodiment of the present invention.

As best shown in FIGS. 1, 11, and 12, upper substantially rigid stabilizing straps 250 are provided between each of the top strap portions 222 and the sealing assembly 212, and lower substantially rigid stabilizing straps 260 are provided between each of the bottom strap portions 232 and the sealing assembly 212. The upper and lower stabilizing straps 250, 260 provide a flexible yet stable connection system between the headgear strap portions 222, 232 and the sealing assembly 212 in order to ensure suitable tension vectors are provided to seal the sealing assembly 212 with both the patient's mouth and nasal passages. The desired vectors to achieve a seal to the nares and mouth region are illustrated in FIG. 171 for example and denoted by $F_X$ and $F_Y$ specifically.

As illustrated, the stabilizing straps 250, 260, also referred to as stabilizing elements or stiffened headgear elements, are each constructed from a rigid or semi-rigid yoke section 244 that is attached to a material backing 246, e.g., via stitching, welding, gluing, or otherwise mechanically affixed. In the illustrated embodiment, the yoke section 244 is manufactured from nylon or polypropylene or polycarbonate. However, other materials of greater or less rigidity are also possible. The stabilizing straps 250, 260 may be constructed from multiple layers, e.g., more than two layers, or maybe constructed from a single layer of substantially rigid material. In an alternative embodiment, the stabilizing straps may be constructed from a relatively soft and rigid material so that a material backing is not needed. The sectional geometry of the yoke section 244 allows flexing across the thickness, i.e., rotation around the Y-axis in FIGS. 11 and 12, to conform to a patient's face, while preventing flexing along the longitudinal axis, i.e., no rotation around the X-axis in FIGS. 11 and 12. In this way, the stabilizing straps 250, 260 act to maintain the position of the top and bottom strap portions 222, 232 relative to each other, and secure the mask system 210 at the correct orientation on the patient's face. In addition, the stabilizing straps 250, 260 act as "outriggers" to the mask system 210 and provide a larger footprint on the patient's face. This arrangement substantially increases the stability of the mask system.

Figure 32:
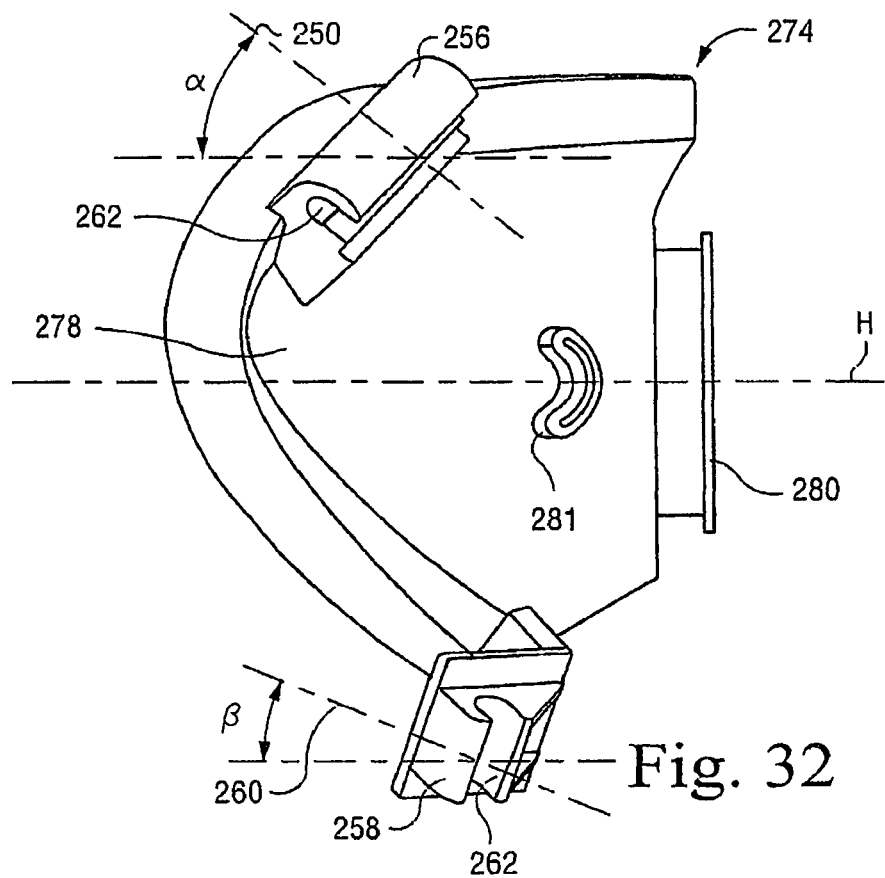
FIG. 32 is a side view of the frame of the mask system shown in FIG. 1.

Another aspect of the design of the headgear assembly 218 is the angle that the stabilizing straps 250, 260 make with respect to the sealing assembly 212 and the patient's face. In the illustrated embodiment, each of the upper stabilizing straps 250 makes an angle α of 40°+/−10° with respect to the horizontal plane H (as defined in FIG. 32) of the sealing assembly 212. This angle α has been chosen as the top strap portions 222 are designed to affect sealing in the roughly orthogonal planes of the nasal openings and the mouth opening of the patient. See the vectors illustrated in FIG. 171 (i.e., along these planes). In this way, tightening the top strap portions 222 will simultaneously draw the nasal prongs 270 of the sealing assembly 212 up and into engagement with the patient's nares while also drawing the cushion 272 of the sealing assembly 212 back and against the patient's face (particularly above the patient's upper lip). Thus, the angle chosen and the resultant force vector when headgear tension is applied allows for effective sealing at both the nasal prongs 270 and the mouth cushion 272. The angle chosen also takes into account the various forces the mask system 210 is subject to, e.g., the force desired to seal against the treatment pressure (as a function of sealing area), and the force desired to offset tube drag and other factors.

In the illustrated embodiment, each of the lower stabilizing straps 260 makes an angle ß of 0° to 30° with respect to the horizontal plane H (as defined in FIG. 32) of the sealing assembly 212. The lower stabilizing straps 260 are aligned in this manner so that the bottom strap portions 232 will extend close to the base of the patient's ear and remain primarily on the bony part of the patient's skull. This arrangement minimizes the sections of bottom strap portions 232 that extend horizontally over the patient's neck. In this way, the headgear assembly 218 remains firmly attached to the patient's head as there is no relative movement (e.g., distance changes) between headgear components when patient is moving or rolling around and therefore stability of the mask system 210 is maximized. By way of explanation, if the headgear extended over the patient's neck it would move or tighten and loosen with head movements of the patient. This angle also ensures that the bottom strap portions 232 intersect with the crown strap 240 at the appropriate location at the base of the occiput of the patient's head.

§ 1.1.3 Attachment to Frame

§ 1.1.3.1 First Embodiment Headgear

As illustrated in FIGS. 1, 11, and 12, the upper stabilizing straps 250 are removably connected to an upper portion of the frame 274, and the lower stabilizing straps 260 are removably connected to a lower portion of the frame 274.

As shown in FIGS. 11 and 12, each of the upper and lower stabilizing straps 250, 260 includes a strap attachment member 254 secured at one end and a frame attachment member 264 secured at the opposite end. The strap attachment member 254 includes a crossbar that enables the end portion of the respective top and bottom strap portion 222, 232 to be wrapped around, in a known manner. The free end of each of the top and bottom strap portions 222, 232 includes a strip of Velcro® material 228,238 that engages the remainder of the strap portion to adjustably pull or secure the strap attachment member 254 in place. Thus, the length of the top and bottom strap portions 222, 232 maybe easily adjusted. However, other adjustment arrangements are possible, e.g., adjustment via ladderlock, ratcheting mechanism, etc.

Figure 13:
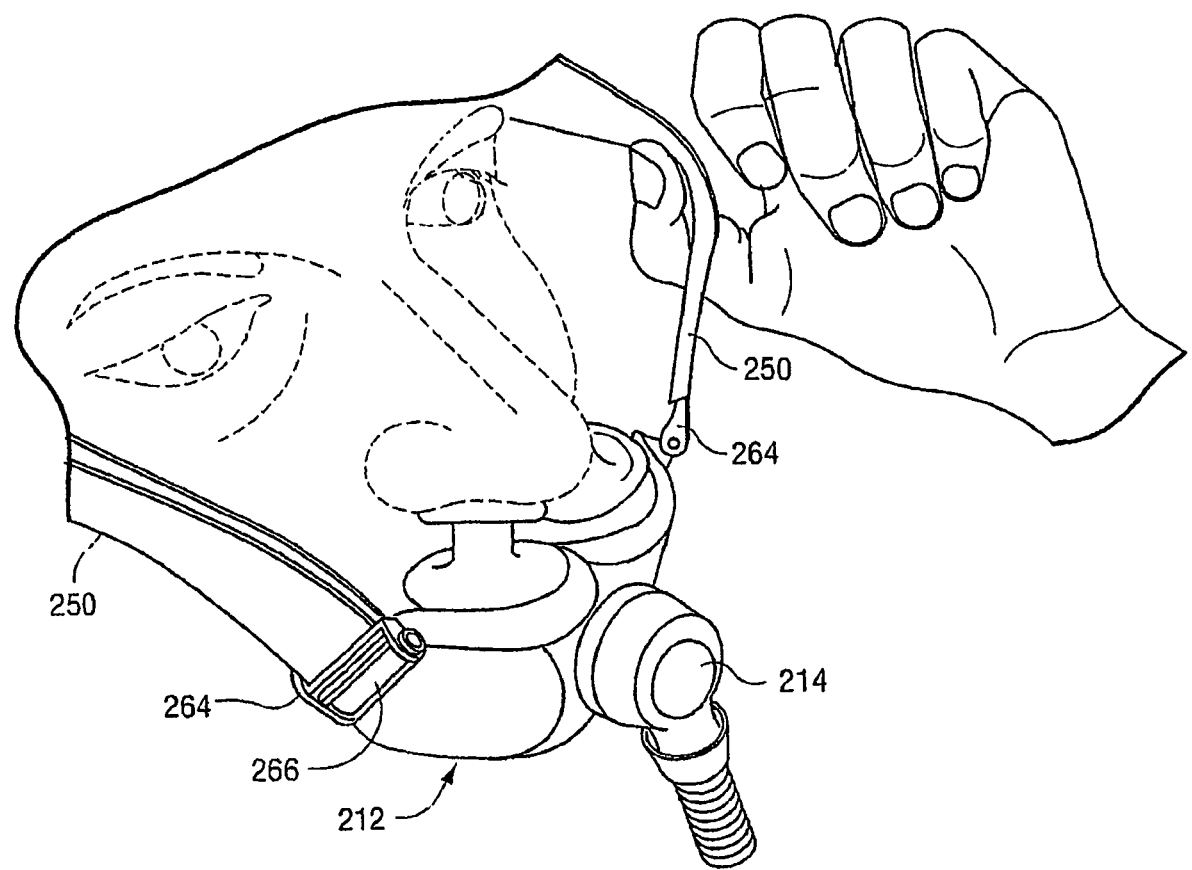
FIG. 13 is a front perspective view of the mask system shown in FIG. 1 on the patient's head with the patient pivoting a stabilizing or stabilizer strap.

As best shown in FIGS. 1 and 13, the frame attachment member 264 of each of the upper and lower stabilizing straps 250, 260 is in the form a swivel attachment that provides a post element 266. The swivel attachment of the upper stabilizing straps 250 is arranged to allow respective upper stabilizing straps 250 to rotate in one plane in order to accommodate a wide range of facial angles, as shown in FIG. 13. The swivel attachment of the lower stabilizing straps 260 is arranged to allow for easy engagement/disengagement.

Figure 14:
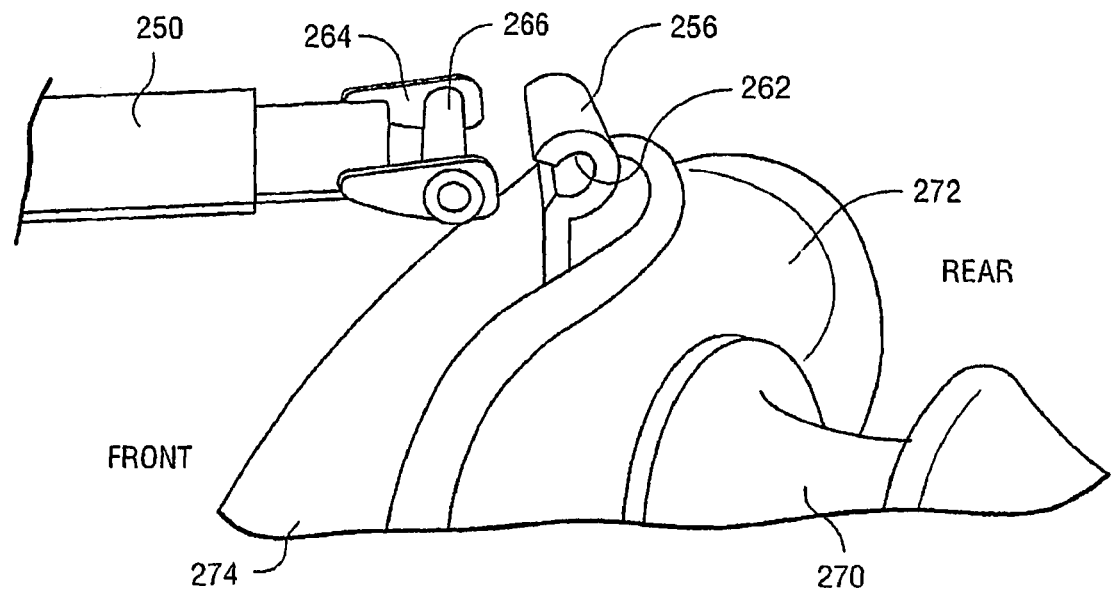
FIG. 14 is an enlarged perspective view of a frame attachment member of the mask system shown in FIG. 1 being engaged with an upper headgear anchor.
Figure 16:
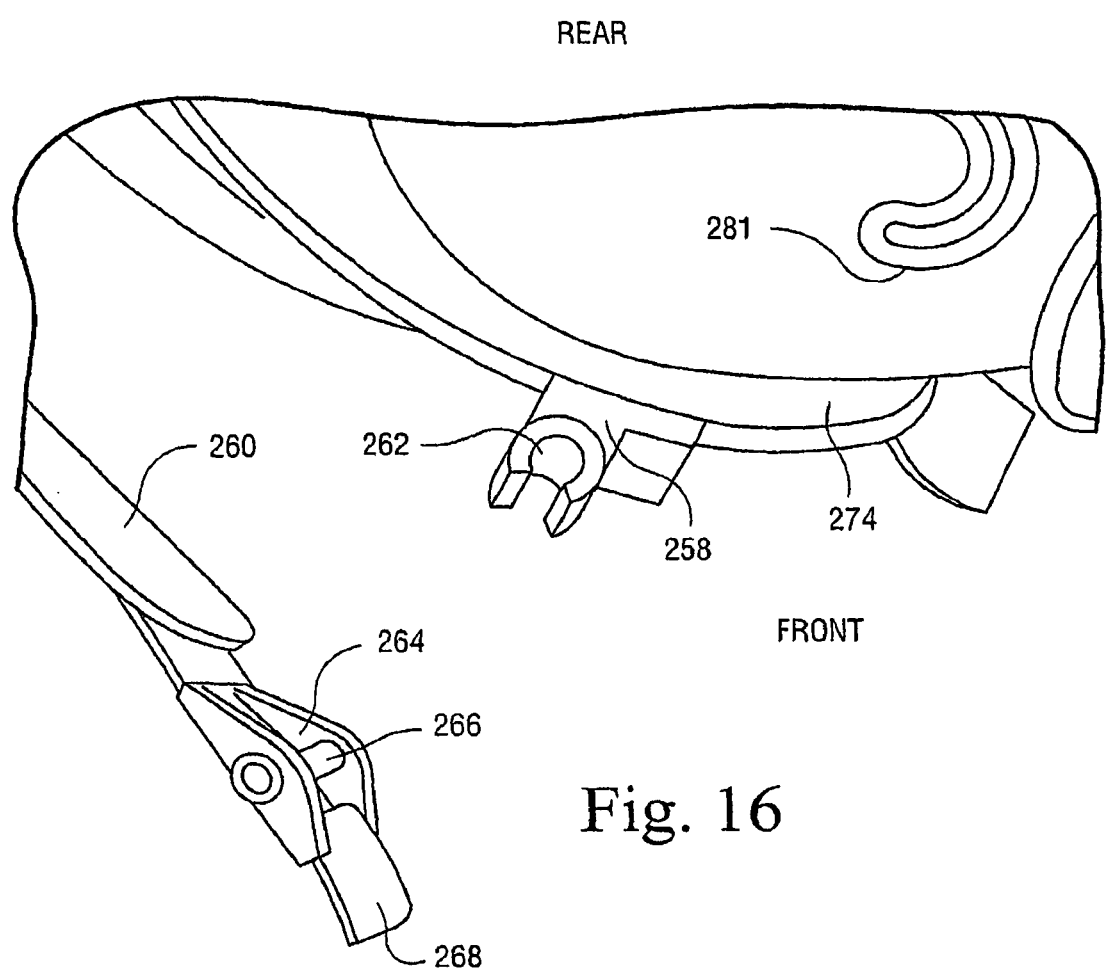
FIG. 16 is an enlarged perspective view of a frame attachment member of the mask system shown in FIG. 1 being engaged with a lower headgear anchor.
Figure 31:
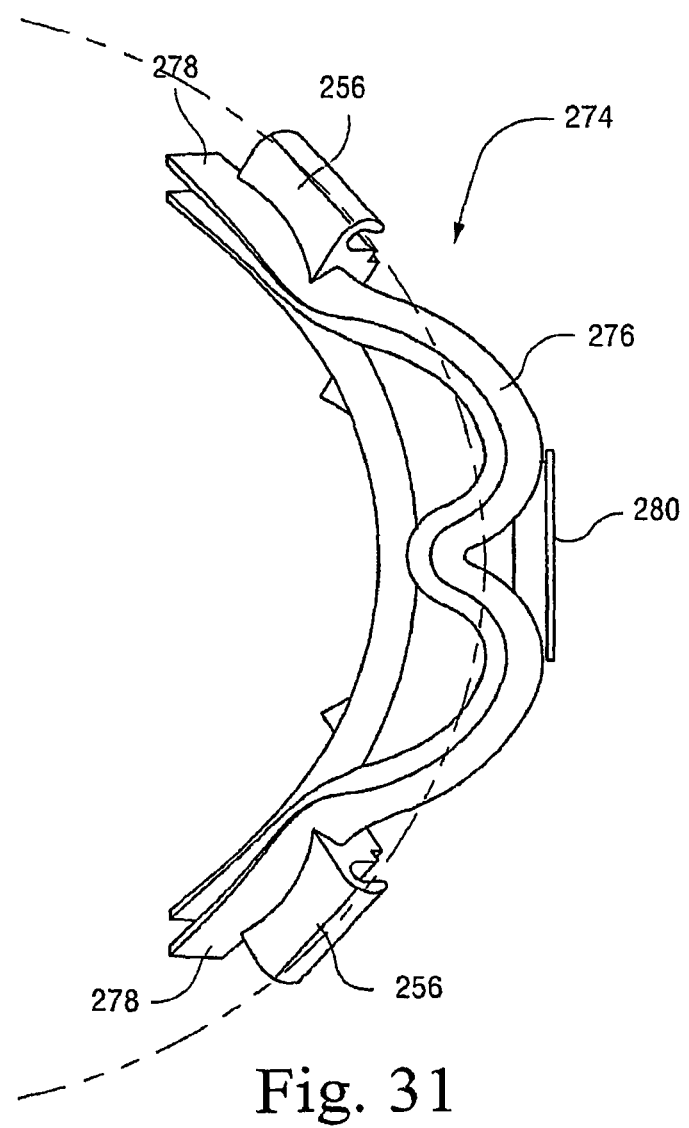
FIG. 31 is a top view of the frame of the mask system shown in FIG. 1.

Specifically, as best shown in FIGS. 1 and 11, the frame 274 includes a main body having a side frame portion 278 on each lateral side thereof. The main body includes an aperture 280 that is coupled to the swivel elbow 214 for delivering breathable gas. Upper and lower anchors 256, 258 are provided on each side frame portion 278 thereof. As best shown in FIGS. 14 and 16, each anchor 256, 258 is in the form of a female connector that provides a slot opening 262. Also, as shown in FIG. 31, the upper anchors 256 are substantially in line with the prongs when the prongs are received in the frame 274 (see arcuate dashed line).

Figure 17:
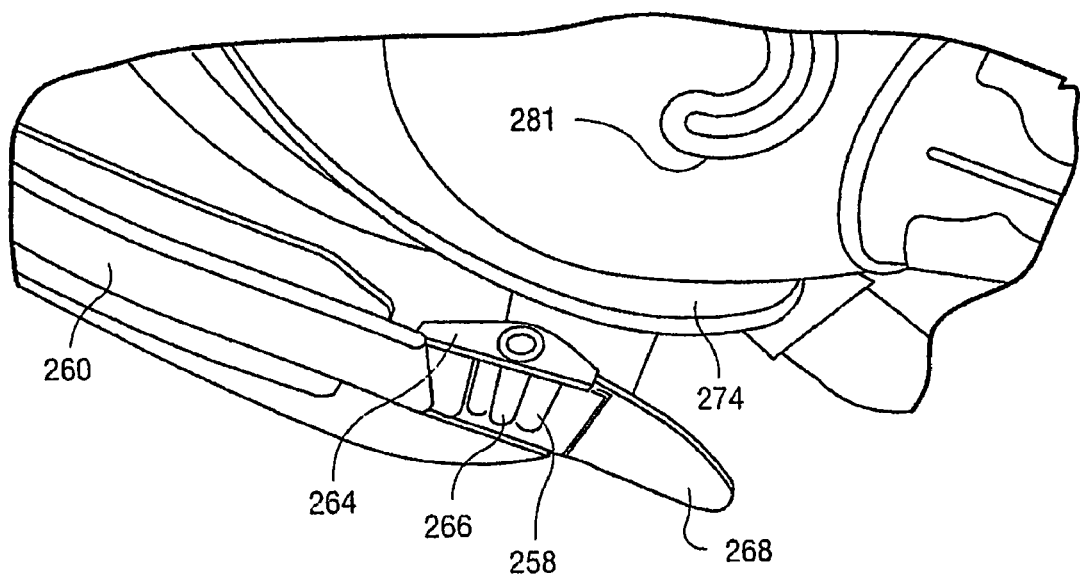
FIG. 17 is an enlarged perspective view of the frame attachment member shown in FIG. 16 engaged with the lower headgear anchor.
Figure 18:
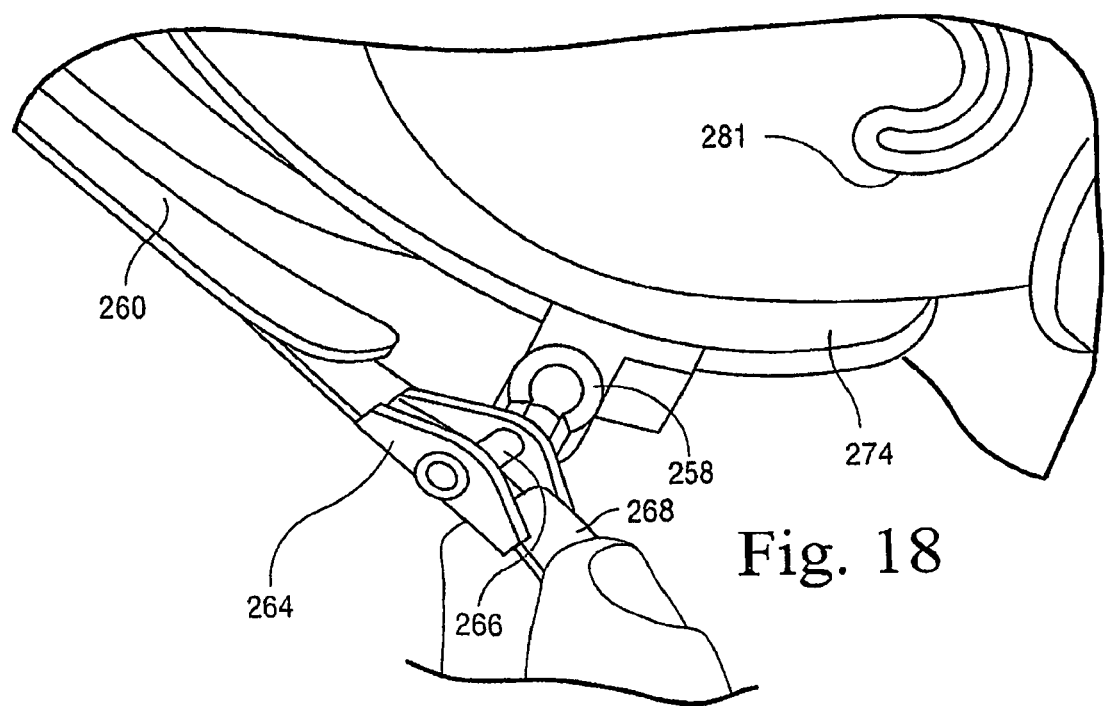
FIG. 18 is an enlarged perspective view of the frame attachment member shown in FIG. 16 being removed from the lower headgear anchor.

In use, each frame attachment member 264 is interlocked with a respective anchor 256, 258 by moving the post element 266 adjacent the respective slot opening 262 such that the post element 266 engages within the respective slot opening 262, e.g., with a snap-fit. The frame attachment members 264 on the ends of the upper stabilizing straps 250 are adapted to releasably interlock with respective upper anchors 256 on the frame 274 (see FIGS. 14-15), and the frame attachment members 264 on the ends of the lower stabilizing straps 260 are adapted to releasably interlock with respective lower anchors 258 on the frame 274 (see FIGS. 16-18). As shown in FIGS. 16-18, a soft flexible finger tab 268 is provided on the end of each frame attachment member 264 of the lower stabilizing straps 260 to facilitate engagement and disengagement of the frame attachment member 264 to the lower anchors 258.

Figure 15:
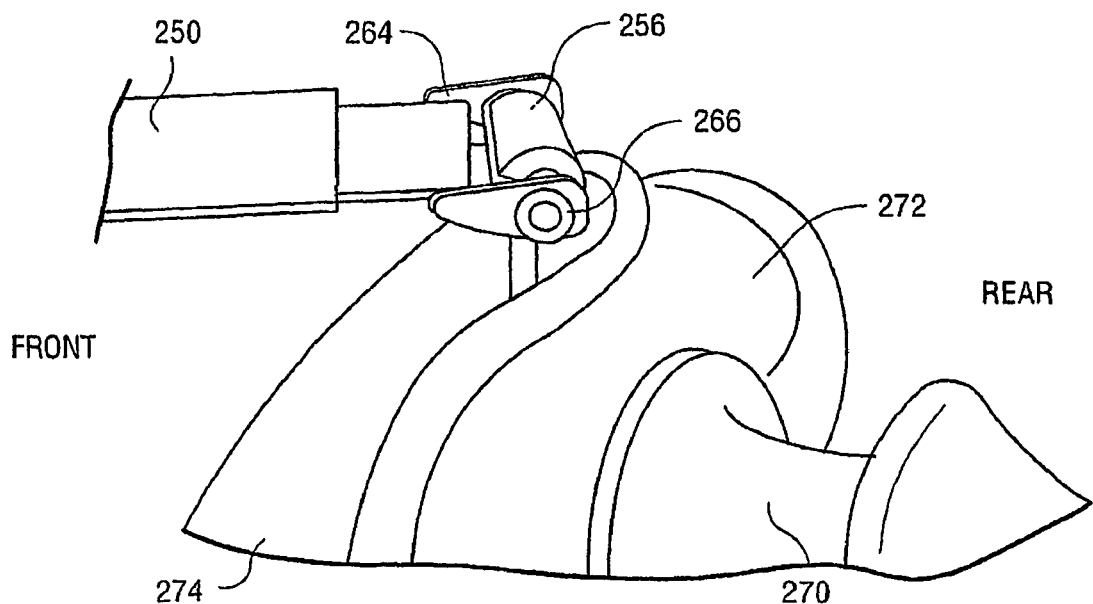
FIG. 15 is an enlarged perspective view of the frame attachment member shown in FIG. 14 engaged with the upper headgear anchor.

As shown in FIGS. 14 and 15, the slot opening 262 of respective upper anchors 256 is oriented towards the front of the sealing assembly 212 in order to eliminate inadvertent disengagement. When in use, the force on the upper stabilizing strap 250 is pulling directly away from the respective slot opening 262, and up against a solid section of the upper anchor 256.

As shown in FIGS. 16-18, the slot opening 262 of respective lower anchors 258 is oriented perpendicular to the front of the sealing assembly 212 in order to allow for easy engagement/disengagement. This arrangement provides the mask system 210 with a quick release system so that the mask system 210 may be removed quickly and easily from the patient's face in the event of an emergency or panic attack, as shown in FIG. 18.

The headgear attachment points, i.e., anchors 256, 258, are located towards. the top and at the lowest point on the frame 274, e.g., see FIG. 1. This arrangement allows the stabilizing straps 250, 260 to articulate and rotate as described above, without the stabilizing straps 250, 260 having to bend as they run over the top of the frame 274. This freedom of rotation allows the stabilizing straps 250, 260 to conform to the patient's face.

§ 1.1.3.2 Second Embodiment

Figure 19:
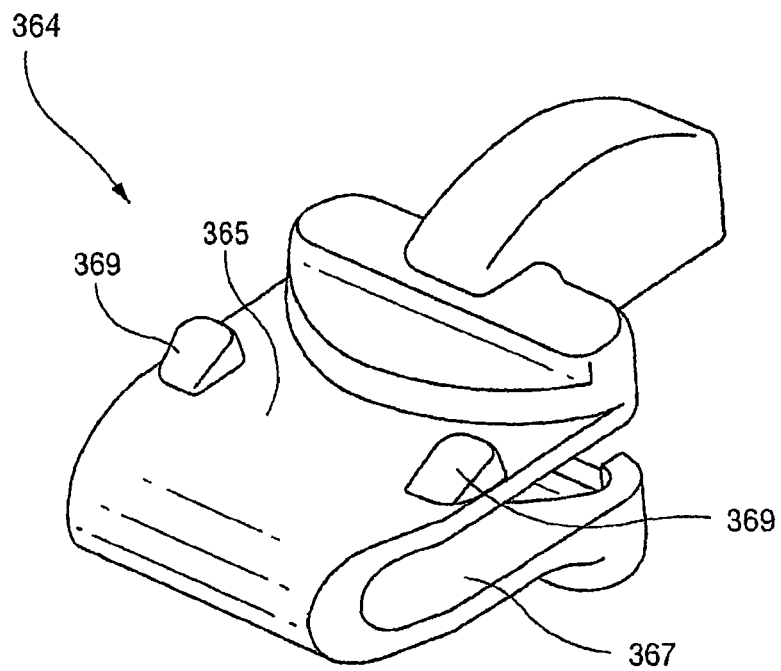
FIG. 19 is a top perspective view of an embodiment of a headgear locking clip.
Figure 20:
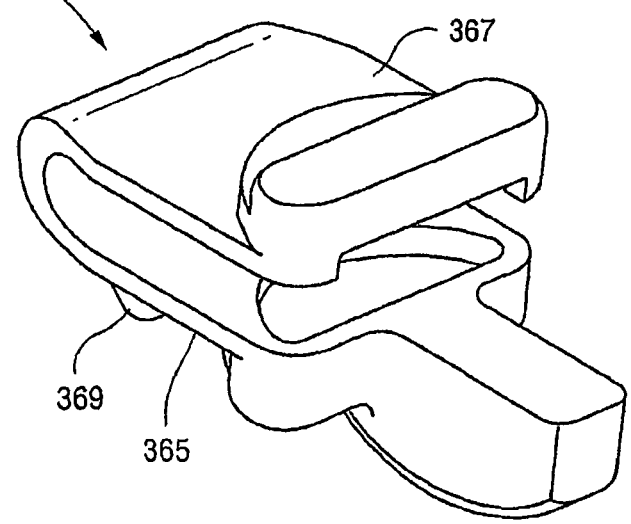
FIG. 20 is a bottom perspective view of the headgear locking clip shown in FIG. 19.
Figure 21:
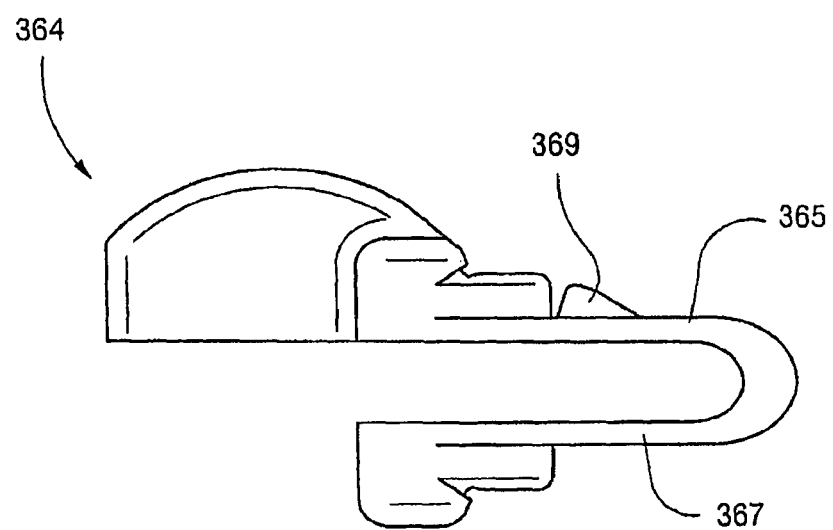
FIG. 21 is a side view of the headgear locking clip shown in FIG. 19.

In an alternative embodiment, the frame attachment member of each of the lower stabilizing straps 260 may be in the form of a locking clip 364. As shown in FIGS. 19-21, the locking clip 364 includes upper and lower arms 365, 367 that are resiliently flexible towards one another. Also, the upper arm 365 includes spaced-apart protrusions 369. In an embodiment, the locking clip 364 is molded in one-piece along with the yoke section 244 of the respective lower stabilizing strap 260. Alternatively, the locking clip 364 maybe formed separately from the yoke section 244 and attached thereto, e.g., by an adhesive or rotational connection, etc.

Figure 22:
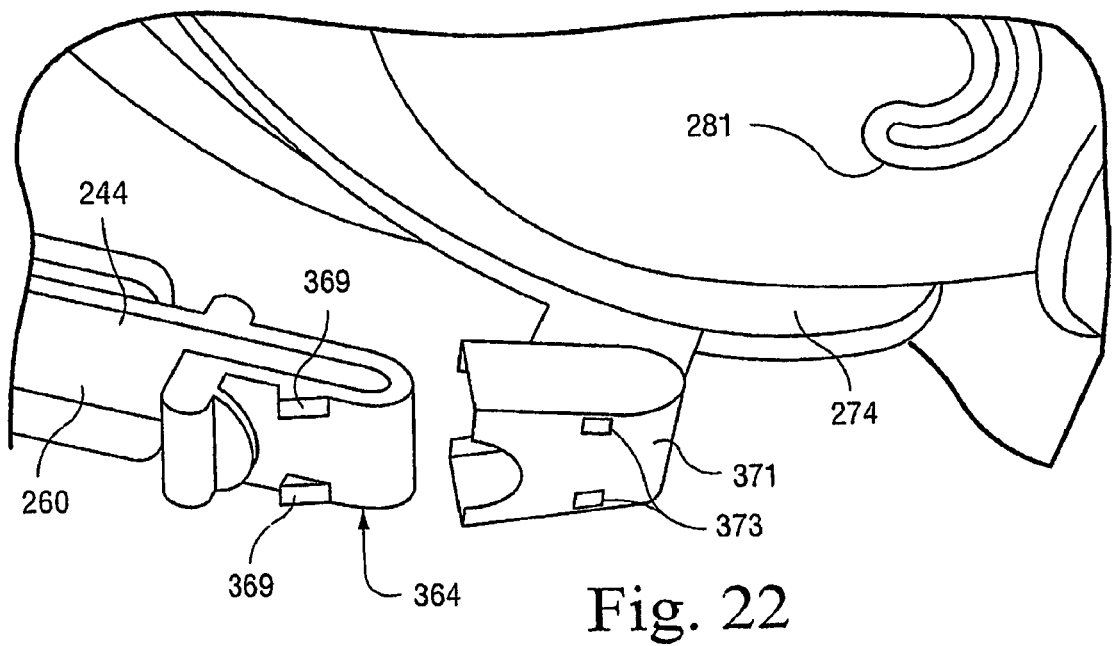
FIG. 22 is an enlarged perspective view of the headgear locking clip shown in FIG. 19 being engaged with a clip receptacle on the frame.
Figure 23:
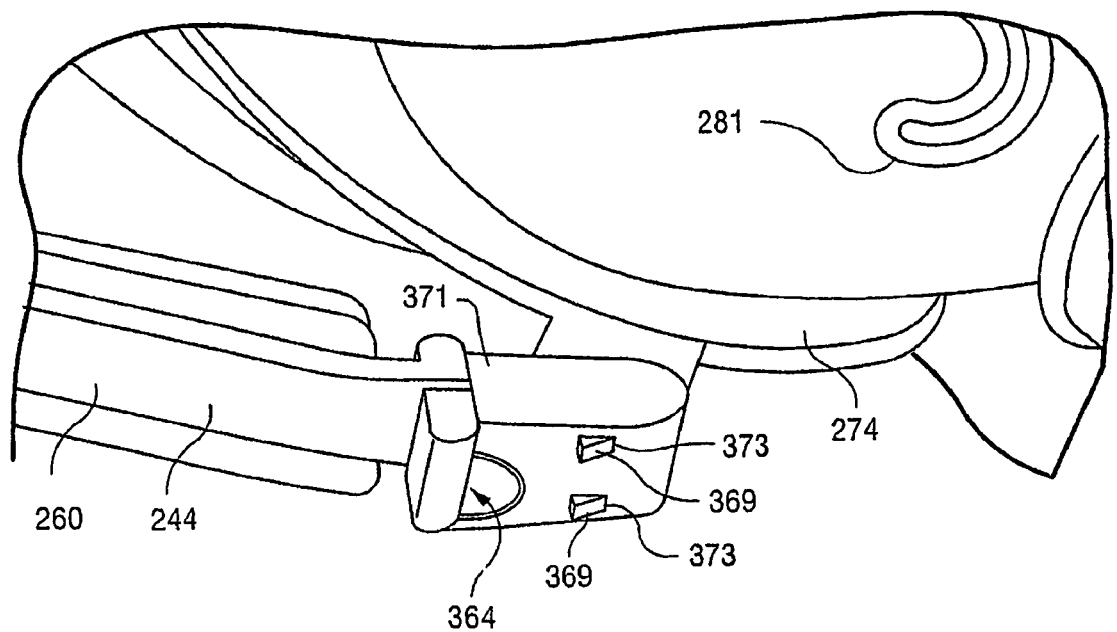
FIG. 23 is an enlarged perspective view of the headgear locking clip shown in FIG. 19 engaged with a clip receptacle on the frame.

As shown in FIGS. 22-23, the frame 274 is provided with clip receptacles 371 on each side frame member thereof. Each clip receptacle 371 includes spaced-apart slots 373. In use, each clip 364 is interlocked with a respective clip receptacle 371 by first moving the clip 364 into the respective clip receptacle 371 such that the protrusions 369 extend through respective slots 373 with a snap fit. The clip 364 may be released from the respective clip receptacle 371 by depressing the arms 365, 367 towards one another until the protrusions 369 release from the slots 373. The clip arrangement may provide audible feedback when the clips 364 are attached to the respective clip receptacles 371.

Also, the clip arrangement may have other suitable designs, such as those disclosed in U.S. patent application Ser. No. 10/390,681, filed Mar. 19, 2003, U.S. patent application Ser. No. 10/655,621, filed Sep. 5, 2003, and U.S. Pat. No. 6,374,826, the contents of each being hereby incorporated by reference in its entirety.

§ 1.1.3.3 Third Embodiment

Figure 24:
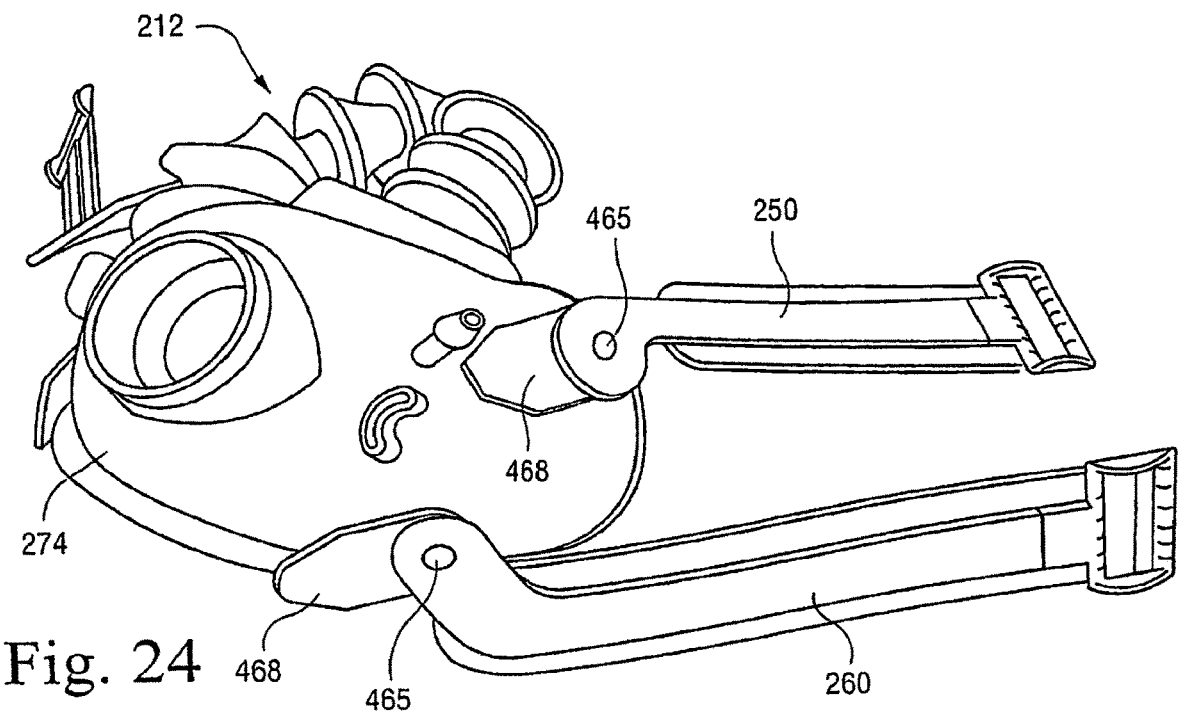
FIG. 24 is a perspective view of an embodiment of a mask system with headgear stabilizing straps attached via a press-stud type interface.
Figure 25:
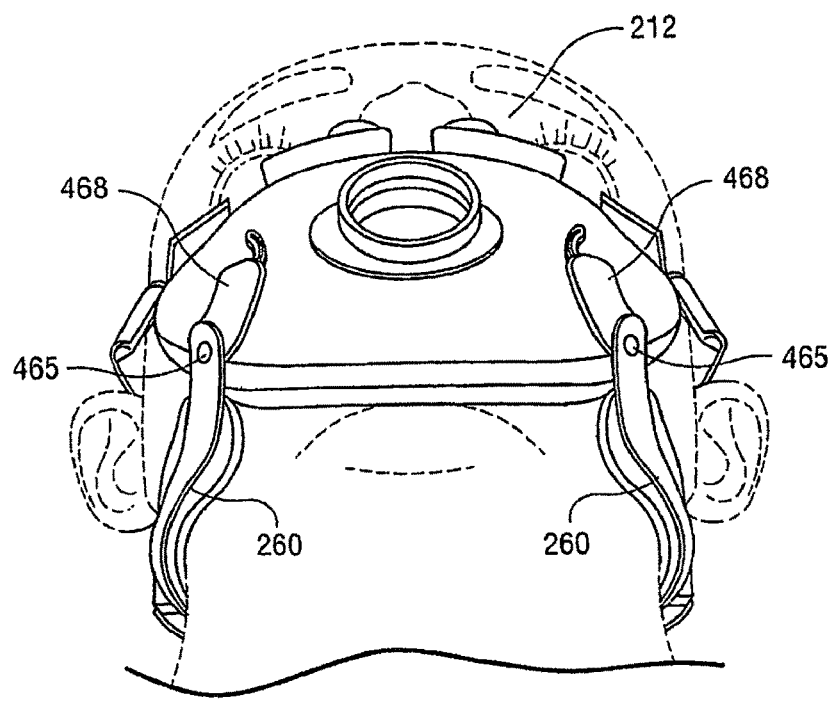
FIG. 25 is a bottom perspective view of the mask system shown in FIG. 24 on the patient's face.

In another alternative embodiment, the frame attachment member of each of the upper and lower stabilizing straps 250, 260 may be in the form of a press-stud type interface. As shown in FIGS. 24-25, the end of each stabilizing strap 250, 260 includes a protruding stud 465. A soft flexible finger tab 468 is provided on the end of each stabilizing strap to facilitate engagement and disengagement to the frame 274.

The frame 274 is provided with stud receivers on each side frame member thereof. In use, each stud 465 is press-fit into a respective stud receiver. This arrangement allows the stabilizing straps 250, 260 to rotate with respect to the frame 274 to allow the mask system to align on the patient's face. In an alternative embodiment, the studs 465 may be provided on the frame 274 and the stud receivers may be provided on the stabilizing straps 250, 260.

§ 1.1.4 Alternative Stabilizing Systems

Figure 26:
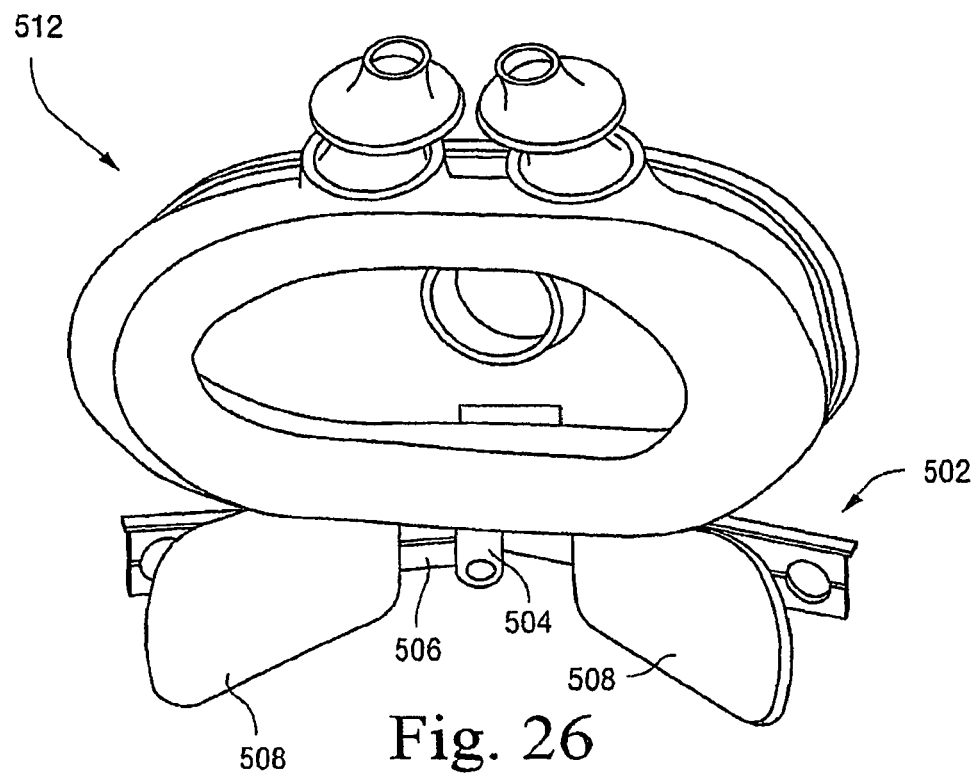
FIG. 26 is a perspective view of an embodiment of a mask system with an adjustable chin support.
Figure 27:
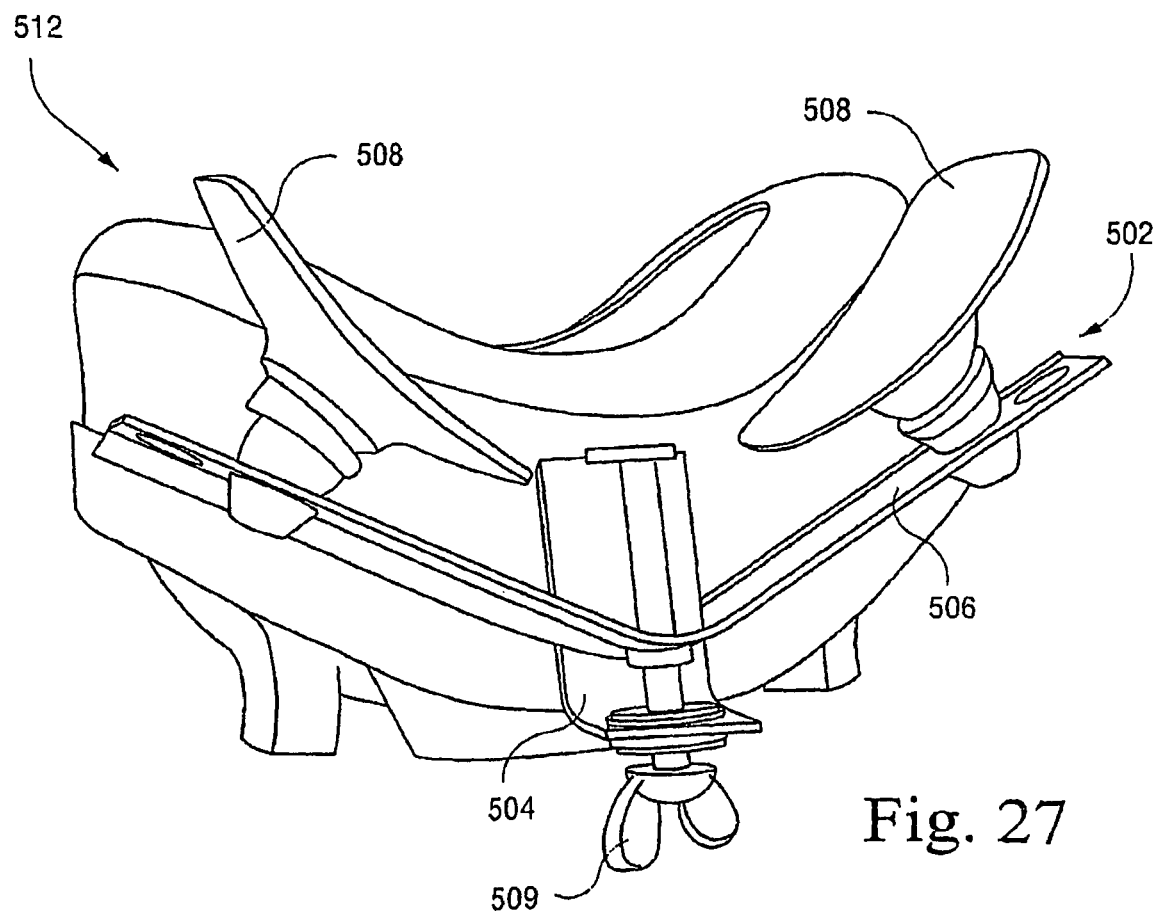
FIG. 27 is a bottom perspective view of the mask system shown in FIG. 26.

FIGS. 26-29 illustrate alternative embodiments for stabilizing the mask system on the patient's face. For example, FIGS. 26-27 show a mask system 512 that includes an adjustable chin support 502. As illustrated, the frame of the mask system 512 includes an extension 504 that supports a V-shaped chin support frame 506. The V-shaped chin support frame 506 has two spaced elastomeric chin cushion elements 508 removably attached thereto and structured to engage a patient's chin. The V-shaped chin support frame 506 is moveably mounted to the frame extension 504 to adjust the position of the chin cushion elements 508 relative to the patient's chin, e.g., by adjusting a thumb screw 509. However, the chin support 502 maybe adjusted in other suitable manners, e.g., via a ratchet-type mechanism, butterfly mechanism, push-button arrangement, tongue/groove arrangement, and/or gear arrangement, as described in U.S. Pat. No. 6,532,961, incorporated herein by reference in its entirety.

Figure 28A:
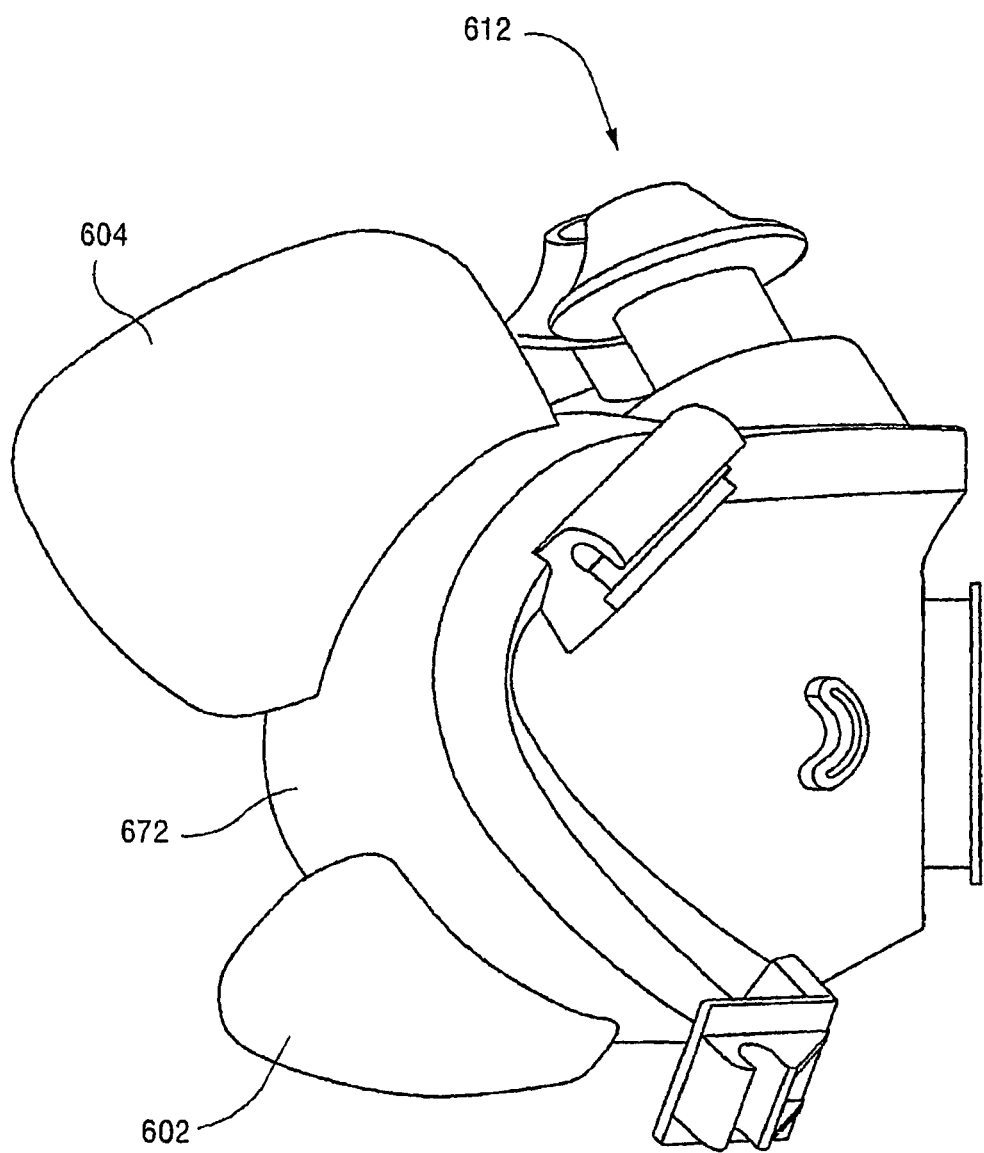
FIG. 28a is a side view of an embodiment of a mask system with chin and cheek supports.
Figure 28B:
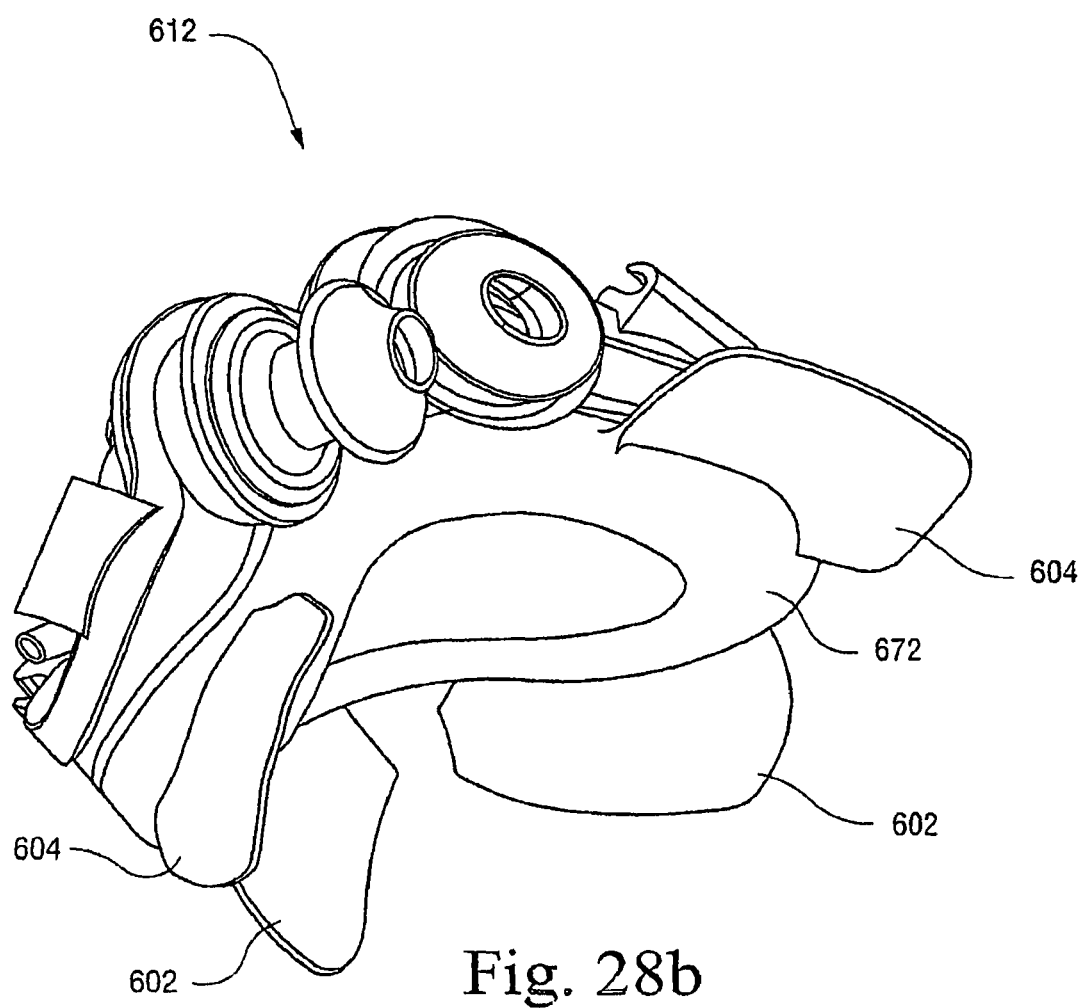

FIGS. 28*a* and 28*b* show a mask system 612 that includes chin and cheek supports 602, 604 integrally formed with the cushion 672. As illustrated, the cushion 672 includes a chin support 602 that extends downwardly from a lower side wall thereof The chin support 602 is contoured to conform to the patient's chin. The cushion 672 also includes a cheek support 604 that extends upwardly from an upper side wall thereof. The cheek support 604 is contoured to conform to the patient's cheeks.

Figure 29:
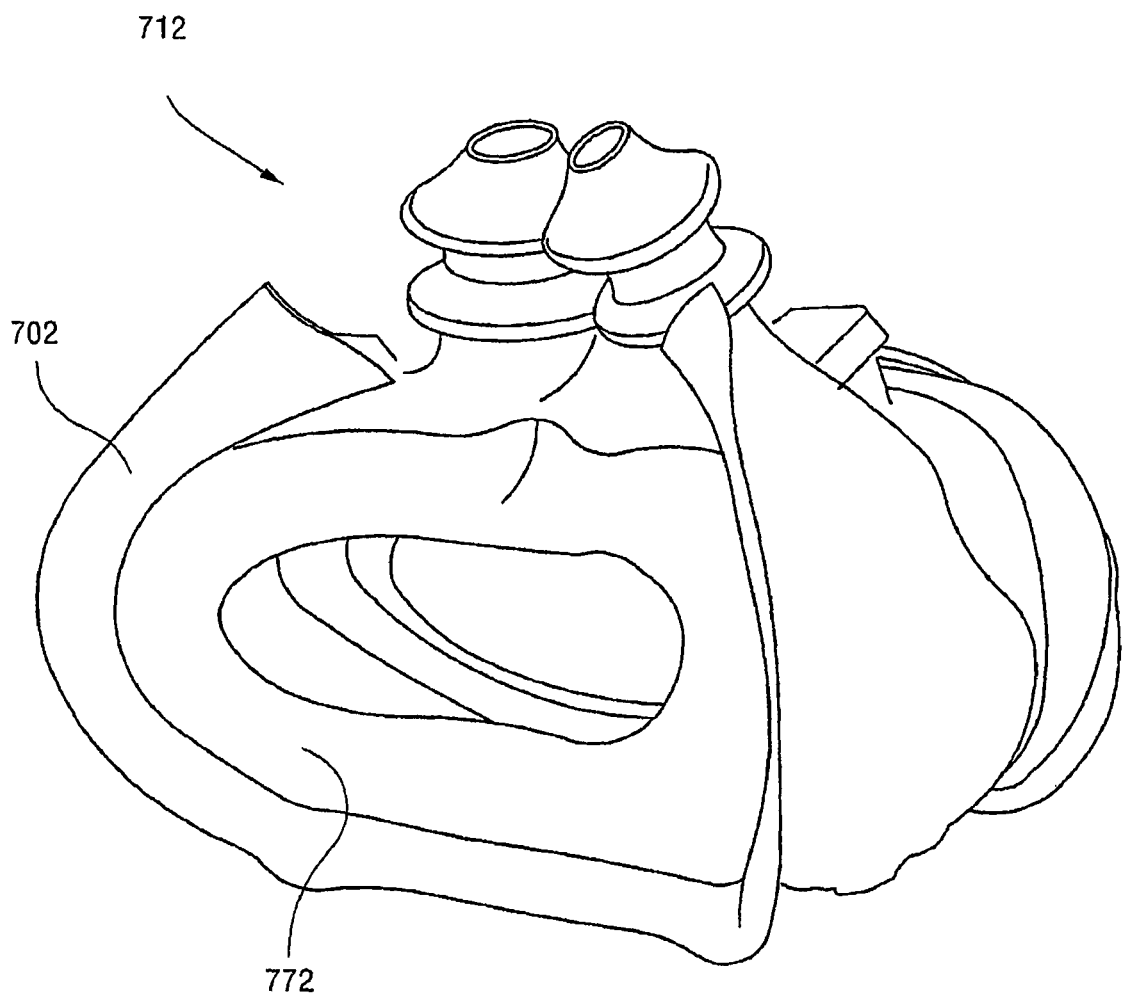
FIG. 29 is a rear perspective view of an embodiment of a mask system with a "scuba mask" style support.
Figure 30:
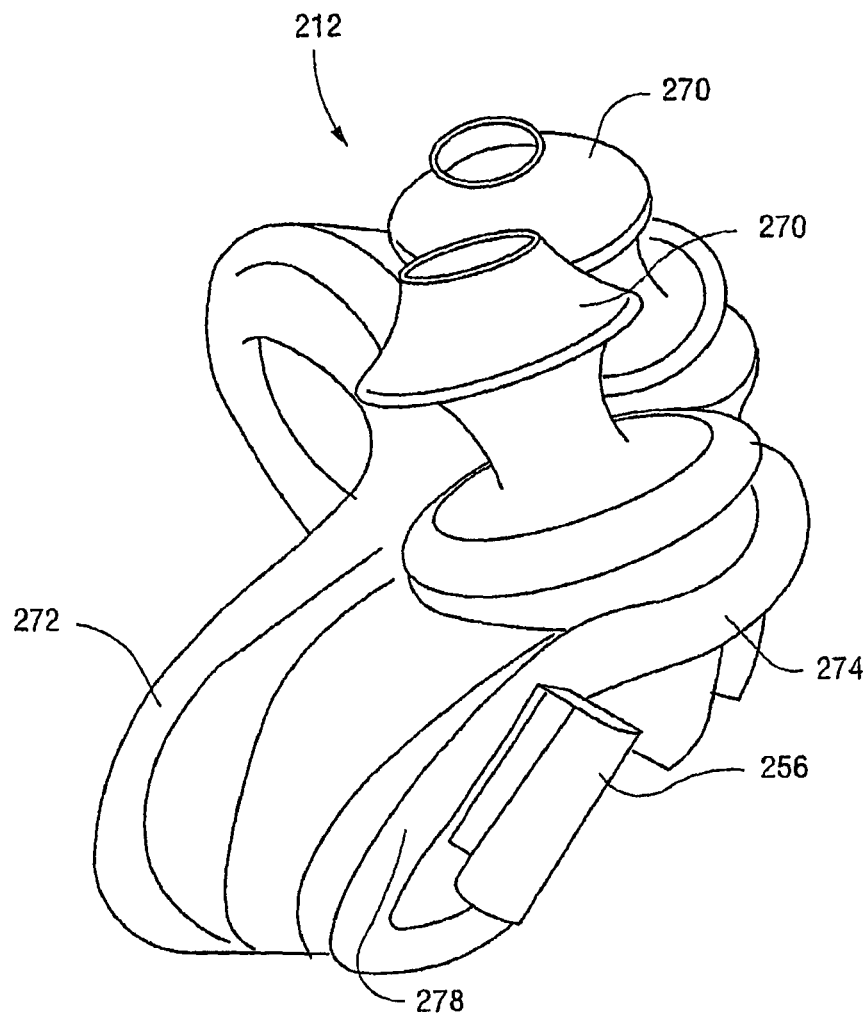
FIG. 30 is a side perspective view of the mask system shown in FIG. 1.

FIG. 29 shows a mask system 712 that includes a scuba-style support 702 integrally formed with the cushion 772. As illustrated, the support 702 extends outwardly from a lower portion and side portions of the cushion 772. The support 702 is, contoured to conform with chin and cheek regions of the patient's face that surround the patient's mouth.

§ 1.2 Mouth Cushion and Frame Shape

As shown in FIGS. 1 and 30-33, the sealing assembly 212 of the mask system 210 includes a mouth cushion 272 structured to sealingly engage around an exterior of a patient's mouth in use and a pair of nasal prongs 270 structured to sealingly communicate with the nasal passages of the patient's nose in use and in particular the base of the patient's nares. The cushion 272 may be integrally formed in one-piece along with the prongs 270, e.g., by silicone in an injection molding process. The cushion 272 is structured to be removably and replaceably attached to a substantially rigid frame 274, e.g., by friction fit, mechanical fastening means, etc. Also, the frame 274 includes an aperture 280 that is coupled to the swivel elbow 214 for delivering breathable gas. Further, one or more vent openings may be provided in the frame and/or swivel elbow for $CO_2$ washout. For example, FIGS. 1, 11, 12, and 32 illustrate the frame 274 including a vent 281. The vent 281 may have a similar form to those disclosed in U.S. Provisional Patent Application No. 60/643,114 to Veliss, filed Jan. 12, 2005, the contents of which are hereby incorporated by reference in their entirety.

In an alternative embodiment, as shown in FIG. 11, opposing ends of the mask system may include cylindrical tubes 282, one of which may be provided with a plug or vent and the other of which may be provided with an elbow 214 for delivering breathable gas. The positions of the elbow and plug/vent maybe interchanged, depending on patient preference.

Also, in another embodiment, the mask system (with or without cylindrical tubes 282) may be ventless such as the ventless design described in U.S. patent application Ser. No. 60/667,052, filed Apr. 1, 2005, the contents of which are hereby incorporated by reference in its entirety.

A low profile is provided by sweeping back the frame 274 immediately around the prongs in order to achieve frame attachment points 256, 258 as close as possible to the face without touching the lips. In a preferred embodiment as shown in FIG. 31, the frame 274 is swept back in side frame portions 278 of the frame 274 such that these side frame portions 278 are about 15+/−5 mm below the frame height at which the frame 274 receives the prongs, i.e., the region 276. This arrangement improves the mouth cushion height to depth ratio and reduces the height of the mask system 210 on the patient's face. In addition, this arrangement allows the headgear attachment points 256, 258 to be as close as possible to the patient's face. Both of these factors combine to improve stability of the mask system 210.

Figure 33:
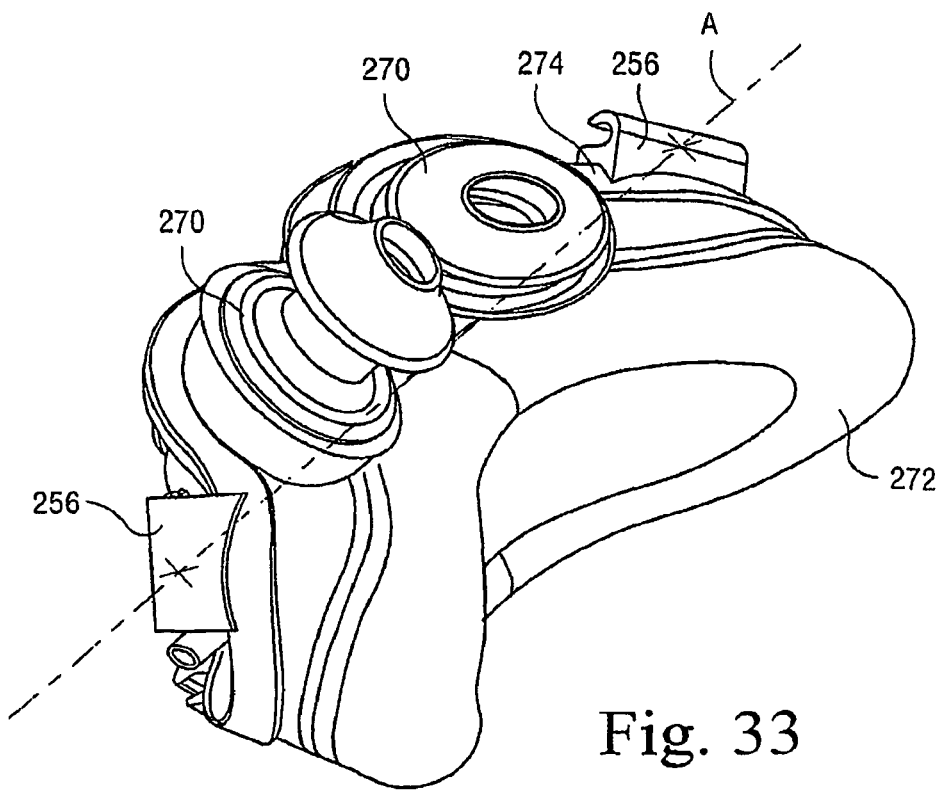
FIG. 33 is a top perspective view of the mask system shown in FIG. 1.

FIG. 33 illustrates the position of the upper headgear anchors 256. As illustrated, the axis A between the centers of the upper anchors 256 lies centrally between the nasal prongs 270 and the upper sealing surface of the mouth cushion 272. This centralized location enables the headgear vector to radiate from these points in an orientation that is optimized for sealing both the nasal prongs 270 and mouth cushion 272. That is, the chosen vector achieves a good balance in compressing the nasal prongs 270 to achieve a comfortable seal in the nose and compressing the mouth cushion 272 to achieve a comfortable seal at the mouth. Concurrently, this vector orientation and location is in a plane such that the headgear stabilizing straps 250, 260 achieve a tangential point of contact with the cheek region on the patient's face. This is advantageous for comfort.

Also, the use of a low profile cushion 272 uses less silicone, which effectively reduces the weight of the mask system 210. Further, the low profile design has the additional benefit of reducing the total internal deadspace volume of the mask system 210.

§ 1.3 Nasal Prong Design

The nasal prongs 270 may be formed separately from the cushion 272, e.g., from silicone in an injection molding process, and then inserted and secured to the cushion 272. However, the nasal prongs 270 may be constructed from other suitable materials, e.g., gel material. This arrangement provides a greater scope of patient fitting by being able to select cushion size and nasal prong size independently. Also, the nasal prongs 270 may be independently aligned (i.e., by rotation of the prongs) with respect to the cushion 272 for optimal fit.

Figure 34A:
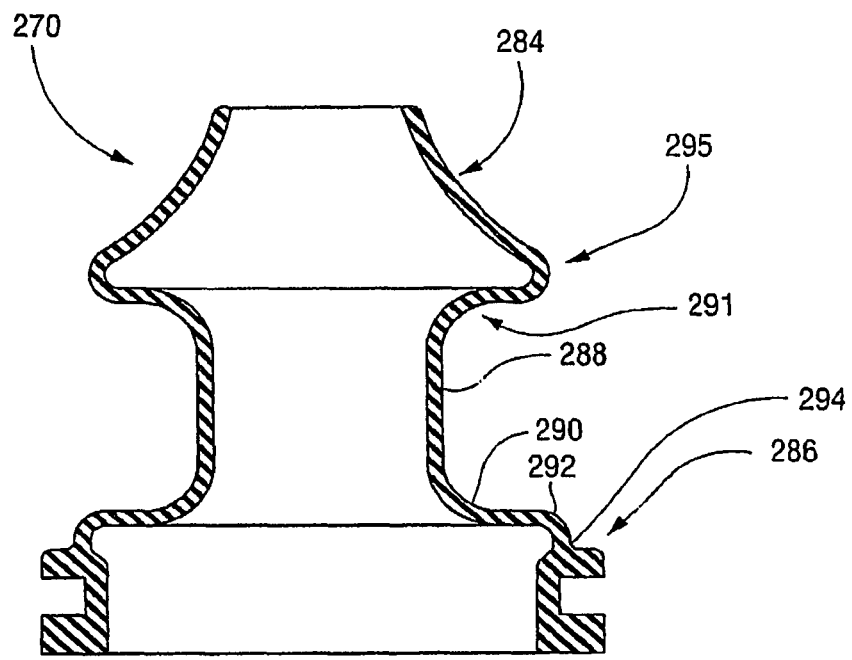
FIG. 34a is a cross-sectional view of an embodiment of an insertable nasal prong.
Figure 34B:
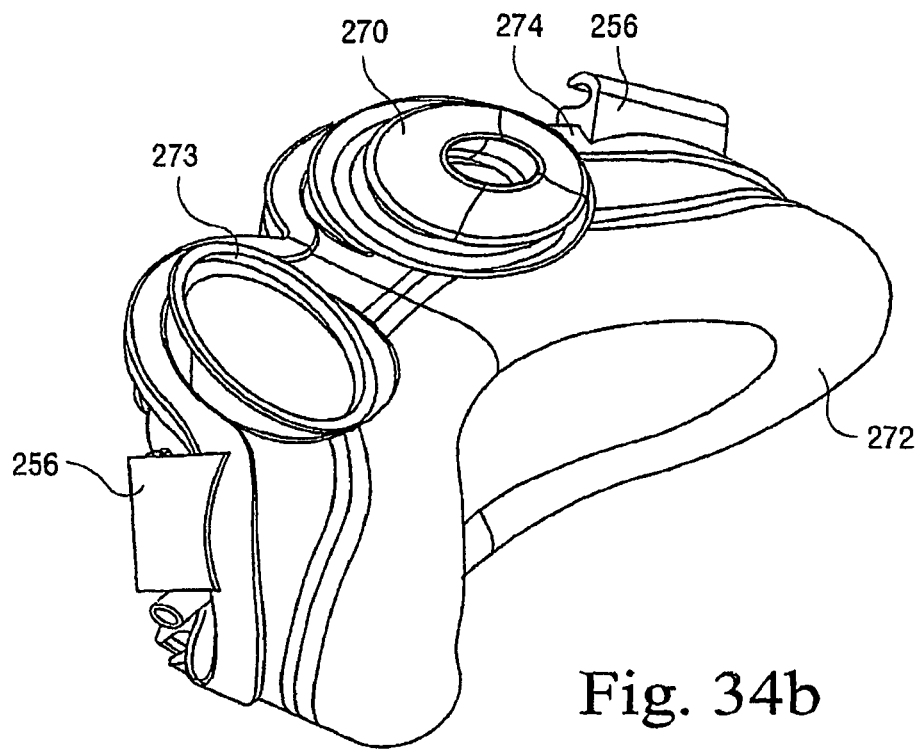

FIG. 34a shows an embodiment of an insertable nasal prong 270. As illustrated, the nasal prong 270 is a single prong that includes a nasal portion 284 that sealingly engages with a respective patient naris or nostril and a base portion 286 that is mountable to the cushion 272, e.g., via an annular recess. For example, FIG. 34b illustrates a cushion 272 with an annular recess 273 adapted to receive the base portion 286 of the prong 270 therein. The base portion 286 of the prong 270 may be secured within the recess 273 via a press-fit or glued butt joint, for example. The single prong arrangement is advantageous because it allows customization of fit, e.g., more angular adjustment of the prong to match nasal angle and possibility of different sizes in each patient nostril. In an alternative embodiment, the prongs 270 may be provided as a pair with a thin silicone section joining the prongs at respective base portions 286. The paired-prong arrangement may improve usability, e.g., unproved ease of assembly and alignment.

In the illustrated embodiment, the nasal prong 270 includes a trampoline-like detail at both top and bottom horizontal segments 291, 290 of the nasal column 288. As illustrated, the sectional thickness, e.g., nominally 0.75 mm, of the nasal portion 284 and nasal column 288 is maintained for a localized area at the base portion 286 of the prong 270, i.e., where the nasal column 288 meets the base portion 286 (either the cushion in the case of an integral assembly or the base portion in the case of insertable prongs), before transitioning into the base portion 286, e.g., nominally >1.5 mm. This section (indicated by horizontal segment 290, radial segment 292, and vertical segment 294) acts as a trampoline in use. In the illustrated embodiment, the size and shape (outline) of the trampoline-like base is closely matched, e.g., identical or close to identical in size, to that of the outer periphery 295 of the nasal portion 284. When the nasal prong 276 is brought into contact with the patient's nose, compression (nasal portion 284 will move towards base portion 286) will occur. Nasal compression is effectively the result of the nasal column 288 receding (rolls back onto itself) into both the nasal portion 284 and base portion 286. Because the thickness of these horizontal sections at the top 291 and bottom 290 of the nasal column 288 are identical, the nasal column 288 will recede by a similar degree at both of these locations.

The inclusion of the trampoline-like detail at the top and base of the nasal column 288 has a two-fold effect. First, the increased flexibility at the top and base of the nasal column 288 allows these transitions to act much like a ball-in-socket arrangement. This allows increased articulation of the nasal prong 270, thereby allowing a greater range of naso-labial angles to be matched. Second, the compression at the top and base of the nasal column 288 will act as a form of suspension. In this way, the mouth cushion 272 can move away from the nasal prongs 270, e.g., move downward or side to side, without disrupting the seal at the patient's nose. As the mouth cushion 272 moves, the nasal prongs 270 can uncompress while still maintaining sufficient load and hence seal at the patient's nose.

In an alternative embodiment, the prong design may be modified to remove the radial and vertical segments 292, 294. However, the inclusion of these segments is preferred as they maximize the trampoline effect.

Figures 5, 34C:
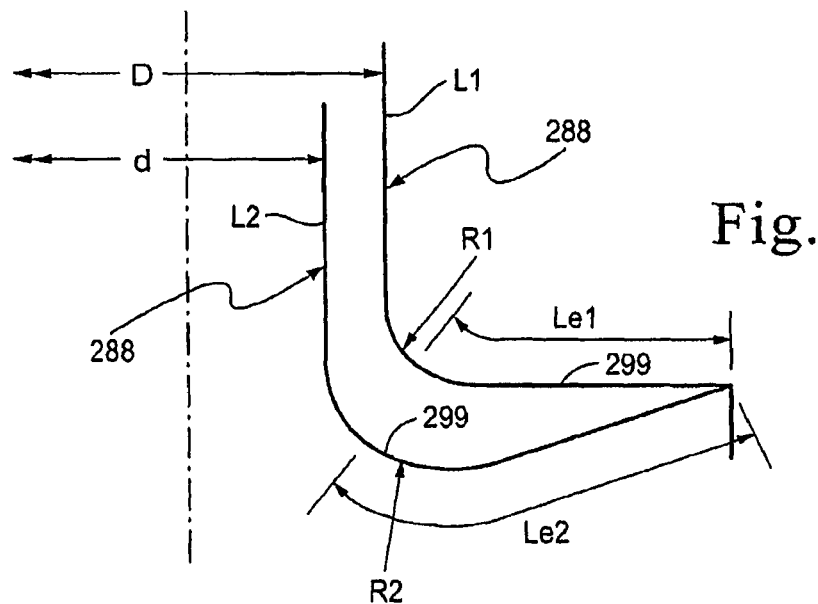
Figures 6, 34C:
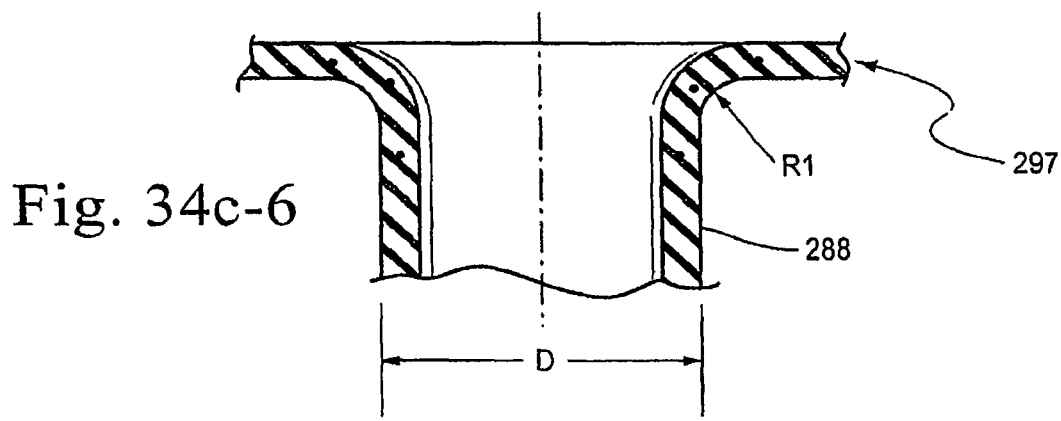

FIGS. 34c-1 to 34c-13 illustrate the trampoline effect of the nasal prong in greater detail. FIGS. 34c-1 and 34c-2 illustrate the nasal prong in its free state. As illustrated, the nasal prong includes a nasal or head portion 284 (also referred to as a pillow), a column or stalk 288, a base portion 286 communicated with the mouth cushion volume 287, an upper trampoline base 297, and a lower trampoline base 299. The stalk 288 transitions into the upper and lower trampoline bases 297, 299 with radius R1.

Figures 4, 158B:
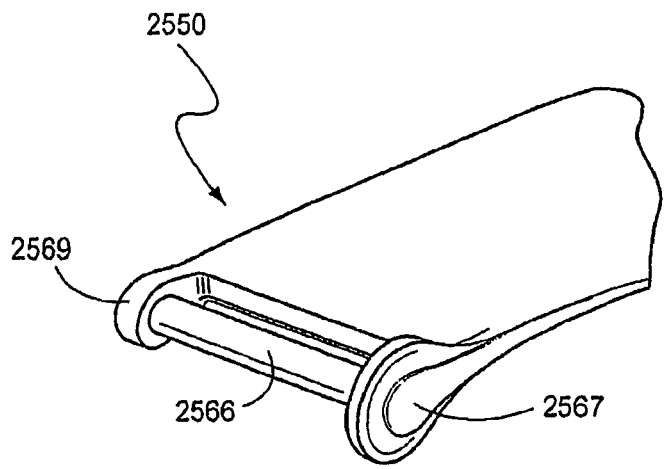
Figures 5, 158B:
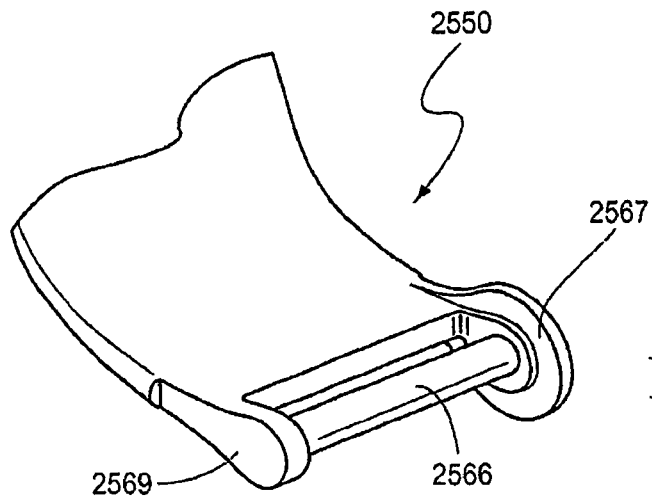
Figures 6, 158B:
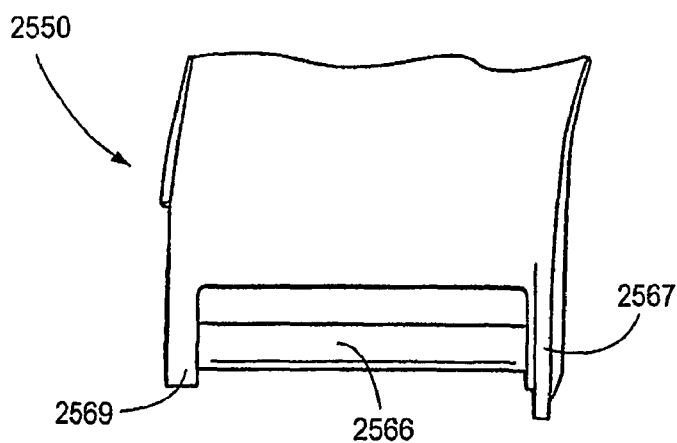

As shown in FIGS. 34c-3 and 34c-4, when the pillow 284 linearly compresses, the upper trampoline base 297 extends into the pillow's head portion and the lower trampoline base 299 extends into the mouth cushion volume 287. The overall effect is that the trampoline bases 297, 299 flex sufficiently so that the head portion of the pillow 284 can adjust to a height and angle to fit most nostrils. The change in height may be represented as H (height in free state) minus h (height in compressed state).

This flexing increases the length of the respective trampoline bases as shown in FIG. 34c-5. Specifically, L1 represents the stalk 288 and trampoline base 299 in its free state, and L2 represents the stalk 288 and trampoline base 299 in its compressed state. As illustrated, the length Le2 of the trampoline base in its compressed or flexed state is greater than the length Le1 of the trampoline base in its free state. The extra material required to increase the length of the trampoline bases comes from the following mechanisms: the trampoline base silicone stretching, and the stalk's end rolling over and being drawn into the trampoline base as shown in FIGS. 34c-6 (showing upper trampoline base 297 in its free state) and 34c-7 (showing upper trampoline base 297 in its compressed state).

Figures 7, 34C:
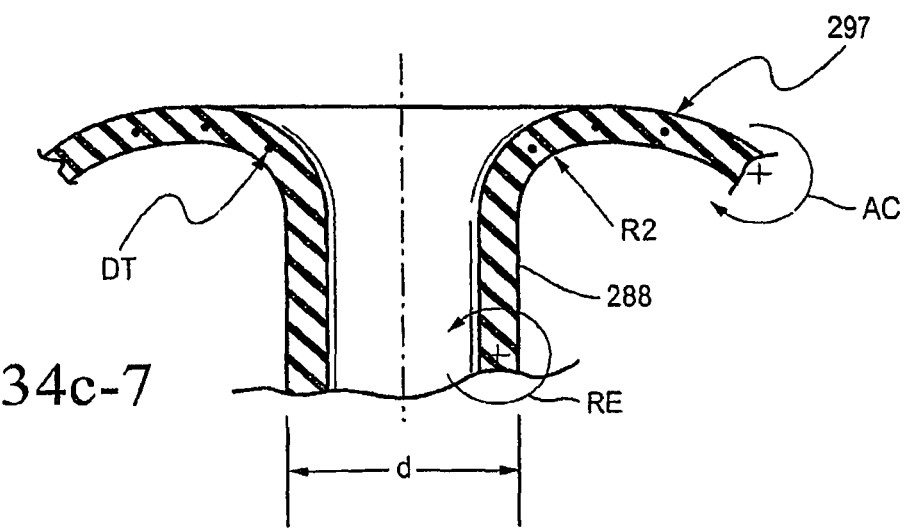
Figures 8, 34C:
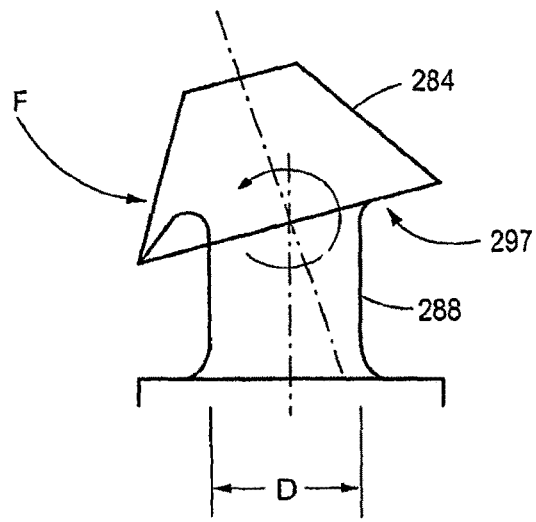
Figures 9, 34C:
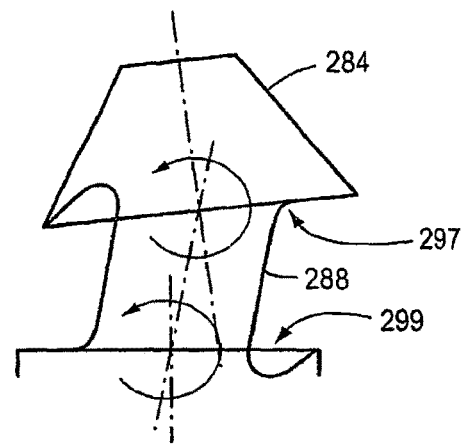
Figures 10, 34C:
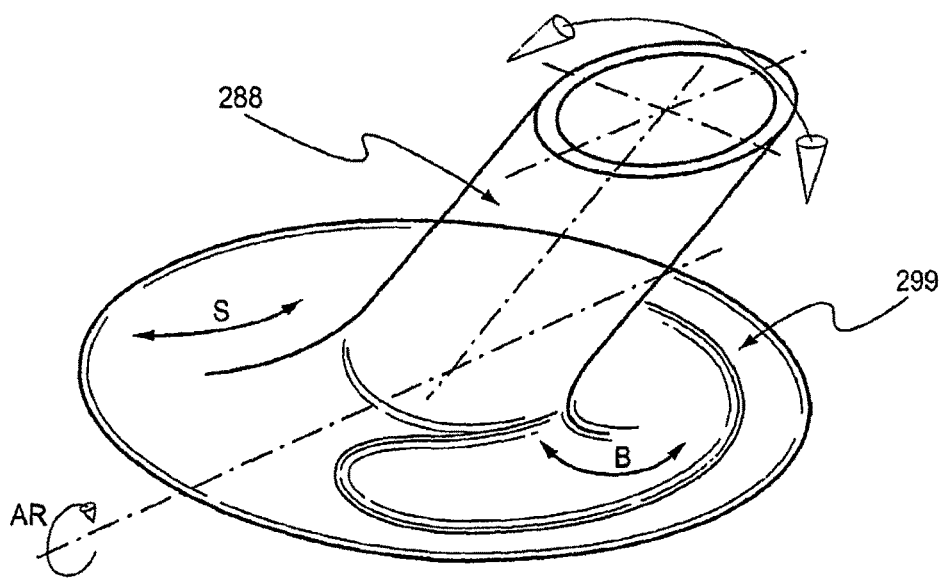
Figures 11, 34C:
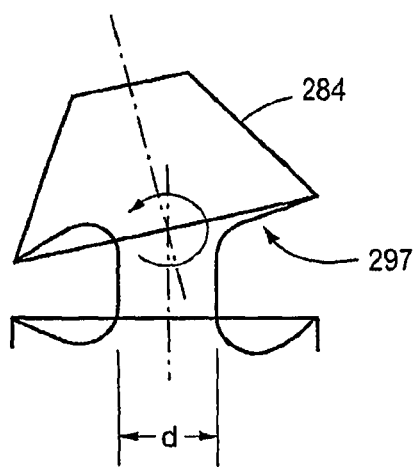
Figures 12, 34C:
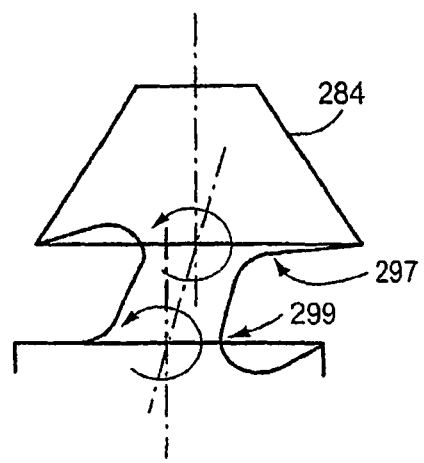
Figures 13, 34C:
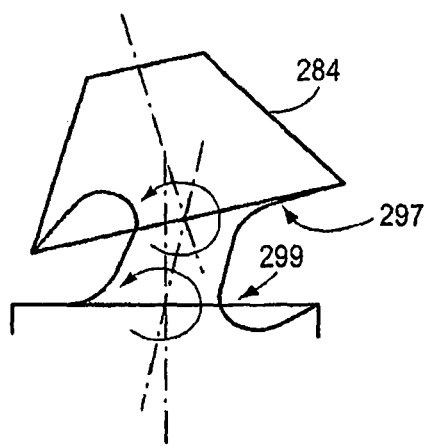

The stalk 288 has an elliptical section which does not readily roll over. When roll over does occur, resistance to this deformation will act against the stalk 288. FIGS. 34c-3, 34c-4, 34c-5, and 34c-7 illustrate the mechanical reactions that occur when the stalk 288 rolls over. As illustrated, the transition radius between stalk 288 and trampoline base 297, 299 increases to R2 due to the flexible nature of the silicone. As a consequence of the radius increasing, the stalk 288 will get thinner, e.g., reduce from D to d as illustrated in FIGS. 34c-1 to 34c-7. The stalk will thin more readily in its weakest plane, which in the case of an elliptical stalk is its minor axis. Also, FIGS. 34c-6 and 34c-7 provide dots DT to show how material moves into the trampoline base. In addition, FIG. 34c-7 shows roll-over action AC and roll-over reaction RE that pulls in the stalk 288.

As shown in FIG. 34c-1, the stalk 288 is a conical tube that merges at 90 degrees into the trampoline bases 297, 299 which are conical surfaces. The nature of the geometry dictates that the stalk 288 is a relatively rigid member and the adjacent trampoline bases 297, 299 are relatively flexible members. As shown in FIGS. 34c-8 and 34c-9, when a non-axial force F is applied to the head portion of the pillow 284 creating a rotational movement to the pillow 284, the pillow 284 will react in such a way that the trampoline base or bases 297, 299 will rotationally flex around the relatively rigid stalk 288. FIG. 34c-8 illustrates the upper trampoline base 297 rotating about the stalk 288, and FIG. 34c-9 illustrates the upper and lower trampoline bases 297, 299 rotating about the stalk 288.

The trampoline base flexing is a combination of one side stretching and the other side buckling according to the direction of rotation. For example, FIG. 34c-10 illustrates stretching S and buckling B of the lower trampoline base 299 as the stalk 288 rotates about axis AR. Therefore, the stalk to trampoline base intersection acts as a junction for articulation.

A trampoline base 297, 299 provided at the top and bottom of the stalk 288 equips the pillow 284 with two articulation junctions, which enables the head portion of the pillow 284 to align to most patient nostrils.

In most instances of mask set-up, the pillows 284 will be subjected to both compression and rotation in order for the head portion of the pillow 284 to adjust in height and angle to conform to the patients nose and attain seal. The trampoline bases 297, 299 will therefore experience the compression and rotation actions mentioned above in unison. FIGS. 34c-11 to 34c-13 illustrate some possible compression and rotation scenarios for the pillow 284. For example, FIG. 34c-11 illustrates the pillow compressed and head portion rotated causing the upper trampoline base 297 to rotate about the stalk. FIG. 34c-12 illustrates the pillow compressed and head portion translated causing the stalk to rotate about top and bottom trampoline bases 297, 299. FIG. 34c-13 illustrates the pillow compressed and head portion rotated causing upper and lower trampoline bases 297, 299 to rotate about the stalk.

Figure 34D:
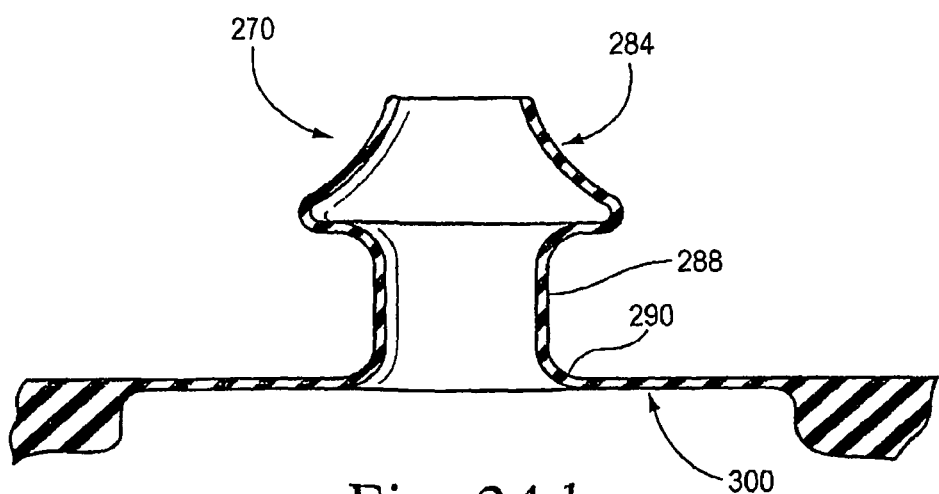
FIG. 34d is a cross-sectional view of a nasal prong according to another embodiment of the present invention.

In an alternative embodiment, a leaf spring 300 may be provided to a base of the nasal prong 270 as shown in FIG. 34d. The leaf spring 300 may provide substantially similar movement and force that is provided by sections 292 and 294 shown above in FIG. 34a, e.g. lower trampoline base.

§ 1.3.1 Nasal Prong Sizes

Figure 35:
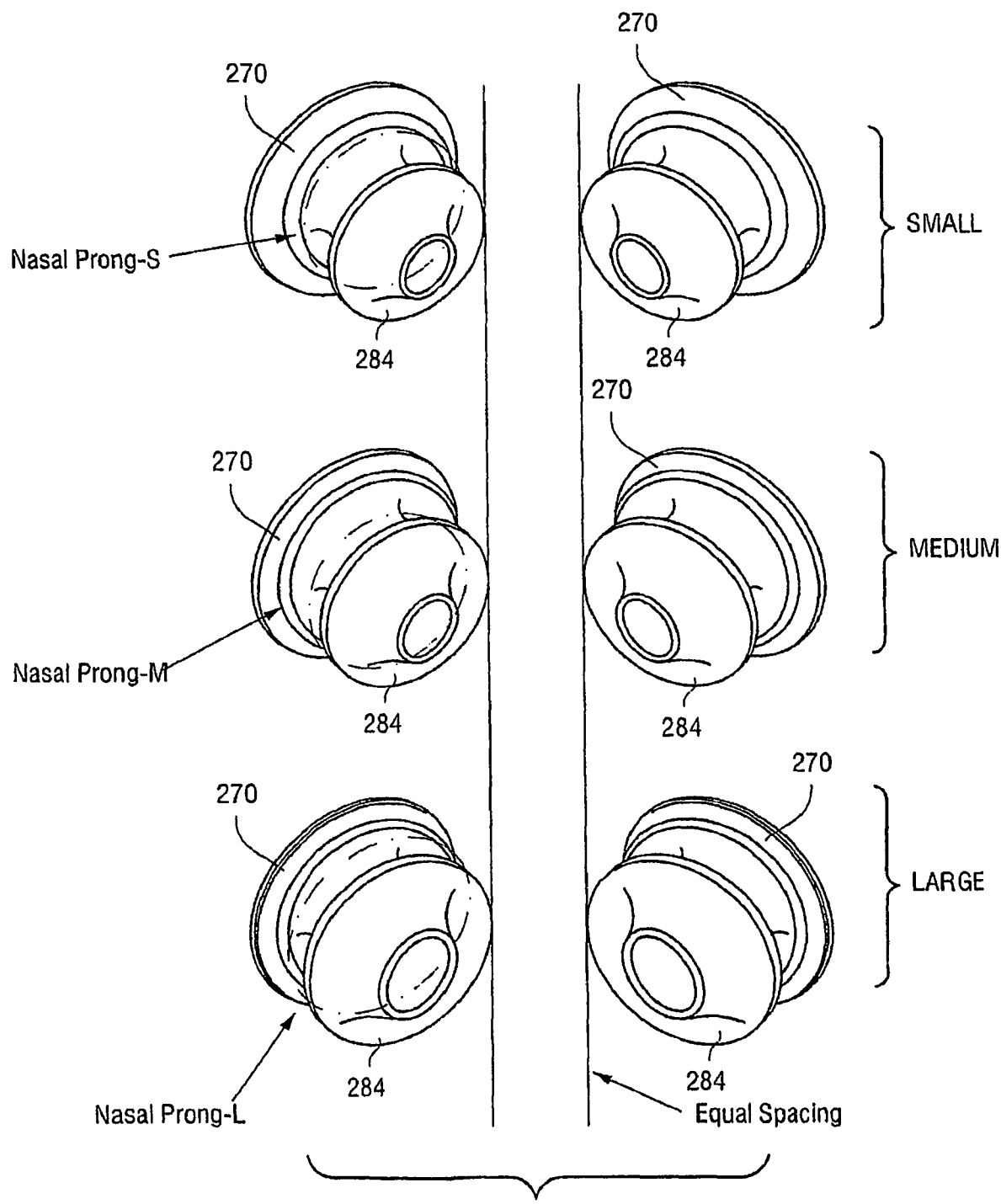
FIG. 35 is a perspective view that illustrates an embodiment of nasal prong sizes.
Figure 36:
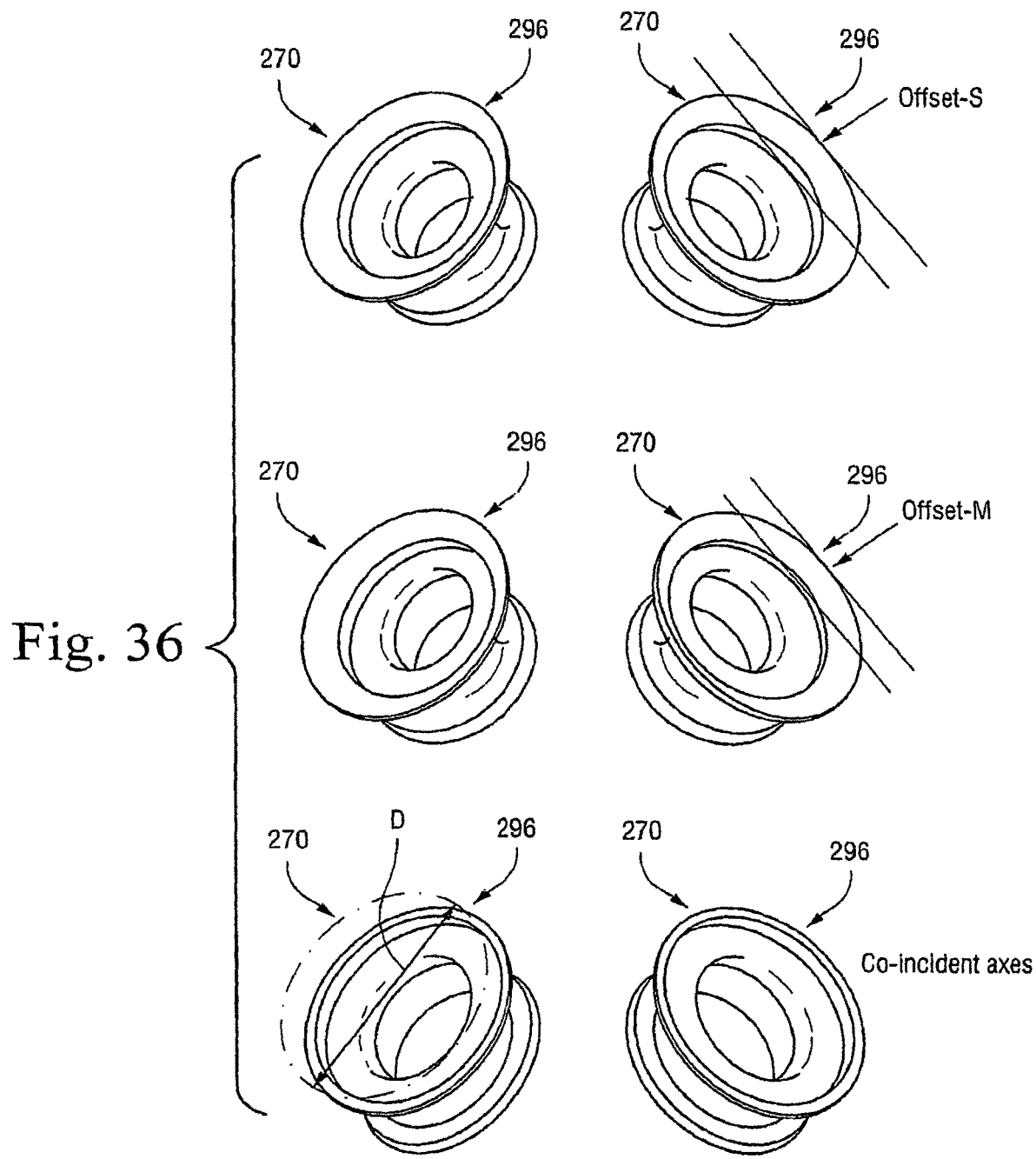
FIG. 36 is a perspective view that illustrates an embodiment of nasal prong base sizes.

In a preferred embodiment, the insertable nasal prongs 270 are provided as a pair. Moreover, the pair may be provided in any one of a number of different nasal prong sizes and may be anatomically shaped. In FIGS. 35-36, the nasal prongs 270 are shown in the position they would take when installed on the mouth cushion 272. In addition, the section that may join each pair together is not shown. For each of these sizes, the spacing between the two nasal portions 284 is substantially the same, even though the nasal portions 284 themselves are of differing sizes. For example, FIG. 35 illustrates three different sizes of nasal prongs 270, i.e., small, medium, and large. As illustrated, the size of the nasal portions 284 changes, but the spacing between the nasal portions 284 remains the same.

Also, as noted above, the size of the trampoline base matches that of the outer periphery 295 of the nasal portion 284 (see FIG. 34a). In order to allow all insertable prong sizes to interface with an identical mouth cushion, each size of prong has the same overall base size. The overall base size 296 (indicated in dashed lines with diameter D in FIG. 36) is the connector or plug that interfaces with the mouth cushion 272. The overall base size 296 is designed to accommodate the largest prong size, as shown in FIG. 36. For the large size, the axis of the prong 270 aligns with the axis of the overall base 296. For the small and medium sizes, the axis of the prong 270 (and trampoline base) is progressively offset toward the centerline of the prong set so that the separation between the nasal portions is identical (Offset-L=0<Offset-M<Offset-S). The section on the base that remains may be greater than about 1.5 mm as above. This ensures that the trampoline base works similarly or identically for all sizes.

§ 1.3.2 Nasal Prong with Articulating Portion

Figure 37:
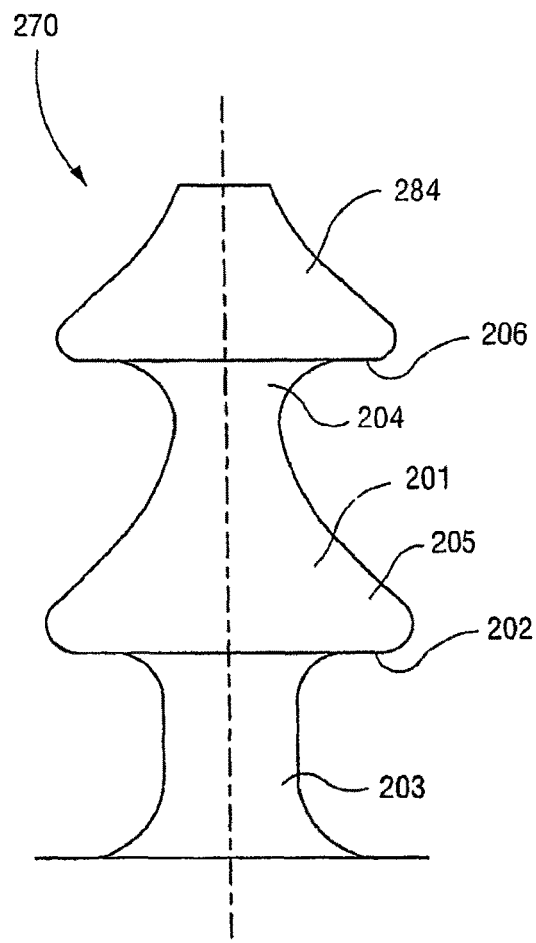
FIG. 37 is a side view of another embodiment of a nasal prong in a free state.
Figure 38:
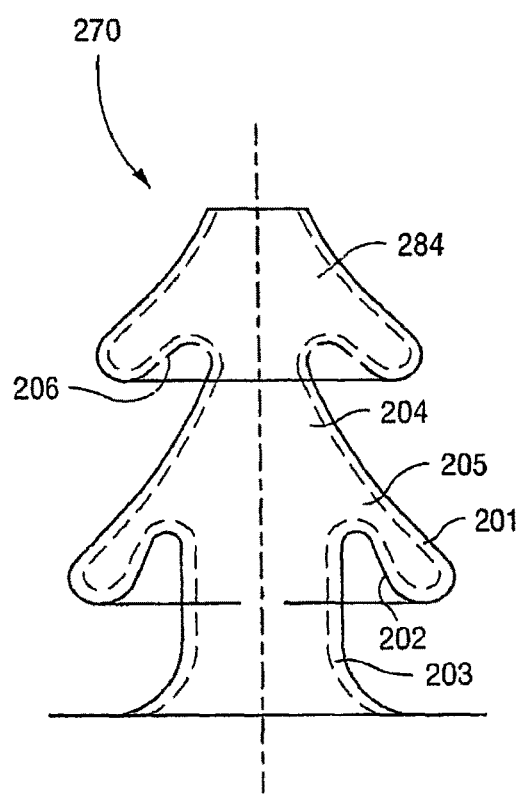
FIG. 38 is a side view of the nasal prong shown in FIG. 37 in a compressed state.

As shown in FIG. 37, the nasal prong 270 may include an articulating portion 201, or double prong configuration, to add flexibility and articulation of the nasal prong 270 with respect to the cushion 272. In the illustrated embodiment, the nasal prong 270 is structured such that it is partially "nestable" or significantly compresses once positioned in the patient's nose. For example, FIG. 37 illustrates the nasal prong 270 in a free state and FIG. 38 illustrates the nasal prong 270 in a compressed state.

In an embodiment, compression of the nasal prong 270 may be of the order of about 40%. To achieve this, the articulating portion 201 is structured such that it has a substantially horizontal lower wall 202. That is, the lower wall 202 of the articulating portion 201 is perpendicular to the lower column 203. This allows the prong 270 to compress as the lower column 203 moves into the articulating portion 201. The nasal portion 284 and upper column 204 of the prong 270 are similarly structured although these are marginally stiffer than the articulating portion 201 and lower column 203. This bias allows the articulating portion 201 and lower column 203 to compress more readily than the nasal portion 284 and upper column 204, although compression of both sections does occur. The upper portion 205 of the articulating portion 201 is designed to accommodate the compression of the lower column 203, i.e., there exists sufficient height in the upper portion 205 of the articulating portion 201 so that the lower column 203 can move into this region. In an embodiment, the articulating portion 201 is structured such that it does not inflate and operate in an extended manner.

The selected geometry of the articulating portion 201 allows the prong 270 to compress when inserted into the patient's nose. Due to the elastic properties of the silicone (or other compressible material), this compression results in a load that assists in sealing at the patient's nose and is reacted at the frame. In effect, the prong 270 acts as a spring.

Figure 39:
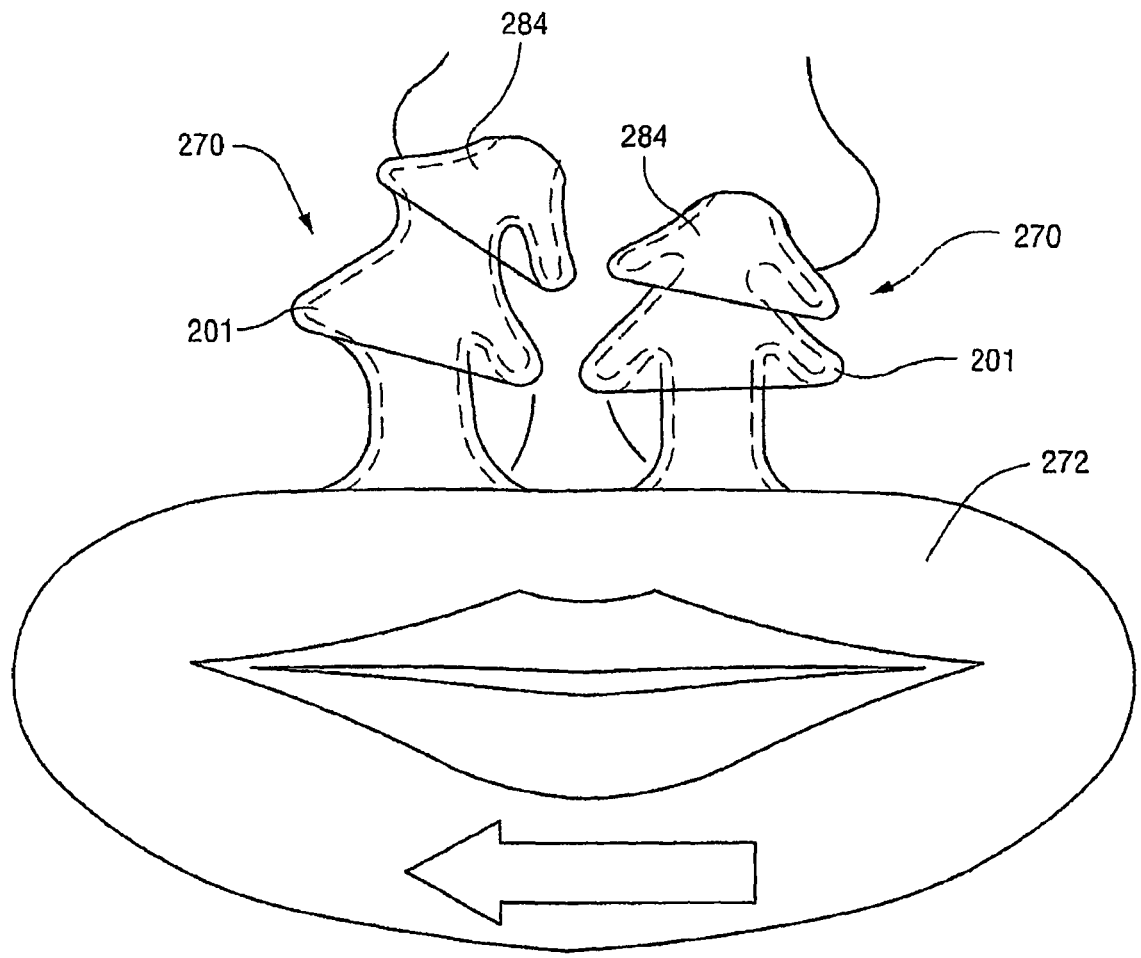
FIG. 39 is a front view illustrating the nasal prong shown in FIG. 37 engaged with the patient's nose and the mouth cushion moving to the side.

The articulating portion 201 allows additional articulation of the prong 270 relative to the frame 274 and mouth cushion 272. In operation, the lower column 203 compresses into the articulating portion 201 as shown in FIGS. 38-39. In this way, this articulating portion 201 acts as a ball-type joint. The geometry of this arrangement is such that the upper and lower columns 204, 203 remain essentially undeformed with the prong 270 pivoting at the junction between the upper column 204 and the lower wall 206, and the lower column 203 and the lower wall 202. Further, the prong 270 is structured such that the lower column 203 is initially aligned with the upper column 204. This arrangement ensures that the load desired to seal the prong 270 at the patient's nose can be effectively transferred via the headgear attached to the frame.

Also, the compressed prong 270 acts to provide a suspension-type effect, similar to that used in vehicles. In this way, the mouth cushion 272 can move away from the prong 270, i.e., move downward or side to side, without disrupting the seal at the patient's nose. As the mouth cushion 272 moves, the prong 270 can uncompress while still maintaining sufficient load and hence seal at the patient's nose (see FIG. 39).

In the illustrated embodiment, both the nasal portion 284 and the articulating portion 201 have a substantially elliptical shape. The shape of the nasal portion 284 ensures substantially even loading across a lower surface, and hence even loading into the patient's nose. This arrangement dictates that the articulating portion 201 is also elliptical in shape so that the load is transferred evenly to the nasal portion 284. However, the prongs 270 may have any other suitable shape, e.g., circular or any other closed section.

§ 2. Second Illustrated Embodiment of Mask System

§ 2.1 General

FIGS. 40-44 illustrate a mask system 10 constructed according to another embodiment of the present invention. As illustrated, the mask system 10 includes a sealing assembly 12 that provides an effective seal with both the patient's mouth and the patient's nasal passages, inlet conduits 14, 16 structured to deliver breathable gas to the patient, and a headgear assembly 18 to maintain the sealing assembly 12 in a desired position on the patient's face.

Figure 40:
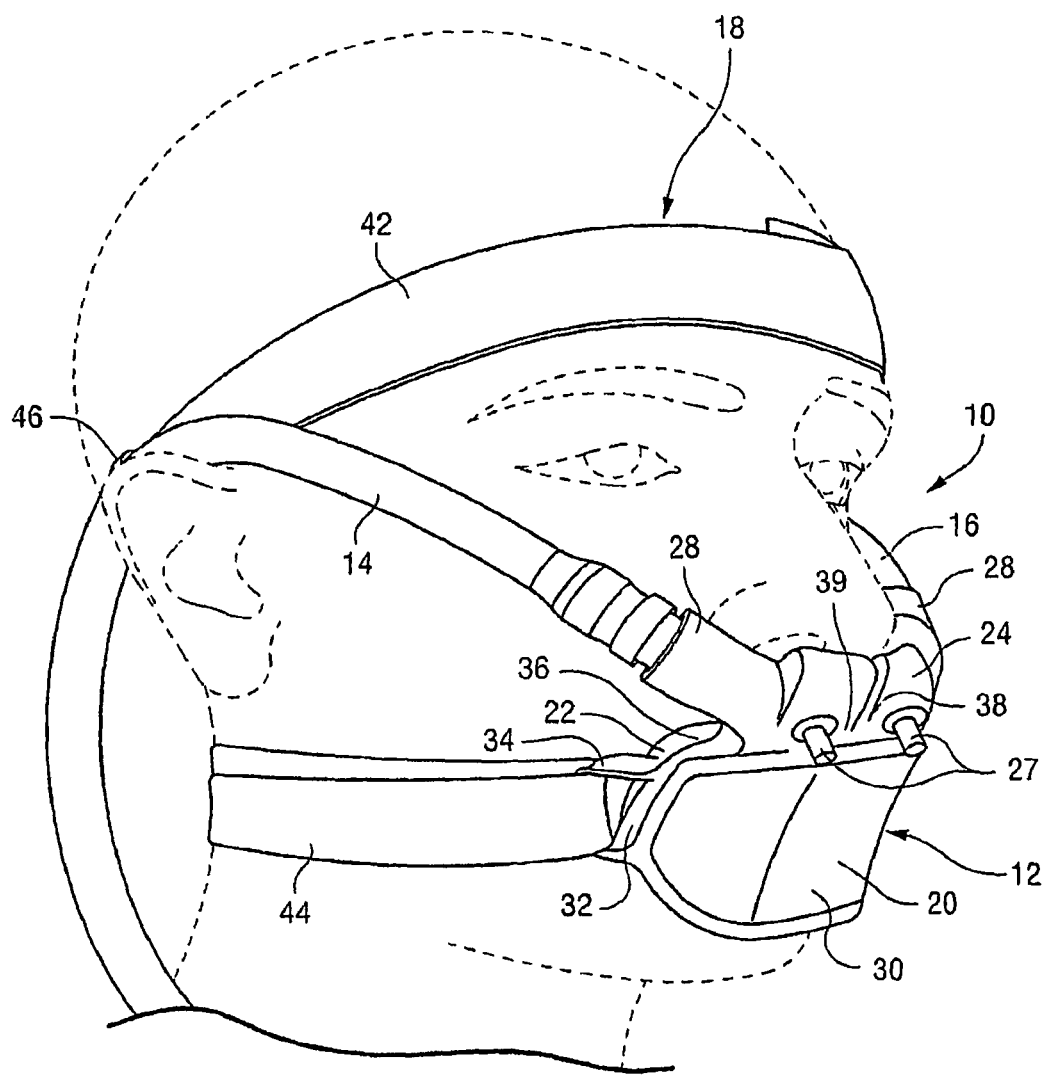
FIG. 40 is a perspective view of a mask system constructed according to another embodiment of the present invention.
Figure 41:
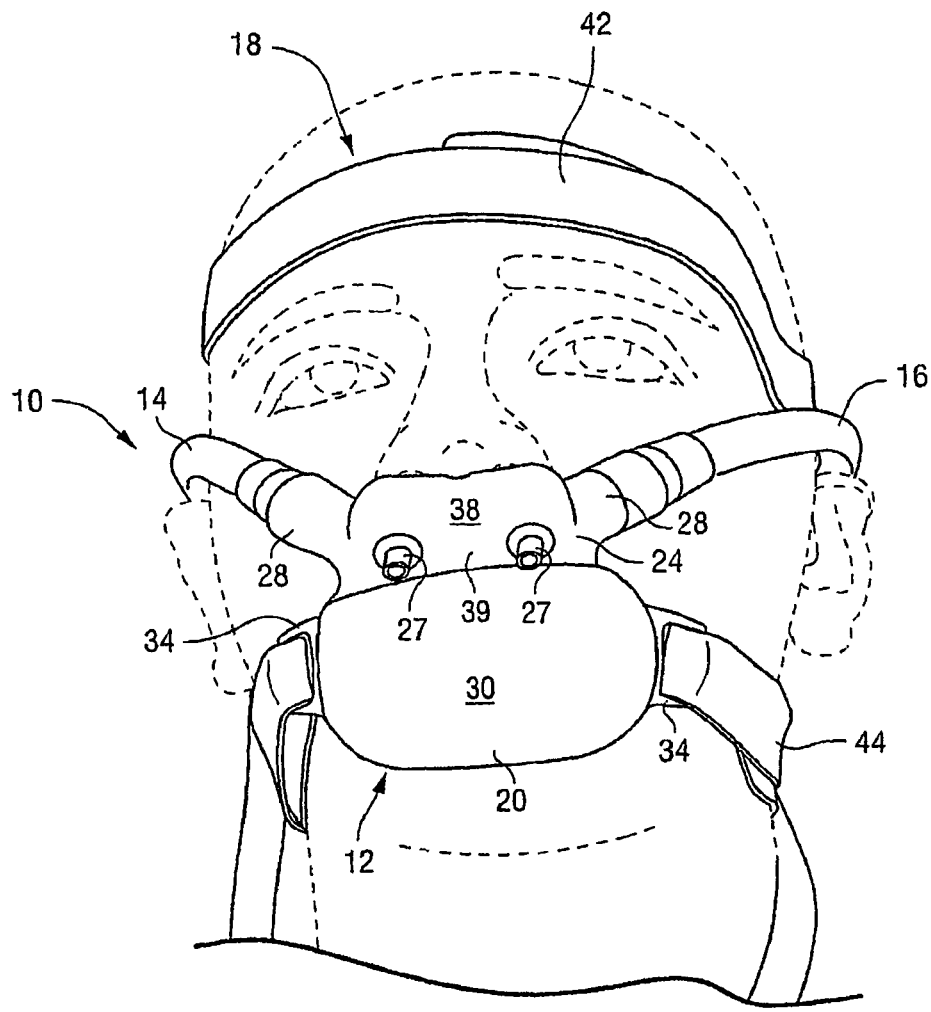
FIG. 41 is a front view of the mask system shown in FIG. 40.

The sealing assembly 12 includes a mouth covering assembly 20 having a cushion 22 structured to sealingly engage around an exterior of a patient's mouth in use and a nasal prong assembly 24 having a pair of nasal prongs 26 structured to sealingly engage with the nasal passages of the patient's nose in use. As illustrated in FIG. 40, the nasal prong assembly 24 is supported by a side wall 32 of the mouth covering assembly 20. In an embodiment, the mouth covering assembly 20 is integrally formed in one-piece along with the nasal prong assembly 24, e.g., by silicone in an injection molding process. However, the mouth covering assembly 20 and nasal prong assembly 24 may be formed separately from one another and then attached to one another. Advantageously, a standard mouth cushion size can be used in conjunction with a variety of nasal prong sizes reducing costs since the multiple moldings desired for different sized prongs may not be as expensive as multiple moldings for different sized mouth cushions.

As illustrated, opposing ends of the nasal prong assembly 24 include tubes 28, e.g., cylindrical tubes, that are adapted to engage respective inlet conduits 14, 16, e.g., via friction fit. The tubes 28 and inlet conduits 14, 16 may have any suitable cross-sectional shape, e.g., cylindrical, elliptical, flatter section, etc. In use, the inlet conduits 14, 16 are supplied with breathable gas under pressure, e.g., via an air delivery device, and the pressurized breathable gas is delivered into opposing ends of the nasal prong assembly 24 via the tubes 28. The mouth covering assembly 20 and nasal prong assembly 24 may be coupled such that gas is allowed to pass between each of these. This allows gas to be delivered to both the patient's nasal passages and mouth. Alternatively, the gas may be allowed to pass through the nasal prong assembly 24 only, such that gas is delivered to only the patient's nasal passages. In this arrangement, the mouth covering assembly 20 just acts as a mouth seal. In another embodiment, the gas may be allowed to pass through the mouth covering assembly 20 only, such that gas is delivered to only the patient's mouth. In this arrangement, the nasal prong assembly 24 is blocked and just acts as a nasal seal.

Figure 43:
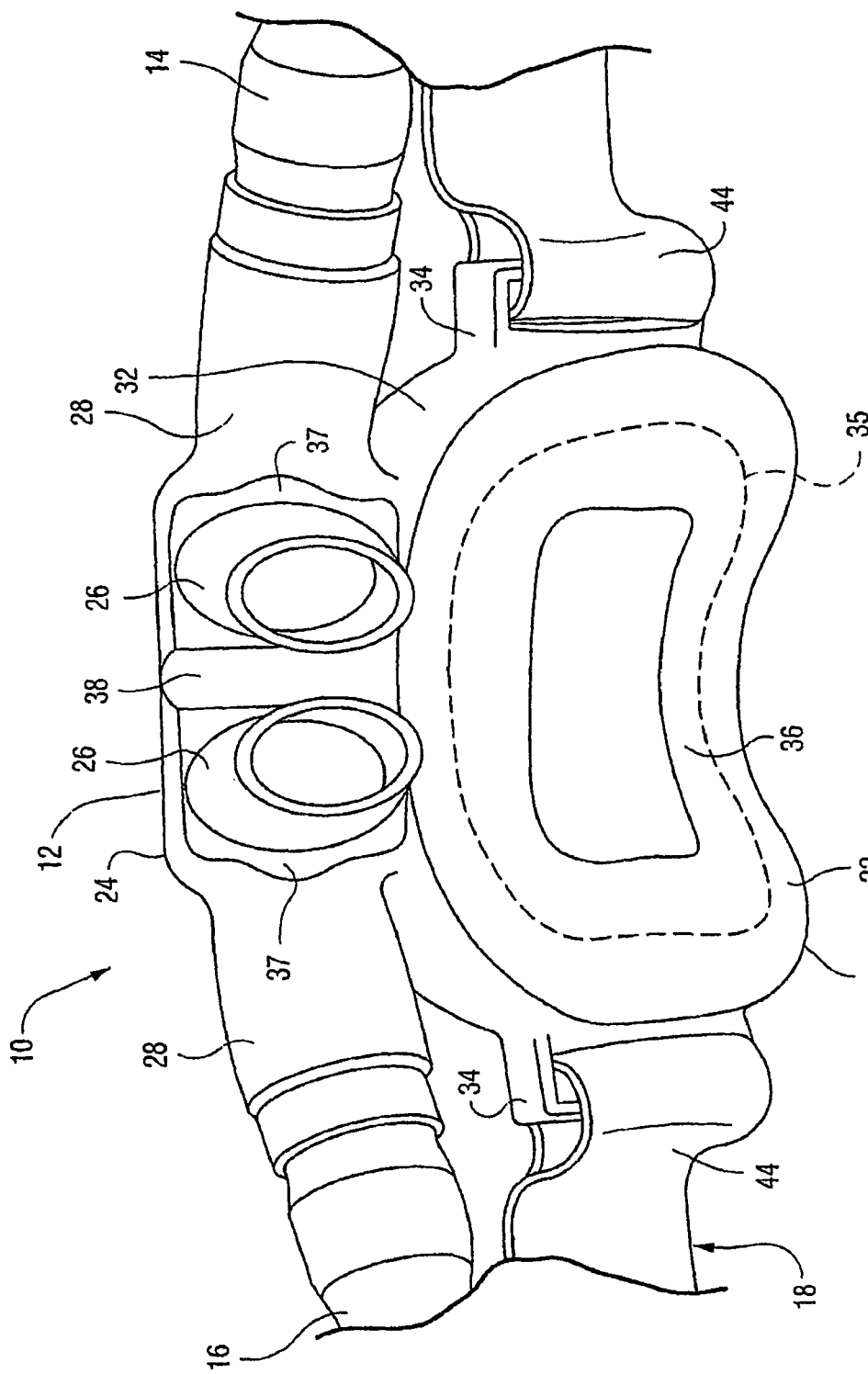
FIG. 43 is an enlarged rear view of the mask system shown in FIG. 40.
Figure 44:
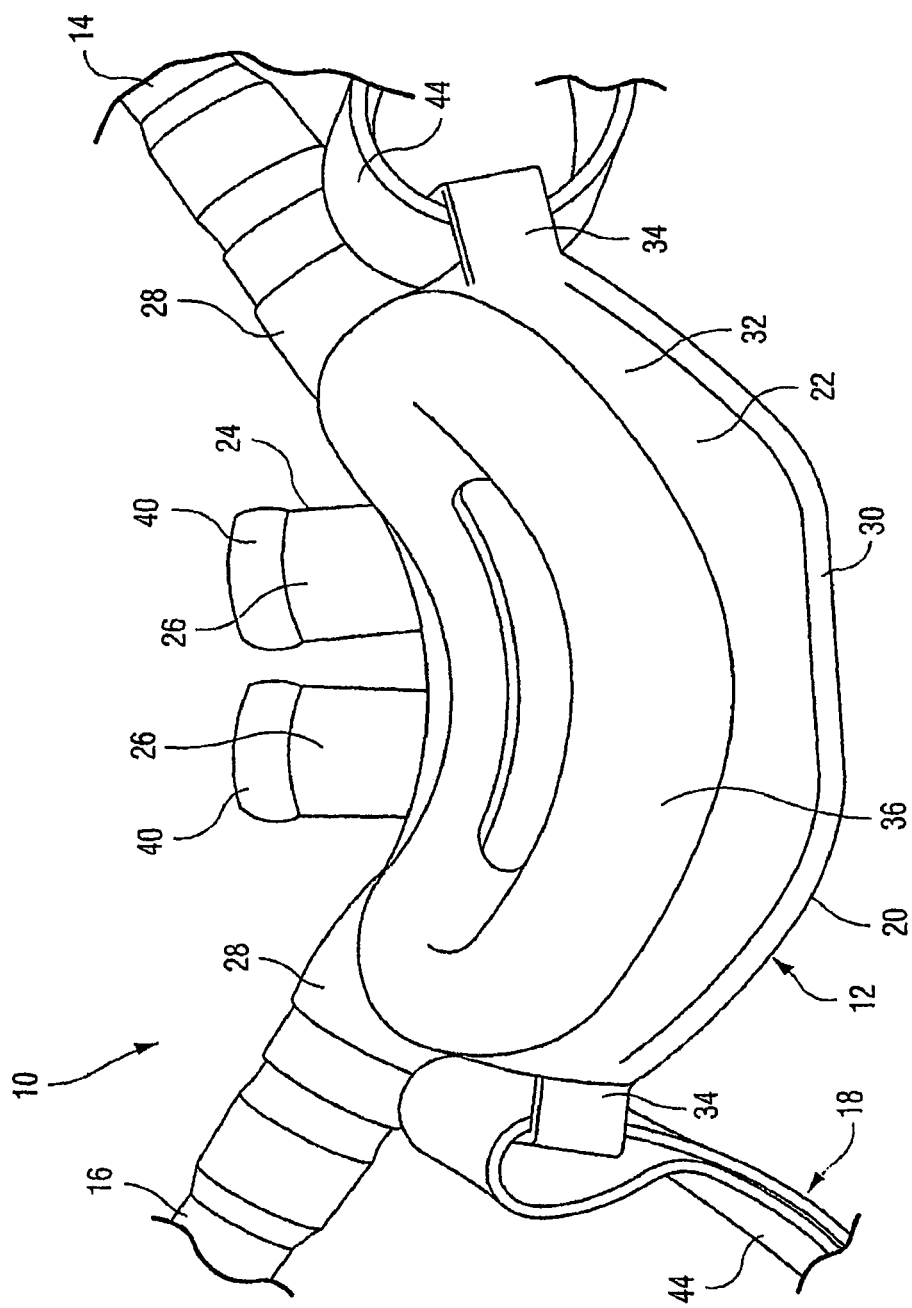
FIG. 44 is an enlarged bottom perspective view of the mask system shown in FIG. 43.

As best shown in FIGS. 43 and 44, the cushion 22 includes a non-face-contacting portion and a face-contacting portion. The non-face-contacting portion includes a front wall 30 and a side wall 32 extending away from the front wall 30. The front and side walls 30, 32 define a chamber for receiving the patient's mouth and a breathable gas when communicated to the nasal prong assembly 24. Also, opposing sides of the cushion 22 include a crossbar 34. Each crossbar 34 extends from the side wall 32 and is adapted to releasably engage a lower strap of the headgear assembly 18.

The face-contacting portion of the cushion 22 includes a membrane 36 that extends from the side wall 32. The membrane 36 is structured to form a seal around the lips of a patient. The face-contacting portion is contoured to follow generally the curvature of the patient's face. The face-contacting portion may include one or more undercushions 35 (see FIG. 43) to provide a support structure for the membrane 36. In an embodiment, the undercushion 35 may have a similar form to those disclosed in U.S. Pat. No. 6,701,927, the contents of which are hereby incorporated by reference in its entirety.

The side wall 32 of the cushion 22 supports the nasal prong assembly 24. As illustrated, the nasal prong assembly 24 includes a hollow body 38 that defines an air chamber, cylindrical tubes 28 extending from the body 38, and a pair of nasal prongs 26 supported by a substantially flat rear wall 37 of the hollow body 38. Each nasal prong 26 is substantially oval in cross-section and includes a flange or widened portion 40 (also referred to as beads) at an upper end thereof (see FIG. 44). The nasal prongs 26 may be angled with respect to the rear wall 37 to properly position the nasal prongs 26 with the nasal passages of the patient.

In the illustrated embodiment, the nasal prongs 26 are in the form of nasal inserts. In use, the nasal prongs 26 are inserted into the patient's nasal passages and retained therein by respective flanges 40. One or more vent ports 27 may be provided in a front wall 39 of the body 38 for CO.sub.2 washout. In an embodiment, the nasal prong assembly 24 and nasal prongs 26 thereof may have a similar form to those disclosed in U.S. Pat. Nos. 6,478,026 and 6,595,215, the contents of which are hereby incorporated by reference in their entirety. However the nasal prongs 26 may be in the form of nasal pillows, nozzles, cannula, nasal puffs, and may sealingly engage with the patient's nasal passages in any suitable manner.

As noted above, the body of the nasal prong assembly 24 may include one or more openings that communicate with one or more openings provided in the side wall of the cushion 22 to allow breathable gas to pass from the air chamber defined by the body 38 to the air chamber defined by the mouth covering assembly 20.

In the illustrated embodiment, the components of the mouth cover assembly 20 and the nasal prong assembly 24 are constructed from a substantially soft material, e.g., silicone, and may be integrally formed. However, certain components may be constructed from a substantially rigid or semi-rigid material, such as the front wall 30, side wall 32, and crossbars or rigid mounting loop 34 of the mouth covering assembly 20.

§ 2.2 Headgear Assembly

Figure 42:
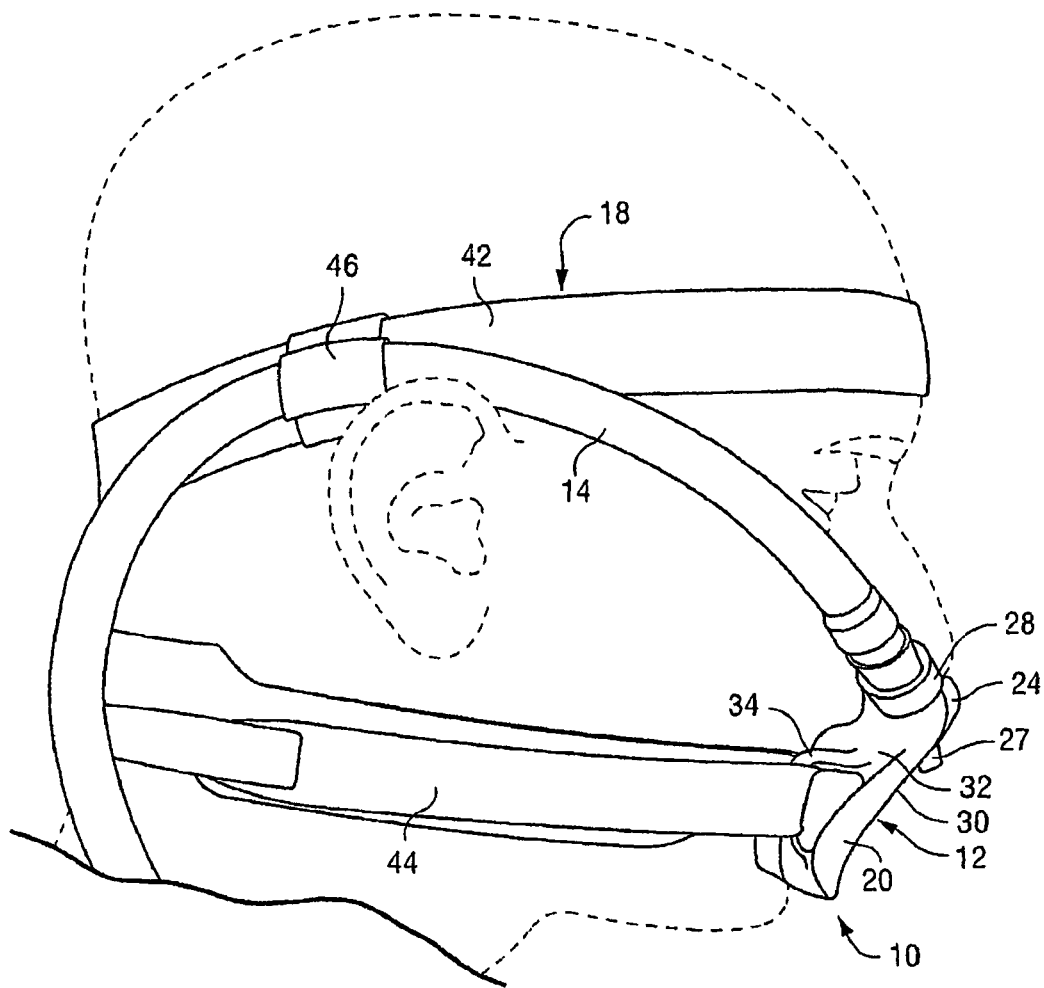
FIG. 42 is a side view of the mask system shown in FIG. 40.

As best shown in FIGS. 40 and 42, the headgear assembly 18 includes an upper strap 42 removably connectable to the inlet conduits 14, 16 and a lower strap 44 removably connectable to the sealing assembly 12. Specifically, the upper strap 42 extends across the patient's forehead and above the patient's ears. Fastening of the upper strap 42 to the patient's head may be provided by a hook and loop material, e.g., Velcro®. The upper strap 42 includes tube retainers 46 that are positioned adjacent the patient's ears in use. As illustrated, the tube retainers 46 retain respective inlet conduits 14, 16 so that the inlet conduits 14, 16 extend up and around the patient's ears. In an embodiment, each tube retainer 46 is a Velcro® strap that is wrapped around the respective inlet conduit 14, 16 and upper strap 42.

The lower strap 44 extends around the patients neck and below the patient's ears. End portions of the lower strap 44 are wrapped around a respective crossbar 34 provided on the cushion 22 and fastened in place, e.g., by a hook and loop material such as Velcro®. However, the lower strap 44 may be attached to the cushion 22 in any other suitable manner, e.g., via a clip arrangement. Also, the upper and lower straps 42, 44 may be joined to one another, e.g., joined to one another at the back of the patient's head similar to the arrangement shown in FIG. 10.

§ 2.3 Low Profile

As best shown in FIG. 42, the sealing assembly 12 has a low profile, which improves the comfort level of the patient, and reduces the forces which may tend to pivot the sealing assembly 12 relative to the patient's face.

§ 3. Third Illustrated Embodiment of Mask System

Figure 45:
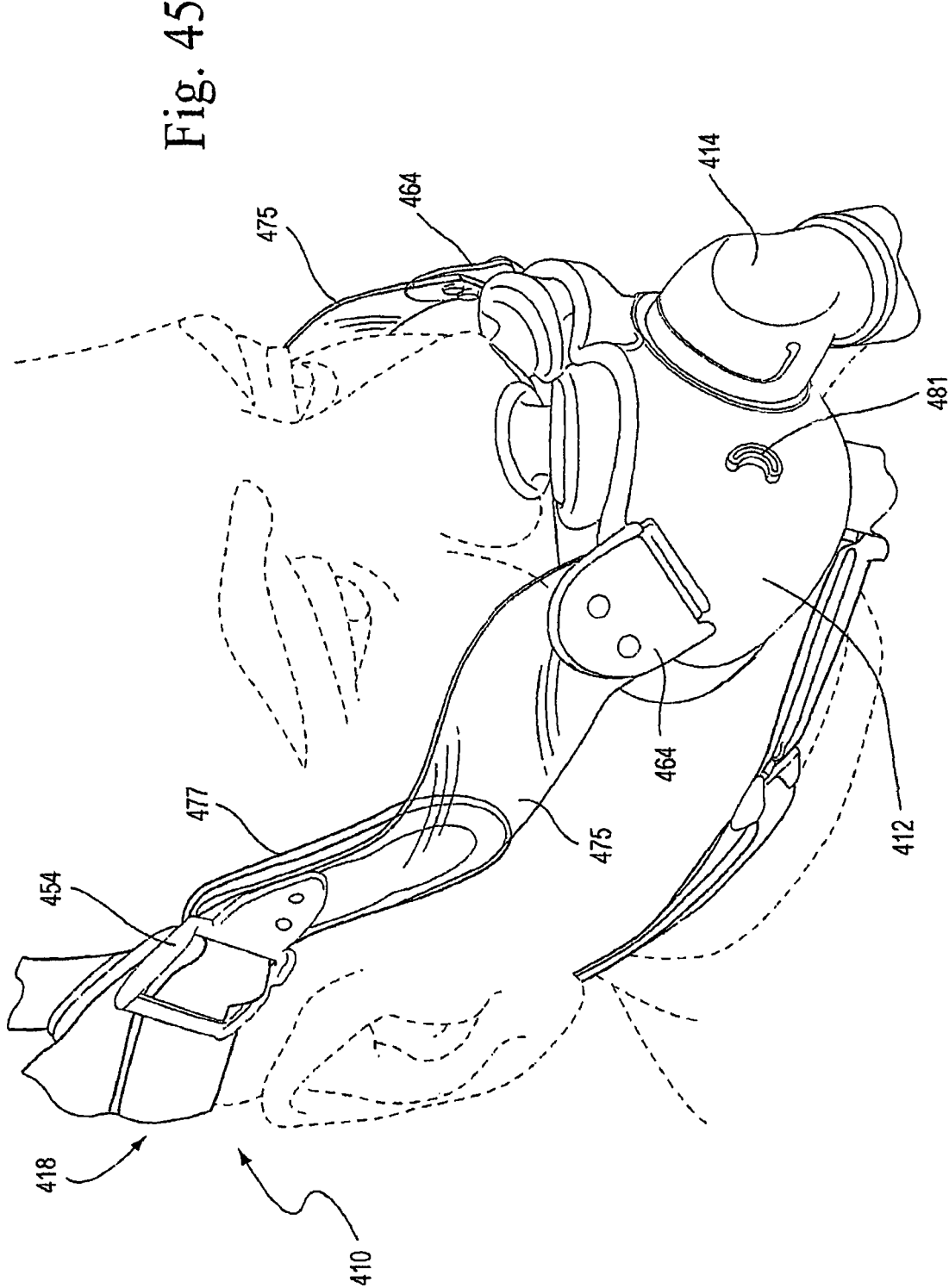
FIGS. 45-47 illustrate a mask system according to still another embodiment of the present invention.
Figure 46:
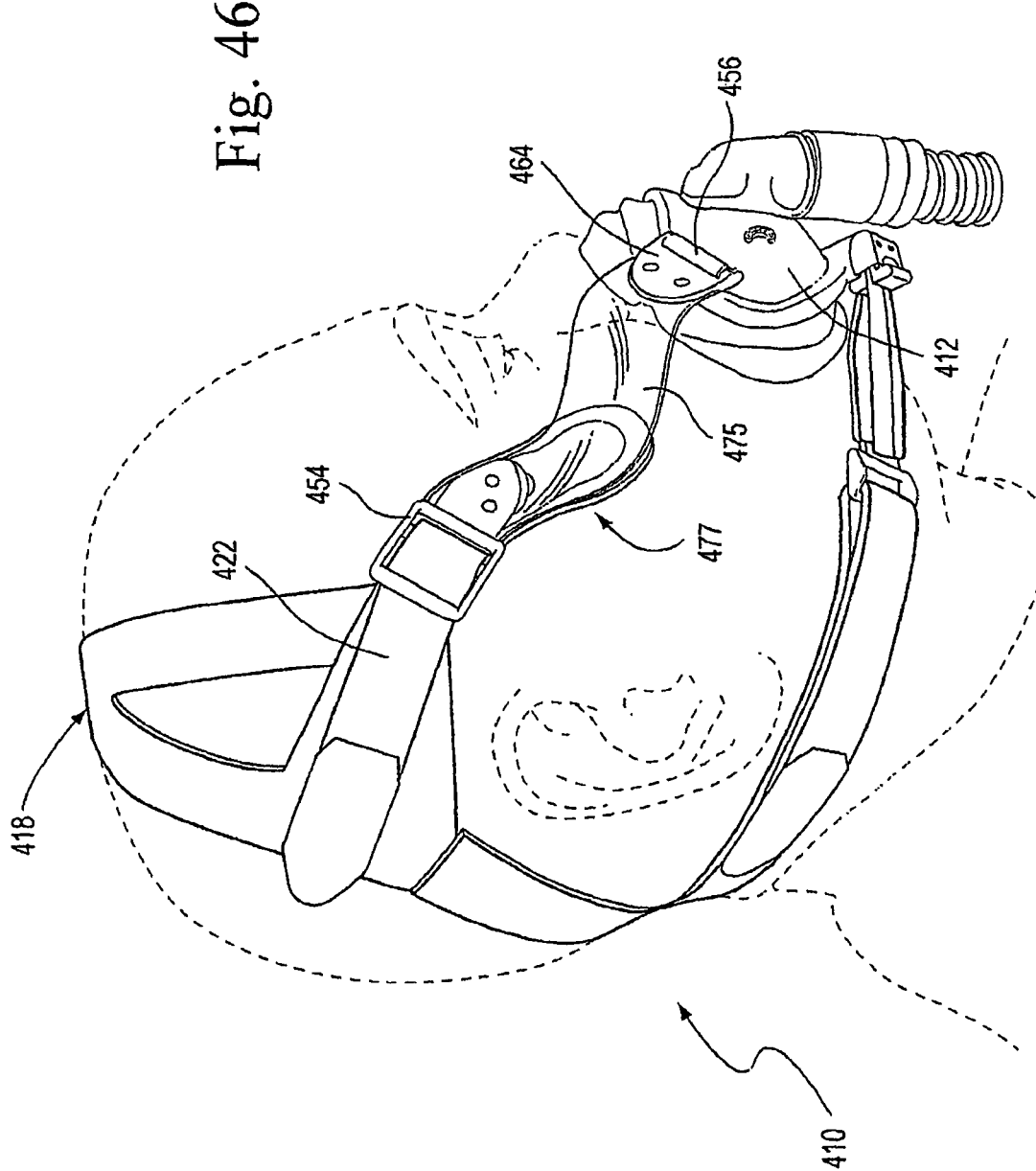
Figure 47:
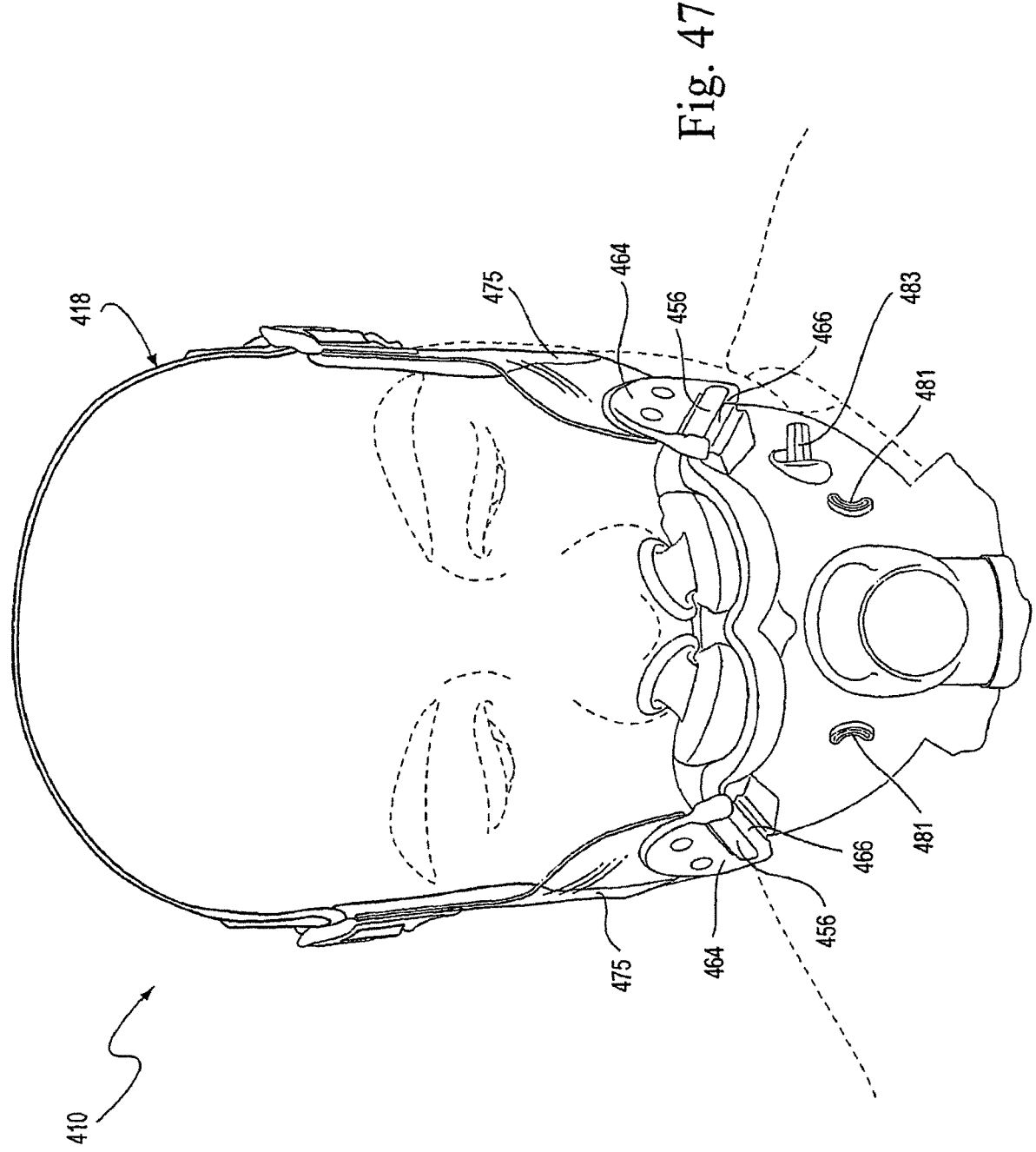

FIGS. 45-47 illustrate a third embodiment of a mask system 410 according to the present invention. Mask system 410 is similar to the mask systems described above, and even includes common elements that have been indicated with similar reference numbers. For example, mask system 410 includes a sealing assembly 412, a swivel elbow 414 and a headgear assembly 418.

The overall architecture of the headgear straps in FIGS. 45-47 is similar to the overall architecture of the headgear straps in FIG. 12. However, one main difference in the embodiment of FIGS. 45-47 relates to the use of a stabilizing structure 475. The stabilizing structure 475 in this example has one end connected to attachment member 464 provided to the frame and a second end that extends toward top strap portion 422. The second end may be connected to a tab or extension of upper strap attachment member or buckle 454. The stabilizing structure 475, attachment member 464, and buckle 454 may be integrally as a one-piece structure. Alternatively, the stabilizing structure 475, attachment member 464, and buckle 454 may be formed separately from one another and then assembled to one another.

Stabilizing structure 475 has a "3D" form and is contoured to sit more flush with the face. In one example, the stabilizing structures are generally "5-shaped", and extend from the patient's temple, along the cheekbones and towards the attachment members 464. The shape also helps to move the stabilizing structure away from the patient's eyes. Because they are generally rigid, stabilizing structures 475 can be slightly spaced from the patient's cheek region, if desired. The stabilizing structures may be made of any rigid or semi-rigid material, e.g., polycarbonate, nylon. The stabilizing structures 475 can also be made of clear material, to minimize obtrusiveness to the patient.

Headgear assembly may include a padded material or soft portion 477 positioned between the stabilizing structure 475 and the patient's face. However, the stabilizing structure 475 may be constructed of a relatively soft material and therefore a padded material may be unnecessary.

Mask system 410 includes a plurality of frame attachment members 464. The frame attachment members 464 associated with the top strap portions are similar to those shown in FIGS. 14 and 15. The frame attachment members associated with the bottom strap portions are similar to those shown in FIGS. 22 and 23.

FIG. 47 also depicts a ports cap 483 for selective attachment of an oxygen delivery cannulae or the like.

§ 4. Fourth Illustrated Embodiment of Mask System

§ 4.1 General

Figure 48:
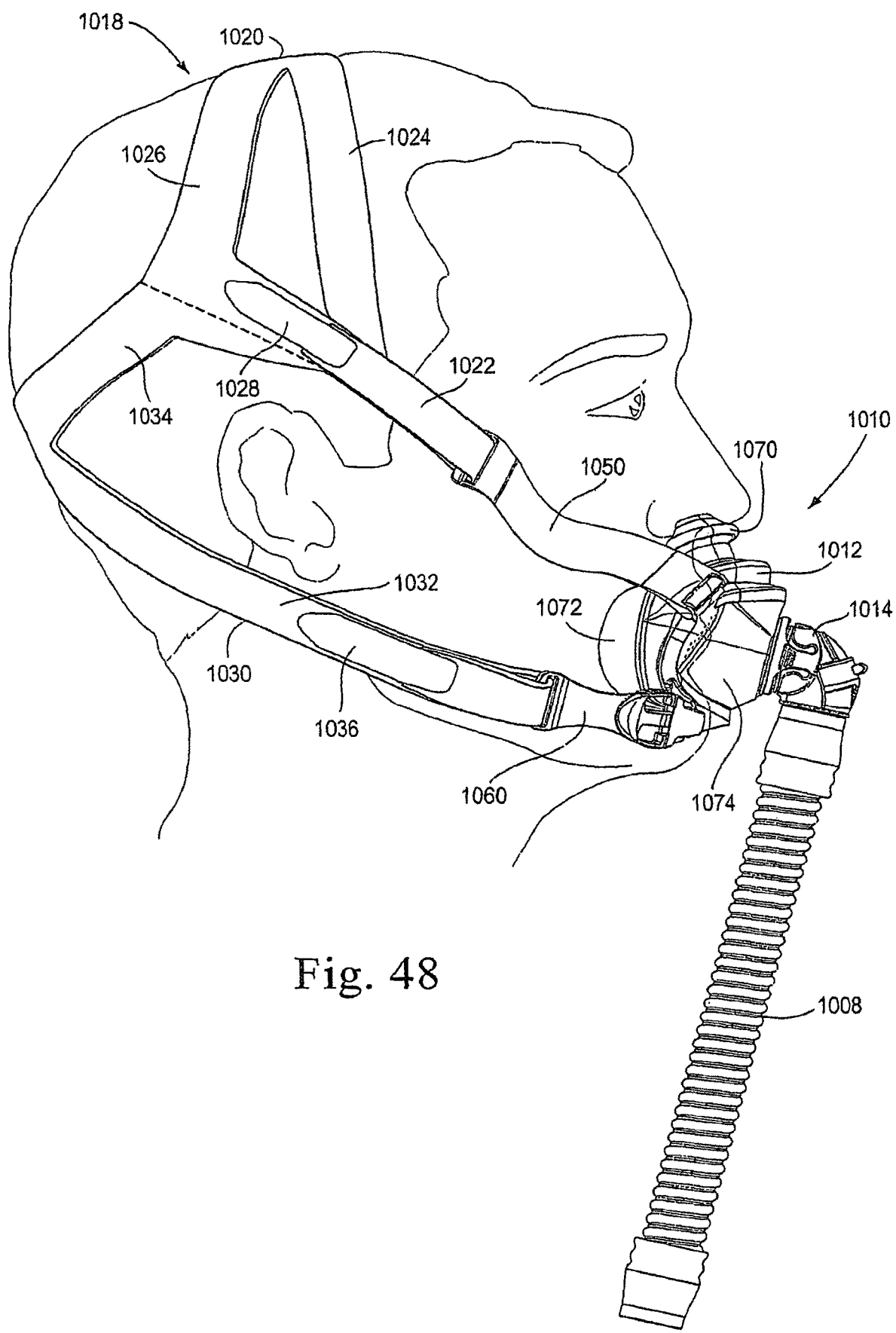
FIG. 48 is a side view of a mask system according to another embodiment of the present invention.
Figure 49:
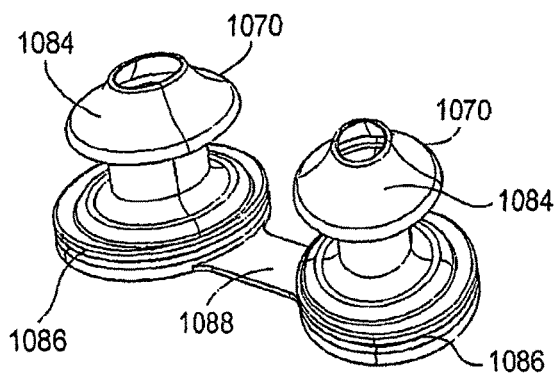
FIGS. 49-52 illustrate a paired prong arrangement according to an embodiment of the present invention.

FIG. 48 illustrates a mask system 1010 according to another embodiment of the present invention. The mask system 1010 may include one or more elements that are similar to those of the mask systems described above. As illustrated, the mask system 1010 includes a sealing assembly 1012 that provides an effective seal with both the patient's mouth and the patient's nasal passages, an elbow assembly 1014, e.g., swivel elbow, and a headgear assembly 1018 to maintain the sealing assembly 1012 in a desired position on the patient's face. The mask system 1010 enables the delivery of therapy in a manner which is unobtrusive, quiet, comfortable, and effective.

The sealing assembly 1012 of the mask system 1010 includes a mouth cushion 1072 structured to sealingly engage around an exterior of a patient's mouth in use and a pair of nasal prongs 1070 structured to sealingly communicate with the nasal passages of the patient's nose in use. The cushion 1072 is structured to be removably and replaceably attached to a substantially rigid frame 1074.

§ 4.2 Nasal Prongs

The nasal prongs 1070 may be formed separately from the cushion 1072, e.g., by silicone in an injection molding process, and then inserted and secured to the cushion 1072. This arrangement provides a greater scope of patient fitting by being able to select cushion size and nasal prong size independently.

It should be understood that nasal prongs, nasal pillows, nozzles, or other device that go up or seal near the patient's nose may be used. In addition, most people can obtain a good nasal seal with at least one of three different sizes of nasal prong. Further, instead of a pair of nasal prongs (one for each nostril), a single sealing cushion (e.g., nasal cushion) that seals around, e.g., just under, both nostrils may be used.

§ 4.2.1 Paired-Prong Arrangement

FIGS. 49-52 illustrate a paired-prong arrangement wherein nasal prongs 1070 are provided as a pair on a single insert. As illustrated, each nasal prong 1070 includes a nasal portion or head portion 1084 adapted to sealingly communicate with a respective patient nasal passage and a base portion 1086. The tip of each prong 1070 is slightly inserted into the nose, with the head portion 1084 engaging the patient's nare. Each head portion 1084 includes a curved area 1085 that provides lift or spring to the head portion 1084. The prongs 1070 are joined at respective base portions 1086 by a bridging or connecting strap 1088, e.g., thin silicone section.

Figure 99:
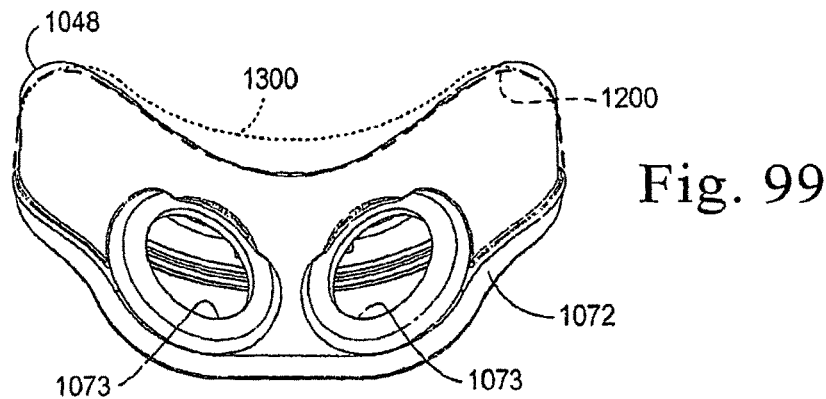
FIG. 99-100 are top and bottom view of the mouth cushion shown in FIG. 90, and illustrate comparison between cushions shown in FIGS. 102 and 103.

The base portions 1086 are adapted to be mounted to the cushion 1072, e.g., via an annular recess that defines a mounting flange. For example, FIG. 99 illustrates a cushion 1072 with spaced-apart annular recesses that define flanges 1073 adapted to engage a respective groove provided in each of the base portions 1086 of the prongs 1070 therein. Each base portion 1086 maybe secured within a respective flange 1073 via a interference-fit or adhesive such as glue, for example. The base portions 1086 are mounted from the breathing chamber side of the cushion 1072 such that the bridging strap 1088 extends along an interior surface of the breathing chamber.

Figure 50:
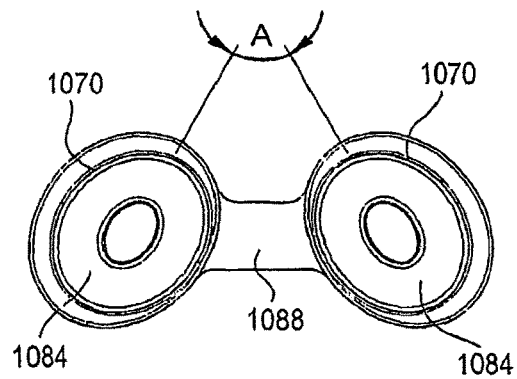
Figure 51:
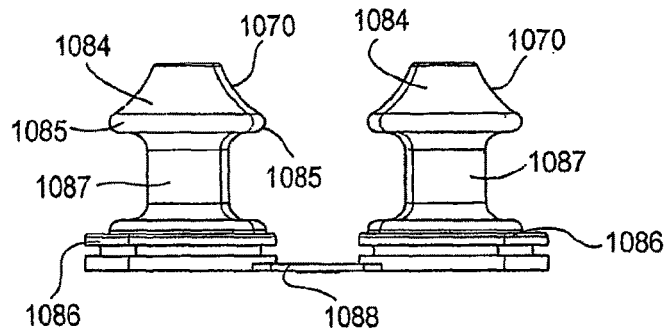

The paired-prong arrangement provides head portions 1084 that are pre-aligned with respect to one another. For example, each head portion 1084 has a general oval-shape with an oval-shaped nasal opening (see FIG. 50). The pair of head portions 1084 may be angled with respect to one another to provide a better fit with the patient's nares. As shown in FIG. 50, the head portions 1084 may define an angle A therebetween of about 50°-60°, e.g., 54°. However, other angles are possible and may be customized based on the patient. The paired-prong arrangement provides correct alignment with the mating cushion 1072 and with the patient's nares. Specifically, the head portions 1084 are pre-angled to match the patient's nares, the base portions 1086 match the oval shape of the flanges 1073, and the connecting strap 1088 may flex or bend to find its position.

Figure 52:
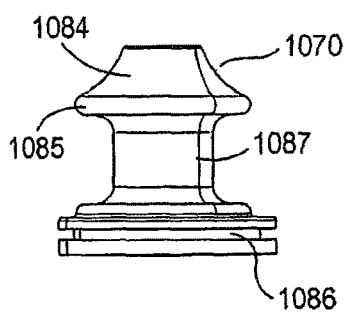
Figure 52B:
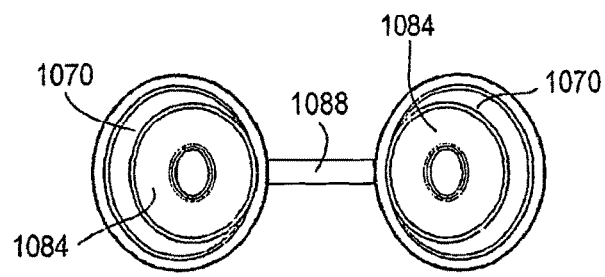
FIGS. 52B-52E illustrate a paired prong arrangement according to another embodiment of the present invention.
Figure 52C:
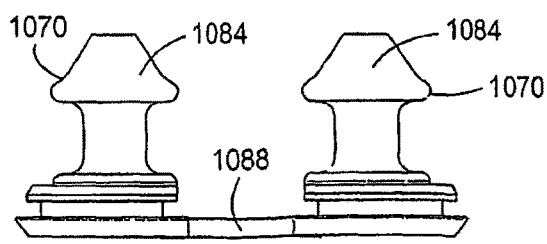
Figure 52D:
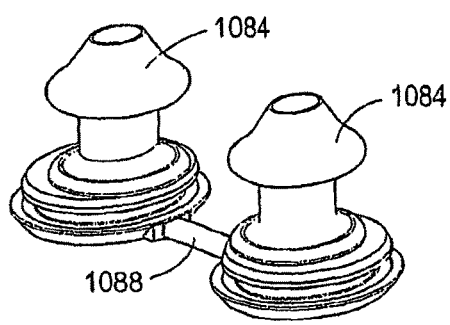
Figure 52E:
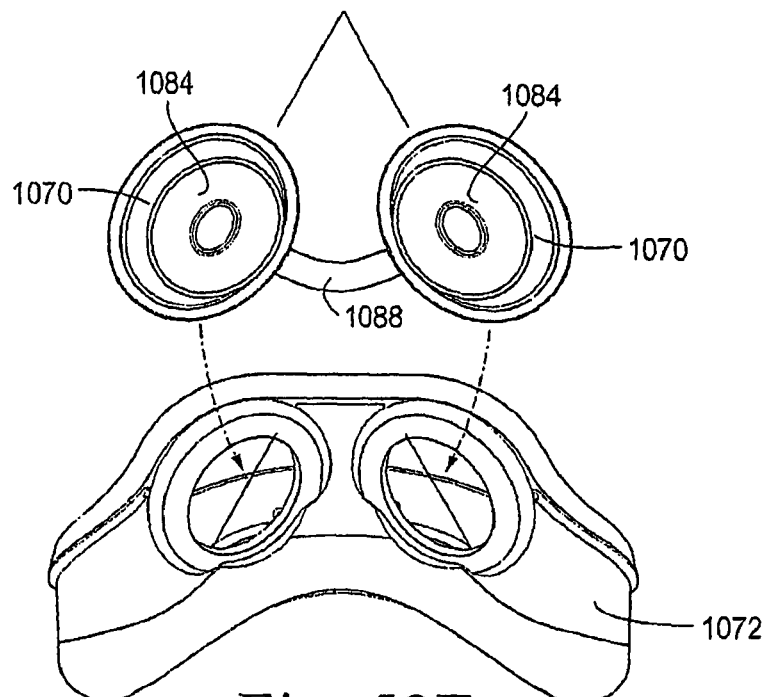
Figure 53:
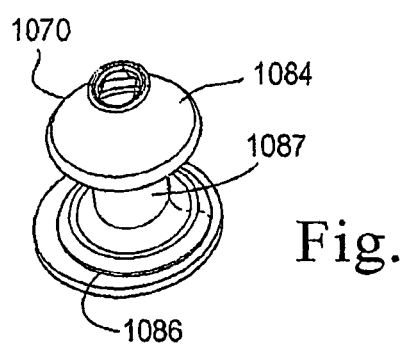
FIGS. 53-56 illustrate a single prong arrangement according to an embodiment of the present invention.
Figure 54:
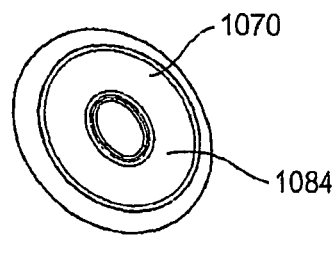
Figure 55:
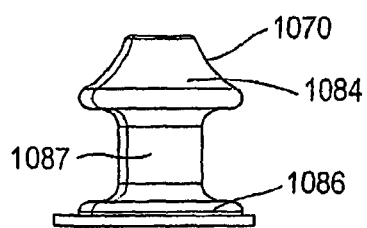
Figure 56:
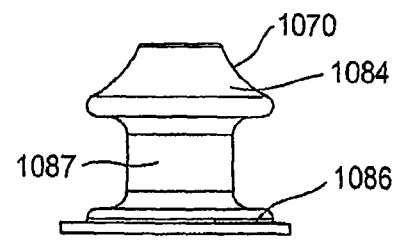

In an alternative embodiment, as shown in FIGS. 52B-52E, the major axes of the elliptical head portions 1084 may be parallel to each other, e.g., molded parallel to one another. The bridging strap 1088 may have a circular cross-section (see FIG. 52D). When assembling the prongs 1070 onto the cushion 1072, the patient must align the prongs 1070 at an angle as shown in FIG. 52E. The bridging strap 1088 is flexible or bendable to achieve the desired angle. The patient can vary the angle for either the left or right prong, which allows customization. The bridging strap 1088 prevents individual left and right prongs 1070 from becoming separated and lost. Also, the symmetrical design (as the left and right prongs 1070 are molded parallel) enables easier assembly onto the cushion. This arrangement also allows the insert to be inserted into the cushion in different orientations, one being rotated 180° from the other.

The paired-prong arrangement provides correct alignment with the mating cushion 1072 and with the patient's nares because each prong is held in angular alignment with respect to the other prong by nature of its connection with the other prong. Also, the paired-prong arrangement prevents accidental loss of component, e.g., loss of nasal prongs. In addition, the paired-prong arrangement may improve ease of assembly. In an embodiment, the prongs 1070 may be configured such that the paired-prong insert can be inserted into the cushion 1072 in from either the breathing chamber side or the outward facing side, for error proofing.

§ 4.2.2 Single-Prong Arrangement

FIGS. 53-56 illustrate a single-prong arrangement wherein a nasal prong 1070 is molded and assembled individually to the cushion 1072. Similar to the above, the nasal prong 1070 includes a head portion 1084 and a base portion 1086 adapted to be mounted to the cushion 1072, e.g., via a press-fit or adhesive.

The single prong arrangement is advantageous because it allows customization of fit. For example, each nasal prong 1070 maybe independently aligned with respect to the cushion 1072 for optimal fit, e.g., angular adjustment of each prong to match nasal angle. Also, the single prong arrangement provides the possibility of different prong sizes in each patient nare, e.g., large prong size for left nare and small prong size for right nare.

§ 4.2.3 Nasal Prong Ribs

Figure 57:
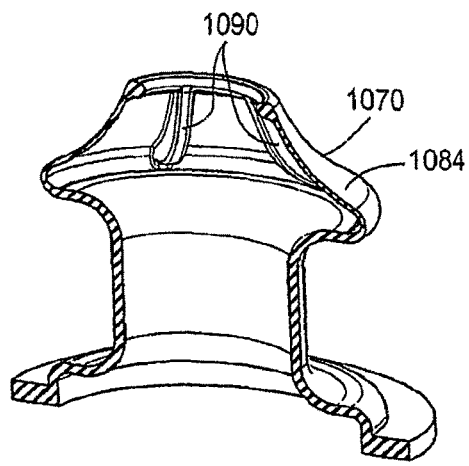
FIGS. 57-58 illustrate a prong including one or more ribs according to an embodiment of the present invention.
Figure 58:
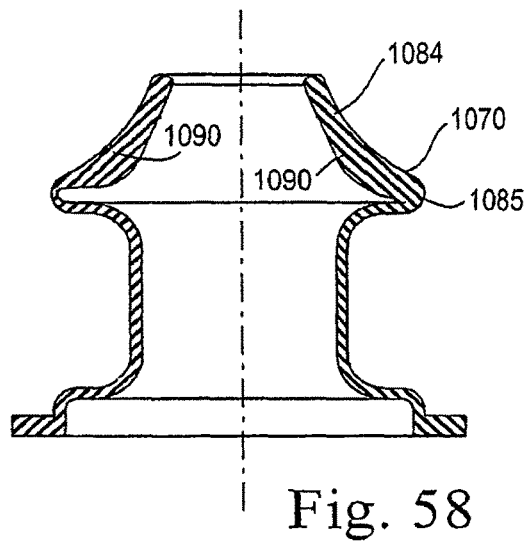
Figure 59:
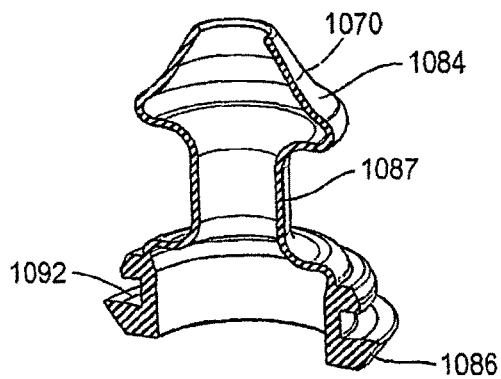
FIGS. 59-62 illustrate a prong including a single wall according to an embodiment of the present invention.
Figure 60:
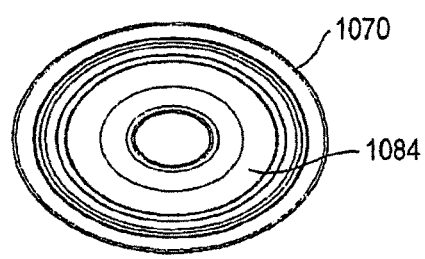
Figure 61:
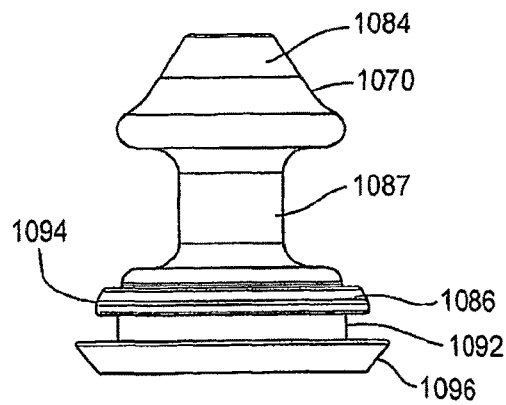
Figure 62:
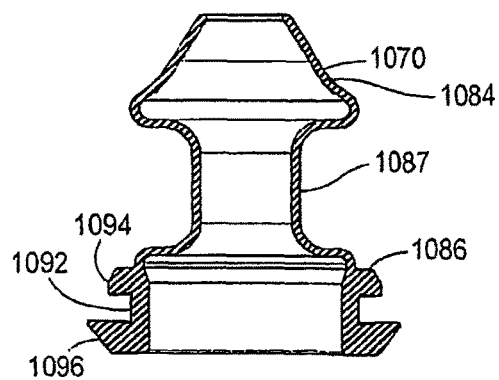

As shown in FIGS. 57 and 58, one or more ribs 1090 may be integrally molded with each nasal prong 1070 to provide axial and radial spring and/or lateral/circumferential structural rigidity/reinforcement, e.g., increased radial strength.

In the illustrated embodiment, multiple ribs 1090 are located internally on the upper section of the nasal portion or head portion 1084. The multiple ribs 1090 provide increased radial strength to allow the use of thin walled head portion 1084 without collapsing. In this way, the head portion 1084 can inflate to a certain degree, to match nasal opening shape, but still retain sufficient rigidity to allow insertion into the nasal opening. Each rib 1090 may be attached or unattached at its base (adjacent the curved area 1085) to control spring rate and stiffness. Also, the cross-sectional thickness of each rib 1090, e.g., rib profile, may vary along its length to control spring rate and stiffness. Clearly, ribs are particularly advantageous where the cushion is formed from a very thin and/or very flexible membrane.

§ 4.2.4 Single-Wall Nasal Prong

FIGS. 59-62 illustrate another embodiment of a nasal prong 1070 having a single-wall head portion 1084. As illustrated, the base portion 1086 of the nasal prong 1070 includes a slot 1092 to facilitate assembly to the cushion 1072. In addition, the upper flange that defines the slot 1092 (e.g., a circumferential groove) includes a curved exterior surface 1094, and the lower flange that defines the slot 1092 includes a chamfered surface 1096. This arrangement provides a tapered lead-in to allow easier assembly to the cushion 1072.

Also, the section of the nasal prong 1070 (where the nasal column 1087 meets the base portion 1086) provides axial spring and compression (e.g., similar to a shock absorber) to compensate for slight variation in angle and distance between the cushion and the patient's nares. Specifically, this section provides a trampoline-type arrangement that allows the nasal column 1087 to move axially into the base portion 1086. This forms a kind of ball joint which accommodates both short and large axial distances to the patient's nares.

Figure 63:
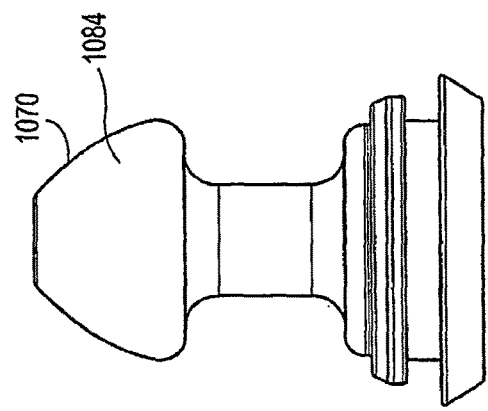
FIGS. 63-65 illustrate prongs having different upper section profiles.
Figure 64:
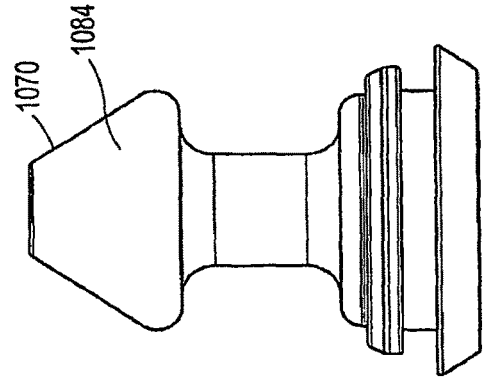
Figure 65:
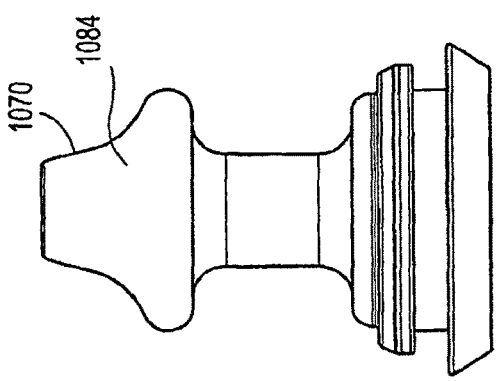

The upper section profile of the head portion 1084 may be varied to better accommodate nares of different patients. For example, the upper section profile may have a convex shape (as shown in FIG. 63), a straight shape (as shown in FIG. 64), or a concave shape (as shown in FIG. 65). In an alternative embodiment, the head portion 1084 may be formed of a deformable material, e.g., foam, so that the head portion 1084 maybe deformed to conform to a patient's nare.

Figure 66:
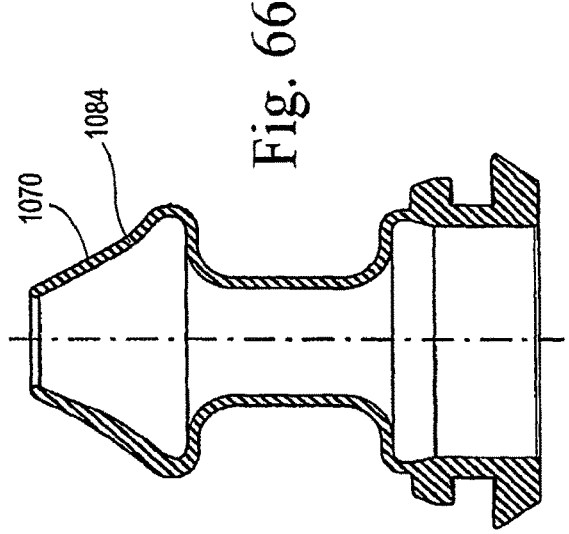
FIG. 66 illustrates a prong having varying wall sections.

Also, the wall section of the head portion 1084 may be varied to control lateral stiffness/rigidity. For example, FIG. 66 illustrates a head portion 1084 having one wall section (the left side) that is thicker than an opposing wall section.

§ 4.2.5 Nasal Prong Length

The nasal prongs are longer than those known in the art, e.g., nasal prongs disclosed in U.S. patent application Ser. No. 10/781,929, filed on Feb. 20, 2004, the entirety incorporated herein by reference. This increased length is desired for a number of reasons.

First, the length of the nasal prong is desired to "reach" to the back of the patient's nose. This is due to the presence of the mouth cushion which spaces the base of the prongs from the patient's face. Specifically, the base of the prongs is positioned "behind" the membrane and undercushion that seal on the patient's upper lip. Thus, the prongs must be longer to extend from the mouth cushion to the patient's nose. In contrast, the nasal prong of the '929 application sits very close to the patient's face so its length is shorter.

Second, the length of the nasal prong is desired to ensure that sealing on all facial geometries can be satisfied, i.e., to match varying naso-labial angles. The mouth cushion precludes rotation of the device to match naso-labial angles. Due to the height of the mask, rotation would result in a large change in distance at the bottom of the mouth cushion, which would present a sealing challenge. In the '929 application, the prongs are provided on a "barrel" that can be rotated to match varying naso-labial angles.

Third, the additional length of the nasal prong section allows greater compression than that achievable in the '929 application. This in turns provides additional sealing at the nose and assists in achieving an appropriate balance of nose and mouth sealing. In addition, compression at the base of the column will act as a form of "suspension". In this way, the mouth cushion can move away from the prong section (i.e., move downward or side to side) without disrupting the seal at the nose. As the mouth cushion section moves, the prong section can uncompress while still maintaining sufficient load and hence seal at the nose. This is not provided in the '929 application as the absence of a mouth cushion means the device is much more difficult to disrupt on the face.

In an embodiment, the column or stalk 1087 has a length in the range of 9-20 mm. In a preferred embodiment, the stalk 1087 has a length of 12 mm.

Figure 66B:
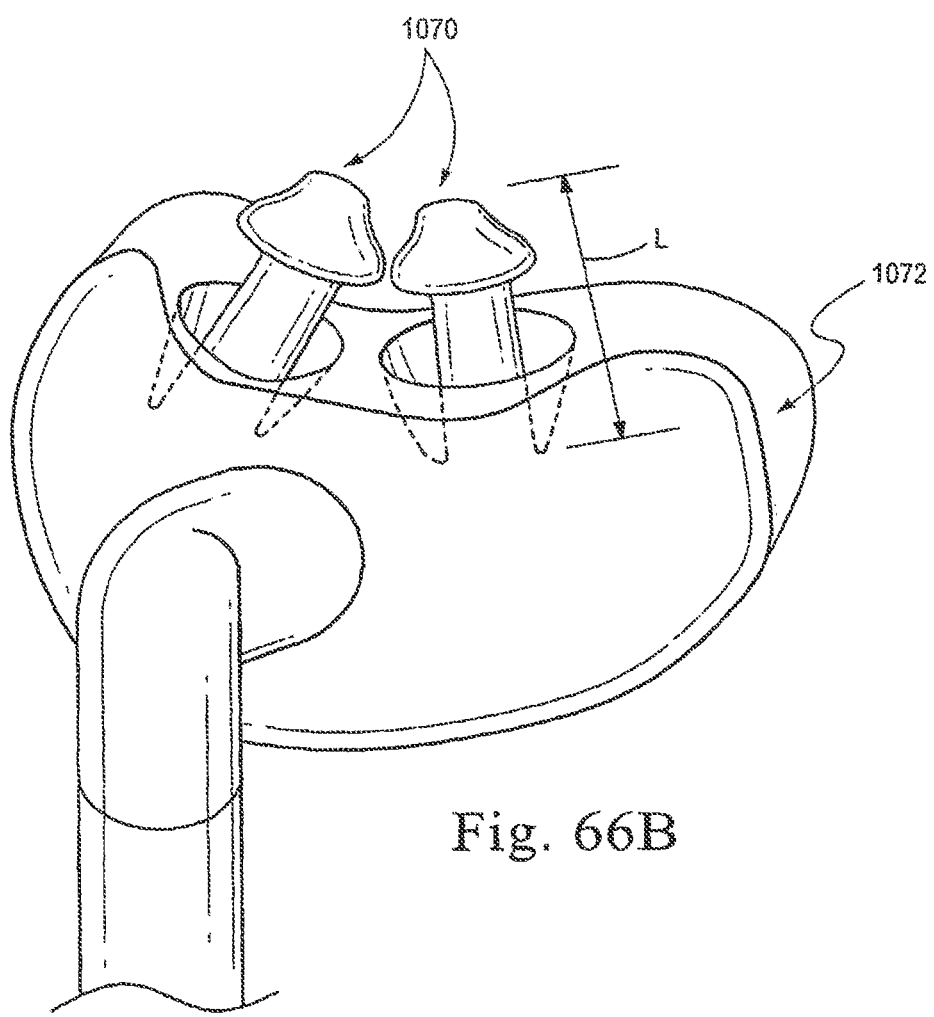
FIG. 66B illustrates nasal prongs according to another embodiment of the present invention.

In an alternative embodiment, nasal prongs 1070 in their free state maybe inset into the mouth cushion 1072 as shown in FIG. 66B. The prongs 1070 shown in FIG. 66B may have a length of up to 70 mm. A similar embodiment is disclosed in PCT Application No. PCT/AU2004/001832, filed Dec. 24, 2004, which is incorporated herein by reference in its entirety.

§ 4.2.6 Articulation

The prong arrangement of the present invention provides independent movement of both ends of the "stalk" or nasal column of the prong. Hence the head portion or pillow section can articulate independent of the base portion or "trampoline" section. This form of independent suspension allows both axial and rotational movement of the top of the prong. It also allows for the head portion and base portion to remain parallel despite movement or bending of the stalk.

To match the varying naso-labial angles, the prongs are designed to articulate at both ends. The geometry used allows the joints at each end to act much like "ball in socket" joints and conform to different facial geometries. The additional length of the prongs allow this articulation (rotation of the prong around its base) without the underside of the prong interfering with the mouth cushion.

§ 4.2.7 Dual-Wall Nasal Prong

FIGS. 67-70 illustrate a nasal prong 1070 having a dual or double-wall head portion 1084. As illustrated, the head portion 1084 includes an inner wall 1002 and an outer wall 1004 that surrounds the inner wall 1002. In an embodiment, the outer wall 1004 is substantially thinner than the inner wall 1002, and no more than 0.65 mm thick. In the illustrated embodiment, the inner and outer walls 1002, 1004 are molded in its in use position. In use, the thin outer wall 1004 inflates and/or allows conformance to the inner periphery of the patient's nare to enhance the seal of the head portion 1084 against the patient's nare. The dual wall nasal prong may reduce the time of mask set-up as it provides more ability to seal, e.g., thin outer wall conforms to the patient's nasal contours. An early generation dual-wall nasal prong is disclosed in PCT Application No. PCT/AU2004/001832, filed Dec. 24, 2004, which is incorporated herein by reference in its entirety. Also, a dual-wall nasal cushion is disclosed in U.S. Pat. No. 6,112,746, which is incorporated herein by reference in its entirety.

The thin outer wall 1004 (also referred to as an outer membrane) may have a thickness in the range of 0.1 mm to 0.65 mm. In a preferred embodiment, the thin outer wall 1004 has a thickness of 0.35 mm. In contrast, the inner wall 1002 (also referred to as an inner membrane) has a thickness of about 0.75 mm, which is substantially similar to the thickness of the base 1086 and the column or stalk 1087. In other arrangements, it would also be possible to eliminate the inner wall, just leaving the thinner outer wall membrane for contact with the patient.

The outer wall 1004 is relatively thin to provide compliance and/or conformance with the patient's nose to enhance the seal of nasal prong 1070. That is, the thinner outer wall 1004 allows superior sealing due to its ability to conform to the nasal contours. The thicker inner wall 1002 supports the thinner outer wall 1004 as the prong 1070 is inserted and/or engaged with the patient's nose, e.g., so the outer wall 1004 does not collapse. When the prong 1070 is pressurized, the outer wall 1004 conforms to the patient's nose and the inner wall 1002 "floats" under the patient's nose, e.g., spaced from the outer wall 1004. An adequate gap, e.g., 0.75 mm, is provided between the inner wall 1002 and the outer wall 1004 to allow movement of the inner wall 1002 without disturbing the seal of the outer wall 1004. The gap between the inner and outer walls 1002, 1004 may vary around the perimeter of the head portion 1084 in use, e.g., depending on set-up and/or movement during use.

The relatively thin wall thickness, e.g., 0.35 mm, is preferably provided to an outer wall of a dual-wall prong configuration. However, the thin wall thickness may be provided to a nasal prong having a single wall configuration. As noted above, the thin membrane allows superior sealing due to its ability to conform to the patient's nasal contours.

Figure 62B:
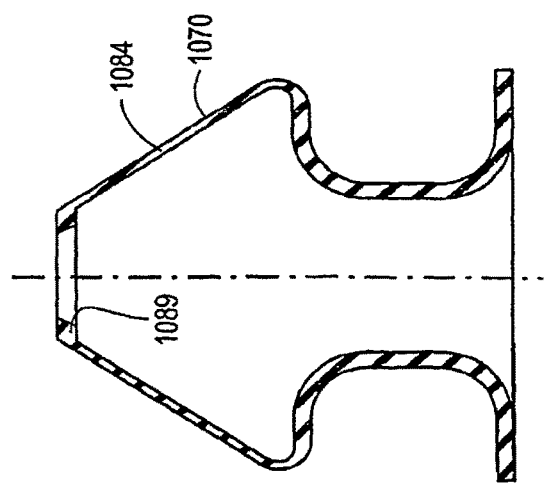
FIG. 62B illustrates a single wall nasal prong having a relatively thin wall thickness with beading around a top section thereof according to an embodiment of the present invention.

For example, a nasal prong having a single wall head portion may have a wall thickness in the range of 0.1 mm to 0.65 mm, e.g., preferably 0.35 mm. In an embodiment, as shown in FIG. 62B, the thin head portion 1084 may include a thicker top section or bead 1089 to prevent excessive flash and/or tearing as the nasal prong 1070 is removed from its mold.

However, the head portion may include other structure to prevent excessive flash and/or tearing. For example, one or more internal ribs may be added to the head portion 1084, e.g., in lieu of or in addition to beading 1089. As shown in FIGS. 57 and 58, ribs 1090 may be provided to a thin, single wall head portion 1084. In another embodiment, a single wall head portion may be provided with a tapered or varying cross-section along its length, e.g., wall thickness tapers from relatively thin to thick.

In an alternative embodiment, instead of a one-piece arrangement, a thin outer membrane may be provided as a separate component that is retro-fit (attached, coupled, glued, etc.) to a single wall nasal prong. For example, a thin outer membrane may be provided to an exterior surface of the head portion and secured in position, e.g., by an elastic ring. The other membrane 1004 need not be made of the same material (e.g., Silicone) as the inner wall 1002, so long as it is patient friendly and compliant.

Figure 70:
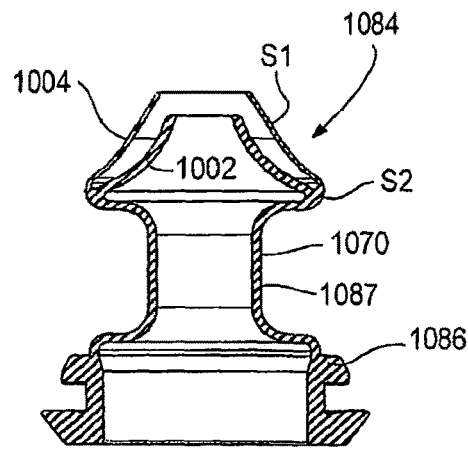

In a preferred embodiment, the head portion 1084 of the dual wall nasal prong includes a substantially straight conical section s1 that ramps down to a relatively large elliptical or curved section s2, e.g., see FIG. 70. The curved section is configured to match the patient's nares opening at the bottom, the conical section improves insertion into the patient's nose, and dual-wall configuration achieves a quicker more effective seal. That is, this profile arrangement has the ability to locate or insert the head portion into the nose easier, which optimizes set-up time. In use, patients may establish a seal about halfway up the head portion. This profile arrangement may also be provided in a single wall nasal prong, e.g., see FIG. 62.

Figure 68:
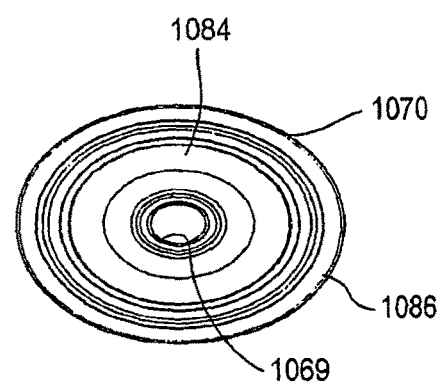
Figure 69:
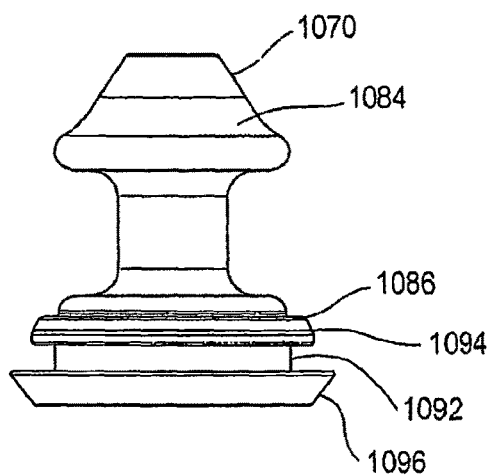

In the illustrated embodiment, the base portion 1086, stalk 1087, head portion 1084, and opening 1069 each include oval or elliptical shapes when viewed in plan view, e.g., see FIG. 68. However, other shapes are possible depending on application, e.g., shape of the patient's nose. For example, the base portion, stalk, head portion, and/or opening may have a circular shape. Also, the nasal prong may be configured such that portions of the prong transition from elliptical to circular shapes, e.g., base portion of the head portion may be generally circular and the head portion and outlet openings may be elliptical and the prong transitions therebetween.

Figure 67:
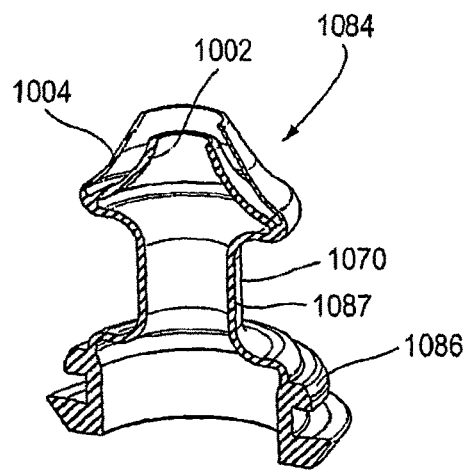
FIGS. 67-70 illustrate a prong including a dual wall according to an embodiment of the present invention.

In the illustrated embodiments, the dual wall nasal prong has an outer wall 1004 that is longer than the inner wall 1002, e.g., see FIGS. 67 and 70. This arrangement may help with sealing and may assist in removal of the dual wall nasal prong from the molding tool. In alternative embodiments, the outer wall 1004 may be of an equivalent length or shorter than the inner wall 1002.

Also, a surface finish may be added to one or more surfaces of the dual-wall nasal prong. The surface finish may help in removing the nasal prong from its molding tool. In addition, the surface finish may help with sealing.

Specifically, a surface finish may be provided on the inner surface of the outer wall 1004 to assist removal of the nasal prong from the tool, e.g., a sliding core. A surface finish provided on the outer surface of the outer wall 1004 may also help removal of the nasal prong from the tool and may assist sealing with the patient's nare. Similarly, a surface finish may be provided on the inner and/or outer surface of the inner wall 1002 to help removal of the nasal prong from the tool. As noted above, beading around the top periphery of the outer wall 1004 may be applied to prevent excessive flash and/or tearing on removal from the tool.

In addition, the molding tool itself may include surface finish, e.g., frosted surface finish, to facilitate removal from the nasal prong. For example, a surface finish may be added to molding tool surfaces that engage the inner surface of the outer wall 1004 and/or the outer surface of the inner wall 1002. However, the entire exterior surface or portions, of the exterior surface of the tool may have a surface finish.

The base portion 1086 of the dual-wall nasal prong is similar to that of the nasal prong having a single-wall, e.g., slot 1092, rounded upper flange 1094, chamfered lower flange 1096, and axial spring section. However, the base of the dual-wall nasal prong may have other suitable constructions, e.g., such as the base shown in FIGS. 55, 56, and 58.

As described above, the nasal prong includes upper and lower trampoline-like bases that provide articulation, a self-adjusting length, and a force for sealing. The trampoline-like base includes two curved sections at the top and bottom thereof, and a straight section at the middle thereof. This structure provides the nasal prong with a form of suspension.

Specifically, the trampoline base detail is provided at both ends of the stalk. The trampoline base detail acts as a universal mechanism to articulate and align the head portion of the pillow to the patient's alar and nasolabial angles, self-adjust the stalk length to suit the patient's nasolabial height, and/or provide a comfortable sealing force to the nares. That is, the trampoline base detail allows rotation of the stalk relative to both the head portion of the pillow and the base portion, and allows reduction in height of the head portion of the pillow relative to the base portion.

FIGS. 70B-1 to 70B-10 illustrate a paired-prong arrangement wherein nasal prongs 1070 are provided as a pair on a single insert. As illustrated, each nasal prong 1070 includes dual-wall head portion such as that described above in FIGS. 67-70. The prongs 1070 are joined at respective base portions by a bridging or connecting strap 1088.

FIGS. 70B-1 to 70B-10 illustrate exemplary dimensions for a paired prong arrangement, e.g., medium size. In the illustrated embodiment, $D_1$ is 10.5 mm, $D_2$ is 22.5 mm, $D_3$ is 33.6 mm, $D_4$ is 38.9 mm, $D_5$ is 41 mm, $D_6$ is 8 mm, $D_7$ is 10.3 mm, $D_8$ is 25.1 mm, $D_9$ is 4.6 mm, $D_{10}$ is 7 mm, $D_1$ is 20.1 mm, $D_{12}$ is 14.2 mm, $D_{13}$ is 9.4 mm, $D_{14}$ is 66.45 mm, and $D_{15}$ is 24.5 mm. Although specific dimensions are provided, it is to be understood that these dimensions are merely exemplary and other dimensions are possible depending on application. For example, the exemplary dimensions may vary by 10-20% or more or less depending on application.

In an embodiment all internal surfaces of each prong 1070 are relatively flash free. In addition, the outer wall 1004 is relatively free from partlines and flash. Also, the free end of the outer wall 1004 is smooth and has a rounded edge, e.g., no sharp edges, and relatively free from flash and tears. Further, the entire paired prong arrangement may be mirror polished, although some selected surfaces may have a non-polished surface finish, e.g., inner surface of outer wall.

In an embodiment, one of the inner and outer walls may be molded in an open position and then inverted to form the dual wall construction. This arrangement simplifies the molding process.

Figure 72:
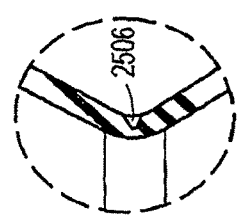
FIGS. 71-77 illustrate a molding process for constructing a prong including a dual wall according to an embodiment of the present invention.
Figure 71:
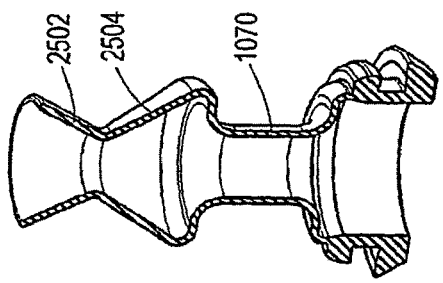
Figure 73:
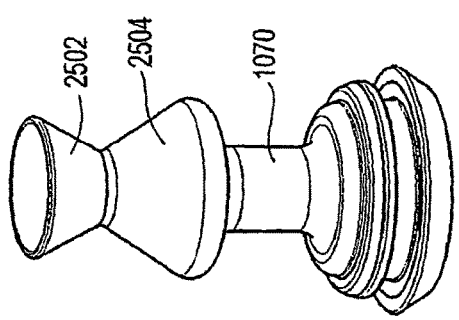
Figure 74:
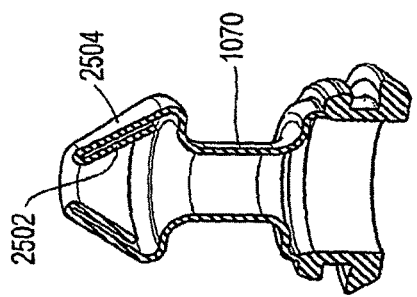
Figure 75:
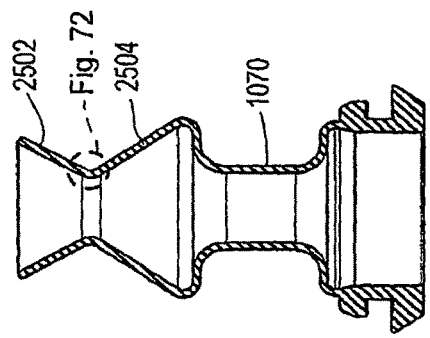
Figure 76:
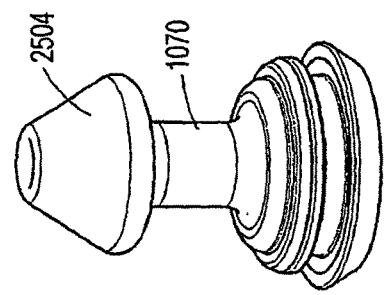
Figure 77:
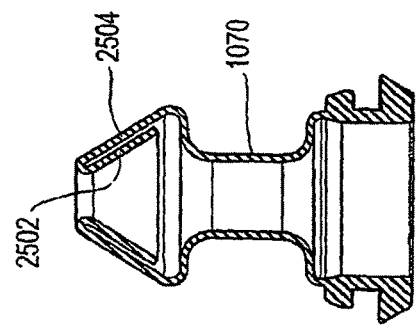

For example, the inner wall 2502 may be molded in an open position (as shown in FIGS. 71-74), and then inverted internally to form the dual wall construction (as shown in FIGS. 75-77). The wall section may be varied to control stiffness/rigidity. For example, one wall (e.g., inner wall 2502) may be thicker than the other, or both walls may be relatively thin. Also, as shown in FIG. 72, an integrated hinge 2506 may be provided between the walls 2502, 2504 to control the fold-over location.

Figure 80:
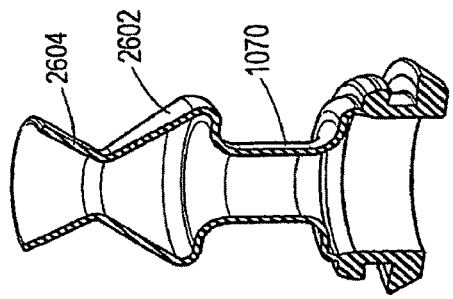
FIGS. 78-83 illustrate a molding process for constructing a prong including a dual wall according to another embodiment of the present invention.
Figure 83:
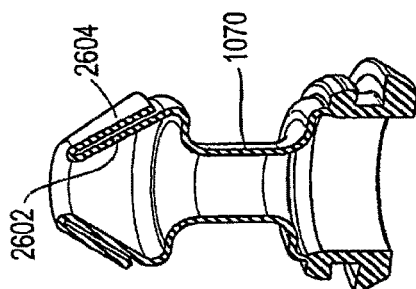
Figure 79:
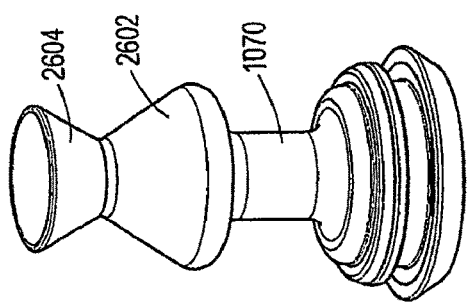
Figure 82:
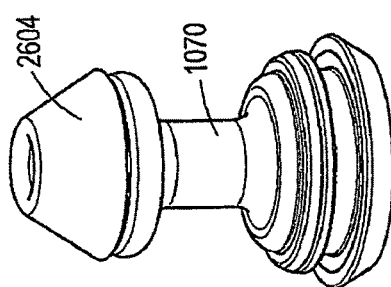
Figure 78:
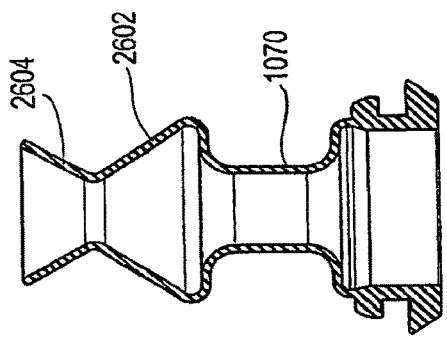
Figure 81:
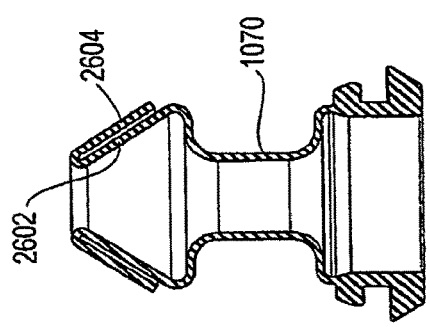

FIGS. 78-83 illustrate an alternative arrangement wherein the outer wall 2604 may be molded in an open position (as shown in FIGS. 78-80), and then inverted externally with respect to the inner wall 2602 to form the dual wall construction (as shown in FIG. 81-83). The wall section may be varied to control stiffness/rigidity (e.g., inner wall 2602 (e.g., 0.7 mm) thicker than outer wall 2604). In an embodiment, the outer wall 2604 acts like a "tacky" filler between the head portion 1084 and the patient's nare.

Figure 84:
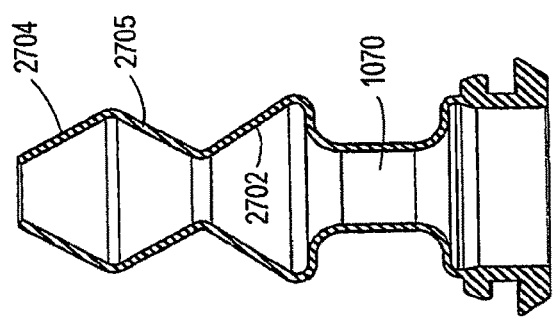
FIGS. 84-89 illustrate a molding process for constructing a prong including a triple wall according to an embodiment of the present invention.
Figure 85:
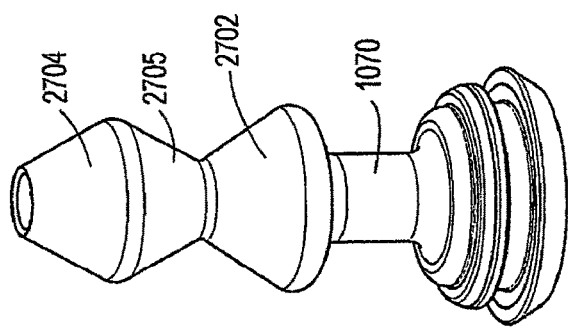
Figure 86:
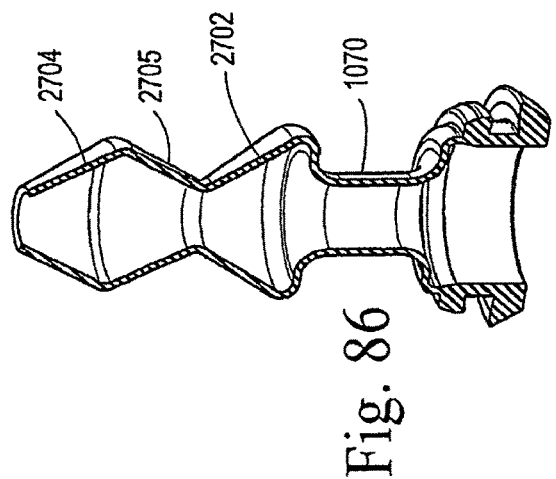
Figure 87:
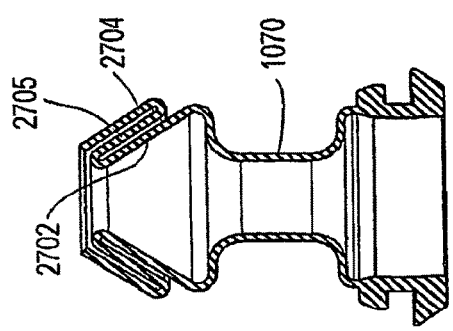
Figure 88:
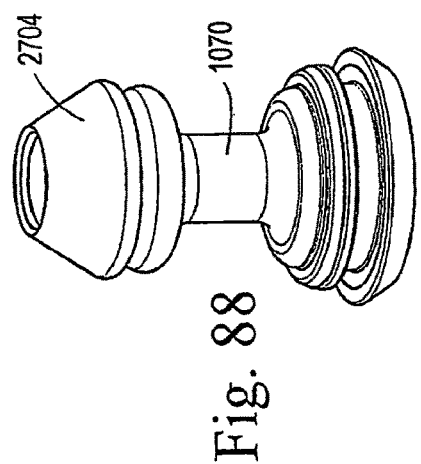
Figure 89:
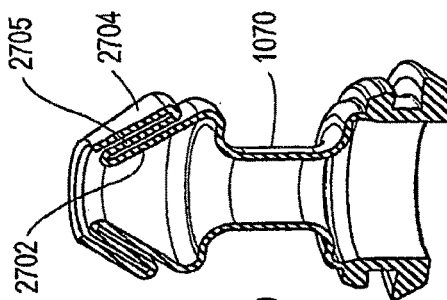

FIGS. 84-89 illustrate a nasal prong 1070 having a triple-wall construction. It should be understood that the nasal prong 1070 may have other suitable multi-wall constructions, e.g., head portion 1084 with two or more walls. As illustrated, first and second outer walls 2704, 2705 may be molded in an open position (as shown in FIGS. 84-86), and then inverted externally with respect to inner wall 2702 to form the triple wall construction (as shown in FIG. 87-89). The wall section may be varied to control stiffness/rigidity. Furthermore, the fold lines may be positioned differently to achieve a different length fold-over portion.

The dual wall arrangement facilitates sealing of the nasal prong in the nares by combining a structure-defining thicker wall with a seal-forming thinner wall. A very thin wall, while suitable for forming a seal, may lack sufficient stiffness by itself to support the necessary structure in use. As discussed above, adding ribs can stiffen a wall otherwise too thin to support itself in use.

The dual-wall nasal prong may be incorporated into other mask systems. For example, the dual-wall nasal prong may be incorporated into a nozzle assembly such as that disclosed in U.S. patent application Ser. No. 10/781,929, filed Feb. 20, 2004, the entirety incorporated herein by reference.

Figure 89B:
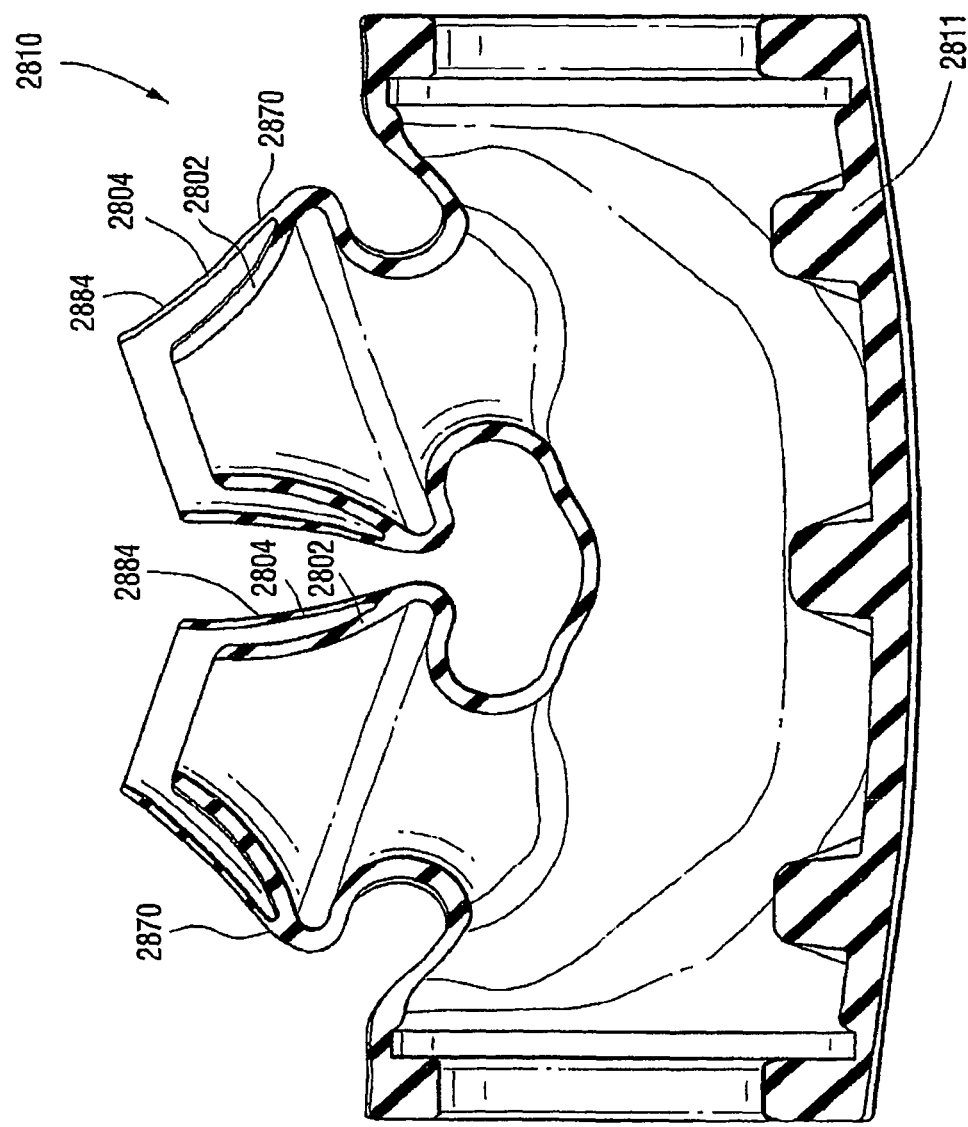
FIG. 89B illustrates a nozzle assembly including a pair of dual-wall nasal prongs according to an embodiment of the present invention.
Figure 90:
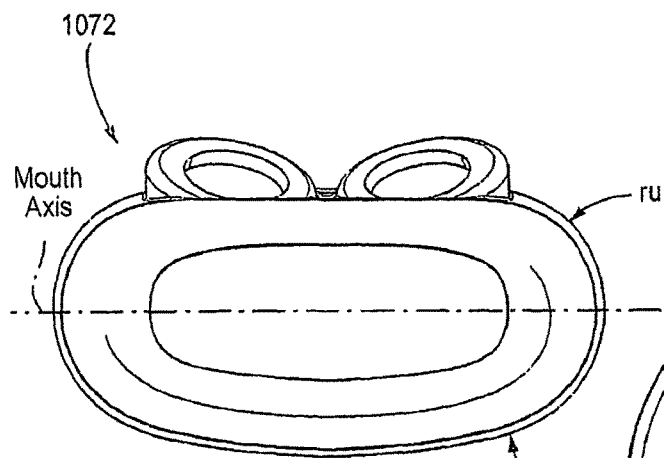
FIG. 90 is a front view of a mouth cushion according to an embodiment of the present invention.
Figure 91:
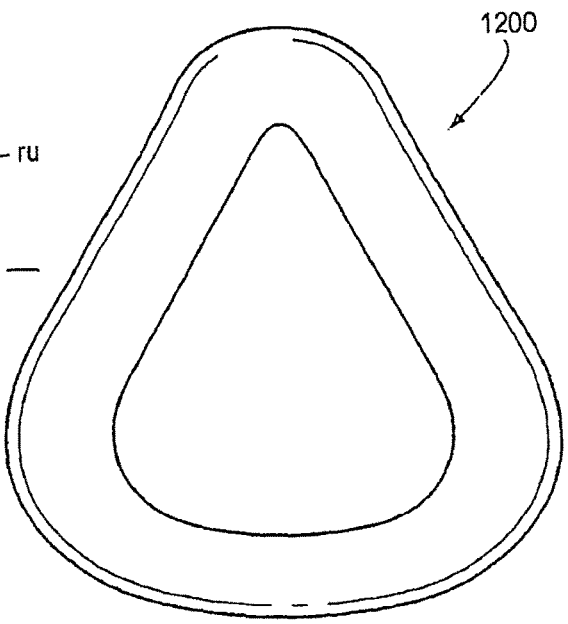
FIG. 91 is a front view of ResMed's full face mask cushion.

FIG. 89B illustrates an embodiment of such an arrangement. As illustrated, the nozzle assembly 2810 includes a base portion 2811 and a pair of dual-wall nasal prongs 2870 provided thereto. The base portion 2811 is adapted to be attached to a frame as described in the '929 application. As described above, each dual-wall nasal prong 2870 includes a head portion 2884 having an inner wall 2802 and an outer wall 2804.

In an embodiment, the outer wall 2804 may have a surface finish applied to improve manufacturability.

§ 4.3 Mouth Cushion

As best shown in FIGS. 94, 96, 106 and 120B-120F, the mouth cushion 1072 includes a non-face-contacting portion 1038 and a face-contacting portion 1040. The non-face-contacting portion 1038 is structured to be removably and replaceably attached to the frame 1074. In the illustrated embodiment, the non-face-contacting portion 1038 includes an arrow-head type design having a tapered end portion 1042 with a sealing lip 1044. The tapered end portion 1042 is adapted to be easily inserted and retained, via a retaining bead 1049, within a channel 1075 provided on the frame 1074 (see FIGS. 121, 167, and 120B-120F). The sealing lip 1044 provides a seal around the perimeter of the cushion 1072 and also retains the cushion 1072 onto the frame 1074. In an embodiment, alignment features, e.g., diamonds or triangles or other details, maybe provided on the cushion 1072 and frame 1074 to aid correct assembly. Cushion attachment to the frame may be similar to that disclosed in U.S. application Ser. No. 10/390,682, which is incorporated herein by reference in its entirety. However, other cushion attachment methods are possible.

The face-contacting portion 1040 of the cushion 1072 includes a side wall 1046, an undercushion 1047 extending away from the side wall 1046, and a membrane 1048 provided to substantially surround the undercushion 1047 and provide a sealing structure for the face-contacting portion 1040. The inner edge of the membrane 1048 defines an aperture that receives the patient's mouth. Also, the side wall 1046 includes spaced-apart prong support structures 1045 that provide annular recesses 1073 adapted to support respective prongs 1070 (e.g., see FIGS. 94, 96, 112, and 113). As illustrated, the prong support structures 1045 provide an angled pedestal that project the prongs at the correct angle to the patient's nares.

§ 4.3.1 Shape of Lower Chin Region in Front and Side Views

Figure 92:
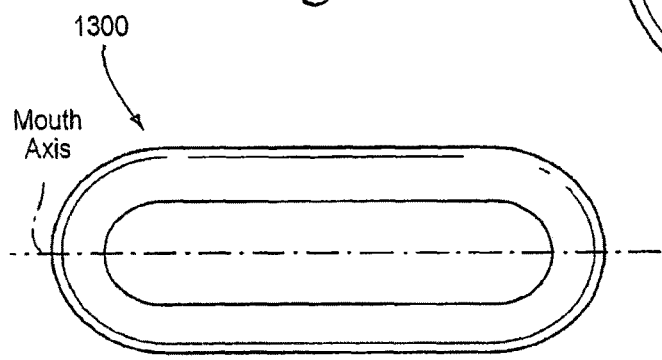
FIG. 92 is a front view of ResMed's mouth mask cushion.

FIGS. 90-98 illustrate the shape of the cushion 1072 with respect to ResMed's full face mask cushion 1200 (shown in isolation in FIGS. 91 and 97) and ResMed's mouth mask cushion 1300 (shown in isolation in FIGS. 92 and 98). As illustrated in the comparison views of FIGS. 93 and 96, the cushion 1072 has a different shape in the lower chin region when viewed from the front and the side.

Figure 93:
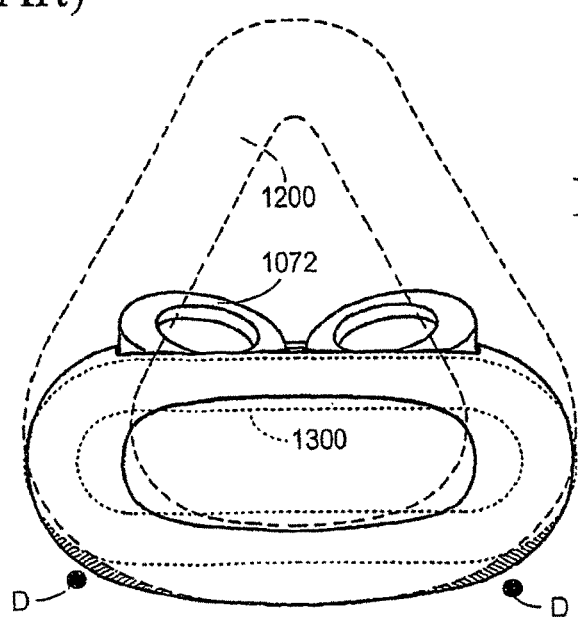
FIG. 93 is a comparison view between cushions of FIGS. 90-92.

Specifically, the cushion 1072 is "squarer" (height to width ratio different) at the lower chin region and lower corners of the patient's mouth (area indicated by dots D) when viewed from the front as shown in FIG. 93, as compared to ResMed's full face mask cushion 1200 which is more curved. This shape of the cushion 1072 covers more of the lower chin region as indicated by the hatched region in FIG. 93. Also, this shape of the cushion 1072 better accommodates variations in facial curvature in the chin region based on anthropometric data. Further, this shape of the cushion 1072 seals around deep lines radiating from the mouth often found on older patients. This provides a better seal when mouth movements occur during sleep. This change in shape in the lower chin region (area indicated by dot D) is also illustrated when viewed from the side as shown in FIG. 96.

In addition, the cushion 1072 is asymmetric about the axis of the mouth (see FIG. 90), whereas ResMed's mouth mask cushion 1300 is symmetrical about the axis of the mouth (see FIG. 92). Also, the cushion 1072 has a smaller outer radius in the chin region (shown as rl in FIG. 90) than the outer radius in the upper lip region (shown as ru in FIG. 90).

Figure 100:
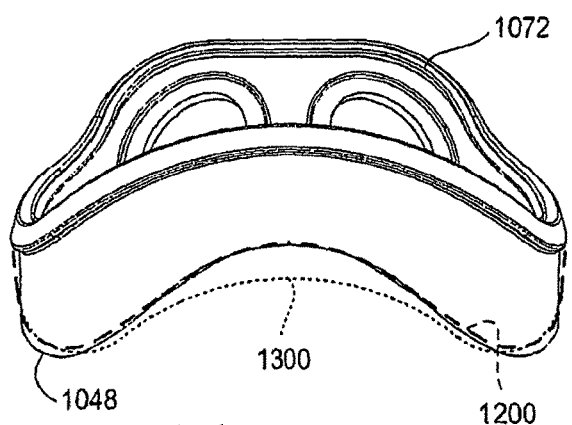
Figure 103:
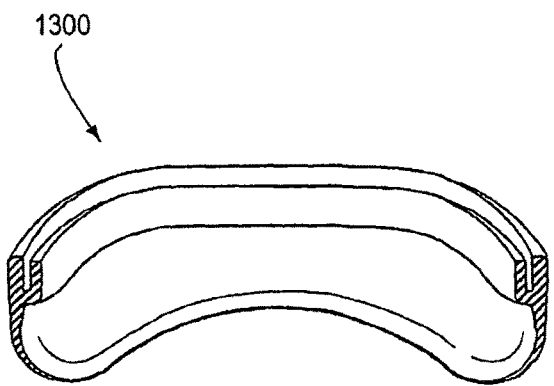
FIG. 103 is a bottom cross-sectional view of ResMed's mouth mask cushion.

§ 4.3.2 Shape of Membrane at Lower Chin and Upper Lip Regions in Top and Bottom Views FIGS. 99-103 illustrate the shape of the cushion 1072 with respect to ResMed's full face mask cushion 1200 (shown in isolation in FIG. 102) and ResMed's mouth mask cushion 1300 (shown in isolation in FIG. 103). As best shown in the comparison views of FIGS. 99 and 100, the membrane 1048 of the cushion 1072 is similar in curvature at the chin and upper lip regions when compared to ResMed's full face mask cushion 1200 at the chin area. The curvature of the cushion membrane 1048 at the chin (when viewed from the bottom as shown in FIG. 100) is substantially similar or the same as the curvature of the cushion membrane 1048 at the upper lip region (when viewed from the top as shown in FIG. 99).

Figure 101:
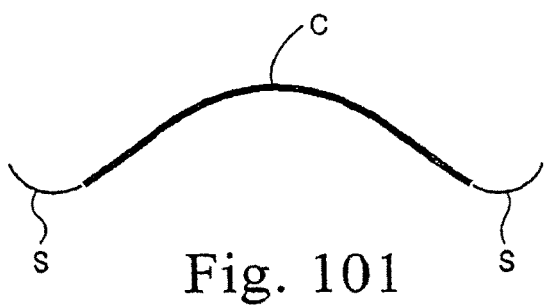
FIG. 101 illustrates a membrane curvature of the mouth cushion shown in FIG. 90.
Figure 102:
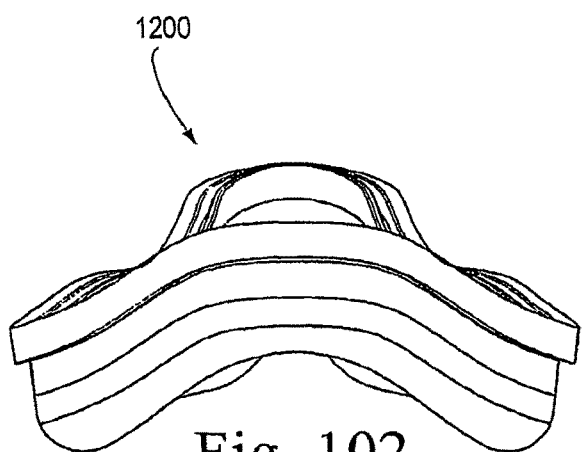
FIG. 102 is a bottom view of ResMed's full face mask cushion.

As shown in FIG. 101, this curvature of the cushion membrane 1048 includes a concave parabolic center region C and two convex curved side regions S joined to the side walls of the cushion 1072. This arrangement is in contrast to the curvature of ResMed's mouth mask cushion 1300 which is defined by a shallower radius (see FIGS. 99 and 100).

§ 4.3.3 Shape of Undercushion in Top and Bottom Views

Figure 107:
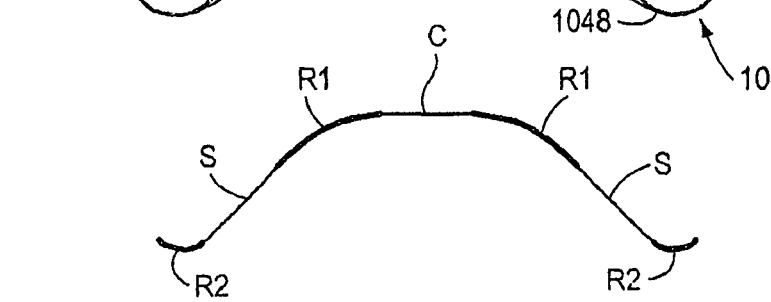
FIG. 107 illustrates an undercushion curvature of the mouth cushion shown in FIG. 90.
Figure 108:
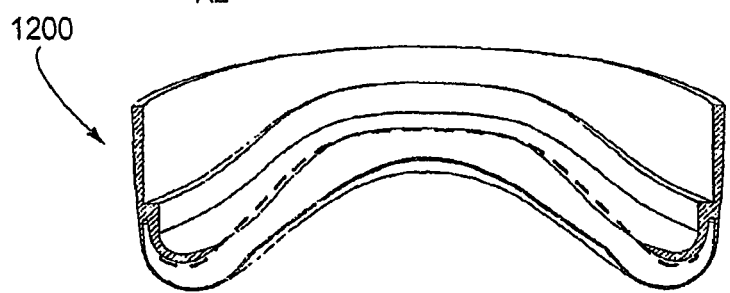
FIG. 108 is a cross-sectional view of ResMed's full face mask cushion.

FIGS. 104-108 illustrate the shape of the undercushion 1047 with respect to ResMed's full face mask cushion 1200 (shown in isolation FIG. 108). ResMed's mouth mask cushion 1300 does not include an undercushion. As illustrated in the comparison views of FIGS. 104 and 106, the undercushion 1047 is the same or similar in curvature at the chin and upper lip regions to ResMed's full face mask undercushion 1200.

Figure 104:
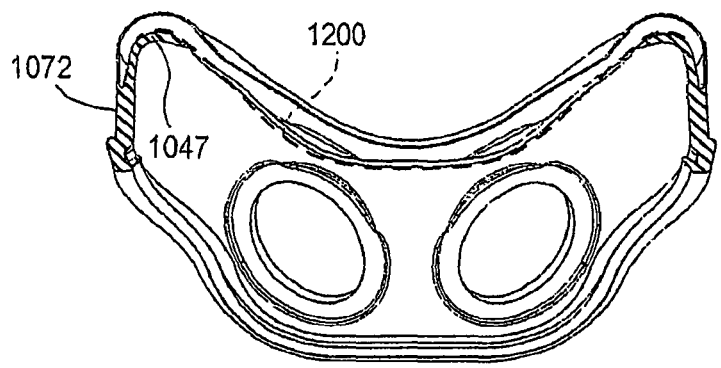
FIGS. 104-106 are cross-sectional views through the mouth cushion shown in FIG. 90, and illustrate comparison between cushion shown in FIG. 108.
Figure 105:
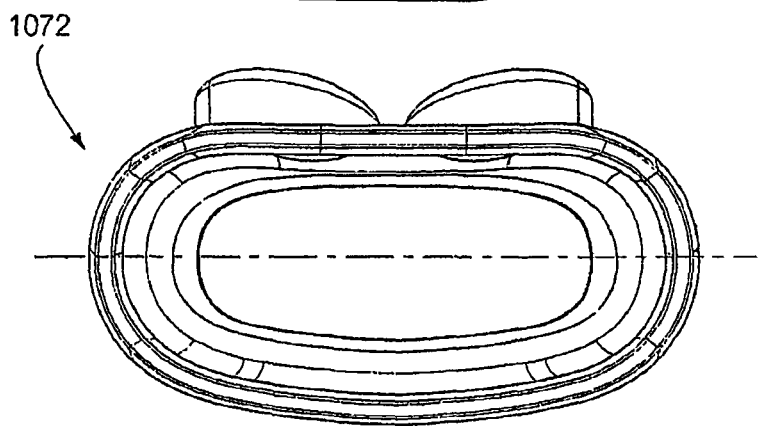
Figure 106:
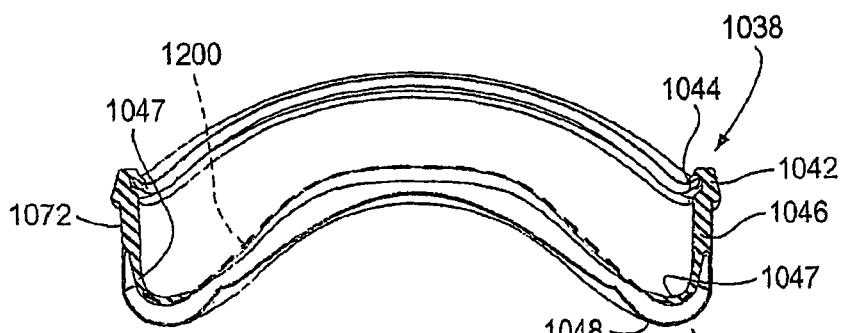

The curvature of the undercushion 1047 at the chin region (as viewed from the bottom in FIG. 106) is the same or similar to the curvature of the undercushion 1047 at the upper lip region (as viewed from the top in FIG. 104). This curvature is illustrated in FIG. 107 and includes a substantially flat center portion C and angled side portions S. The center and side portions are joined together by curved/radii portions R1. The side portions S merge into a second smaller radius R2 where the cross-sectional cut has been made.

§ 4.3.4 Width of Undercushion and Membrane at Upper Lip and Chin Regions

Figure 109:
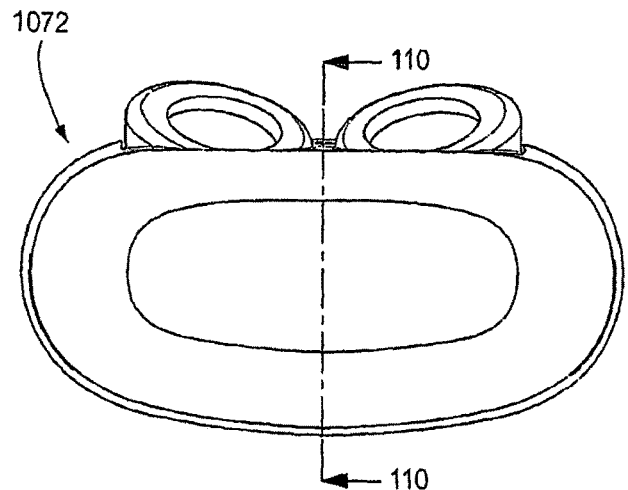
FIGS. 109-111 illustrate the width of the mouth cushion shown in FIG. 90.
Figure 110:
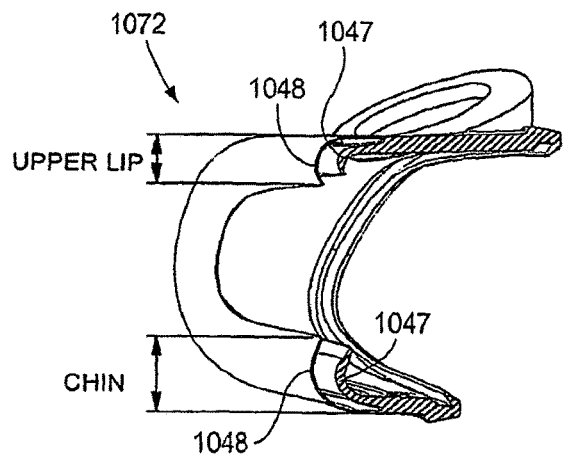
Figure 111:
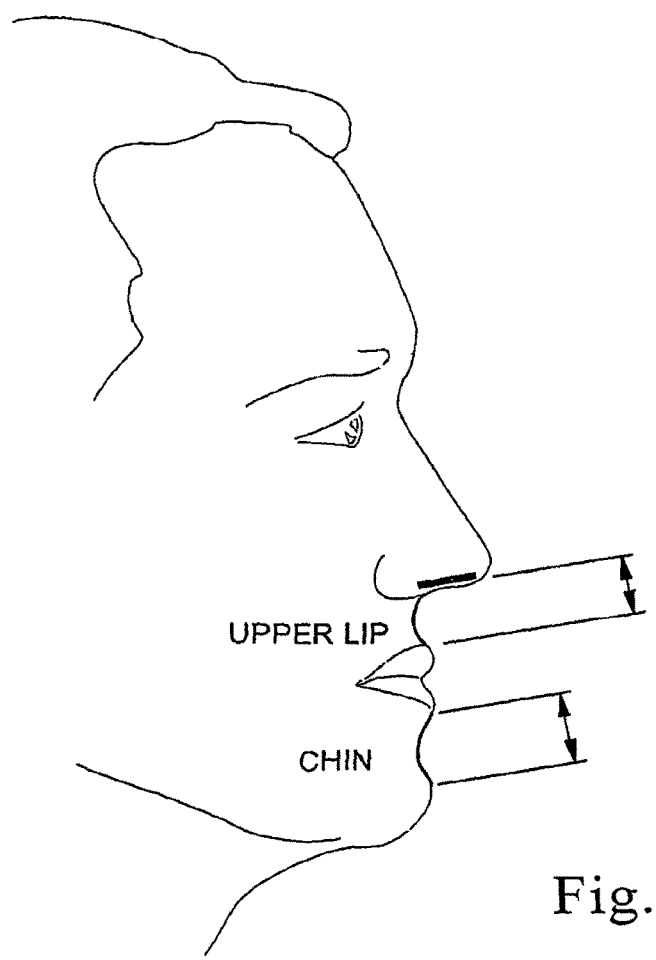

As shown in FIGS. 109-110, the width of the undercushion 1047 and the membrane 1048 at the upper lip region is less than the width of the undercushion 1047 and the membrane 1048 at the chin region. The width of the undercushion 1047 in the upper lip region is smaller such that it fits in the relatively narrow region between the nares and the upper lip (see FIG. 111) and anthropometric variations in patient population.

Figure 111B:
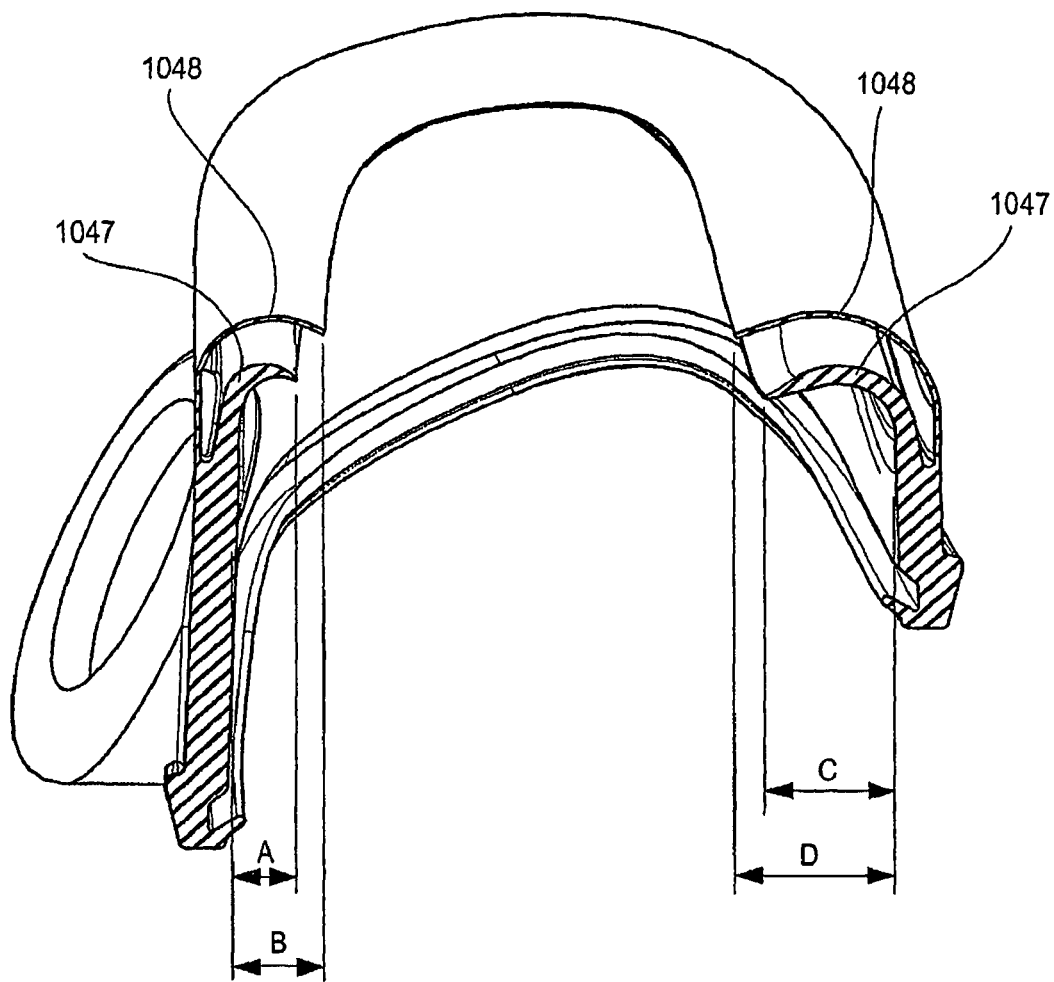
FIG. 111B illustrates exemplary widths of the mouth cushion shown in FIG. 110.

In an embodiment, the width of the undercushion 1047 and membrane 1048 at the upper lip is between 20% to 80% of the width of the undercushion 1047 and membrane 1048 at the chin region. For example, as shown in FIG. 111B, dimension A may be about 4 mm, dimension B may be about 6 mm, dimension C may be about 8.8 mm, and dimension D may be about 11 mm. These dimensions may be similar for small and large size cushions. Although specific dimensions are provided, it is to be understood that these dimensions are merely exemplary and other dimensions are possible depending on application. For example, the exemplary dimensions may vary by 10-20% or more or less depending on application.

§ 4.3.5 Cushion Wall Cross-Section

As shown in FIGS. 112-119, the cross-section of the cushion 1072 varies along the perimeter of the cushion 1072. In the illustrated embodiment, there are three distinct cross-sections that define the shape of the membrane 1048 and undercushion 1047 along their perimeters. As illustrated, cross-sections A, B, and C are provided in upper lip, side, and chin regions of the cushion 1072. It is noted that the cross-section B is symmetrical on both sides of the cushion 1072. However, alternative embodiments may utilize more than three cross-sections.

Elements that define each cross-section A, B, and C (for both the undercushion 1047 and the membrane 1048) include angles $\beta$ and $\alpha$ between the cushion side wall 1046 and the tip of the undercushion 1047 and the tip of the membrane 1048, respectively (see FIG. 117), widths $W_1$ and $W_2$ from the cushion side wall 1046 to the tip of the undercushion 1047 and membrane 1048, respectively (see FIG. 118), heights $H_1$ and $H_2$ from the top of the cushion side wall 1046 to the tip of the undercushion 1047 and membrane 1048, respectively (see FIG. 119), and radii r1 and r2 between the cushion side wall 1046 and the tip of the undercushion 1047 and membrane 1048, respectively (see FIG. 118). The undercushion 1047 and membrane 1048 of the illustrated embodiments also include straight portions s1 and s2, respectively, at some cross-sections. However, other elements maybe included to define each cross-section.

In an embodiment, the shape or profile of the cushion 1072 may be defined by three points selected at common points of each of the three cross-sections. At each of the three points, x, y, and z coordinates are defined, where x dimensions are measured from an anthropometrical datum, y dimensions are measured from a vertical symmetry line, and z dimensions are measured from the cushion height. The shape of the cushion 1072 smoothly varies between the three points along its perimeter.

§ 4.4 Frame

As best shown in FIGS. 120-124 and 167, the frame 1074 includes a main body 1076 having a side frame portion 1078 on each lateral side thereof. The main body 1076 includes an aperture 1080 and a flanged collar member 1082 that surrounds the aperture 1080. The elbow assembly 1014 is coupled to the flanged collar member 1082 in a manner as described below. The frame 1074 also includes the channel 1075 for retaining the cushion 1072 as described above.

In the illustrated embodiment, a vent assembly 1079 is provided in each side frame portion 1078. of the frame 1074 for $CO_2$ washout. The vent assembly may be configured such as those disclosed in U.S. Provisional Patent Application No. 60/795,615, entitled "Nasal Assembly" and filed Apr. 28, 2006, which is incorporated herein by reference in its entirety. However, one or more vent openings may be provided in the swivel elbow 1014 for $CO_2$ washout.

As shown in FIGS. 124B-124I, the vent assembly 1079 is provided in each side frame portion 1078 of the frame 1074, adjacent the upper anchors 1041 described below. Each vent assembly 1079 includes an array or pattern of relatively small holes 1011 arranged in a plurality of columns, e.g., 3-10 columns, and in the example illustrated, 5 columns. The 5 columns are vertically staggered with respect to one another. Also, the first hole in each column cooperate to form an axis A that is angled at an angle .alpha. (when viewed from the front as shown in FIG. 124E) of about 15-35.degree., e.g., 25.degree., with respect to vertical axis V. As best shown in the side view of FIG. 124G, each hole is provided along a plane P (approximate plane shown in FIG. 124G due to frame angle in side view) that forms an angle .beta. of about 20-40.degree., e.g., 30.degree., with respect to vertical axis V. As shown in the bottom view of FIG. 124H, each hole has a longitudinal axis L that is angled at an angle of about −10.degree. to 45.degree., e.g., 0.degree., with respect to transverse axis T. Each column includes 2-6 holes, e.g., 4 holes. In the illustrated embodiment, each hole 1011 has a generally part conic shape, including opposed walls that converge from a larger diameter to a smaller diameter, as viewed in the direction of exhausted gas. The smaller diameter may be about 0.7 mm, the larger diameter may be about 1 mm, the included angle of the cone may be about 10.degree. and the height of the cone may be about 1.7 mm. However, other vent arrangements are possible.

As illustrated, the holes 1011 are located away from the aperture 1080 to avoid air flow interference. Also, the holes 1011 are located near headgear attachment points where the frame 1074 is relatively flat to the users face for the anchor structures. In addition, the holes 1011 are positioned on relatively flat portions of the frame 1074 so that air may be vented perpendicularly from the general plane of the patient's face to avoid air jetting towards a bed partner. Thus, this vent arrangement optimizes mask operation and is synergistic in that it utilizes an area of the frame 1074 which is relatively flat to the patient's face for two purposes, i.e., anchor structure and perpendicular venting. Aesthetics of the frame 1074 are also improved significantly by reducing the number of relatively flat areas that are provided on the frame 1074.

§ 4.4.1 Anchor Points for Headgear Assembly

Each side frame portion 1078 includes upper and lower anchors 1041, 1043 for attaching the headgear assembly 1018. As best shown in FIGS. 120-124 and 167, each upper anchor 1041 is in the form of a female connector that provides a slot opening 1062, and each lower anchor is in the form of a clip receptacle 1071. Attachment of the frame 1074 to the headgear assembly 1018 will be described in greater detail below.

Figure 120:
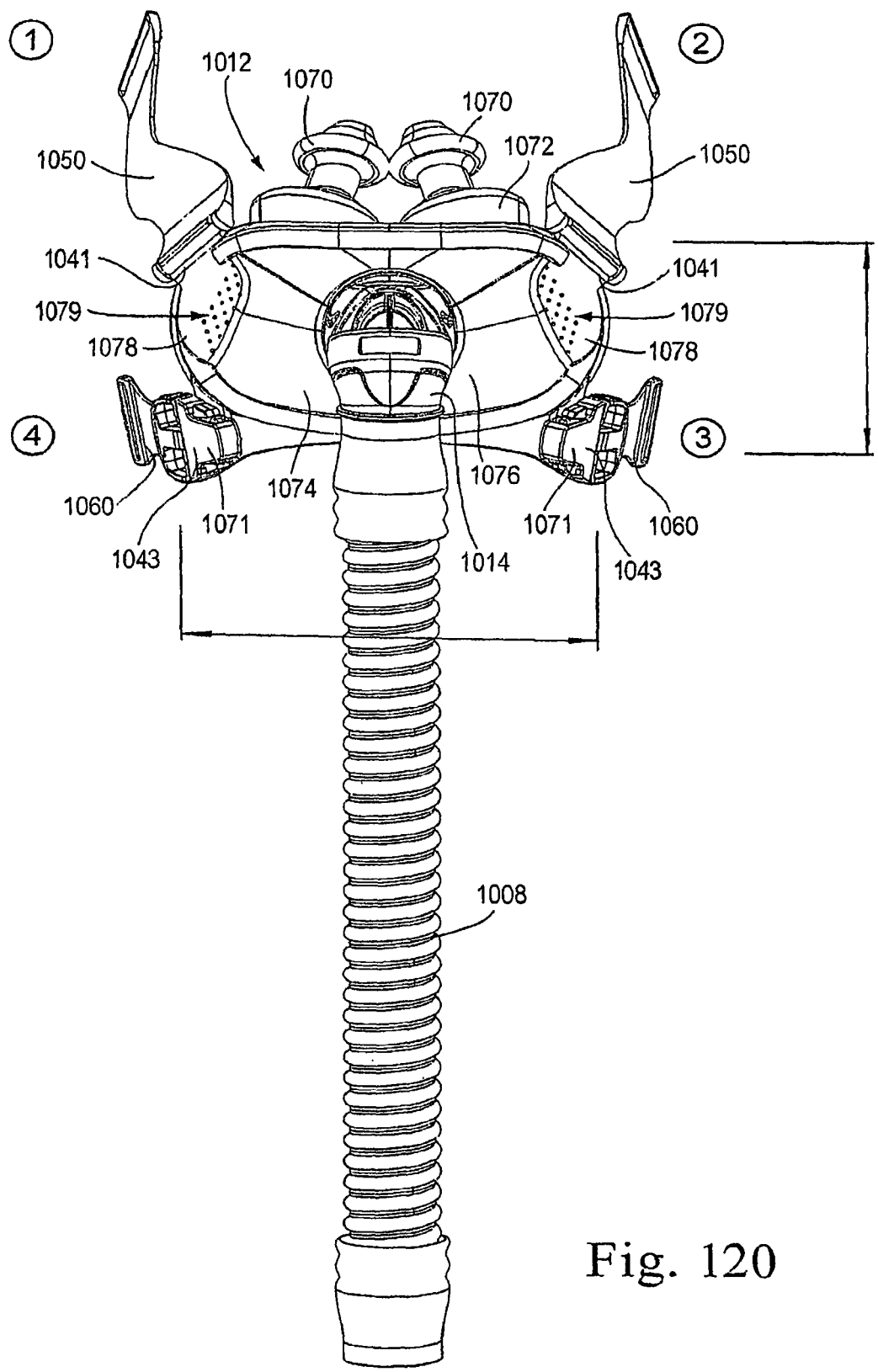
FIG. 120 illustrates a frame and upper and lower stabilizing elements of the mask system shown in FIG. 48.
Figure 120B:
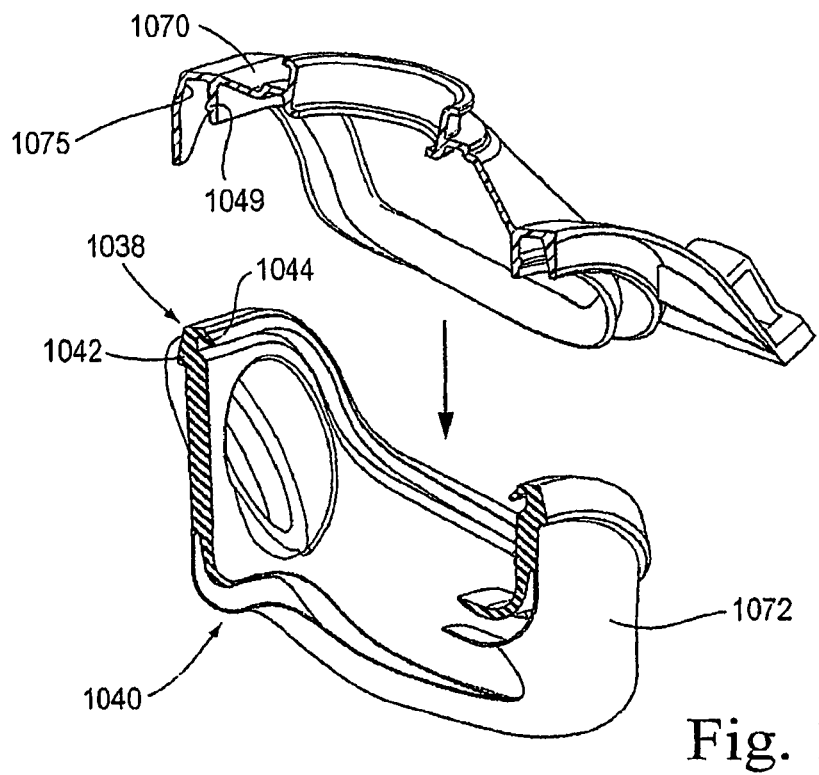
FIGS. 120B-120F illustrate cushion attachment to the frame.
Figure 120C:
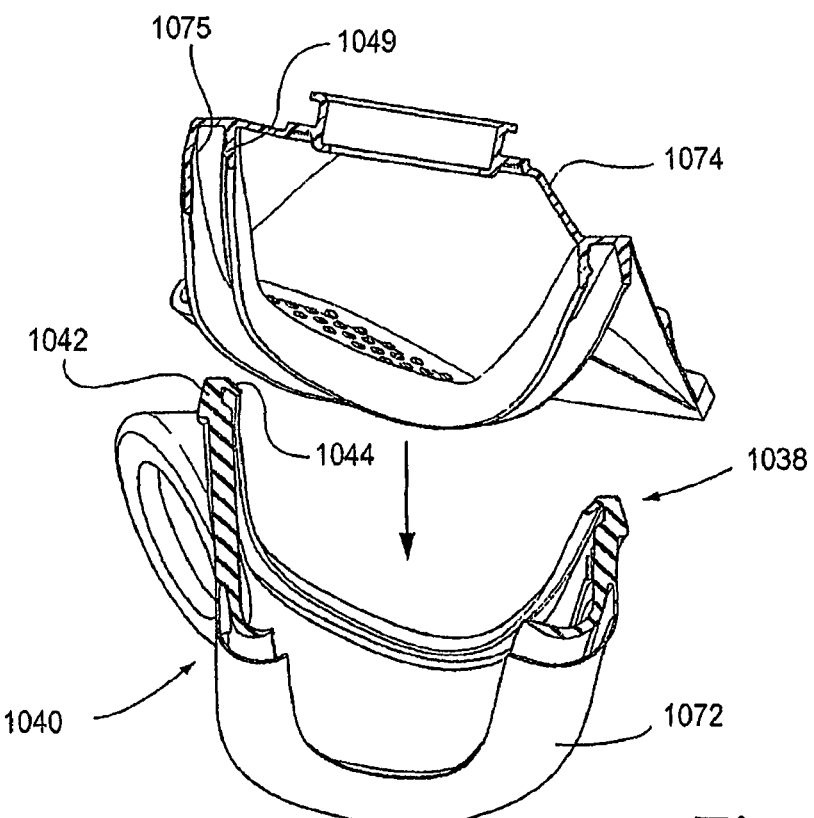
Figure 120E:
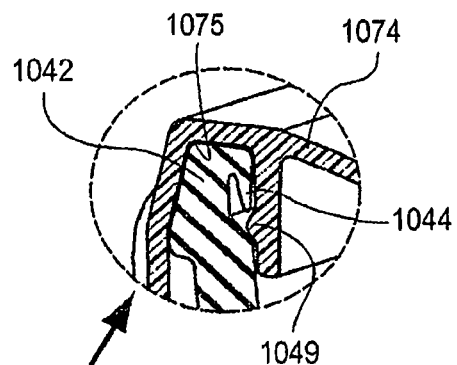
Figure 120D:
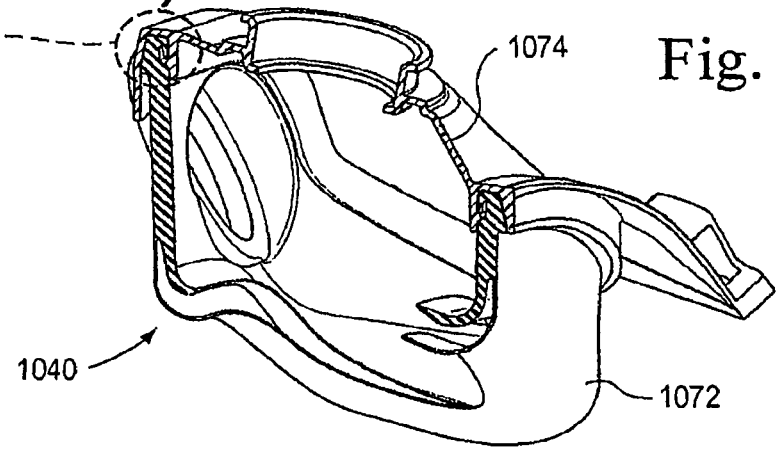
Figure 120F:
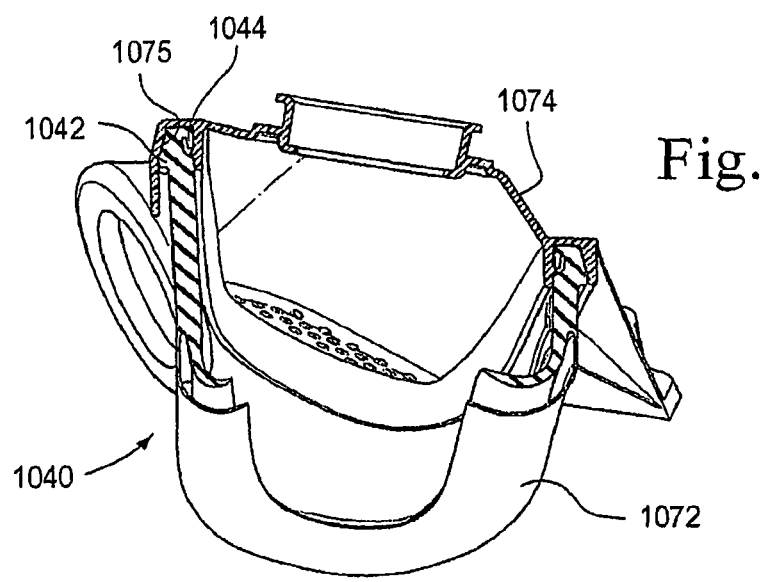
Figure 121:
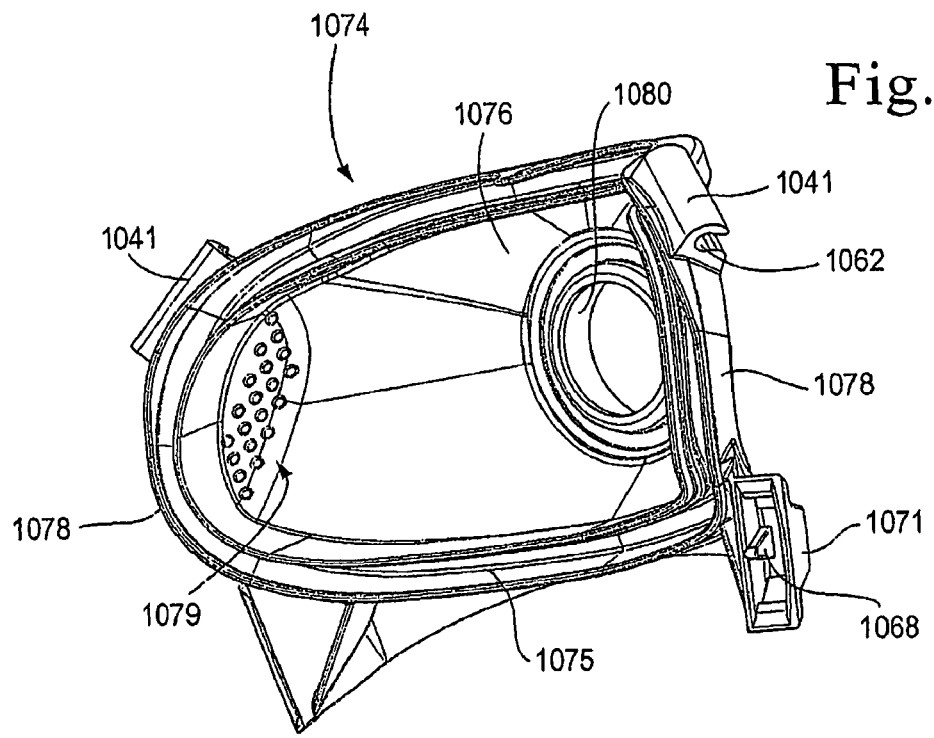
FIGS. 121-124 illustrate other views of the frame and upper and lower stabilizing elements.
Figure 167:
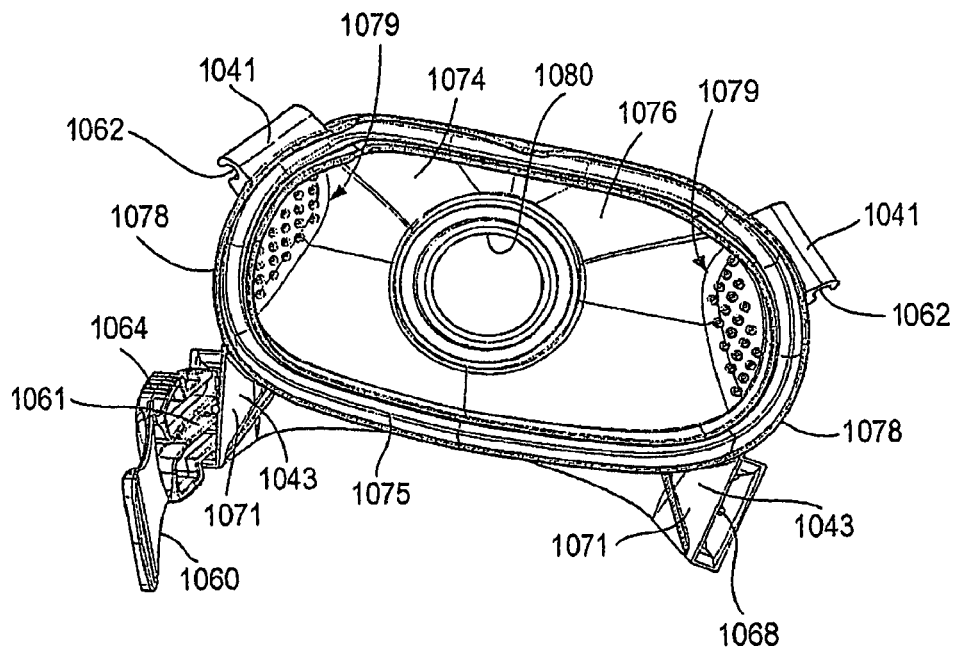
FIGS. 167-170 illustrate assembly of the lower stabilizing element shown in FIGS. 159-166 to clip receptacles provided on the frame.
Figure 168:
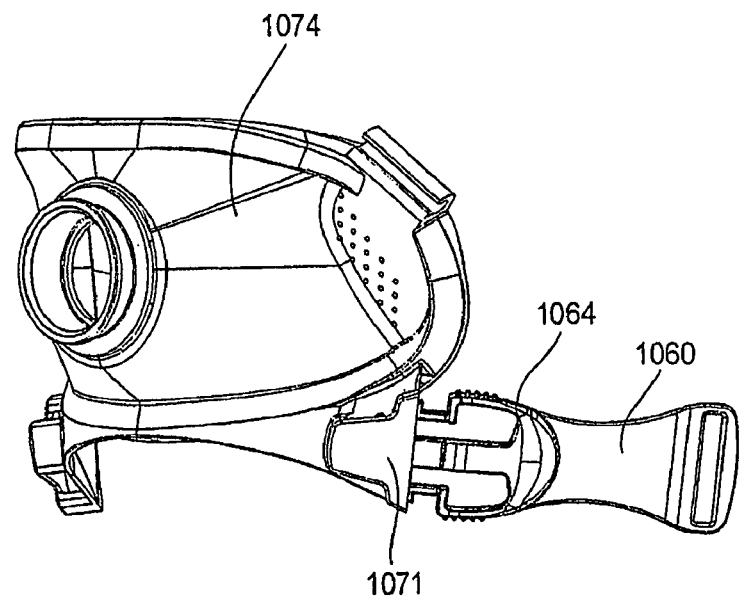
Figure 169:
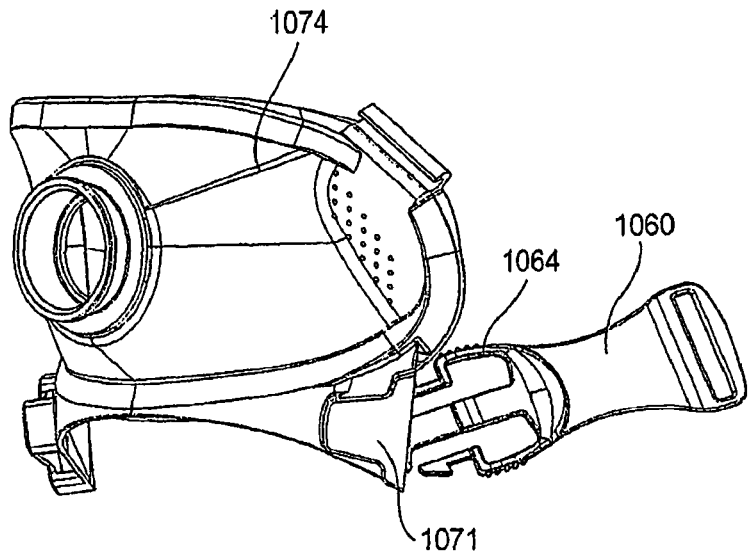
Figure 170:
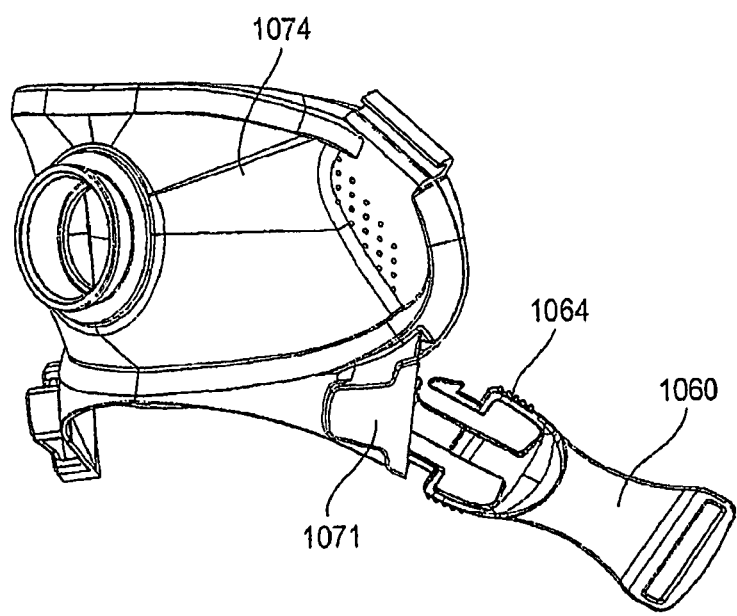

The frame 1074 provides four anchor points (as shown in FIGS. 120 and 167) for securing the mask system 1010 onto the patient's face. As illustrated, the anchor points are located at the vertical and horizontal extremities of the frame 1074 to provide maximum stability by acting as "outrigger" elements.

§ 4.5 Elbow Assembly

As shown in FIGS. 125-140, the elbow assembly 1014, e.g., swivel elbow, includes an elbow 1051, an anti-asphyxia valve (AAV) 1052, and a clip member 1053 to secure the AAV 1052 to the elbow 1051.

Figure 155:
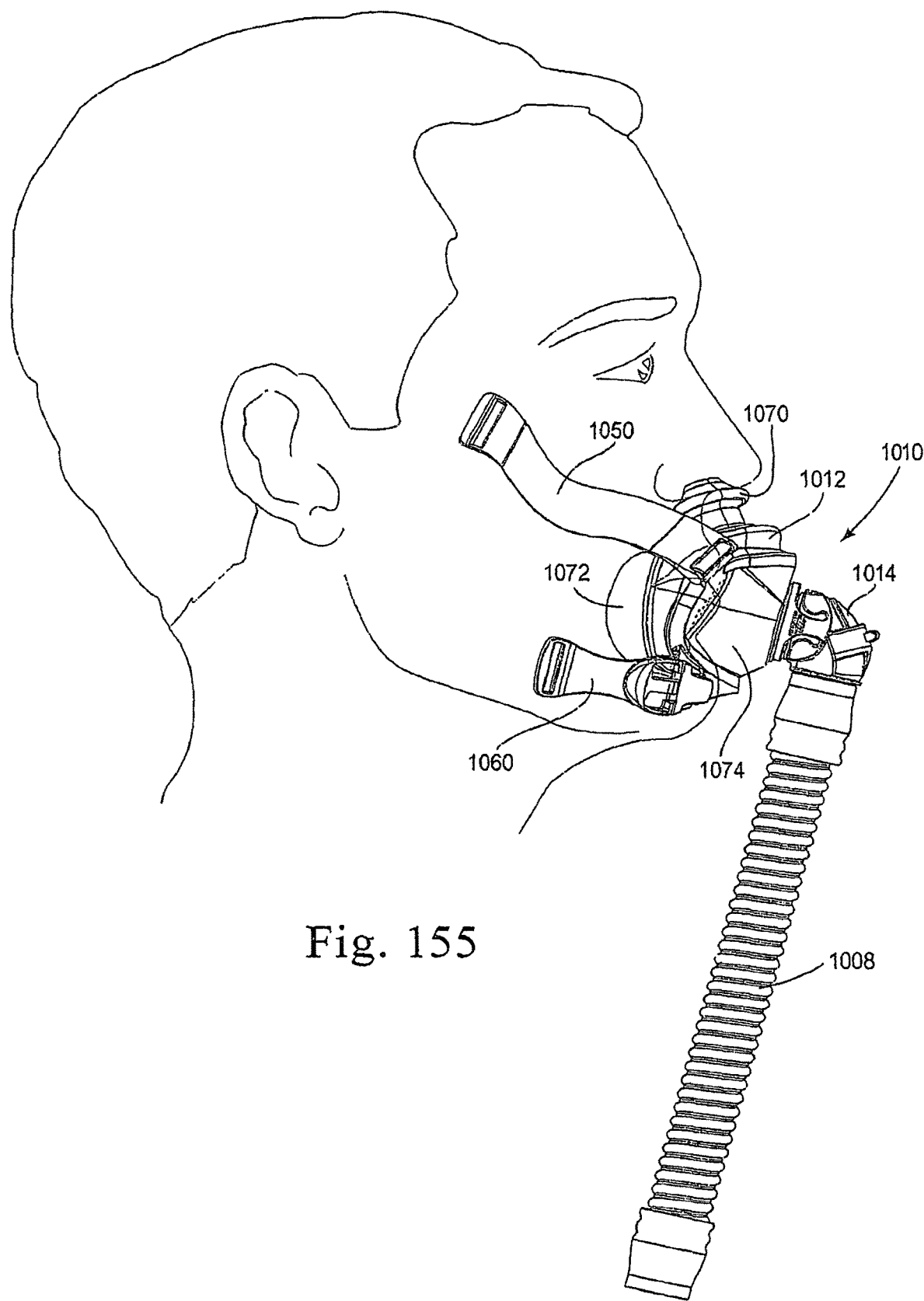
FIG. 155 illustrates the mask system shown in FIG. 48 with upper and lower stabilizing elements positioned on a patient's face.

The elbow 1051 includes a first portion 1081 connectable to the frame 1074 and a second portion 1083 connectable to an air delivery tube 1008 (see FIGS. 48, 155, and 120). The first portion 1081 of the elbow 1051 is releasably connected to the flanged collar member 1082 of the frame 1074 in a snap-fit manner as is known from U.S. Patent Application Publication No. 2003/0196656, which is incorporated herein by reference in its entirety.

The elbow 1051 also includes a slot 1091 to receive the AAV 1052, a port 1093 that is selectively closed by a flap portion 1063 of the AAV 1052 (depending on the presence of pressurized gas), and two recesses or protrusions (not visible) for attaching the clip member 1053 with a snap-fit.

The AAV 1052 interlocks with the clip member 1053 to provide a sub-assembly that is removably attached to the elbow 1051 with a snap-fit. Specifically, the AAV 1052, e.g., constructed of flexible silicone or other elastic material, includes an arrowhead-shaped protrusion 1095 that removably interlocks with a slot 1097 provided on the clip member 1053, e.g., constructed of rigid plastic. As illustrated, the inside edges of the slot 1097 are filleted to allow for easier assembly of the AAV 1052. In addition, the arrowhead shape of the protrusion 1095 facilitates assembly. However, the inside edges of the slot 1097 may have a conical fillet or chamfer, for example, to facilitate assembly. Also, the protrusion 1095 of the AAV 1052 may have a filleted, curved, chamfered, or tapered end to facilitate assembly.

The clip member 1053 includes two tabs 1099 that interlock with respective recesses/protrusions (not shown) provided to the elbow 1051. In addition, the clip member 1053 includes structure to prevent incorrect assembly of the AAV 1052 to the elbow 1051.

Figure 140:
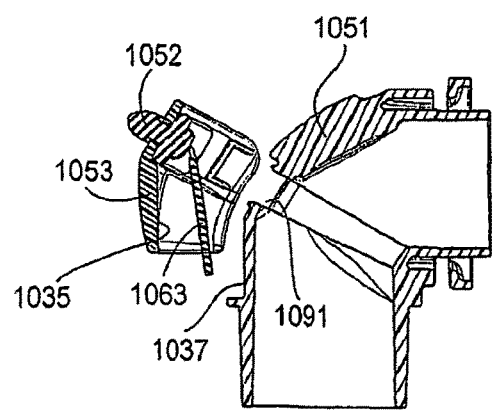

Specifically, the clip member 1053 includes recessed sides 1033 and a central vertical rib 1035 integrally molded with the clip member 1053. When the clip member 1053 is assembled to the elbow 1051, the recessed sides 1033 and central vertical rib 1035 are located against the elbow outer surface 1037, e.g., flush against the elbow outer surface, to prevent the AAV 1052 from being assembled between the clip member 1053 and the elbow 1051. For example, if the clip member 1053 is assembled to the elbow 1051 with the AAV 1052 in an incorrect orientation (as shown in FIG. 140 and in dashed lines in FIGS. 137 and 138), the flap portion 1063 of the AAV 1052 will be positioned between the central vertical rib 1035 and the elbow outer surface 1037, which prevents the clip member 1053 from interlocking with the elbow 1051. It would then be evident to a user that the AAV 1052 had not been correctly installed.

In addition, as shown in FIG. 140, the flap portion 1063 of the AAV 1052 is longer than the clip member 1053 is wide such that if the AAV 1052 is incorrectly assembled, the flap portion 1063 will extend outside of the clip member 1053 and thereby provide a visual and tactile cue to the patient that the AAV 1052 has been incorrectly assembly to the elbow 1051.

In an embodiment, material, e.g., wall thickness, surrounding the port 1093 of the elbow 1051 may be cut-away to reduce material. However, sufficient material is maintained to allow surface area for engaging the flap portion 1063 of the AAV 1052 in use.

Alternative embodiments of the elbow assembly 1014 are disclosed in PCT Application No. PCT/AU2006/000031, which is incorporated herein by reference in its entirety.

§ 4.6 Headgear Assembly

As best shown in FIGS. 141-154, the headgear assembly 1018 includes an upper headgear section 1020 and a lower headgear section 1030 that is attached to the upper headgear section 1020. Upper stabilizing elements 1050 are provided between the upper headgear section 1020 and the frame 1074, and lower stabilizing elements 1060 are provided between the lower headgear section 1030 and the frame 1074.

The headgear assembly preferably includes elastic straps, e.g., a pair of upper and a pair of lower elastic straps, and preferably includes the rigid or semi-rigid stabilizing elements. The stabilizing elements may be separate from the elastic straps, may comprise a sub-assembly with the elastic straps, or may form part of the mask frame In any event, the headgear assembly defines a sealing force vector having sufficient magnitude and direction to effect a seal against both the mouth and lower nasal region.

Unlike prior art mask systems including a nasal mask alone, nasal prongs alone, or a full-face mask, the mask system 1010 provides a sealing force against two surfaces which are almost at right angles to one another, namely the mouth and the nares. The headgear straps and stabilizing elements are configured and arranged to achieve sufficient sealing force components in both directions. The headgear of prior art masks typically only provide a sealing force in one direction or substantially in one direction.

The magnitude of the sealing force relates to several factors including the elasticity of the headgear straps and how tightly they are tightened. The direction of the sealing force relates to where the headgear strap is attached to the frame and where it engages with the patient's head.

The upper straps connect to upper stabilizing elements that in turn connect to the mask frame in a region which in use lies generally between the nose and mouth. In use, the upper straps pass over the patient's temples and connect with a rear headgear portion that generally engages the occiput of a patient's head. The upper stabilizing elements allow a sufficient force component to seal with the nares without obscuring the vision of the patient.

Furthermore, by engagement with rigid or bony regions of the patient's skull and avoiding non-rigid (e.g., muscle and tendon), the seal provided by the headgear assembly 1018 is less likely to be disrupted by movement of the patient's head.

§ 4.6.1 Headgear Sections

As shown in FIGS. 141, the upper headgear section 1020 includes upper straps 1022, bridge straps 1024, and front crown straps 1026. The free end of each upper strap 1022 includes a tab of Velcro® material 1028 for use in securing the upper stabilizing elements 1050 to the upper headgear section 1020 (see FIG. 143). The Velcro® tab 1028 may be secured to the upper strap 1022 by ultrasonic welding, for example. In the illustrated embodiment, the bridge straps 1024 are formed, e.g., punched, from the same piece of material as the upper straps 1022 and the front crown straps 1026 such that the bridge straps 1024 are separated from respective upper straps 1022 as shown in FIG. 141. Then, the bridge straps 1024 are attached to respective upper straps 1022 to form a three-dimensional shape. This arrangement is similar to that shown in FIG. 4d.

As shown in FIG. 142, the lower headgear section 1030 includes lower straps 1032 and rear crown straps 1034. The free end of each lower strap 1032 includes a tab of Velcro® material 1036 for use in securing the lower stabilizing elements 1060 to the lower headgear section 1030 (see FIG. 143). The Velcro® tab 1036 maybe secured to the lower strap 1032 by ultrasonic welding, for example.

Figure 144:
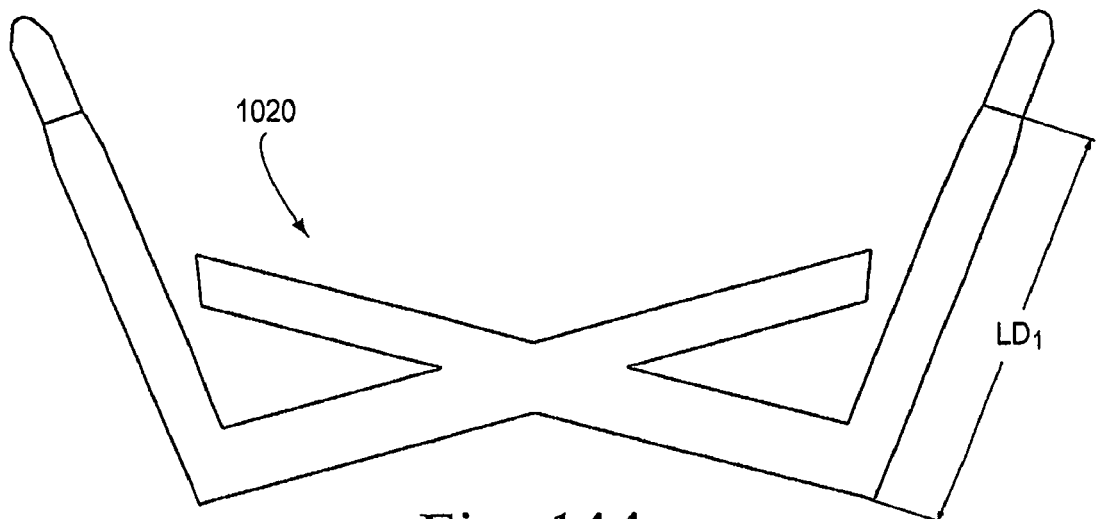
FIGS. 144-146 illustrate exemplary dimensions for large, medium, and small upper headgear sections.
Figure 145:
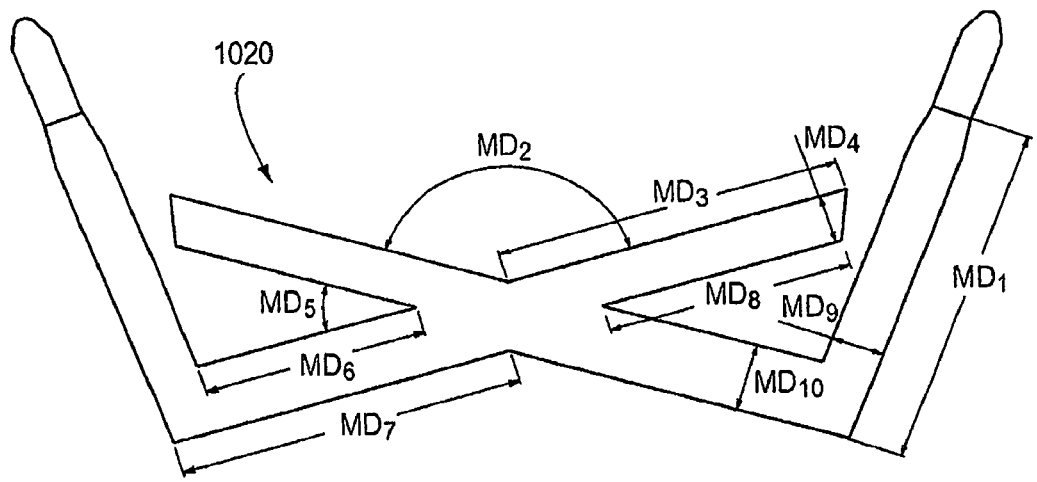
Figure 146:
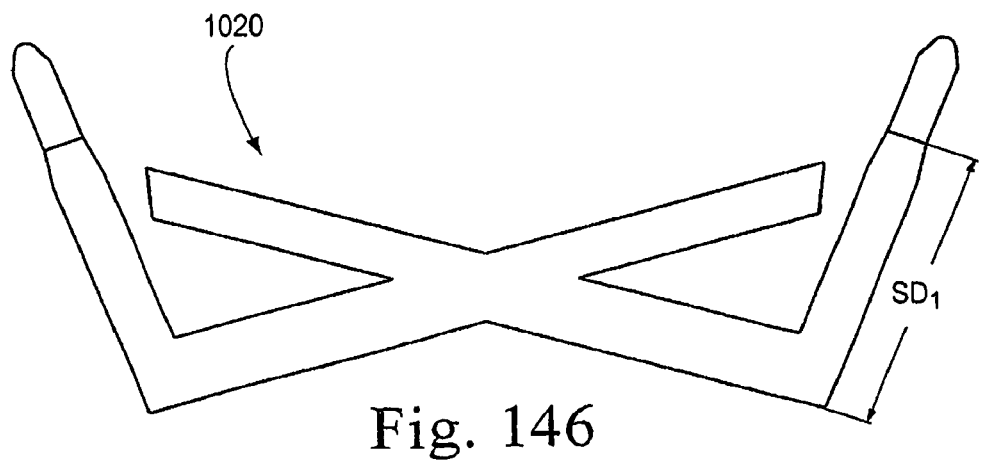
Figure 150:
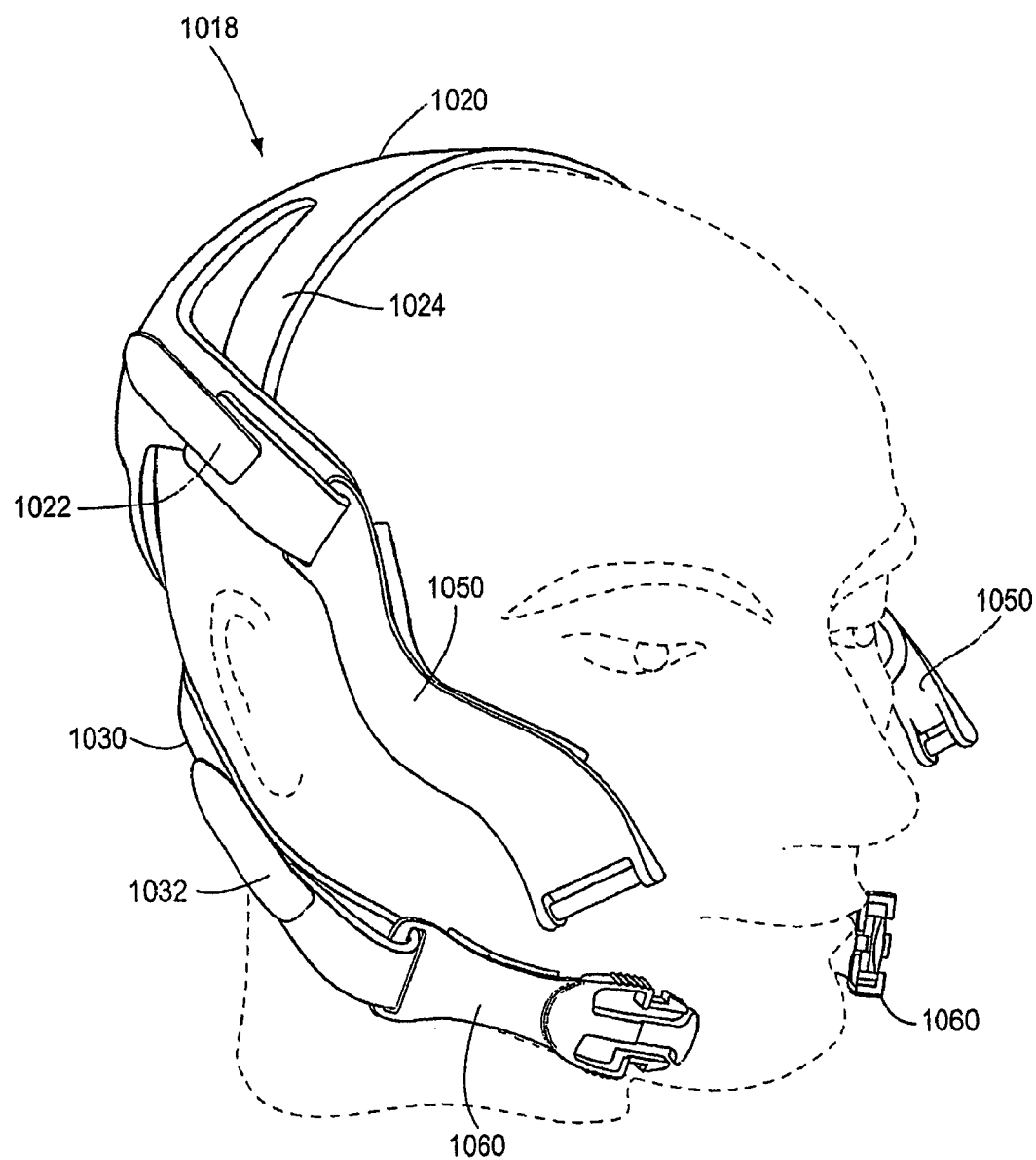
FIGS. 150-154 illustrate the headgear assembly of FIGS. 141-143 with upper and lower stabilizing elements assembled and positioned on a patient's head.
Figure 151:
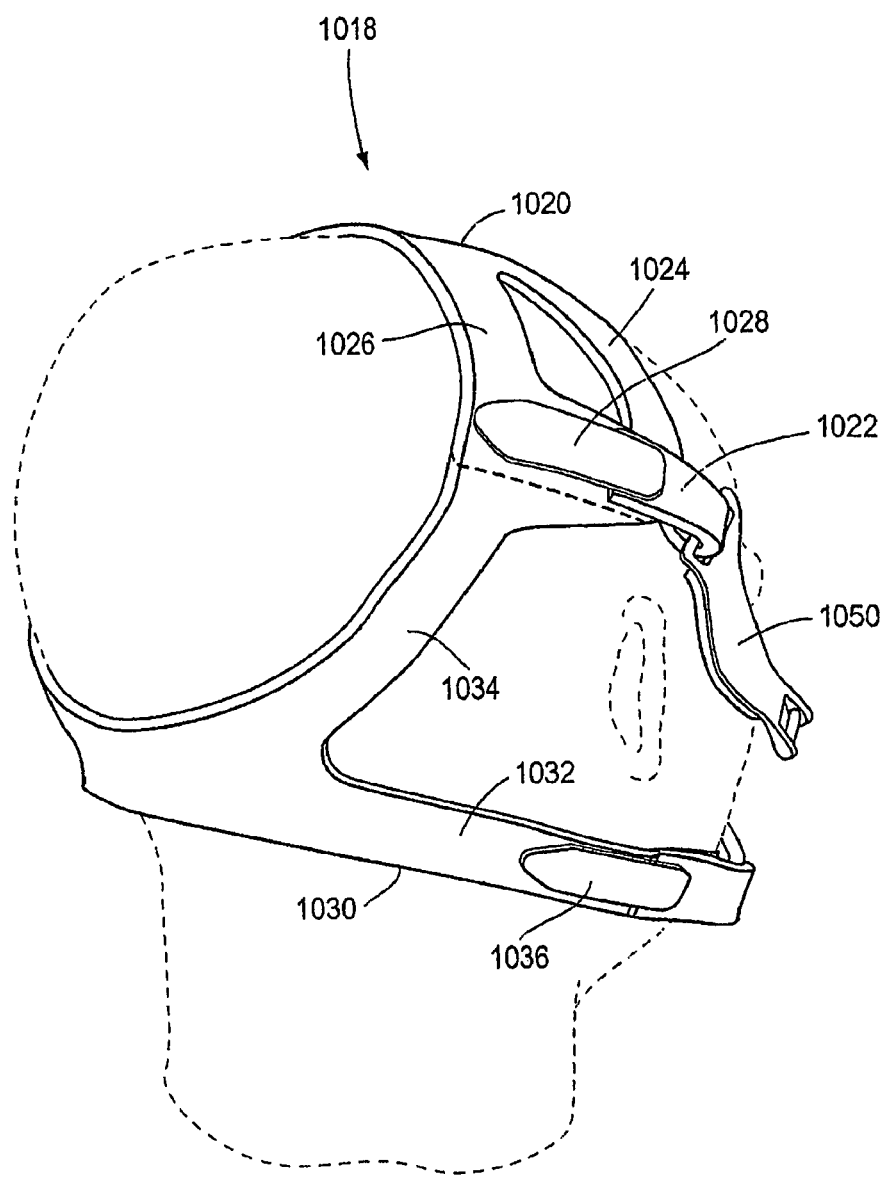
Figure 152:
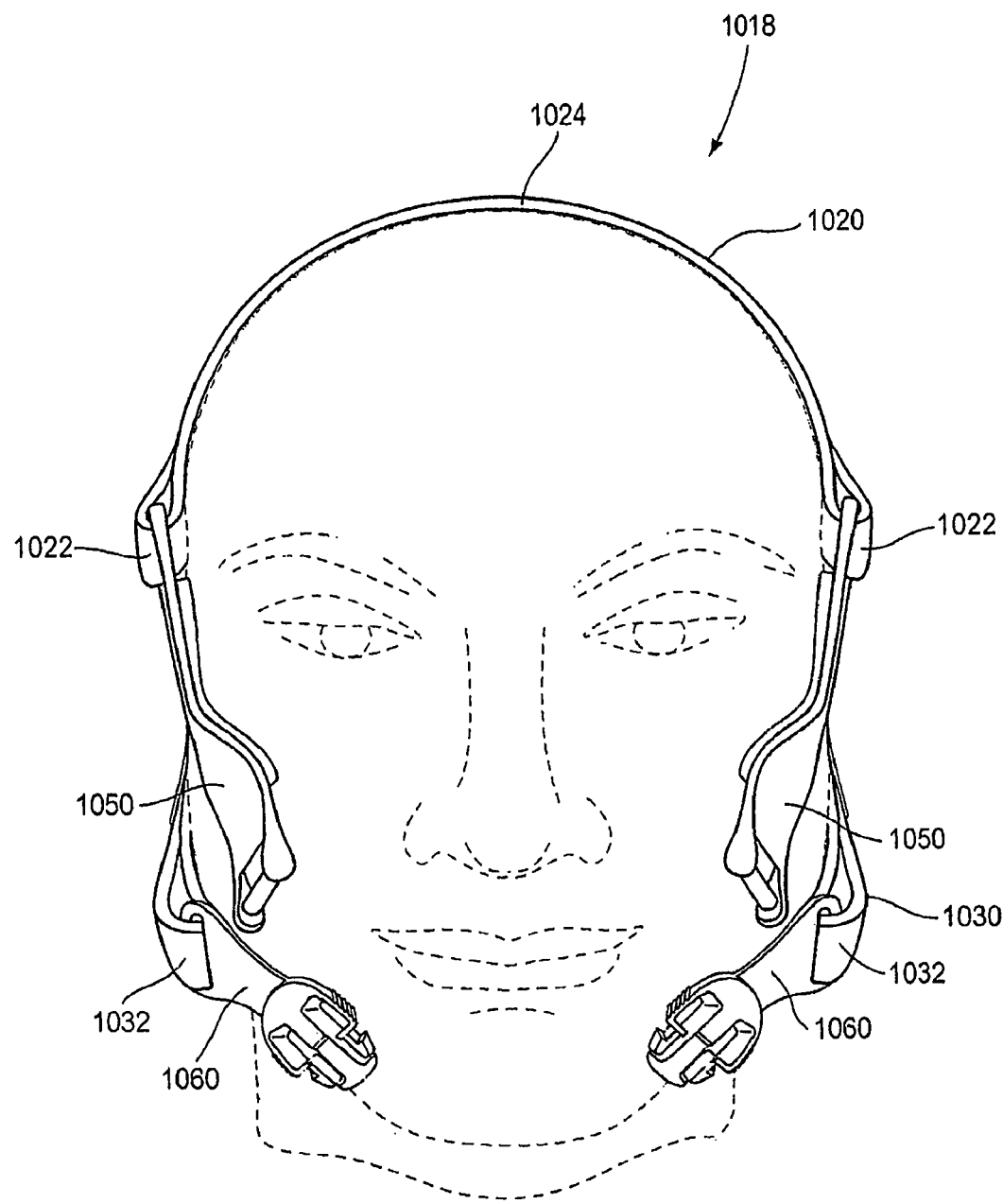
Figure 153:
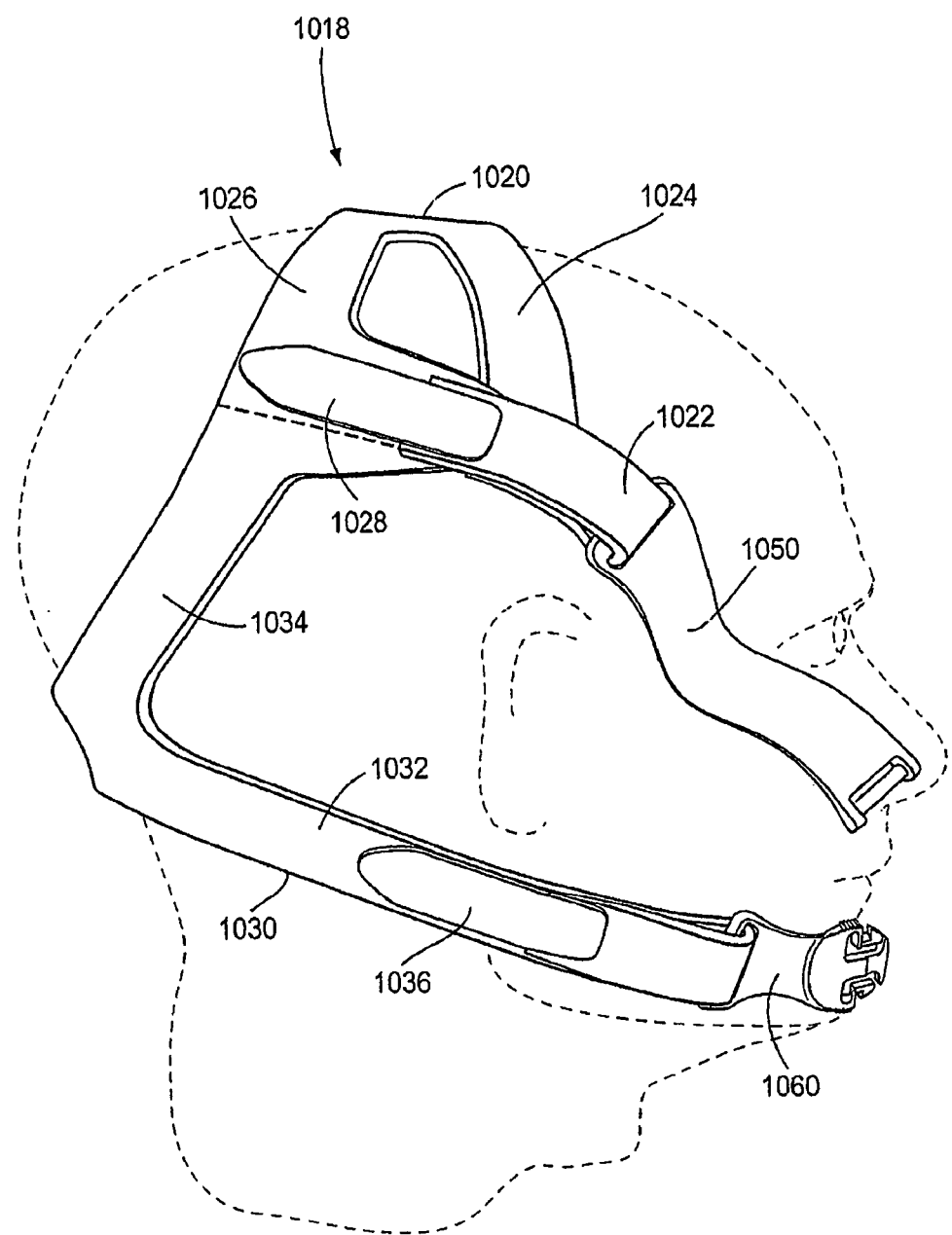
Figure 154:
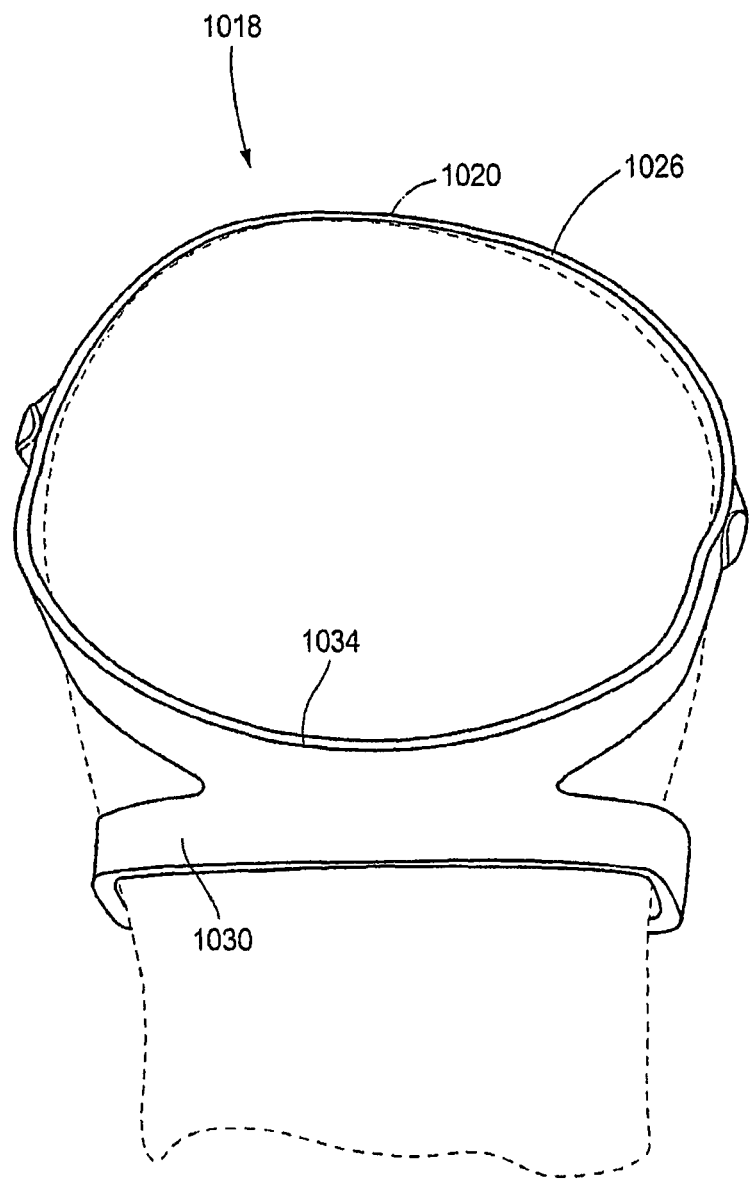

FIGS. 141 and 142 illustrate the two-dimensional upper and lower headgear sections 1020, 1030, and FIGS. 144-149 illustrate dimensions of embodiments of the upper and lower headgear sections 1020, 1030. Specifically, FIGS. 144-146 illustrate exemplary dimensions for large, medium, and small upper headgear sections 1020, respectively, and FIGS. 147-149 illustrate exemplary dimensions for large, medium, and small lower headgear sections 1030, respectively. In an embodiment, as shown in FIGS. 144-146, $LD_1$ is 153 mm, $MD_1$ is 128 mm, $MD_2$ is 147.degree., $MD_3$ is 119 mm, $MD_4$ is 18 mm, $M_5$ is 33.degree., $MD_6$ is 76.9 mm, $MD_7$ is 118.9 mm, $MD_8$ is 84 mm, $MD_9$ is 18 mm, $MD_{10}$ is 25 mm, and $SD_1$ is 107 mm. In an embodiment, as shown in FIGS. 147-148, $LD_1$ is 245 mm, $MD_1$ is 220 mm, $MD_2$ is 147.degree., $MD_3$ is 18 mm, $MD_4$ is 25 mm, $MD_5$ is 107.9 mm, $MD_6$ is 67 mm, $MD_7$ is 33.degree., $MD_8$ is 25.degree., and $SD_1$ is 220 mm. Although specific dimensions of the upper and lower headgear sections 1020, 1030 are provided, it is to be understood that these dimensions are merely exemplary and other dimensions are possible depending on application. For example, the exemplary dimensions may vary by 10-20%.

The two-dimensional first and second headgear sections 1020, 1030 are attached to one another, e.g., machine sewn butt joints, to form a three-dimensional anatomically shaped headgear assembly 1018. FIGS. 141 and 142 illustrate the attachment points in dotted lines, e.g., A joins to A, B joins to B, C joins to C, and D joins to D. As illustrated, the free end of each rear crown strap 1034 includes a widened portion 1019 to facilitate attachment.

FIGS. 150-154 illustrate the three-dimensional headgear assembly 1018 positioned on the patient's head. As illustrated, the crown straps 1026, 1034 cooperate to form a round-shaped crown strap that cups the parietal bone and occipital bone of the patient's head. FIG. 141 illustrates a cross-over point Y where the upper headgear section 1020 crosses over the crown of the patient's head, and FIG. 142 illustrates a cross-over point Z where the lower headgear section 1030 crosses over the lower occiput of the patient's head (i.e., bony structure at the back of the patient's head).

§ 4.6.2 Stabilizing Elements

As best shown in FIGS. 48 and 155, the upper and lower stabilizing elements 1050, 1060 provide a stable connection system between the upper and lower straps 1022, 1032 and the sealing assembly 1012 in order to protect and ensure the seal with both the patient's mouth and the patient's nasal passages. That is, the upper and lower stabilizing elements 1050, 1060 maintain the position of the upper and lower straps 1022, 1032 relative to each other, and secure the mask system 1010 at the correct orientation on the patient's face. The upper and lower stabilizing elements 1050, 1060 also act as "outriggers" to the frame 1074 to provide a larger footprint on the patient's face. This increases the stability of the mask system.

§ 4.6.2.1 Upper Stabilizing Elements

Figure 156:
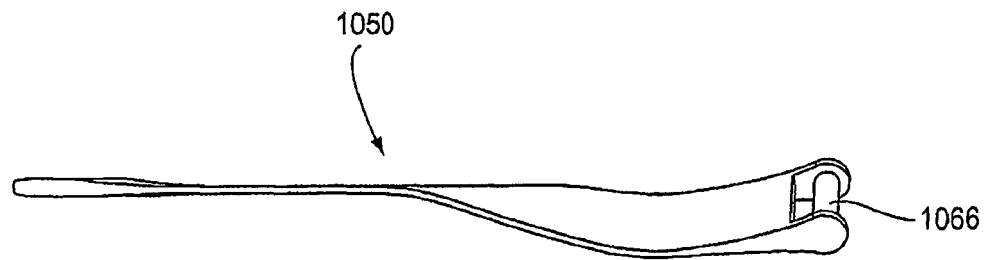
FIGS. 156-158 illustrate an upper stabilizing element according to an embodiment of the present invention.
Figure 157:
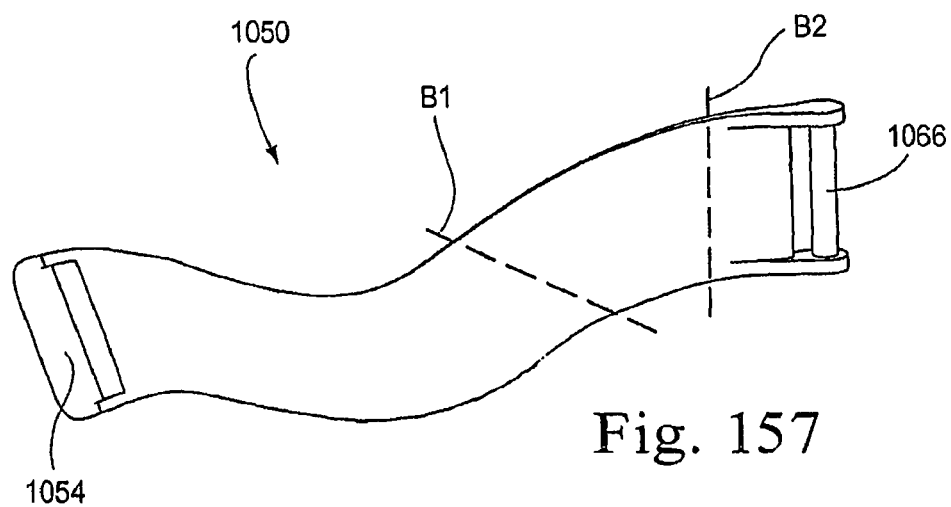

As shown in FIGS. 156-158 (illustrating a left side upper stabilizing element, the right side upper stabilizing element being symmetrical in design to the left side), each upper stabilizing element 1050 is constructed from a rigid or semi-rigid material, e.g., plastic material or nylon, and includes a three-dimensional shape so as to contour or conform to the shape of a patient's face. As shown by the dotted lines in FIG. 157, each upper stabilizing element 1050 includes at least one bending plane, e.g., two distinct bending planes B1 and B2, that allows flexing to conform to the shape of a patient's face.

One end of each upper stabilizing element 1050 includes a crossbar 1054 that enables the end portion of a respective upper headgear strap 1022 to be wrapped around, in a known manner. Each upper strap 1022 includes the Velcro® band. 1028 that engages the remainder of the strap to adjustably secure the crossbar 1054 in place. The opposite end of each upper stabilizing element 1050 includes a post element 1066. Each post element 1066 engages within a respective slot opening 1062 provided to the frame 1074, e.g., with a snap-fit. This attachment is similar to that shown in FIGS. 11-15 described above.

FIGS. 158b-1 to 158b-6 illustrate an alternative embodiment of the upper stabilizing element 2550 that includes structure to prevent misassembly with the frame 1074. As illustrated, the post element 2566 of the upper stabilizing element 2550 is supported by opposing end portions 2567, 2569. One of the end portions 2567 is relatively larger than the other of the end portions 2569. The enlarged end portion 2567 provides a key to facilitate assembly of the upper stabilizing element 2550 to the frame 1074 in the correct orientation.

Figure 122:
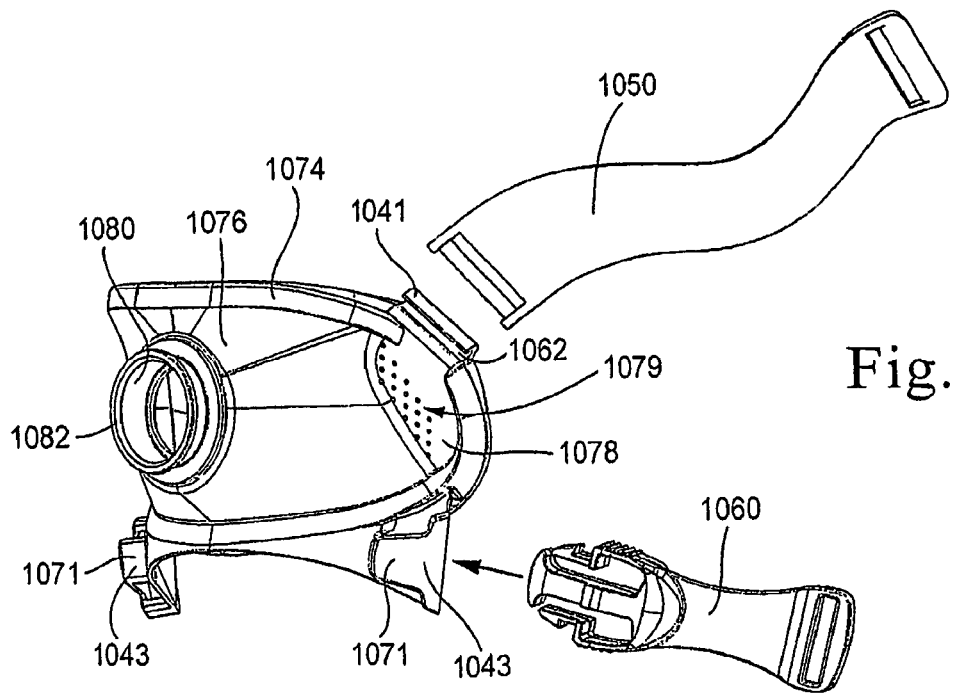
Figure 123:
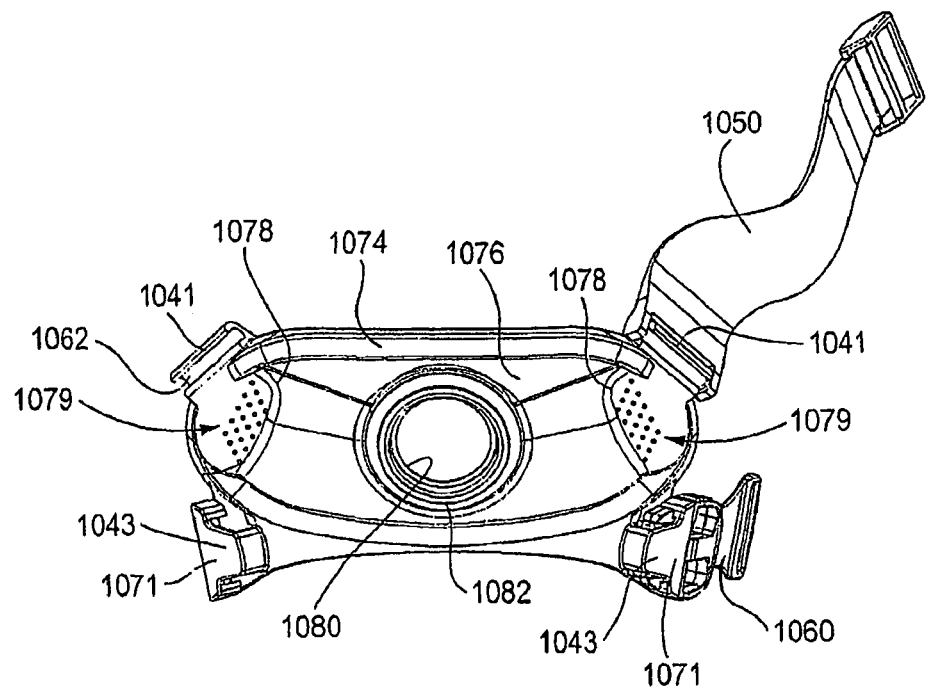
Figure 124:
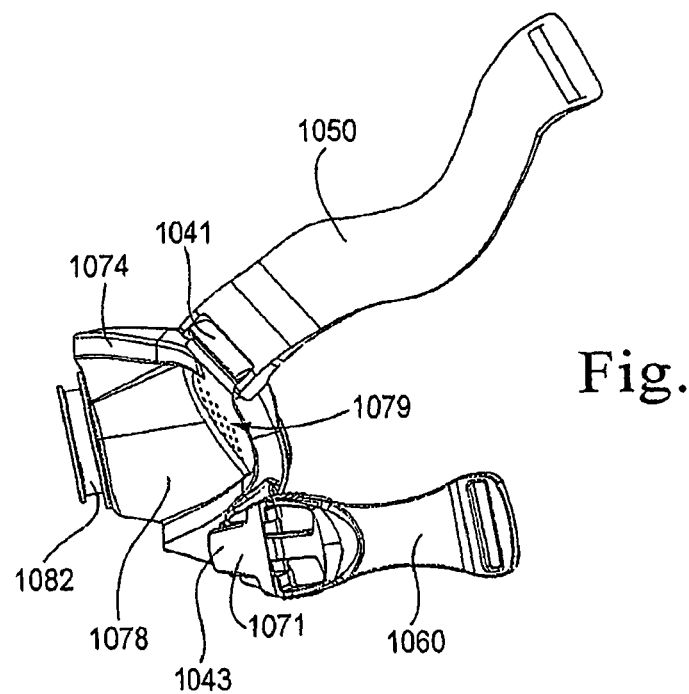
Figure 124B:
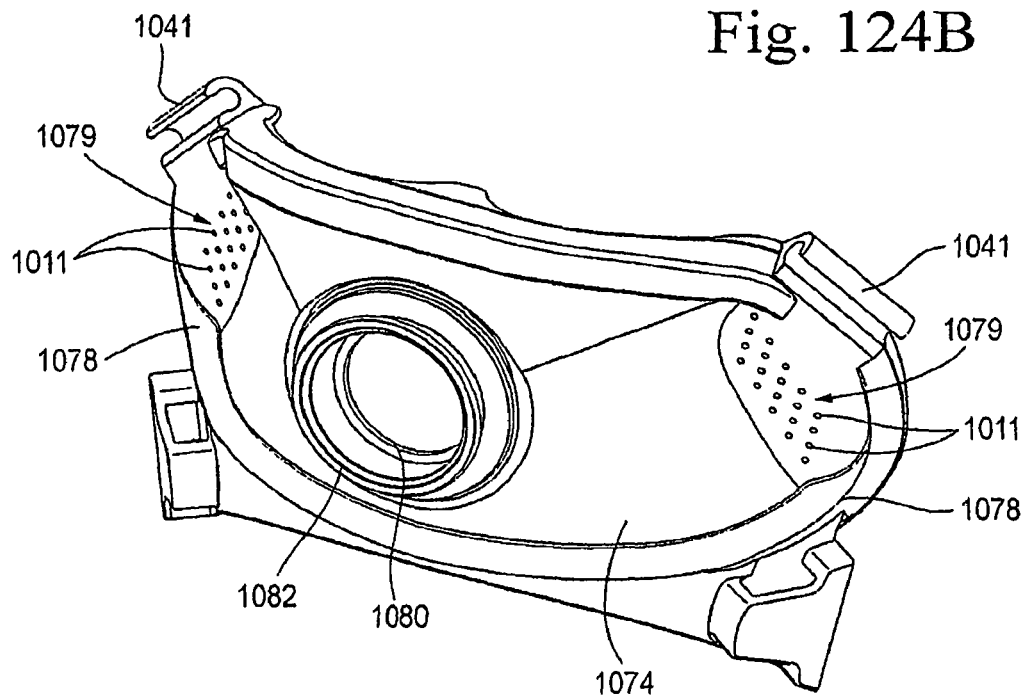
Figure 124C:
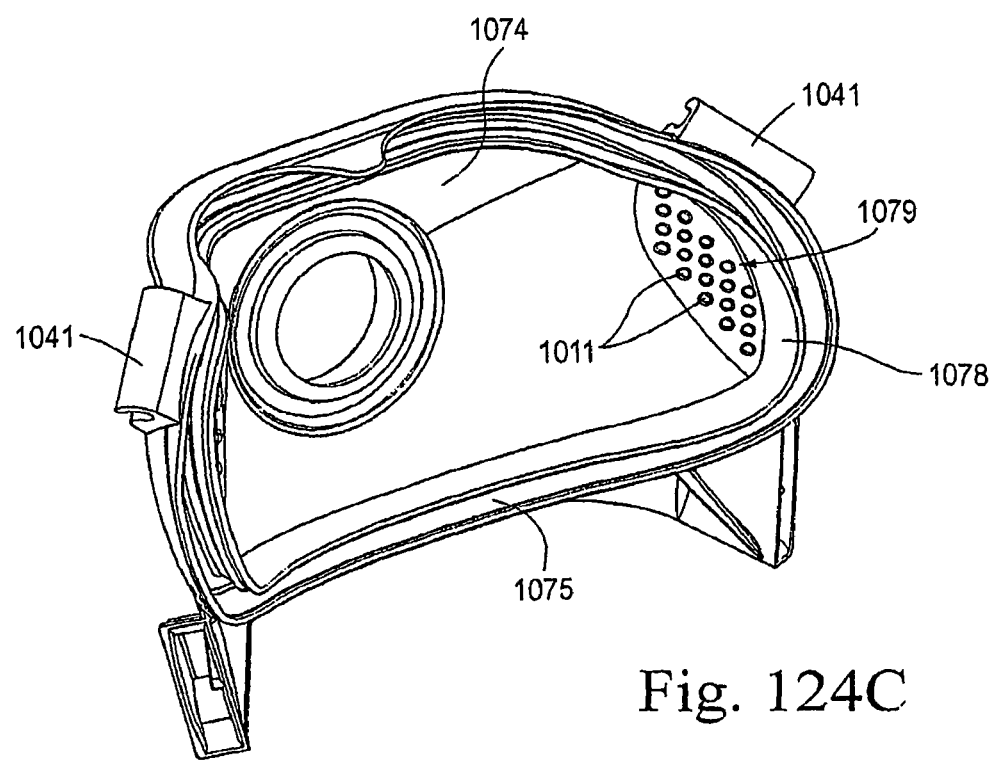
Figure 124F:
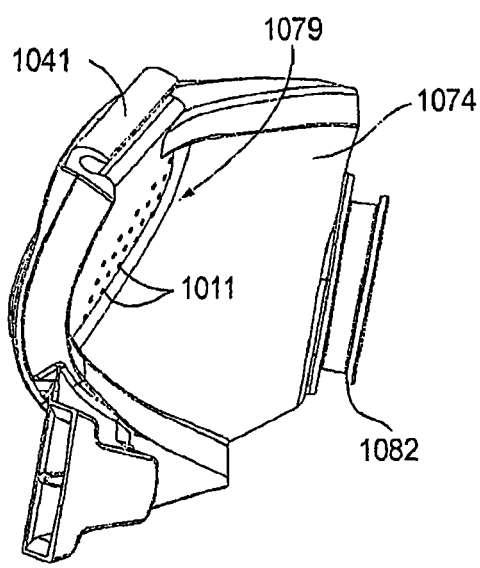
Figure 124G:
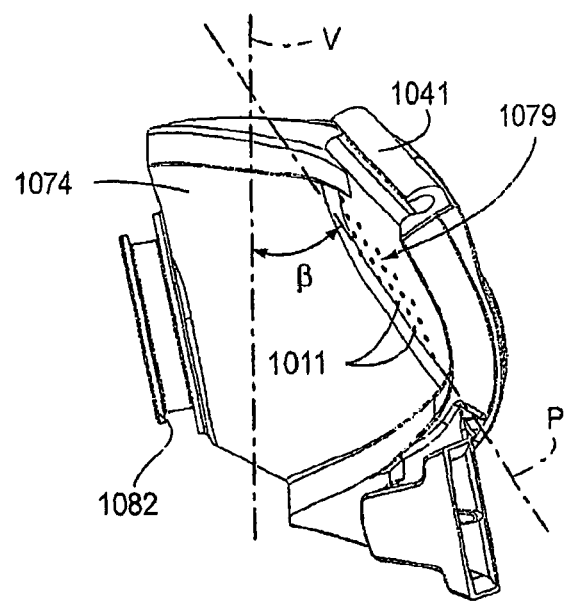
Figure 135:
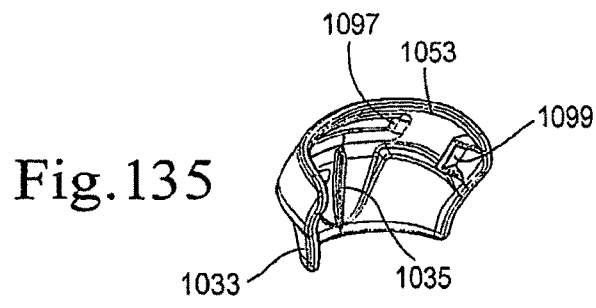
Figure 136:
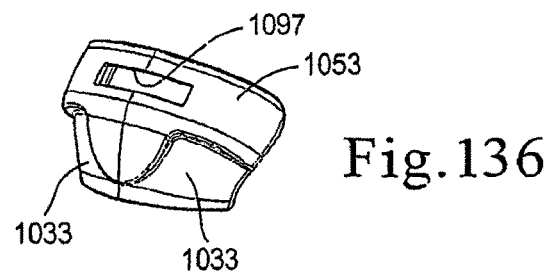
Figure 137:
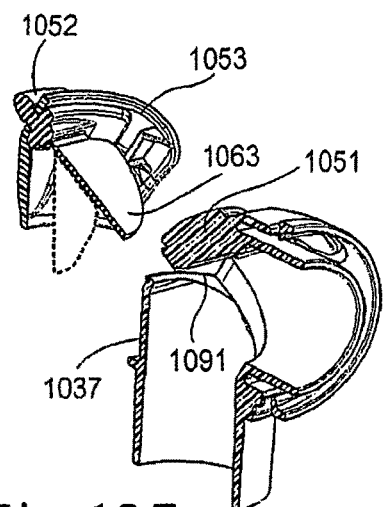
Figure 138:
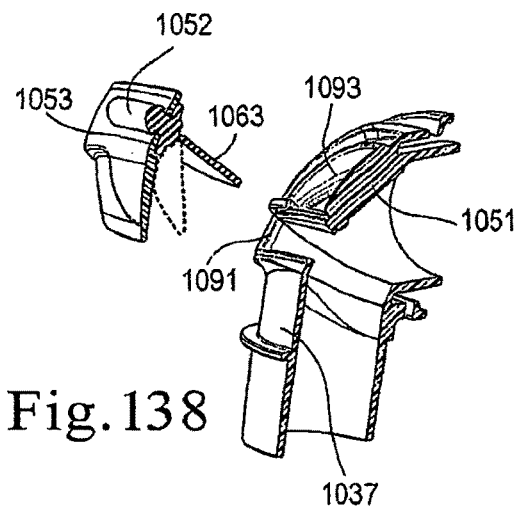
Figure 139:
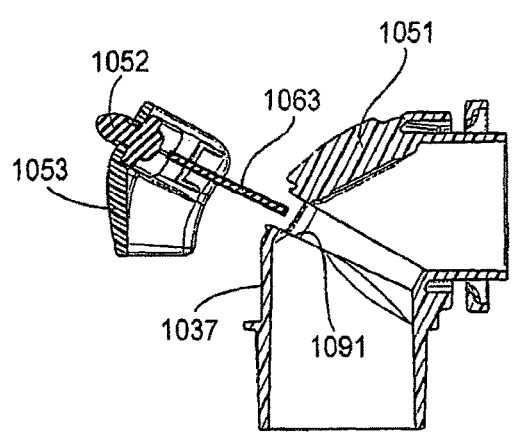

As shown in FIGS. 122, 124b and 124c for example, each upper anchor 1041 of the frame 1074 is structured such that sufficient space is provided on only one side of the upper anchor 1041 to accommodate the enlarged end portion 2567. Thus, if the upper stabilizing element 2550 is attempted to be engaged in the wrong orientation with the upper anchor 1041, the enlarged end portion 2567 will prevent the post element 2566 from interlocking with the respective slot opening 1062 of the upper anchor 1041.

Figures 1, 158C:
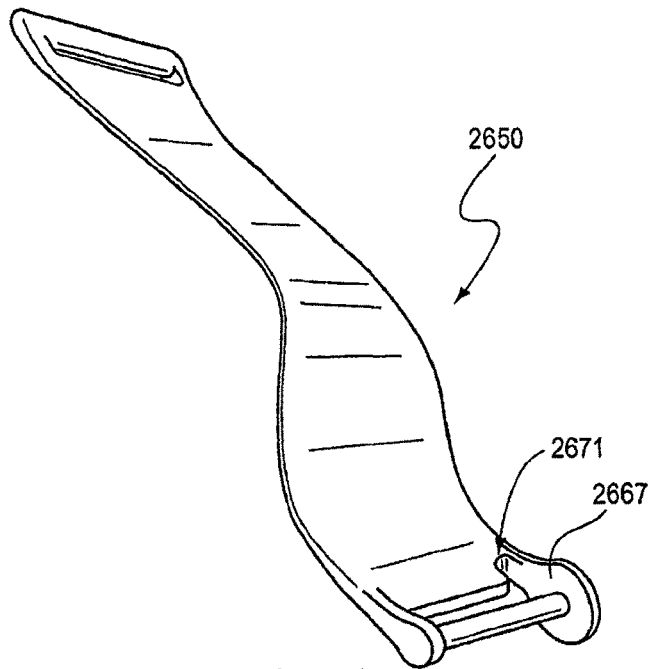
Figures 2, 158C:
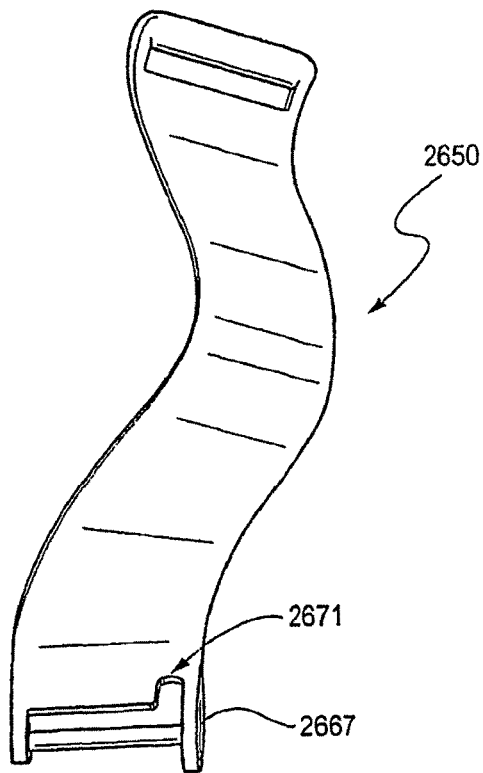
Figures 3, 158C:
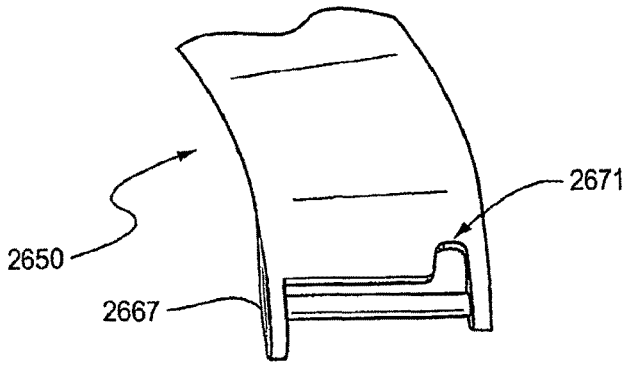
Figures 4, 158C:
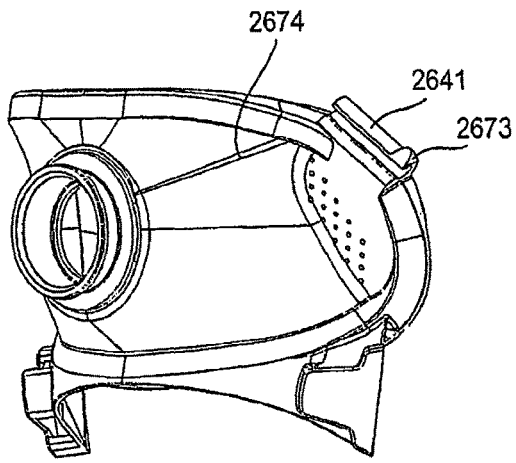
Figure 159:
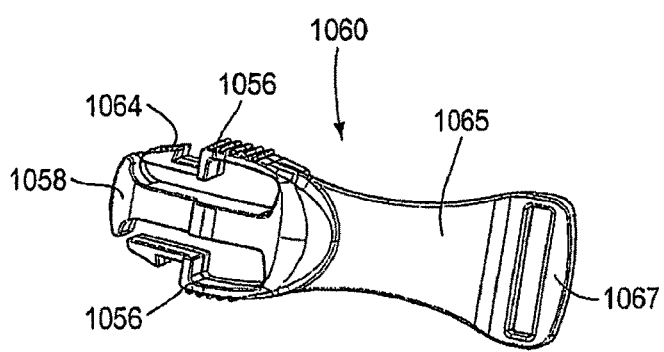
FIGS. 159-166 illustrate a lower stabilizing element according to an embodiment of the present invention.
Figure 160:
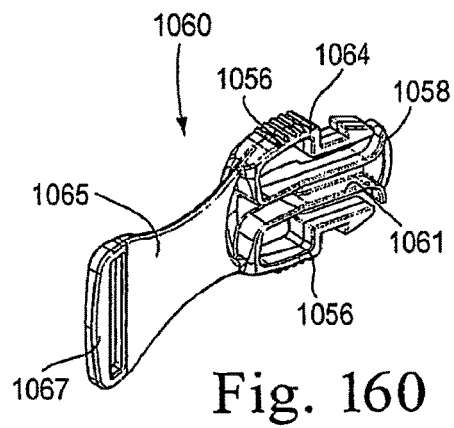

FIGS. 158c-1 to 158c-4 illustrate another embodiment of an upper stabilizing element 2650 and a frame 2674 having an upper anchor 2641 structured to accommodate such upper stabilizing element 2650. FIGS. 158c-1 and 158c-2 show a right side upper stabilizing element 2650, and FIG. 158c-3 shows a left side upper stabilizing element 2650. Similar to the embodiment described above, each upper stabilizing element 2650 includes an enlarged end portion 2667 to prevent misassembly with the respective upper anchor 2641 of the frame 2674. In addition, each upper stabilizing element 2650 includes a keyway or groove 2671 that is adapted to receive a key 2673 provided on a respective upper anchor 2641. The keyway 2671 of the right side stabilizing element 2650 is on the same side of the enlarged end portion 2667 (see FIG. 158c-2), and the keyway 2671 of the left side stabilizing element 2650 is on the opposite side of the enlarged end portion 2667 (see FIG. 158c-3).

FIG. 158c-4 shows the right side of frame 2674. As illustrated, the key 2673 is provided on an outer side of the right upper anchor 2641. the left upper anchor (not shown) will have the key located on the inner side thereof. This arrangement ensures that the right side stabilizing element 2650 can only attach to the right side anchor 2641, and the left side stabilizing element 2650 can only attach to the left side anchor. Specifically, the key 2673 on the right side anchor 2641 only allows the keyway 2671 of the right side stabilizing element 2650 to pass, and the enlarged end portion 2667 of the right side stabilizing element 2650 can only fit on the outer side of the right anchor 2641. Similarly, the key on the left side anchor only allows the keyway 2671 of the left side stabilizing element 2650 to pass, and the enlarged end portion 2667 of the left side stabilizing element 2650 can only fit on the outer side of the left anchor. Thus, the enlarged end portion 2667 and key 2673/keyway 2671 ensure that only the correct orientation of the upper stabilizing elements 2650 can take place.

§ 4.6.2.2 Lower Stabilizing Elements

As shown in FIGS. 159-166, each lower stabilizing element 1060 is constructed from a rigid or semi-rigid material, e.g., plastic material, and allows flexing to conform to a patient's face. Specifically, each lower stabilizing element 1060 includes a locking clip 1064 and a tail section 1065.

Figure 161:
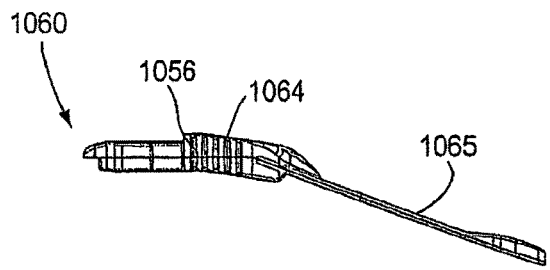
Figure 162:
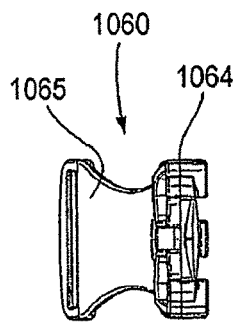
Figure 165:
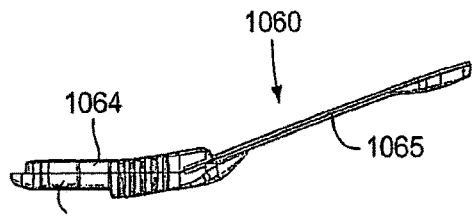

The tail section 1065 includes a crossbar 1067 that enables the end portion of a respective lower strap 1032 to be wrapped around, in a known manner. Each lower strap 1032 includes the Velcro® band 1036 that engages the remainder of the strap to adjustably secure the crossbar 1067 in place. As best shown in FIGS. 161 and 165, the tail section 1065 is angled with respect to the locking clip 1064 towards the patient's face so as to conform to the patient's face. In addition, the tail section 1065 is relatively thin to allow flexing under the influence of headgear tension so as to contour to the shape of a patient's face.

In some embodiments, the tail section 1065 may be markedly shorter or deleted altogether. In this way, the locking clip acts as described in U.S. patent application Ser. No. 10/390,681, filed Mar. 19, 2003, the contents being hereby incorporated by reference in its entirety.

§ 4.6.2.3 Locking Clip

Each locking clip 1064 includes two spring arms 1056 and a central tab 1058 between the two spring arms 1056. Each clip 1064 is interlocked with a respective clip receptacle 1071 provided to the frame 1074 with a snap-fit. Clip attachment is similar to that disclosed in U.S. patent application Ser. No. 10/390,681, filed Mar. 19, 2003, U.S. patent application Ser. No. 10/655,621, filed Sep. 5, 2003, and U.S. Pat. No. 6,374,826, the contents of each being hereby incorporated by reference in its entirety.

Figure 166:
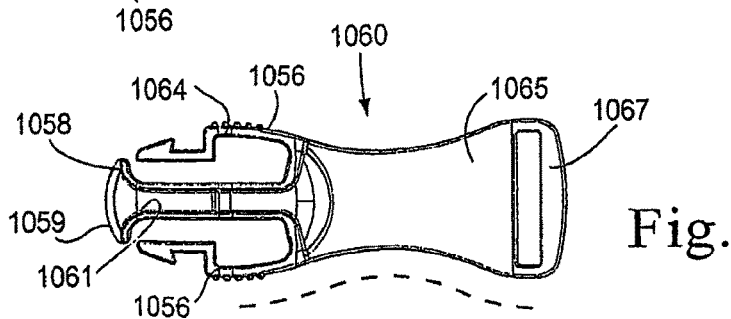

As best shown in dashed lines in FIG. 166, each spring arm 1056 and the adjacent tail section 1065 are contoured to provide an ergonomic grip and to provide a tactile cue to help differentiate the lower stabilizing element 1060 from the frame 1074 during disassembly. Also, each spring arm 1056 has raised grips to facilitate finger grip.

Figure 163:
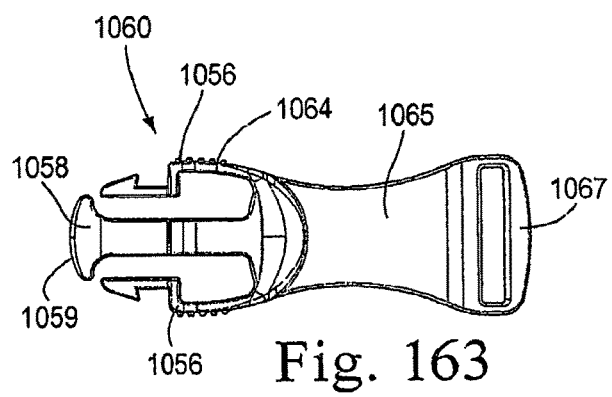
Figure 164:
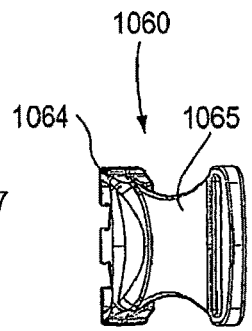

The central tab 1058 has a rounded front face surface 1059 (when viewed from the top and bottom as shown in FIGS. 163 and 166) to improve ease of assembly into the clip receptacle 1071. Also, as shown in FIGS. 163 and 166, the front of the central tab 1058 has a bull-nose shape to prevent the locking clip 1064 from becoming caught/tangled with other parts during manufacture and assembly as well as to prevent the locking clip 1064 from becoming caught on the frame 1074 and receptacle 1011 during fitting.

In addition, the rear side of the central tab 1058 has a central channel 1061 with a wide open mouth that is adapted to engage a tapered rib 1068 (see FIGS. 121 and 167) provided in the clip receptacle 1071. This arrangement facilitates entry and assembly of the locking clip 1064 into the clip receptacle 1071. Specifically, an error with alignment of the locking clip 1064 to the clip receptacle 1071 during assembly is compensated for by the wide open mouth of the channel 1061, i.e., wide open mouth allows insertion at wider range of angles, as shown in FIGS. 167-170.

§ 4.6.2.4 Backing Material

A padded backing material or soft portion may be applied on the rear surface of the upper and lower stabilizing elements 1050, 1060 (i.e., the surface facing the patient's face) to provide comfort and to prevent skin irritation (particularly when the patient is sleeping on his/her side). The backing material may be constructed from the same material as the headgear straps, e.g., Breathe-O-Prene™ manufactured by Accumed Technologies Inc. However, other suitable materials could be used, e.g., foam or cotton. The backing material maybe secured to the upper and lower stabilizing elements 1050, 1060 in any suitable manner, e.g., glued or stitched.

§ 4.6.2.5 Positioning

FIGS. 48, 155, 171, and 172 illustrate the positioning of the upper and lower stabilizing elements 1050, 1060 on the patient's face in use. As illustrated, the upper stabilizing element 1050 is contoured so that it does not obscure the forward field of view or appear in the patient's peripheral vision. Also, the upper stabilizing element 1050 is contoured so that it conforms to the shape of the patient's face, particularly at the upper cheek area. The relatively thin cross-section coupled with the inherent flexibility of the plastic material and applied headgear strap tension also assist the upper stabilizing element 1050 to conform to the shape of the patient's face.

The lower stabilizing element 1060 is angled (as viewed in FIGS. 161 and 165) in order to contour to the shape of the patient's face, particularly at the chin region. The relatively thin cross-section of the tail section 1065 coupled with the inherent flexibility of the plastic material and applied headgear strap tension also assist the lower stabilizing element 1060 to conform to the shape of the patient's face.

As shown in FIG. 171, the headgear assembly provides a force in the Y-direction $F_Y$ to seal under the patient's nares and top of mouth and a force in the X-direction $F_X$ to seal around the patient's lower mouth. The sealing plane and sealing force against the patient's nares is indicated at SN, and the sealing plane and sealing force against the patient's mouth is indicated at SM.

Specifically, the pair of upper straps 1022 defines a first force vector ($F_Y$) that provides a force in the Y-direction and the pair of lower straps 1032 defines a second force vector ($F_X$) that provides a force in the X-direction. As illustrated, the first force vector $F_Y$ extends from the upper cheek to the crown and the second force vector $F_X$ extends from the lower chin to the lower occiput (i.e., the area where bone meets muscle at the back of the patient's head). The curved configuration of the upper stabilizing elements 1050 offsets the first force vector $F_Y$ so that the headgear assembly does obscure the patient's vision, e.g., headgear assembly is sufficiently clear of the patient's eyes. For example, the dashed line L in FIG. 171 illustrates a line of force that would cause the mask to move such that the patient's vision would be obscured.

One aspect of this system is the angle that the upper stabilizing element 1050 makes to the mask frame and face. The angle that has been chosen is designed to affect sealing in the planes of the nasal opening and the mouth opening. In this way, tightening the upper straps 1022 will simultaneously draw the nasal prongs "up" into engagement with the nares while also drawing the mouth cushion "back" against the face (particularly above the upper lip). The angle chosen, and the resultant force vector when headgear tension is applied, allows for optimal sealing at both the nasal pillows and also at the mouth cushion. The chosen angle takes into account the various forces the mask is subject to. These include the force desired to seal against the treatment pressure (as a function of sealing area), and the force desired to offset tube drag and other factors. This angle provides the optimal balance between nose and mouth seal.

In an alternative embodiment, instead of the headgear assembly positioning and retaining both the mouth cushion and nasal pillows in a sealing position, only one of the pair is retained by the headgear assembly, and the other of the two is indirectly positioned. That is, the headgear assembly may provide a sealing force for one of the nares and mouth, and provide a platform for a force for sealing the other of the nares and mouth.

For example, the mouth cushion may be held in a sealing position on the face by the headgear assembly and the nasal prongs may be pushed into position under the nose by a spring mechanism extending from the mouth cushion. Thus, the headgear assembly may provide a sealing force for the patient's mouth, and the mouth cushion is used as a platform for a spring force to spring the prongs into sealing engagement with the patient's nares.

In another example, the nasal prongs may be held in position by headgear and the mouth cushion may be positioned by a spring mechanism extending from the nasal prongs. Thus, the headgear assembly may provide a sealing force for the patient's nares and provide a platform for a spring force to spring the mouth cushion into sealing engagement with the patient's mouth. In both examples, a force is provided in two directions to seal the patient's nose and mouth.

Figure 172:
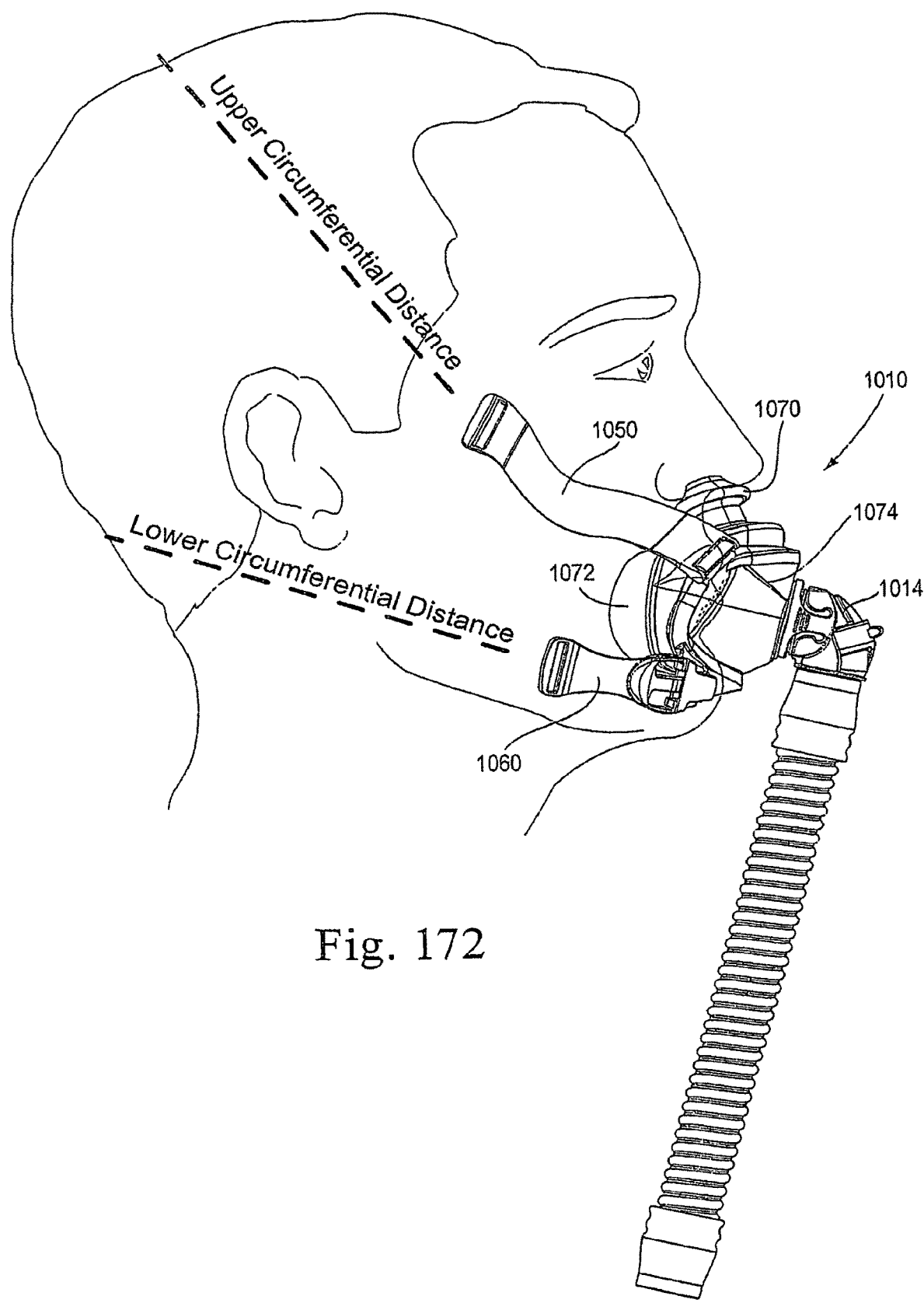
FIG. 172 illustrates dimensional stability provided by the headgear assembly according to an embodiment of the present invention.

As shown in FIG. 172, the lower circumferential distance from lower chin to the lower occipital region, i.e., the distance spanned by the lower headgear straps 1032, and the upper circumferential distance from the upper lip to the crown, i.e., the distance spanned by the upper headgear straps 1022, remains substantially constant even when the patient's head is rotated sideways or up or down. This dimensional stability allows the mask system 1012 to be more securely retained onto the patient's face, i.e., the headgear strap tension is less likely to dramatically change if the upper and lower circumferential distances are kept substantially constant.

§ 4.6.2.6 Alternative Embodiments of Upper Stabilizing Elements

FIGS. 173-175 illustrate alternative embodiments of the upper stabilizing elements. For example, as shown in FIG. 173, the frame 1074 may include an extension 1077 that supports an upper stabilizing element 1550. As illustrated, the upper stabilizing element 1550 has a curved configuration. Intermediate and end portions of the upper stabilizing element are also supported on the frame by support elements 1555. Each end of the upper stabilizing element includes a crossbar element 1557 that enables attachment to a respective upper strap 1022.

As shown in FIG. 174, the frame 1074 may include an extension 1077 that supports an upper stabilizing element 1650. As illustrated, the upper stabilizing element 1650 is bent into a generally U-shaped configuration. Intermediate and end portions of the upper stabilizing element 1650 are also supported on the frame by support elements 1655. Each end of the upper stabilizing element 1650 includes a crossbar element 1657 that enables attachment to a respective upper strap 1022.

As shown in FIG. 175, the frame 1074 may include an extension 1077 that supports a pair of upper stabilizing elements 1750. As illustrated, each upper stabilizing element 1750 has a curved configuration. Support elements 1755 extend between the pair of upper stabilizing elements 1750. Also, each end of the upper stabilizing elements 1750 includes a crossbar element 1757 that enables attachment to a respective upper strap 1022.

Figure 176:
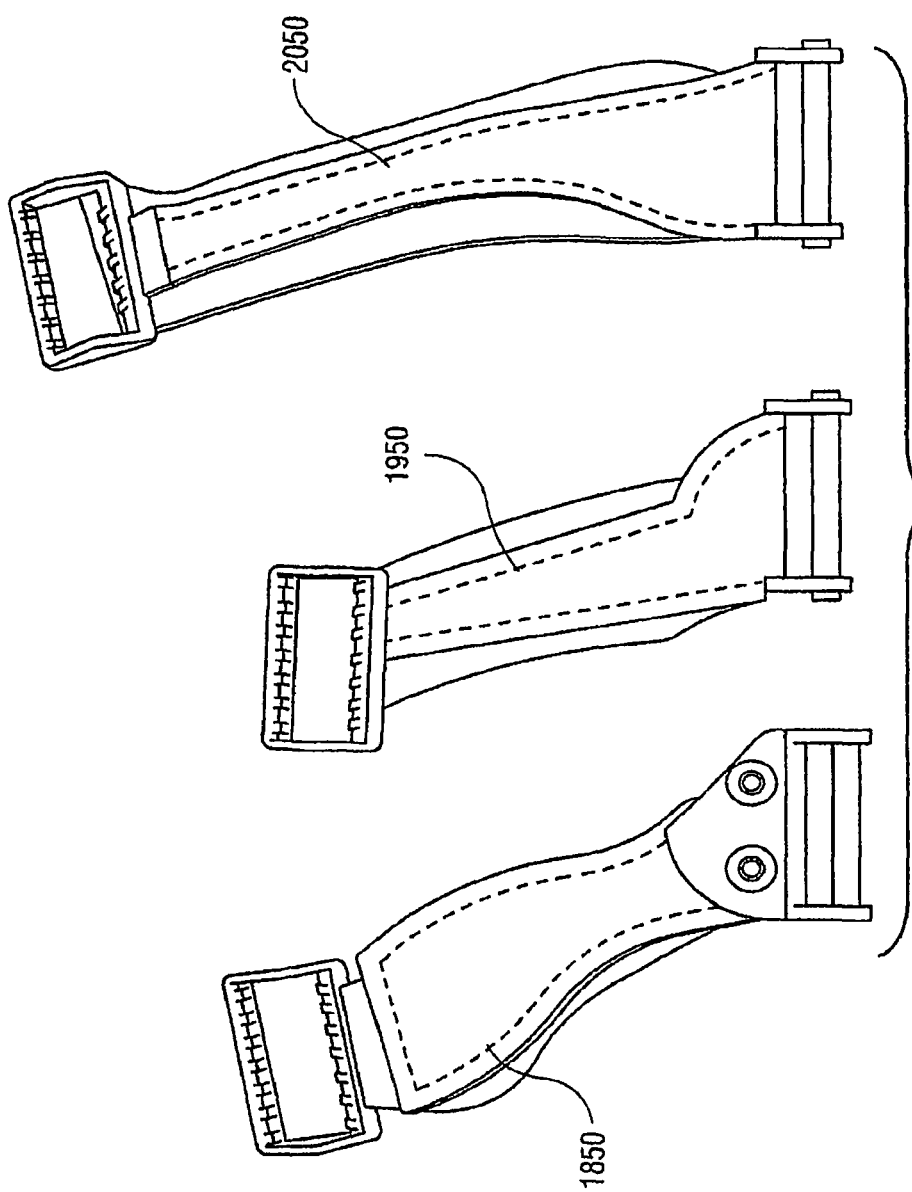
FIGS. 176-177 illustrate alternative arrangements of upper stabilizing elements.
Figure 177:
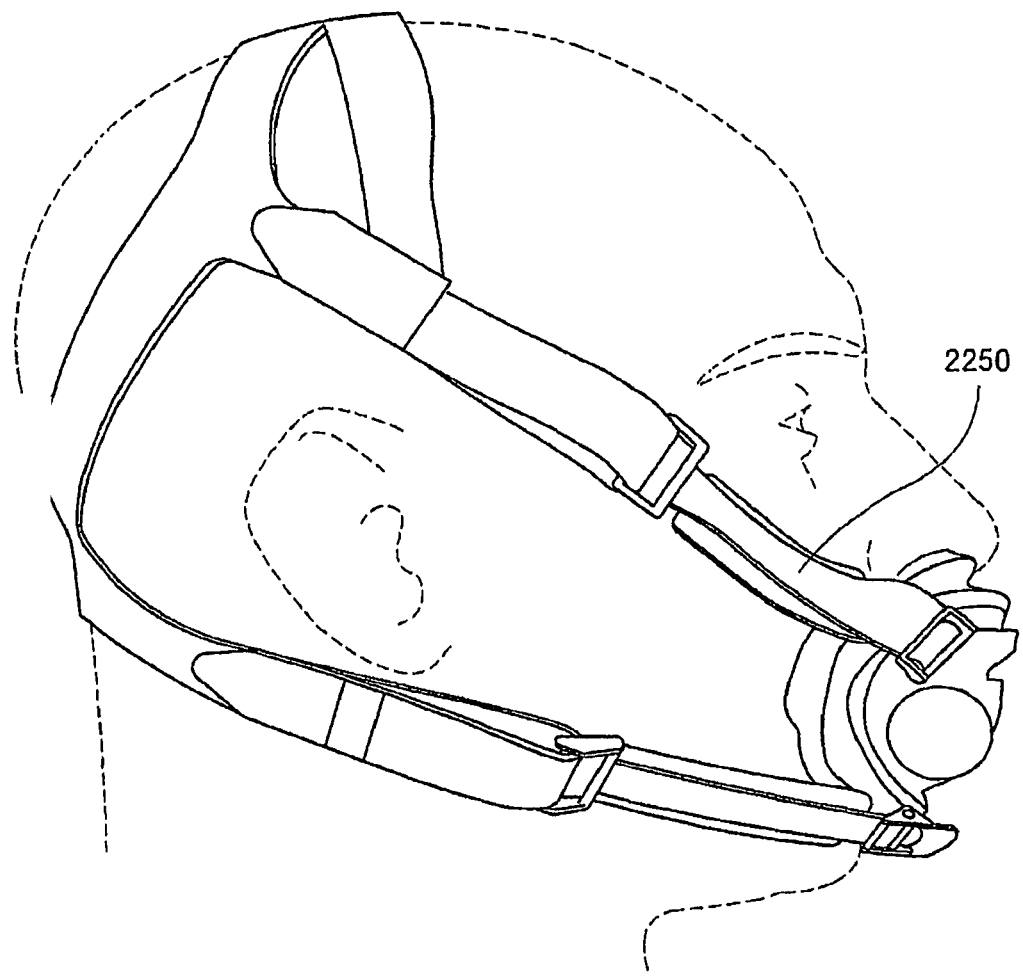
Figures 178, 179:
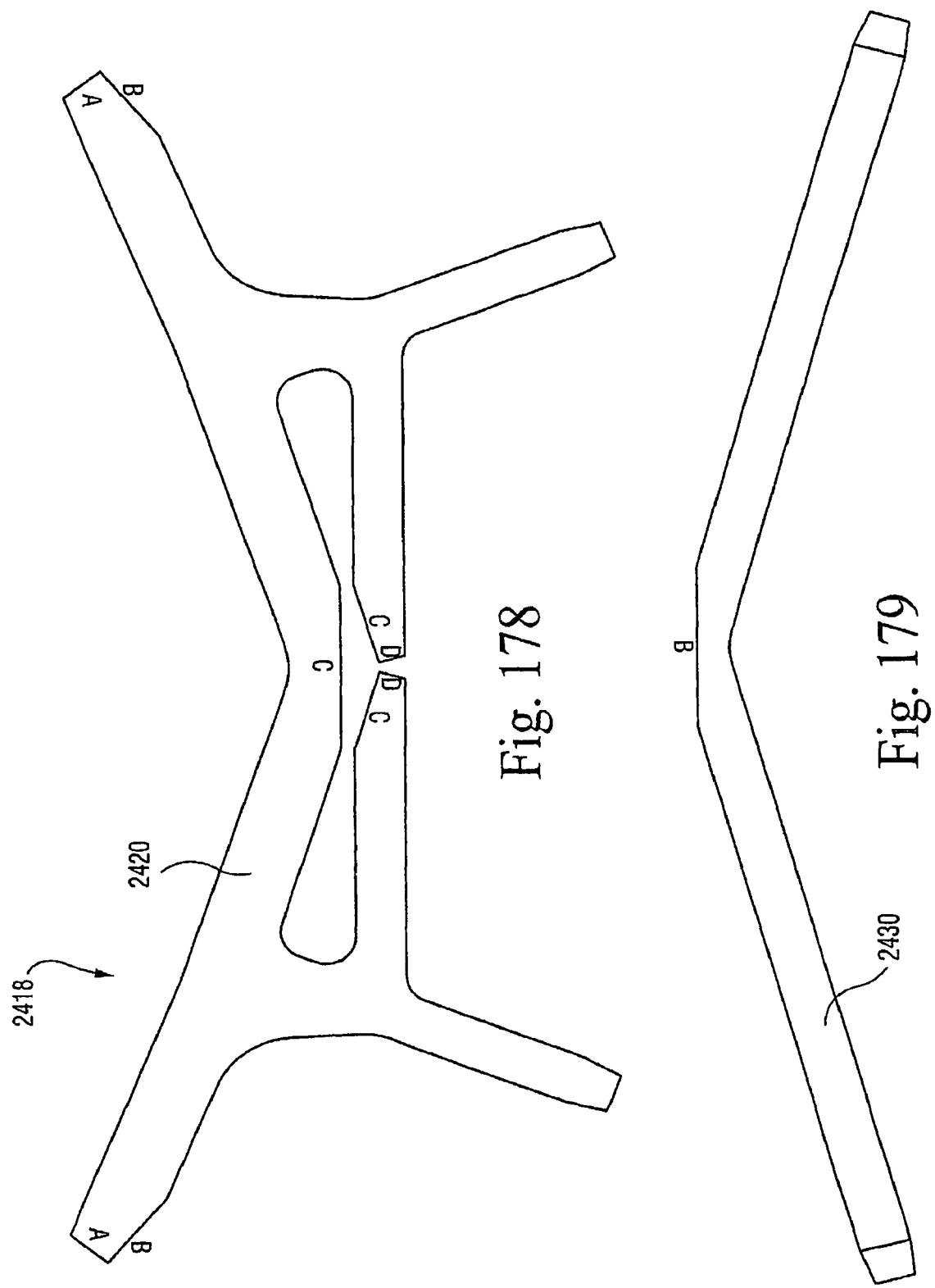
FIGS. 178-181 illustrate a headgear assembly according to another embodiment of the present invention.
Figure 180:
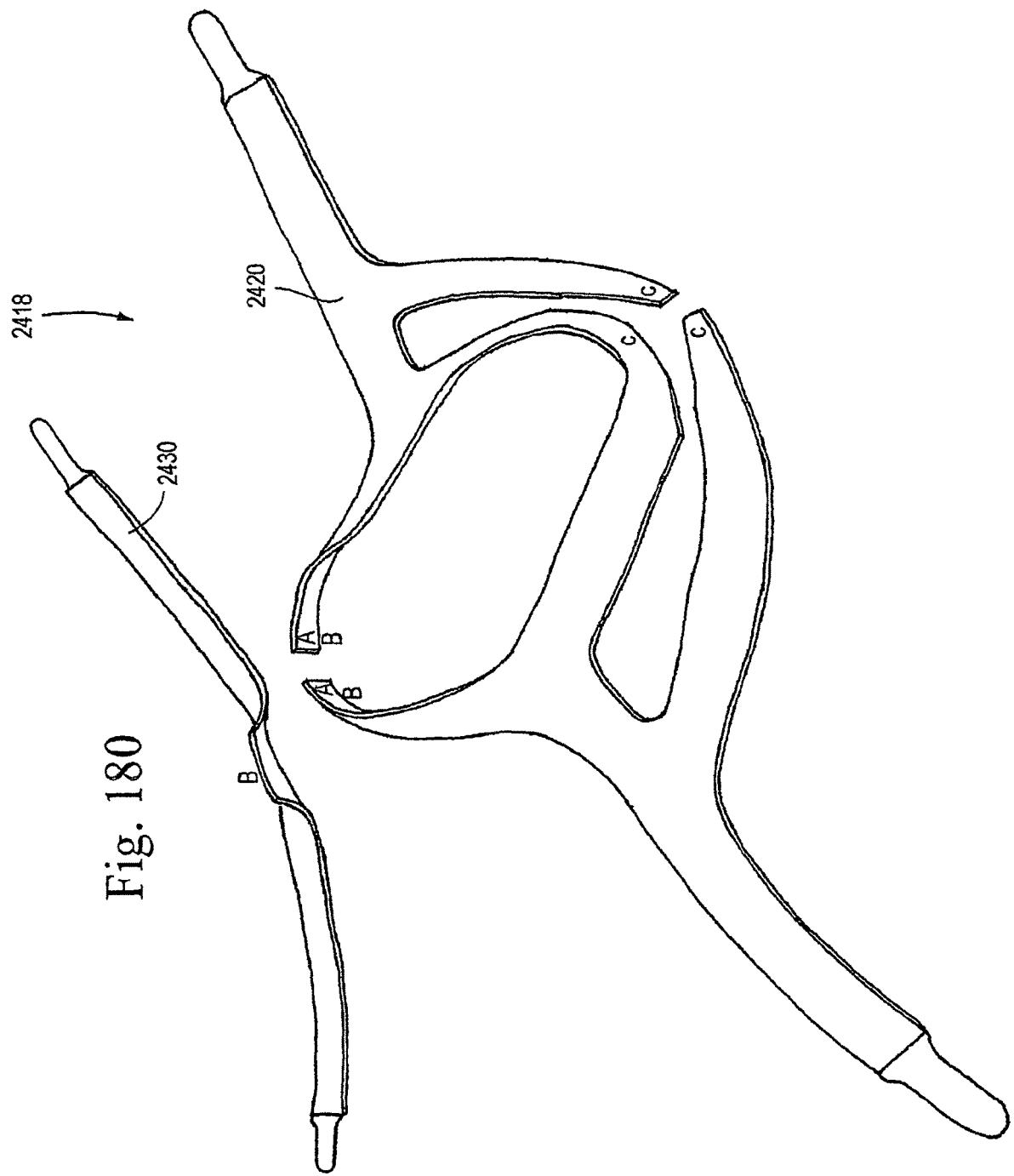
Figure 181:
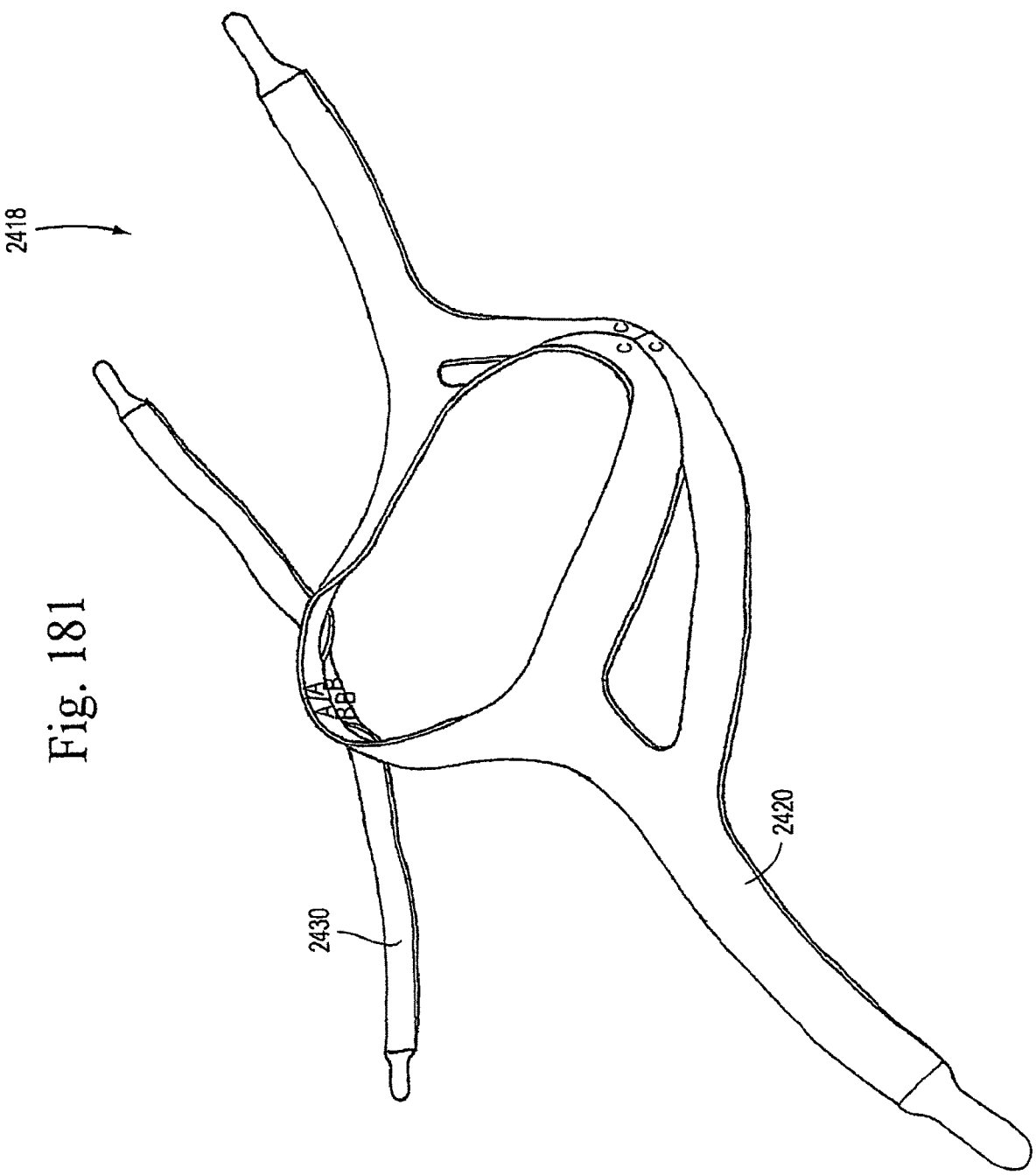
Figure 186:
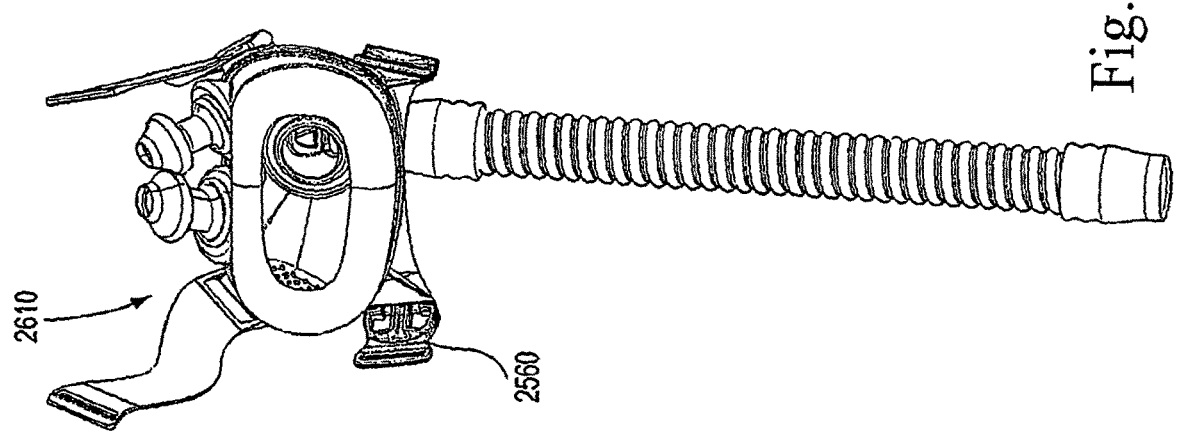
Figure 185:
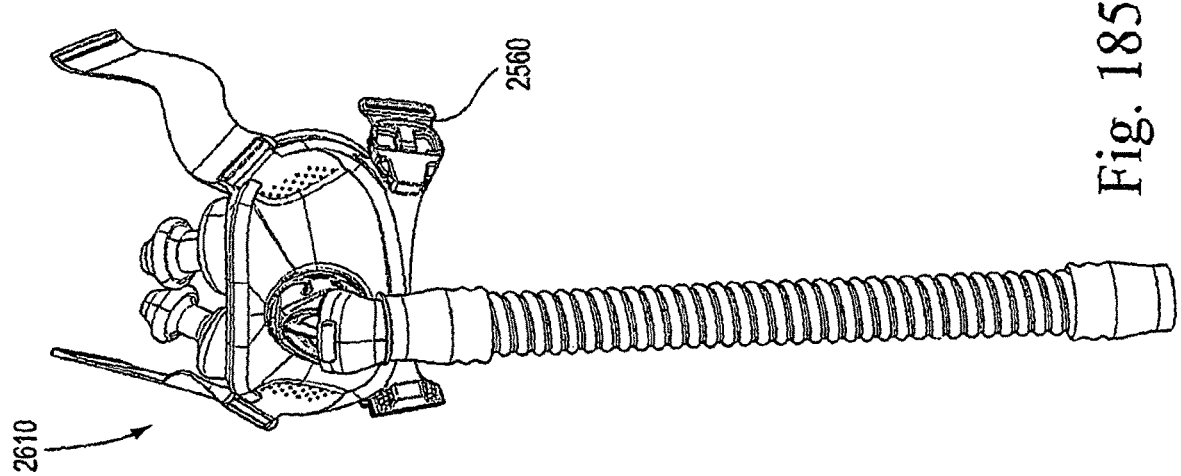
Figure 190:
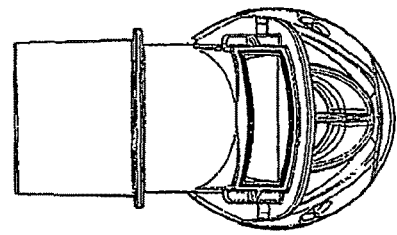
FIGS. 190-193 illustrate an elbow according to another embodiment of the present invention.
Figure 191:
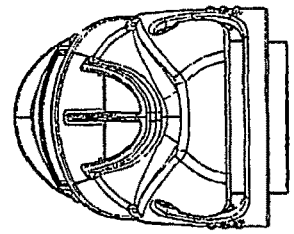
Figure 192:
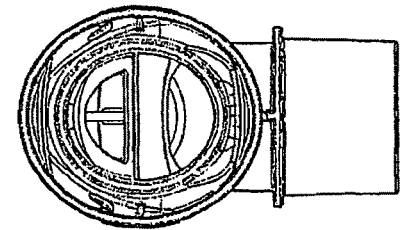
Figure 193:
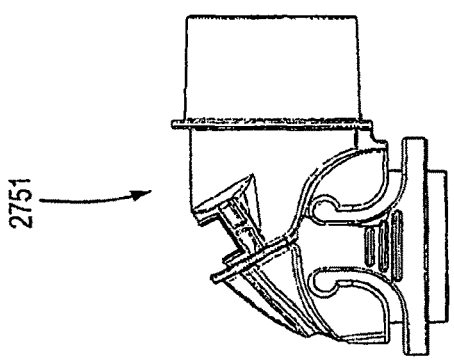

FIGS. 176-177 illustrate alternative arrangements for moving the upper stabilizing elements away from the patient' eyes. For example, FIG. 176 illustrate upper stabilizing elements 1850, 1950, 2050 having different shapes. FIG. 177 illustrates an upper stabilizing element 2250 with an inverted profile to clear the patient's eyes. In another embodiment, the attachment points 1041 on the frame 1074 may be wider, e.g., by a distance Δd as shown in FIGS. 124E, for moving the upper stabilizing elements 1050 away from the patient's eyes. In yet another embodiment, the upper stabilizing element may have an alternative connection to the frame 1074, such as those shown in FIGS. 173-175.

§ 5. Alternative Embodiments

FIGS. 178-181 illustrate another embodiment of a headgear assembly 2418 including upper and lower headgear sections 2420, 2430 attached to one another. In the illustrated embodiment, the headgear assembly 2418 may include a different stitching pattern or attachment arrangement with respect to the headgear assemblies described above, which may facilitate alignment and assembly. Specifically, instead of joints that are angled with respect to one another, the joints are relatively flat, i.e., not angled. FIGS. 178-181 illustrate the attachment points, e.g., A joins to A, B joins to B, and C joins to C.

As illustrated, the headgear assembly 2418 provides a right-angled joining geometry that makes the end portions easier to align for joining. Also, the headgear assembly 2418 moves the joint area away from where the velcro fastens to the headgear, which prevents potential damage to the joints, e.g., sewn joints.

FIGS. 182-184 illustrate another embodiment of a lower stabilizing element 2560 including a locking clip 2564 and a tail section 2565. The locking clip 2564 is adapted to be interlocked with a respective clip receptacle provided to the mask frame and the tail section 2565 is adapted to be attached to a headgear strap.

As illustrated, the tail section 2565 is markedly shorter than the tail section 1065 of lower stabilizing element 1060 described above. Also, the lower stabilizing element 2560 may not require a padded backing because it is shorter and does not contact the patient's face or does not contact the patient's face as much as the lower stabilizing element 1060. This arrangement provides one less assembly step, e.g., assembly of backing material, and less material is provided, thereby reducing costs.

FIGS. 185-189 illustrate another embodiment of a mask system 2610. As illustrated, the mask system 2610 is substantially similar to the mask system 1010 described above. In contrast, the mask system 2610 may include lower stabilizing elements 2560 such as those shown in FIGS. 182-184. Also, the mask system 2610 may have a "large" size, wherein D1 is about 126 mm, D2 is about 119 mm, D3 is about 151 mm, D4 is about 120 mm, and D5 is about 349 mm. These dimensions are merely exemplary and other dimensions are possible depending on application, e.g., size.

FIGS. 190-193 illustrate another embodiment of an elbow 2751 for a mask system. In this embodiment, the elbow 2751 may be a rib formed from a thicker wall section of the elbow.

Figure 194:
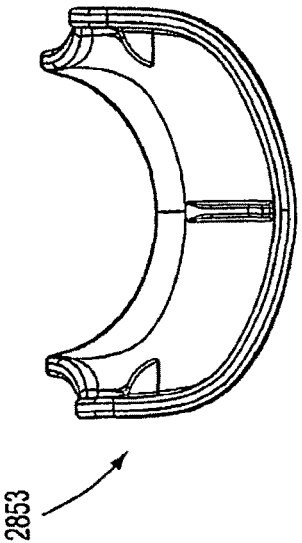
FIGS. 194-196 illustrate a clip member according to another embodiment of the present invention.
Figure 196:
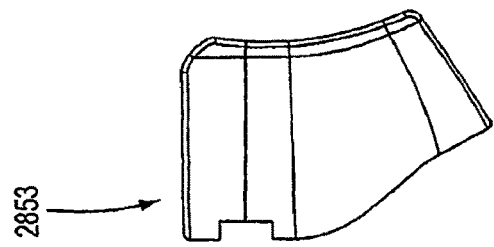
Figure 195:
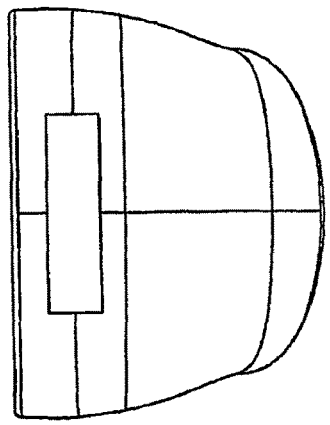

FIGS. 194-196 illustrate another embodiment of a clip member 2853 for securing an AAV to an elbow. In this embodiment, the clip member 2853 may include an arcuate raised portion that mirrors the shape of the vent.

Figure 197:
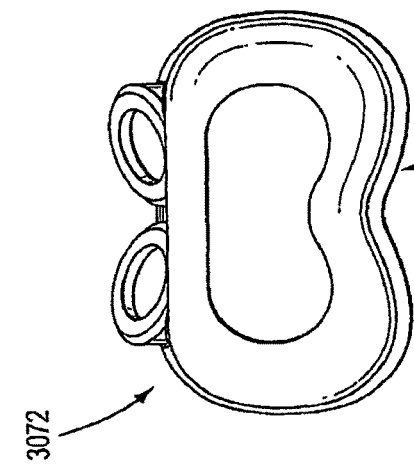
FIG. 197 illustrates a mouth cushion with a "boomerang profile" according to another embodiment of the present invention.

FIG. 197 illustrates another embodiment of a mouth cushion 3072 with a "boomerang profile". Specifically, the mouth cushion 3072 includes a chin section 3015 that is shaped like a boomerang or an inverted U and is designed to rest between the lower lip and the mental protuberance of the patient in use. A full-face cushion including a boomerang profile is disclosed in U.S. patent application Ser. No. 10/655,622, filed Sep. 5, 2003, which is incorporated herein by reference in its entirety.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask system for delivery of respiratory therapy to a patient, the mask system comprising:
   a sealing assembly that defines a breathing chamber configured to contemporaneously provide air to both a nose of the patient and a mouth of the patient, the sealing assembly shaped to be positioned entirely below a nasal bridge of the patient and avoid the nasal bridge of the patient when providing air to both the nose and the mouth, the sealing assembly including:
   (i) a nasal cushion structured to seal nares of the patient and provide air from the breathing chamber to the nose of the patient,
   (ii) a mouth cushion structured to seal around the mouth of the patient and provide air from the breathing chamber to the mouth of the patient, the mouth cushion integrally formed with the nasal cushion,
   (iii) conduit connections, including a first conduit connection and a second conduit connection on respective sides of the sealing assembly,
   (iv) lower headgear connections on the respective sides of the sealing assembly, the lower headgear connections being spaced apart from the conduit connections, the conduit connections being positioned entirely above all headgear connections of the sealing assembly when the mask system is worn by the patient and viewed from in front of the patient, and
   (v) one or more vent ports positioned entirely within a central region of the sealing assembly located (a) between each of the conduit connections, (b) between each of the lower headgear connections, (c) below the conduit connections, and (d) above the lower headgear connections, when the mask system is worn by the patient and viewed from in front of the patient;
   a pair of air delivery conduits including a first air delivery conduit and a second air delivery conduit to provide air to the breathing chamber, the first air delivery conduit being structured to releasably connect with the first conduit connection and the second air delivery conduit being structured to releasably connect with the second conduit connection; and
a headgear assembly structured to maintain the sealing assembly on a face of the patient, the headgear assembly including:
(i) an upper portion structured to connect with the first air delivery conduit above a first ear of the patient and the second air delivery conduit above a second ear of the patient, and
(ii) a lower portion structured to connect with the lower headgear connections, wherein the upper portion of the headgear assembly and the lower portion of the headgear assembly are joined together.

2. The mask system of claim 1, wherein the sealing assembly comprises silicone.

3. The mask system of claim 2, wherein the nasal cushion and the mouth cushion of the sealing assembly are integrally formed as a one-piece component.

4. The mask system of claim 1, wherein the upper portion of the headgear assembly and the lower portion of the headgear assembly are attached to one another to form a three-dimensional anatomically shaped headgear assembly.

5. The mask system of claim 1, wherein the sealing assembly includes a rigid component connected to a front, non-face contacting portion of the mouth cushion.

6. The mask system of claim 5, wherein the rigid component includes the lower headgear connections.

7. The mask system of claim 6, wherein the lower headgear connections are configured to connect using crossbars.

8. The mask system of claim 6, wherein the first conduit connection and the second conduit connection are formed in the nasal cushion.

9. The mask system of claim 5, wherein the rigid component is attached to the mouth cushion.

10. The mask system of claim 5, wherein the nasal cushion includes means for sealing with the nares of the patient.

11. The mask system of claim 10, wherein the mouth cushion includes means for sealing with the mouth of the patient.

12. The mask system of claim 11, wherein:
the headgear assembly includes means for attaching to the sealing assembly;
the sealing assembly includes means for attaching to the headgear assembly; and
the headgear assembly includes means for retaining the headgear on a head of the patient.

13. The mask system of claim 1, wherein the lower portion of the headgear assembly and the upper portion of the headgear assembly join together at a back of a head of the patient when the mask system is worn by the patient.

14. The mask system of claim 1, wherein the one or more vent ports comprise multiple vent ports arranged horizontally with respect to each other when the mask system is worn by the patient and viewed from in front of the patient.

15. The mask system of claim 1, wherein the conduit connections are attached to the sealing assembly at an angle with respect to a horizontal plane of the sealing assembly when the mask system is worn by the patient and viewed from in front of the patient, so that each of the pair of air delivery conduits connects with the sealing assembly at the angle with respect to the horizontal plane and extends upwards away from the sealing assembly and to behind a respective ear of the patient when the mask system is worn by the patient and viewed from in front of the patient.

16. The mask system of claim 1, wherein:
the first conduit connection includes a first tube shaped to receive a portion of the first air delivery conduit within the first tube; and
the second conduit connection includes a second tube shaped to receive a portion of the second air delivery conduit within the second tube.

17. The mask system of claim 1, wherein the nasal cushion and the mouth cushion are integrally formed as a unitary structure made from silicone.

18. A mask system for delivery of respiratory therapy to a patient, the mask system comprising:
a sealing assembly that defines a breathing chamber configured to contemporaneously provide air to both a nose of the patient and a mouth of the patient, the sealing assembly shaped to be positioned entirely below a nasal bridge of the patient and avoid the nasal bridge of the patient when providing air to both the nose and the mouth, the sealing assembly including:
(i) a nasal cushion structured to seal nares of the patient and provide air from the breathing chamber to the nose of the patient,
(ii) a mouth cushion structured to seal around the mouth of the patient and provide air from the breathing chamber to the mouth of the patient, the mouth cushion integrally formed with the nasal cushion from silicone as a unitary structure,
(iii) conduit connections, including a first conduit connection and a second conduit connection, attached to respective sides of the nasal cushion,
(iv) a rigid front wall connected to a non-face contacting portion of the mouth cushion,
(v) lower headgear connections attached to respective sides of the rigid front wall, the lower headgear connections being spaced apart from the conduit connections, the conduit connections being positioned entirely above all headgear connections of the sealing assembly when the mask system is worn by the patient and viewed from in front of the patient, and
(vi) one or more vent ports positioned entirely within a central region of the sealing assembly located (a) between each of the conduit connections, (b) between each of the lower headgear connections, (c) below the conduit connections, and (d) above the lower headgear connections, when the mask system is worn by the patient and viewed from in front of the patient;
a pair of air delivery conduits including a first air delivery conduit and a second air delivery conduit to provide air to the breathing chamber, the first air delivery conduit being structured to releasably connect with the first conduit connection and the second air delivery conduit being structured to releasably connect with the second conduit connection; and
a headgear assembly structured to maintain the sealing assembly on a face of the patient, the headgear assembly including:
(i) an upper portion structured to connect with the first air delivery conduit above a first ear of the patient and the second air delivery conduit above a second ear of the patient, and
(ii) a lower portion structured to connect with the lower headgear connections, wherein the upper portion of the headgear assembly and the lower portion of the headgear assembly are joined together at a back of a head of the patient when the mask system is worn by the patient.

19. The mask system of claim 18, wherein the conduit connections are attached to the sealing assembly at an angle with respect to a horizontal plane of the sealing assembly when the mask system is worn by the patient and viewed from in front of the patient, so that each of the pair of air delivery conduits connects with the sealing assembly at the angle with respect to the horizontal plane and extends upwards away from the sealing assembly and to behind a respective ear of the patient when the mask system is worn by the patient and viewed from in front of the patient.

20. The mask system of claim 18, wherein the one or more vent ports comprise multiple vent ports arranged horizontally with respect to each other when the mask system is worn by the patient and viewed from in front of the patient.

21. The mask system of claim 18, wherein the first conduit connection and the second conduit connection are formed in the nasal cushion.

22. The mask system of claim 18, wherein the lower headgear connections are configured to connect using crossbars.

\* \* \* \* \*